(12) United States Patent
Abdel-Magid et al.

(10) Patent No.: US 7,524,837 B2
(45) Date of Patent: Apr. 28, 2009

(54) BENZOTRIAZAPINONE SALTS AND METHODS FOR USING SAME

(75) Inventors: Ahmed F. Abdel-Magid, Ambler, PA (US); Judith H. Cohen, North Wales, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 553 days.

(21) Appl. No.: 10/833,232

(22) Filed: Apr. 27, 2004

(65) Prior Publication Data

US 2005/0026911 A1 Feb. 3, 2005

Related U.S. Application Data

(60) Provisional application No. 60/469,659, filed on May 12, 2003.

(51) Int. Cl.
*C07D 401/04* (2006.01)
(52) U.S. Cl. ........................ 514/183; 540/501
(58) Field of Classification Search ................. 540/501; 514/183
See application file for complete search history.

(56) References Cited

U.S. PATENT DOCUMENTS

| | | | | |
|---|---|---|---|---|
| 4,255,431 A | 3/1981 | Junggren et al. | ........... | 514/338 |
| 4,472,409 A | 9/1984 | Senn-Bilfinger | ........... | 514/338 |
| 4,758,579 A | 7/1988 | Kohl et al. | ........... | 514/338 |
| 5,045,552 A | 9/1991 | Souda et al. | ........... | 514/338 |
| 5,091,381 A | 2/1992 | Kim et al. | ........... | 514/183 |
| 6,080,743 A * | 6/2000 | Acklin et al. | ........... | 514/249 |

FOREIGN PATENT DOCUMENTS

| | | |
|---|---|---|
| EP | 0 508 796 A1 | 10/1992 |
| EP | 0 514 133 A1 | 11/1992 |
| EP | 0 645 378 B1 | 8/2000 |
| WO | WO 93/12817 A1 | 7/1993 |
| WO | WO 93/19063 | 9/1993 |
| WO | WO 03/041714 A1 | 5/2003 |
| WO | WO 93/16999 | 9/2003 |

OTHER PUBLICATIONS

Mutt V., *Gastrointestinal Hormones*, Glass G.B.J., ed., Raven Press, New York, p. 169-221.
Nisson G., *Gastrointestinal Hormones*, Glass G.B.J., ed., Raven Press, New York, p. 127-167.
Tracy H.J. and Gregory R.A., "Physiological Properties of a Series of Synthetic Peptides structurally related to Gastrin 1," *Nature* (London), Dec. 5, 1964, 204, 935-938.
M.G. Bock et al., "Benzodiapine Gastrin and Brain Cholecystokinin Receptor Ligands: L-365,260," *J. Med. Chem.*, 1989, 32, 13-16.
S.B. Kalindjian et al., "A New Class of Non-peptidic Cholecystokinin-B/Gastrin Receptor Antagonists Based on Dibenzobicyclo[2.2.2]octane," *J. Med. Chem.*, 1994, 37, 3671-3.

A. Nishida et al., "Pharmacological Profile of (R)-1-[2,3-Dihydro-1-2'-methyl-phenacyl)-2-oxo-5-phenyl-1H-1,4-benzodiazepin-3-yl]-3-(3-methylphenyl)urea (YM022), a New Potent and Selective Gastrin/Cholecystokinin-B Receptor Antagonist, in Vitro and in Vivo," *Journal of Pharmacology and Experimental Therapeutics*, 1994, 269(2), 725-731.
Stella, V. J. et al., "Prodrugs: A Chemical Approach to Targeted Drug Delivery," *Directed Drug Delivery*, 1985, Humana Press, New Jersey, pp. 247-267.
Stella, V. J. et al., "Prodrugs—Do They Have Advantages in Clinical Practice?" *Drugs*, 1985, 29, pp. 455-473.
R. J. Booth, et. al., "Polymer-Supported Quenching Reagents for Parallel Purification," *J. Am. Chem. Soc.*, (1997), 119, 4882-6.
M. S. Chambers, et. al., "L-708,474: The C5-Cyclohexyl Analogue of L-365,260, A Selective High Affinity Ligand for the $CCK_B$/Gastrin Receptor," *Bioorg. Med. Chem. Lett.* (1993), 3(10), 1919-24.
M. Gaudry, A. Marquet, "1-Bromo-3-Methyl-2-Butanone," *Org. Synth.*, (1976), 55, 24-7.
T. S. Sorensen, "The Equilibria and Kinetics of the Cyclohexenyl-Cyclopentenyl Cation Rearrangement," *J. Am. Chem. Soc.*, (1969), 91, 6398-403.
G. Semple, et. al., "A Facile Large Scale Synthesis of Optically Active 3-Amino-5-(2-Pyridyl)-1,4-Benzodiazepin-2-One Derivatives," *Synth. Commun.*, (1996), 26(4), 721-7.
Mutt V., *Gastrointestinal Hormones*, Glass G.B.J., ed., Raven Press, New York, p. 169-221, (1980).
Nisson G., *Gastrointestinal Hormones*, Glass G.B.J., ed., Raven Press, New York, p. 127-167, (1980).
Tracy H.J. and Gregory R.A., "Physiological Properties of a Series of Synthetic Peptides structurally related to Gastrin 1," *Nature* (London), Dec. 5, 1964, 204, 935-938.
M.G. Bock et al., "Benzodiapine Gastrin and Brain Cholecystokinin Receptor Ligands: L-365,260," *J. Med. Chem.*, 1989, 32, 13-16.
S.B. Kalindjian et al., "A New Class of Non-peptidic Cholecystokinin-B/Gastrin Receptor Antagonists Based on Dibenzobicyclo[2.2.2]octane," *J. Med. Chem.*, 1994, 37, 3671-3.

(Continued)

*Primary Examiner*—Bruck Kifle
(74) *Attorney, Agent, or Firm*—Woodcock Washburn LLP

(57) ABSTRACT

This invention relates to pharmaceutically acceptable salts of compounds of formula (I)

(I)

Such salts are useful, for example, for the treatment of gastrin related disorders.

15 Claims, No Drawings

OTHER PUBLICATIONS

A. Nishida et al., "Pharmacological Profile of (R)-1-[2,3-Dihydro-1-2'-methyl-phenacyl)-2-oxo-5-phenyl-1H-1,4-benzodiazepin-3-yl]-3-(3-methylphenyl)urea (YM022), a New Potent and Selective Gastrin/Cholecystokinin-B Receptor Antagonist, in Vitro and in Vivo," *Journal of Pharmacology and Experimental Therapeutics*, 1994, 269(2), 725-731.

Stella, V. J. et al., "Prodrugs: A Chemical Approach to Targeted Drug Delivery," *Directed Drug Delivery*, 1985, Humana Press, New Jersey, pp. 247-267.

Stella, V. J. et al., "Prodrugs—Do They Have Advantages in Clinical Practice?" *Drugs*, 1985, 29, pp. 455-473.

R. J. Booth, et. al., "Polymer-Supported Quenching Reagents for Parallel Purification," *J. Am. Chem. Soc.*, (1997), 119, 4882-6.

M. S. Chambers, et. al., "L-708,474: The C5-Cyclohexyl Analogue of L-365,260, A Selective High Affinity Ligand for the $CCK_B$/Gastrin Receptor," *Bioorg. Med. Chem. Lett.* (1993), 3(10), 1919-24.

M. Gaudry, A. Marquet, "1-Bromo-3-Methyl-2-Butanone," *Org. Synth.*, (1976), 55, 24-7.

T. S. Sorensen, "The Equilibria and Kinetics of the Cyclohexenyl-Cyclopentenyl Cation Rearrangement," *J. Am. Chem. Soc.*, (1969), 91, 6398-403.

G. Semple, et. al., "A Facile Large Scale Synthesis of Optically Active 3-Amino-5-(2-Pyridyl)-1,4-Benzodiazepin-2-One Derivatives," *Synth. Commun.*, (1996), 26(4), 721-7.

H. Shinagawa, et. al., "Synthesis and Biological Properties of a New Series of Anti-MRSA β-Lactams; 2-(Thiazol-2-ylthio)carbapenems," *Bioorg. Med. Chem.*, (1997), 5(3), 601-21.

J. L. Castro et al., "Controlled Modification of Acidity in Cholecystokinin B Receptor Antagonists: N-(1,4-Benzodiazepin-3-yl)-N'-[tetrazol-5-ylamino)phenyl]ureas," *J. Med. Chem.* (1996), 39, 842-9.

P. Hodge, G. Richardson, "Conversion of Acids into Acid Chlorides and Alcohols into Alkyl Chlorides using a Polymer-supported Phosphine in Carbon Tetrachloride," *J. C. S. Chem. Commun.*, (1975), 622-623.

A. Cappelli, et. al., "Novel Potent and Selective Central $5-HT_3$ Receptor Ligands Provided with Different Intrinsic Efficacy. 2. Molecular Basis of the Intrinsic Efficacy Receptors," *J. Med. Chem.*, (1999), 42, 1556-75.

Biggs, et. al., "Monoquaternary Neuromuscular Blocking Agents Based on 1-Tetralone and 1-Indanone," *J. Med. Chem.* (1976), 19(4), 472.

A. L. J. Beckwith, et. al., "Stereoelectronic Effects in Hydrogen-atom Transfer Reactions of Substituted Cyclohexyl Radicals," *J. Chem. Soc. Perkin Trans. II*, (1983), 661-8.

J. A. Robl, "Synthesis of 2-(4-Fluorophenyl)-4-isopropyl-3-quinolinecarbaldehyde: A New Route to 2,3,4-Substituted Quinolines," *Synthesis*, 1991, 56-58.

T. R. Kelly et al., "Total Synthesis of Dimethyl Sulfomycinamate," *J. Org. Chem.*, (1996), 61, 4623-4633.

Y. Matsushita, et. al., "A Convenient Synthesis of Methyl 4-Substituted Benzoates via Diels-Alder Reaction in the Presence of Palladium on Activated Carbon," *Syn. Comm.*, (1994), 24(22), 3307-13.

E. Lee, et al., "Oxyanion Orientation in Anionic Oxy-Cope Rearrangements," *J. Org. Chem.* (1994), 59, 1444-56.

J. P. Weichert, et. al., "Polyiodinated Triglyceride Analogs as Potential Computed Tomography Imaging Agents for the Liver," *J. Med. Chem.* (1995), 38, 636-46.

Black et al., "Further analysis of anomalous $pK_B$ values for histamine $H_2$-receptor antagonists on the mouse isolated stomach assay," *Br. J. Pharmacol.*, 1985, 86, 581-7.

Lennon et al., "The I.M.A.G.E. Consortium: An Integrated Molecular Analysis of Genomes and Their Expression," *Genomics* 33, 151-152 (1996).

Kozak M., "Compilation and analysis of sequences upstream from the translational start site in eukaryotic mRNAs," *Nucleic Acids Res.* Jan. 25, 1984;12(2):857-72.

Eissele, R., et al., "Effect of gastrin receptor blockade on endocrine cells in rats during achlorhydria," *Gastroenterology*, 103, 1596-1601, 1992.

* cited by examiner

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: Synthetic Construct

<400> SEQUENCE: 1
tctgaattcg ccgccatgga gctgcta                                    27

<210> SEQ ID NO 2
<211> LENGTH: 27
<212> TYPE: DNA
<213> ORGANISM: Artificial Sequence
<220> FEATURE:
<223> OTHER INFORMATION: Synthetic Construct

<400> SEQUENCE: 2

```
gtatctagac tcagccaggg cccagtg                                    27

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
taatacgact cactatagg                                             19

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
attaaccctc actaaaggg                                             19

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tgtccggact actcatggtg                                            20
```

BENZOTRIAZAPINONE SALTS AND METHODS FOR USING SAME

CROSS REFERENCE TO RELATED APPLICATIONS

This application claims the benefit of U.S. Provisional Application No. 60/469,659, filed May 12, 2003, which is incorporated herein by reference in its entirety.

This invention relates to gastrin and cholecystokinin (CCK) receptor ligands. (The receptor previously known as the $CCK_B$/gastrin receptor is now termed the $CCK_2$ receptor). The invention also relates to methods for preparing such ligands and to compounds which are useful intermediates in such methods. The invention further relates to pharmaceutical compositions comprising such ligands and methods for preparing such pharmaceutical compositions.

Gastrin and the cholecystokinins are structurally related neuropeptides which exist in gastrointestinal tissue and the central nervous system (Mutt V., *Gastrointestinal Hormones*, Glass G. B. J., ed., Raven Press, New York, p. 169; Nisson G., ibid., p. 127).

Gastrin is one of the three primary stimulants of gastric acid secretion. Several forms of gastrin are found including 34-, 17- and 14-amino acid species with the minimum active fragment being the C-terminal tetrapeptide (TrpMetAspPhe-$NH_2$) which is reported in the literature to have full pharmacological activity (Tracy H. J. and Gregory R. A., *Nature* (London), 1964, 204, 935). Much effort has been devoted to the synthesis of analogues of this tetrapeptide (and the N-protected derivative Boc-TrpMetAspPhe-$NH_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal mobility, gall bladder contraction, pancreatic enzyme secretion and are known to have a trophic action on the pancreas. They also inhibit gastric emptying and have various effects in the central nervous system.

Compounds which bind to cholecystokinin and/or gastrin receptors are important because of their potential pharmaceutical use as antagonists, inverse agonists or partial agonists of the natural peptides. Such compounds are described herein as ligands. The term ligand as used herein means either an antagonist, partial or full agonist, or an inverse agonist. Usually, the term ligand refers to an antagonist.

A number of gastrin ligands have been proposed for various therapeutic applications, including the prevention of gastrin-related disorders including gastrointestinal ulcers, dyspepsia, reflux oesophagitis (gastroesophageal reflux disease (GERD), both erosive and non-erosive) by reduction in gastric acid secretion and/or improving impaired motor activity at the lower oesophageal sphincter, Zollinger-Ellison syndrome, Barrett's oesophagus (specialized intestinal metaplasia of distal oesophagus), ECL cell hyperplasia, rebound hypersecretion (following cessation of anti-secretory therapy), ECL-derived gastric polyps most commonly found in patients with atrophic gastritis both with (pernicious anaemia) or without vitamin B12 deficiency, antral G cell hyperplasia and other conditions in which lower gastrin activity or lower acid secretion is desirable. The hormone has also been shown to have a trophic action on cells and so an antagonist may be expected to be useful in the treatment of cancers, particularly in the GI tract, more particularly in the stomach, oesophagus and colo-rectal areas. Tumours found in other organs such as the pancreas, lung (small cell lung carcinomas) and thyroid (thyroid medullary tumours) may also be treated.

Other possible uses are in the potentiation of opiate (for example morphine) analgesia. Moreover, ligands for cholecystokinin receptors in the brain (so-called $CCK_2$ receptors) have been claimed to possess anxiolytic activity.

A known antagonist of the $CCK_2$ receptor is L-365,260 (M. G. Bock et al., *J. Med Chem.*, 1989, 32, 13-16), which is based on a benzodiazepine structure. In the rat stomach assay described hereinbelow, L-365,260 was shown to have an affinity of $pK_B$=7.61±0.12 for the $CCK_2$ receptor (S. B. Kalindjian et al., *J. Med. Chem.*, 1994, 37, 3671-3).

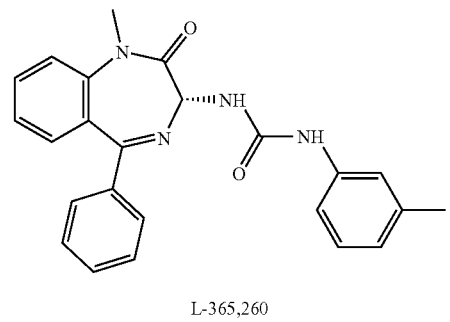

L-365,260

More recently, another benzodiazepine, YF476, was developed as a potent $CCK_2$ antagonist (A. Nishida et al., *Journal of Pharmacology and Experimental Therapeutics*, 1994, 269, 725-731). In rat cortical membranes, YF476 was found to have an affinity $pK_i$ of 10.17±0.03 for the $CCK_2$ receptor.

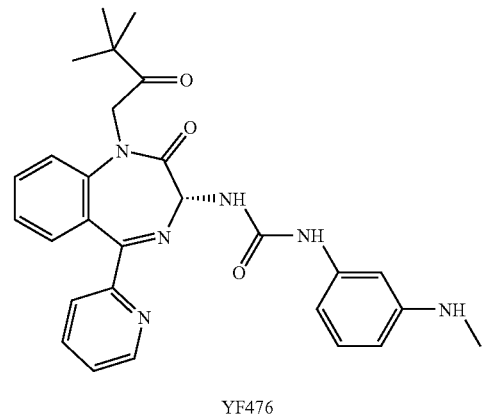

YF476

L-365,260 and YF476 are structurally closely related. Both compounds are 1,4-benzodiazepines. The carbon at position three of these 1,4-benzodiazepines is a chiral centre. In both cases, the optimal compounds have an R-configuration at this centre. Indeed, all 1,4-benzodiazepines that have found utility as gastrin antagonists have a chiral centre on the diazepine ring, and it has been found that better gastrin receptor antagonism is exhibited by one configuration relative to the other.

The requirement for a single enantiomer of the known 1,4-benzodiazepine gastrin ligands is undesirable. The synthesis of single enantiomers from achiral precursors, as in these cases, is a costly and relatively complex procedure. This generally requires, for example, either a separation step, usually inefficient as one enantiomer is discarded, or the use of an often expensive chiral auxiliary during the synthesis, coupled with an increase in chemical steps. For these reasons, a drug candidate with no stereocentres on the seven-membered ring would offer a distinct advantage over chiral alternatives.

U.S. Pat. No. 5,091,381 describes benzotriazepines which are said to bind to peripheral benzodiazepine receptors.

EP-A-0645378 describes a class of bicyclic compounds which are said to inhibit squalene synthetase.

It is an object of the present invention to provide potent and selective gastrin and CCK receptor ligands. It is a further object of the present invention to provide gastrin and CCK receptor ligands which have no chiral centre on the 7-membered ring and which can therefore be prepared using straightforward synthetic methods.

One aspect of the present invention relates to pharmaceutically acceptable salts of compounds having formula (I):

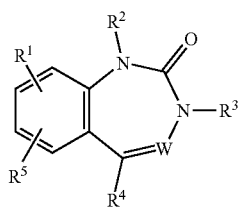

(I)

wherein:
W is N or $N^+$—$O^-$;
$R^1$ and $R^5$ are independently H, $C_1$ to $C_6$ alkyl, ($C_1$ to $C_6$ alkyl)oxy, thio, ($C_1$ to $C_6$ alkyl)thio, carboxy, carboxy ($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino, ($C_1$ to $C_6$ alkyl)aminocarbonyl, di($C_1$ to $C_6$ alkyl)aminocarbonyl, [N-Z]($C_1$ to $C_6$ alkyl)carbonylamino, formyloxy, formamido, ($C_1$ to $C_6$ alkyl)aminosulfonyl, di($C_1$ to $C_6$ alkyl)aminosulfonyl, [N-Z]($C_1$ to $C_6$ alkyl)sulfonylamino or cyano; or $R^1$ and $R^5$ together form a methylenedioxy group;
$R^2$ is H or an optionally substituted $C_1$ to $C_{18}$ hydrocarbyl group wherein up to three C atoms may optionally be replaced by N, O and/or S atoms;
$R^3$ is —$(CR^{11}R^{12})_m$—X—$(CR^{13}R^{14})_p$—$R^9$;
m is 0, 1, 2, 3 or 4;
p is 0, 1 or 2;
X is a bond, —$CR^{15}$=$CR^{16}$—, —C≡C—, C(O)NH, NHC(O), C(O)NMe, NMeC(O), C(O)O, NHC(O)NH, NHC(O)O, OC(O)NH, NH, O, CO, $SO_2$, $SO_2$NH, C(O)NHNH,

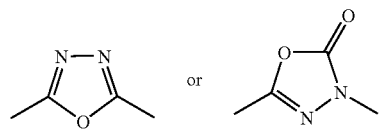

$R^9$ is H; $C_1$ to $C_6$ alkyl; or phenyl, naphthyl, pyridyl, benzimidazolyl, indazolyl, quinolinyl, isoquinolinyl, tetrahydroisoquinolinyl, indolinyl, isoindolinyl, indolyl, isoindolyl or 2-pyridonyl, all optionally substituted with 1, 2 or 3 groups independently selected from
-L-Q wherein:
L is a bond, or a group of the formula —$(CR^{17}R^{18})_v$—Y—$(CR^{17}R^{18})_w$, wherein v and w are independently 0, 1, 2 or 3, and Y is a bond, —$CR^{15}$=$CR^{16}$—, phenyl, furanyl, thiophenyl, pyrrolyl, thiazolyl, imidazolyl, oxazolyl, isoxazolyl, pyrazolyl, isoxazolonyl, piperazinyl, piperidinyl, morpholinyl, pyrrolidinyl, isothiazolyl, triazolyl, oxadiazolyl, thiadiazolyl, pyridyl or pyridazyl; and
Q is H, ($C_1$ to $C_6$ alkyl)oxy, [N-Z]($C_1$ to $C_6$ alkyl)oxy($C_1$ to $C_6$ alkyl)amino, thio, ($C_1$ to $C_6$ alkyl)thio, carboxy($C_1$ to $C_6$ alkyl)thio, carboxy, carboxy($C_1$ to $C_6$ alkyl), carboxy ($C_1$ to $C_6$ alkenyl), [N-Z]carboxy($C_1$ to $C_6$ alkyl)amino, carboxy($C_1$ to $C_6$ alkyl)oxy, formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, amino, [N-Z]($C_1$ to $C_6$ alkyl)amino, aminocarbonyl, ($C_1$ to $C_6$ alkyl)aminocarbonyl, di($C_1$ to $C_6$ alkyl)aminocarbonyl, [N-Z]($C_1$ to $C_6$ alkyl)carbonylamino, $C_5$ to $C_8$ cycloalkyl, [N-Z]($C_1$ to $C_6$ alkyl)carbonyl($C_1$ to $C_6$ alkyl)amino, halo, halo($C_1$ to $C_6$ alkyl), sulfamoyl, [N-Z]($C_1$ to $C_6$ alkyl)sulfonylamino, ($C_1$ to $C_6$ alkyl)sulfonylaminocarbonyl, carboxy($C_1$ to $C_6$ alkyl)sulfonyl, carboxy ($C_1$ to $C_6$ alkyl)sulfinyl, tetrazolyl, [N-Z]tetrazolylamino, cyano, amidino, amidinothio, $SO_3H$, formyloxy, formamido, $C_3$ to $C_8$ cycloalkyl, ($C_1$ to $C_6$ alkyl)sulphamoyl, di($C_1$ to $C_6$ alkyl)sulphamoyl, ($C_1$ to $C_6$ alkyl)carbonylaminosulfonyl, 5-oxo-2,5-dihydro[1,2,4]oxadiazolyl, carboxy($C_1$ to $C_6$ alkyl)carbonylamino, tetrazolyl($C_1$ to $C_6$ alkyl)thio, [N-Z]tetrazolyl ($C_1$ to $C_6$ alkyl)amino, 5-oxo-2,5-dihydro[1,2,4] thiadiazolyl, 5-oxo-1,2-dihydro[1,2,4]triazolyl, [N-Z] ($C_1$ to $C_6$ alkyl)amino($C_1$ to $C_6$ alkyl)amino, or a group of the formula

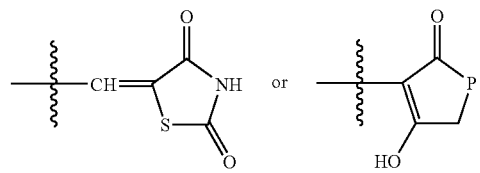

wherein P is O, S or $NR^{19}$;
Z is H, $C_1$ to $C_6$ alkyl, t-butoxycarbonyl, acetyl, benzoyl or benzyl;
$R^4$ is an optionally substituted $C_1$ to $C_{18}$ hydrocarbyl group wherein up to three C atoms may optionally be replaced by N, O and/or S atoms;
$R^{11}$, $R^{12}$, $R^{13}$, $R^{14}$, $R^{15}$, $R^{17}$, $R^{18}$ and $R^{19}$ are independently H or $C_1$ to $C_3$ alkyl; and
$R^{16}$ is H, $C_1$ to $C_3$ alkyl, or acetylamino.

Preferably, W is N. In certain preferred embodiments, $R^3$ is —$CH_2$—X—$R^9$, X is C(O)NH, $R^9$ is phenyl-L-Q, L is a bond an d/or Q is 5-oxo-2,5-dihydro[1,2,4]oxadiazolyl.

In one aspect, the present invention relates to methods of treating a gastrin related disorder comprising administering a therapeutically effective amount of a salt of formula (I) to a patient in need of such treatment.

Typical gastrin related disorders are gastrointestinal ulcers, dyspepsia, reflux oesophagitis (gastroesophageal reflux disease (GERD), both erosive and non-erosive), Zollinger-Ellison syndrome, Barrett's oesophagus (specialized intestinal metaplasia of distal oesophagus), ECL cell hyperplasia, rebound hypersecretion (following cessation of anti-secretory therapy), ECL-derived gastric polyps, cancers of the GI tract, more particularly in the stomach, oesophagus and colo-rectal areas, as well as tumours found in other organs such as the pancreas, lung (small cell lung carcinomas) and thyroid (thyroid medullary tumours) and anxiety. The potentiation of opiate induced analgesia may also provide a role for the gastrin ligands of the present invention.

Further, the present invention provides pharmaceutically acceptable salts of compounds of formula (IIa)

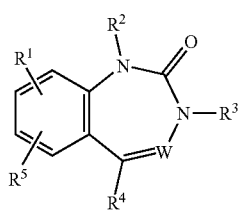

(IIa)

wherein:

W is N or $N^+$—$O^-$;

$R^1$ and $R^5$ are independently H, $C_1$ to $C_6$ alkyl, ($C_1$ to $C_6$ alkyl)oxy, thio, ($C_1$ to $C_6$ alkyl)thio, carboxy, carboxy ($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino, ($C_1$ to $C_6$ alkyl)aminocarbonyl, di($C_1$ to $C_6$ alkyl)aminocarbonyl, [N-Z]($C_1$ to $C_6$ alkyl)carbonylamino, formyloxy, formamido, ($C_1$ to $C_6$ alkyl)aminosulfonyl, di($C_1$ to $C_6$ alkyl)aminosulfonyl, [N-Z]($C_1$ to $C_6$ alkyl)sulfonylamino or cyano; or $R^1$ and $R^5$ together form a methylenedioxy group;

$R^2$ is —$(CH_2)_s$—$C(O)$—$(CH_2)_t$—$R^8$ s is 0, 1, 2 or 3;

t is 0, 1, 2 or 3;

$R^8$ is selected from H, OH, $C_1$ to $C_{12}$ alkyl, ($C_1$ to $C_{12}$ alkyl)oxy, $C_3$ to $C_{12}$ cycloalkyl, phenyl, naphthyl, pyridyl, pyrrolyl, imidazolyl, pyrazolyl, pyridazinyl, pyrimidinyl, triazolyl, furanyl, thienyl, furazanyl, oxazolyl, isoxazolyl, thiazolyl, thiazinyl, indolyl, indolinyl, isoindolyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxanyl (all optionally substituted with 1, 2 or 3 groups independently selected from $C_1$ to $C_6$ alkyl, ($C_1$ to $C_6$ alkyl)oxy, thio, ($C_1$ to $C_6$ alkyl)thio, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino or cyano);

$R^3$ is —$(CR^{11}R^{12})_m$—X—$(CR^{13}R^{14})_p$—$R^9$;

m is 0, 1, 2, 3 or 4 (preferably 1 or 2);

p is 0, 1 or 2;

X is a bond, —$CR^{15}$=$CR^{16}$—, —C≡C—, C(O)NH, NHC(O), C(O)NMe, NMeC(O), C(O)O, NHC(O)NH, NHC(O)O, OC(O)NH, NH, O, CO, $SO_2$, $SO_2$NH, C(O)NHNH,

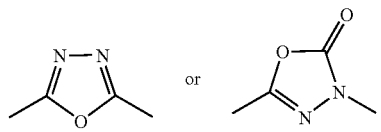

or $R^9$ is H; $C_1$ to $C_6$ alkyl; or phenyl, naphthyl, pyridyl, benzimidazolyl, indazolyl, quinolinyl, isoquinolinyl, tetrahydroisoquinolinyl, indolinyl, isoindolinyl, indolyl, isoindolyl or 2-pyridonyl, all optionally substituted with 1, 2 or 3 groups independently selected from

-L-Q wherein:

L is a bond, or a group of the formula —$(CR^{17}R^{18})_v$—Y—$(CR^{17}R^{18})_w$, wherein v and w are independently 0, 1, 2 or 3, and Y is a bond, —$CR^{15}$=$CR^{16}$—, phenyl, furanyl, thiophenyl, pyrrolyl, thiazolyl, imidazolyl, oxazolyl, isoxazolyl, pyrazolyl, isoxazolonyl, piperazinyl, piperidinyl, morpholinyl, pyrrolidinyl, isothiazolyl, triazolyl, oxadiazolyl, thiadiazolyl, pyridyl or pyridazyl; and Q is H, ($C_1$ to $C_6$ alkyl)oxy, [N-Z]($C_1$ to $C_6$ alkyl)oxy($C_1$ to $C_6$ alkyl)amino, thio, ($C_1$ to $C_6$ alkyl)thio, carboxy($C_1$ to $C_6$ alkyl)thio, carboxy, carboxy($C_1$ to $C_6$ alkyl), carboxy ($C_1$ to $C_6$ alkenyl), [N-Z]carboxy($C_1$ to $C_6$ alkyl)amino, carboxy($C_1$ to $C_6$ alkyl)oxy, formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, amino, [N-Z]($C_1$ to $C_6$ alkyl)amino, aminocarbonyl, ($C_1$ to $C_6$ alkyl)aminocarbonyl, di($C_1$ to $C_6$ alkyl)aminocarbonyl, [N-Z]($C_1$ to $C_6$ alkyl)carbonylamino, $C_5$ to $C_8$ cycloalkyl, [N-Z]($C_1$ to $C_6$ alkyl)carbonyl($C_1$ to $C_6$ alkyl)amino, halo, halo($C_1$ to $C_6$ alkyl), sulfamoyl, [N-Z]($C_1$ to $C_6$ alkyl)sulfonylamino, ($C_1$ to $C_6$ alkyl)sulfonylaminocarbonyl, carboxy($C_1$ to $C_6$ alkyl)sulfonyl, carboxy ($C_1$ to $C_6$ alkyl)sulfinyl, tetrazolyl, [N-Z]tetrazolylamino, cyano, amidino, amidinothio, $SO_3H$, formyloxy, formamido, $C_3$ to $C_8$ cycloalkyl, ($C_1$ to $C_6$ alkyl)sulphamoyl, di($C_1$ to $C_6$ alkyl)sulphamoyl, ($C_1$ to $C_6$ alkyl)carbonylaminosulfonyl, 5-oxo-2,5-dihydro[1,2,4]oxadiazolyl, carboxy($C_1$ to $C_6$ alkyl)carbonylamino, tetrazolyl($C_1$ to $C_6$ alkyl)thio, [N-Z]tetrazolyl($C_1$ to $C_6$ alkyl)amino, 5-oxo-2,5-dihydro[1,2,4]thiadiazolyl, 5-oxo-1,2-dihydro[1,2,4]triazolyl, [N-Z]($C_1$ to $C_6$ alkyl)amino($C_1$ to $C_6$ alkyl)amino, or a group of the formula

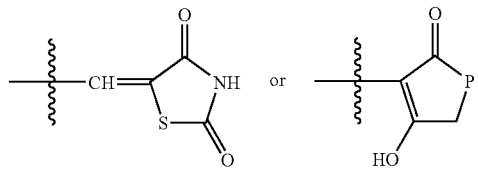

wherein P is O, S or $NR^{19}$;

Z is H, $C_1$ to $C_6$ alkyl, t-butoxycarbonyl, acetyl, benzoyl or benzyl;

$R^4$ is an optionally substituted $C_1$ to $C_{18}$ hydrocarbyl group wherein up to three C atoms may optionally be replaced by N, O and/or S atoms;

$R^{11}$, $R^{12}$, $R^{13}$, $R^{14}$, $R^{15}$, $R^{17}$, $R^{18}$ and $R^{19}$ are independently H or $C_1$ to $C_3$ alkyl; and $R^{16}$ is H, $C_1$ to $C_3$ alkyl, or acetylamino;

with the proviso that $R^2$ is not $CH_2CO_2H$ or $C(O)CH_3$ when $R^4$ is phenyl.

Further, the present invention provides pharmaceutically acceptable salts of compounds of formula (IIb)

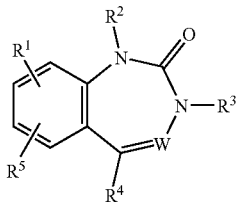

(IIb)

wherein:

W is N or $N^+$—$O^-$;

$R^1$ and $R^5$ are independently H, $C_1$ to $C_6$ alkyl, ($C_1$ to $C_6$ alkyl)oxy, thio, ($C_1$ to $C_6$ alkyl)thio, carboxy, carboxy ($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo(C, to $C_6$ alkyl), aminosulfonyl, ($C_1$ to $C_6$ alkyl)sulfonylamino, ($C_1$ to $C_6$ alkyl)aminocarbonyl, di($C_1$ to $C_6$ alkyl)aminocarbonyl, [N-Z]($C_1$ to $C_6$ alkyl)carbonylamino, formyloxy, formamido, ($C_1$ to $C_6$ alkyl)aminosulfonyl, di($C_1$ to $C_6$ alkyl)aminosulfonyl, [N-Z]($C_1$ to $C_6$ alkyl)sulfonylamino or cyano; or $R^1$ and $R^5$ together form a methylenedioxy group;

$R^2$ is H or an optionally substituted $C_1$ to $C_{18}$ hydrocarbyl group wherein up to three C atoms may optionally be replaced by N, O and/or S atoms;

$R^3$ is —$(CR^{11}R^{12})_m$—X—$(CR^{13}R^{14})$—$R^9$;

m is 0, 1, 2, 3 or 4 (preferably 1 or 2);

p is 0, 1 or 2;

X is a bond, —$CR^{15}$=$CR^{16}$—, —C≡C—, C(O)NH, NHC(O), C(O)NMe, NMeC(O), C(O)O, NHC(O)NH, NHC(O)O, OC(O)NH, NH, O, CO, $SO_2$, $SO_2$NH, C(O)NHNH,

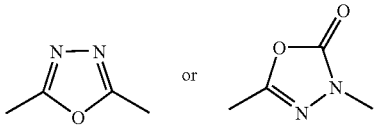

$R^9$ is H; $C_1$ to $C_6$ alkyl; or phenyl, naphthyl, pyridyl, benzimidazolyl, indazolyl, quinolinyl, isoquinolinyl, tetrahydroisoquinolinyl, indolinyl, isoindolinyl, indolyl, isoindolyl or 2-pyridonyl, all optionally substituted with 1, 2 or 3 groups independently selected from

-L-Q wherein:

L is a bond, or a group of the formula —$(CR^{17}R^{18})_v$—Y—$(CR^{17}R^{18})_w$, wherein v and w are independently 0, 1, 2 or 3, and Y is a bond, —$CR^{15}$=$CR^{16}$—, phenyl, furanyl, thiophenyl, pyrrolyl, thiazolyl, imidazolyl, oxazolyl, isoxazolyl, pyrazolyl, isoxazolonyl, piperazinyl, piperidinyl, morpholinyl, pyrrolidinyl, isothiazolyl, triazolyl, oxadiazolyl, thiadiazolyl, pyridyl or pyridazyl; and Q is H, ($C_1$ to $C_6$ alkyl)oxy, [N-Z]($C_1$ to $C_6$ alkyl)oxy($C_1$ to $C_6$ alkyl)amino, thio, ($C_1$ to $C_6$ alkyl)thio, carboxy($C_1$ to $C_6$ alkyl)thio, carboxy, carboxy($C_1$ to $C_6$ alkyl), carboxy ($C_1$ to $C_6$ alkenyl), [N-Z]carboxy($C_1$ to $C_6$ alkyl)amino, carboxy($C_1$ to $C_6$ alkyl)oxy, formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, amino, [N-Z]($C_1$ to $C_6$ alkyl)amino, aminocarbonyl, ($C_1$ to $C_6$ alkyl)aminocarbonyl, di($C_1$ to $C_6$ alkyl)aminocarbonyl, [N-Z]($C_1$ to $C_6$ alkyl)carbonylamino, $C_5$ to $C_8$ cycloalkyl, [N-Z]($C_1$ to $C_6$ alkyl)carbonyl($C_1$ to $C_6$ alkyl)amino, halo, halo($C_1$ to $C_6$ alkyl), sulfamoyl, [N-Z]($C_1$ to $C_6$ alkyl)sulfonylamino, ($C_1$ to $C_6$ alkyl)sulfonylaminocarbonyl, carboxy($C_1$ to $C_6$ alkyl)sulfonyl, carboxy ($C_1$ to $C_6$ alkyl)sulfinyl, tetrazolyl, [N-Z]tetrazolylamino, cyano, amidino, amidinothio, $SO_3H$, formyloxy, formamido, $C_3$ to $C_8$ cycloalkyl, ($C_1$ to $C_6$ alkyl)sulphamoyl, di($C_1$ to $C_6$ alkyl)sulphamoyl, ($C_1$ to $C_6$ alkyl)carbonylaminosulfonyl, 5-oxo-2,5-dihydro[1,2,4]oxadiazolyl, carboxy($C_1$ to $C_6$ alkyl)carbonylamino, tetrazolyl($C_1$ to $C_6$ alkyl)thio, [N-Z]tetrazolyl ($C_1$ to $C_6$ alkyl)amino, 5-oxo-2,5-dihydro[1,2,4]thiadiazolyl, 5-oxo-1,2-dihydro[1,2,4]triazolyl, [N-Z]($C_1$ to $C_6$ alkyl)amino($C_1$ to $C_6$ alkyl)amino, or a group of the formula

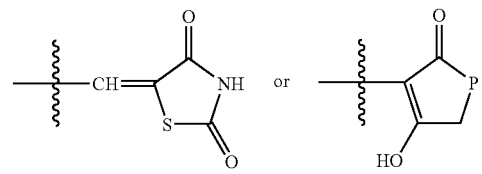

wherein P is O, S or $NR^{19}$;

Z is H, $C_1$ to $C_6$ alkyl, t-butoxycarbonyl, acetyl, benzoyl or benzyl;

$R^4$ is of formula

—$(CH_2)_q$-T-$R^{10}$ wherein:

q is 0, 1, 2 or 3;

T is a bond, O, S, NH or N($C_1$ to $C_6$ alkyl); and $R^{10}$ is $C_1$ to $C_{12}$ alkyl, $C_3$ to $C_{12}$ cycloalkyl, phenyl, naphthyl, pyridyl, pyrrolyl, imidazolyl, pyrazolyl, pyridazinyl, pyrimidinyl, triazolyl, furanyl, thienyl, furazanyl, oxazolyl, isoxazolyl, thiazolyl, thiazinyl, indolyl, indolinyl, isoindolyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxanyl (all optionally substituted with 1, 2 or 3 groups independently selected from $C_1$ to $C_6$ alkyl, ($C_1$ to $C_6$ alkyl)oxy, $C_3$ to $C_8$ cycloalkyl, ($C_3$ to $C_8$ cycloalkyl)oxy, thio, ($C_1$ to $C_6$ alkyl)thio, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino or cyano);

$R^{11}, R^{12}, R^{13}, R^{14}, R^{15}, R^{17}, R^{18}$ and $R^{19}$ are independently H or $C_1$ to $C_3$ alkyl; and $R^{16}$ is H, $C_1$ to $C_3$ alkyl, or acetylamino;

with the proviso that $R^{10}$ is not phenyl or substituted phenyl when q is 0 and T is a bond.

Preferably $R^1$ and $R^5$ are both H. However, it will be appreciated the benzo-fused ring system may have one or two substituents on the benzene ring as indicated hereinabove. The substituents may have subtle steric and/or electronic effects which modify the activity of the compound at the gastrin receptor. However, the presence or otherwise of certain substituents on the benzene ring is not crucial to the overall pharmacological activity of the present compounds.

Preferably, in the compound of formula (IIa) or (IIb), W is N.

Preferably, in the compound of formula (I) or (IIb) $R^2$ is of formula:

wherein:

$R^6$ and $R^7$ are independently selected from H, $C_1$ to $C_6$ alkyl or OH; or $R^6$ and $R^7$ together represent an =O group;

n is 0 or 1;

s is 0, 1, 2 or 3;

t is 0, 1, 2 or 3; and $R^8$ is selected from H, $C_1$ to $C_{12}$ alkyl, ($C_1$ to $C_{12}$ alkyl)oxy, $C_3$ to $C_{12}$ cycloalkyl, phenyl, naphthyl, pyridyl, pyrrolyl, imidazolyl, pyrazolyl, pyridazinyl, pyrimidinyl, triazolyl, furanyl, thienyl, furazanyl, oxazolyl, isoxazolyl, thiazolyl, thiazinyl, indolyl, indolinyl, isoindolyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxanyl (all optionally substituted with 1, 2 or 3 groups independently selected from $C_1$ to $C_6$ alkyl, ($C_1$ to $C_6$ alkyl)oxy, thio, ($C_1$ to $C_6$ alkyl)thio, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino or cyano).

A preferred group of compounds according to the present invention is where $R^2$ is of formula:

—(CH$_2$)C(O)$R^8$ wherein:

$R^8$ is a branched $C_3$ to $C_{12}$ alkyl group (such as tert-butyl, sec-butyl, isopropyl, isobutyl or isovaleryl); or $R^8$ is a $C_3$ to $C_{12}$ cycloalkyl (such as cyclopentyl, cyclohexyl, cycloheptyl or adamantyl) phenyl, pyridyl, pyrrolidinyl or piperidinyl group (all optionally substituted with 1, 2 or 3 $C_{1-6}$ alkyl groups).

Preferably, $R^{11}$, $R^{12}$, $R^{13}$, $R^{14}$, $R^{15}$, $R^{16}$, $R^{17}$, $R^{18}$ and $R^{19}$ are all H.

A preferred group of compounds according to the present invention is where $R^3$ is of formula:

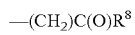

wherein:

X is C(O)NH or NHC(O), more preferably X is C(O)NH.

Preferably, $R^9$ is phenyl substituted with a carboxy, carboxy($C_1$ to $C_6$ alkyl), tetrazolyl, tetrazolyl-N—($C_1$ to $C_6$ alkyl)amino, carboxy($C_1$ to $C_6$ alkyl)thio, carboxy($C_1$ to $C_6$ alkyl)sulfonyl, ($C_1$ to $C_6$ alkyl)amino, or 5-oxo-2,5-dihydro[1,2,4]oxadiazolyl group; or $R^9$ is a N-[carboxy($C_1$ to $C_6$ alkyl)]indolinyl or N-[carboxy($C_1$ to $C_6$ alkyl)]indolyl group.

When $R^9$ is a substituted phenyl group, the substituent is preferably at the 3-position of the phenyl group.

Preferably, in compounds according to formula (I) or (IIa), $R^4$ is of formula:

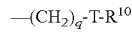

wherein:

q is 0, 1, 2 or 3;

T is a bond, O, S, NH or N($C_1$ to $C_6$ alkyl); and $R^{10}$ is $C_1$ to $C_{12}$ alkyl, $C_3$ to $C_{12}$ cycloalkyl, phenyl, naphthyl, pyridyl, pyrrolyl, imidazolyl, pyrazolyl, pyridazinyl, pyrimidinyl, triazolyl, furanyl, thienyl, furazanyl, oxazolyl, isoxazolyl, thiazolyl, thiazinyl, indolyl, indolinyl, isoindolyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxanyl (all optionally substituted with 1, 2 or 3 groups independently selected from $C_1$ to $C_6$ allyl, ($C_1$ to $C_6$ alkyl)oxy, $C_3$ to $C_8$ cycloalkyl, ($C_3$ to $C_8$ cycloalkyl)oxy, thio, ($C_1$ to $C_6$ alkyl)thio, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino or cyano).

More preferably, in compounds according to formula (I) or (IIa), $R^4$ is selected from $C_{1-12}$ alkyl (such as tert-butyl, sec-butyl, isopropyl, isobutyl or isovaleryl), $C_{3-12}$ cycloalkyl (such as cyclopentyl, cyclohexyl, cycloheptyl or adamantyl), pyridyl or phenyl (all of which may be optionally substituted with 1, 2 or 3 groups selected from OMe, NMe$_2$, CF$_3$, Me, F, Cl, Br or I).

In all compounds of the present invention, preferably q is 0 and T is a bond. More preferably $R^4$ is $C_3$-$C_{12}$ cycloalkyl, and more preferably, $R^4$ is cyclohexyl.

Certain compounds of the invention exist in various regioisomeric, enantiomeric, tautomeric and diastereomeric forms. It will be understood that the invention comprehends the different regioisomers, enantiomers, tautomers and diastereomers in isolation from each other as well as mixtures.

Compounds of the present invention wherein W is N may be prepared by the representative procedure shown in Reaction Scheme 1.

Reaction Scheme 1

I.

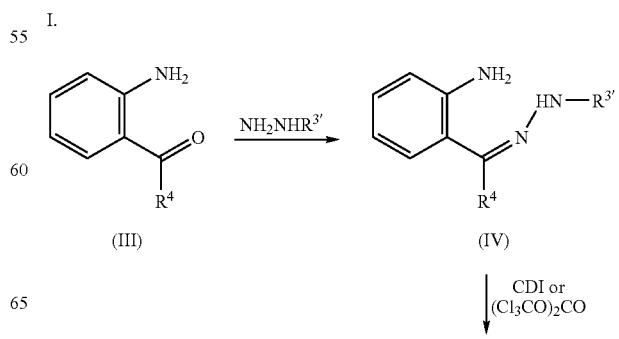

-continued

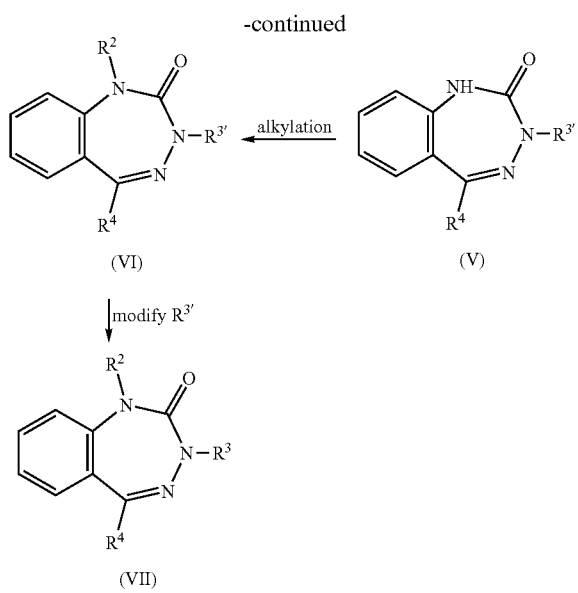

Ketone (III) is reacted with $NH_2NHR^{3'}$ (wherein $R^{3'}$ represents either $R^3$ or a suitable precursor thereof) to form hydrazone (IV). The hydrazone (IV) is then cyclised using a bifunctional carbonyl reagent to form benzotriazepinone (V). Bifunctional carbonyl reagents are well known to the person skilled in the art and include, for example, carbonyldiimidazole (CDI), triphosgene, phosgene or cyanogen bromide. Alkylation under standard conditions followed by modification of $R^{3'}$ affords the desired benzotriazepinone (VII).

Compounds wherein W is $N^+$—$O^-$ may be prepared by treating compound VII directly or an appropriately protected derivative of compound VI, with an oxidising agent such as MCPBA. Such derivatives of compound VI yield the desired N-oxide following deprotection.

$R^{3'}$ groups which are suitable precursors of $R^3$ will depend on the particular nature of $R^3$. For example, when $R^3$ is —$(CH_2)_mC(O)NH$—$(CH_2)_p$—$R^9$, a suitable $R^{3'}$ group would be —$(CH_2)_mCO_2(C_{1-6}$ alkyl). In this case, the requisite $R^3$ groups may be readily accessed via an ester hydrolysis followed by a simple amide coupling reaction. The skilled person will be aware of many other suitable $R^{3'}$ groups, depending on the nature of $R^3$.

Alkylation may be performed by, for example, displacement of an alkyl halide in the presence of a base. Methods of alkylation will be readily apparent to the person skilled in the art.

Hence, the present invention also provides a method of making pharmaceutically acceptable salts of compounds according to formula (I), formula (IIa), or formula (IIb).

It is an important advantage of the synthesis described hereinabove that no chiral centres are generated in the benzotriazepinone ring system during the synthesis.

The invention also comprehends derivative compounds ("pro-drugs") which are degraded in vivo to yield the species of formula (IIa) or (IIb). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, 1985, pp. 112-176, and *Drugs*, 1985, 29, pp. 455-473.

Pro-drug forms of the pharmacologically-active compounds of the invention will generally be compounds according to formula (II) having an acid group which is esterified or amidated. Included in such esterified acid groups are groups of the form —$COOR^a$, wherein $R^a$ is $C_1$ to $C_5$ alkyl, phenyl, substituted phenyl, benzyl, substituted benzyl, or one of the following:

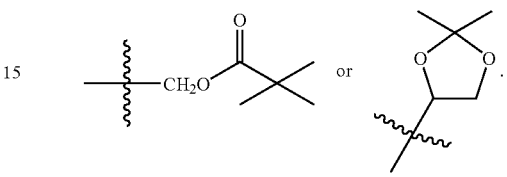

Amidated acid groups include groups of the formula —$CONR^bR^c$, wherein $R^b$ is H, $C_1$ to $C_5$ alkyl, phenyl, substituted phenyl, benzyl, or substituted benzyl, and $R^c$ is —OH or one of the groups just recited for $R^b$.

Compounds of formula (II) having an amino group may be derivatised with a ketone or an aldehyde such as formaldehyde to form a Mannich base. This will hydrolyse with first order kinetics in aqueous solution.

Another aspect of the present invention is a pharmaceutical composition comprising a pharmaceutically acceptable salt of a compound of formula (I) or (II), substantially as described herein before, with a pharmaceutically acceptable diluent or carrier.

Yet another aspect of the present invention is a method of making a pharmaceutical composition comprising a pharmaceutically acceptable salt of a compound of formula (I) or (II), substantially as described herein before, comprising mixing said salt with a pharmaceutically acceptable diluent or carrier.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, zinc, aluminum, and ammonium, and salts with organic bases. Suitable organic bases include choline, tert-butylamine, N-methyl-D-glucamine, arginine, benzathine, diolamine, olamine, procaine, ethanolamine, diethanolamine, triethanolamine, and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, benzylsulfate, napsylate, nitrate, oleate, pamoate, phosphate, polygalacturonate, stearate, succinate, sulfate, sulfosalicylate, tannate, tartrate, terephthalate, tosylate and triethiodide.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained be conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 µg/kg and 50 mg/kg, especially between 10 µg/kg and 10 mg/kg, eg. between 100 µg/kg and 2 mg/kg.

In a further aspect of the present invention there are provided pharmaceutical compositions comprising a pharmaceutically acceptable salt of a compound according to formula (I) and a proton pump inhibitor. Compositions comprising a $CCK_2$/gastrin antagonist and a proton pump inhibitor are described in International patent application WO93/12817, incorporated herein by reference.

In one aspect of the present invention the proton pump inhibitor is
- omeprazole which is 5-methoxy-2-[[(4-methoxy-3,5-dimethyl-2-pyridinyl)-methyl]sulfinyl]-1H-benzimidazole;
- BY308;
- SK&F 95601 which is 2-[[(3-chloro-4-morpholino-2-pyridyl)methyl]sulfinyl]-5-methoxy-(1H)-benzimidazole;
- SK & 96067 which is 3-butyryl-4-(2-methylphenylamino)-8-methoxyquinoline;
- 5-trifluoromethyl-2-[4-methoxy-3-methyl-2-pyridyl-methyl]-thio-[1H]-benzimidazole;
- or pharmaceutically acceptable salts thereof.

These proton pump inhibitors are described and claimed in U.S. Pat. Nos. 4,472,409 and 4,255,431. These patents are incorporated herein by reference.

In a further aspect of the present invention, the proton pump inhibitor is
- lansoprazole which is 2-[[[3-methyl-4-(2,2,2-trifluoroethoxy)-2-pyridinyl]methyl]sulfinyl]-1H-benzimidazole;
- pantoprazole which is 5-(difluoromethoxy)-2-[[(3,4-dimethoxy-2-pyridinyl)methyl]sulfinyl]-1H-benzimidazole;
- perprazole;
- rabeprazole which is 2-[[4-(3-methoxypropoxy)-3-methylpyridin-2-yl]methylsulfinyl]-1H-benzimidazole;
- [[4-(2,2,2-trifluoroethoxy)-3-methyl-2-pyridyl]-methyl] sulfenamide;
- (Z)-5-methyl-2-[2-(1-naphthyl)ethenyl]-4-piperidinopyridine HCl;
- 2-(4-cyclohexyloxy-5-methylpyridin-2-yl)-3-(1-naphthyl)-1-propanol;
- methyl 2-cyano-3-(ethylthio)-3-(methylthio)-2-propenoate;
- 2-((4-methoxy-2-pyridyl)methylsulphinyl)-5-(1,1,2,2-tetrafluoroethoxy)-1H-benzimidazole sodium;
- 2-[[[4-(2,2,3,3,4,4,4-heptafluorobutoxy)-2-pyridyl]methyl)sulfinyl]-1H-thieno [3,4-d]imidazole;
- 2-[[[4-(2,2,2-trifluoroethoxy)-3-methyl-2-pyridyl]methyl]sulfinyl]-1H-benzimidazole;
- 2-[[[4-(2,2,2-trifluoroethoxy)-3-methyl-2-pyridyl]methyl]sulfinyl]-1H-benzimidazole;
- 2-methyl-8-(phenylmethoxy)-imidazo(1,2-A)-pyridine-3-acetonitrile;
- (2-((2-dimethylaminobenzyl)sulfinyl)-benzimidazole);
- 4-(N-allyl-N-methylamino)-1-ethyl-8-((5-fluoro-6-methoxy-2-benzimidazolyl) sulfinylmethyl)-1-ethyl 1,2,3,4-tetrahydroquinolone;
- 2-[[(2-dimethylaminophenyl)methyl]sulfinyl]-4,7-dimethoxy-1H-benzimidazole;
- 2-[(2-(2-pyridyl)phenyl)sulfinyl)-1H-benzimidazole;
- (2-[(2-amino-4-methylbenzyl)sulfinyl]-5-methoxybenzo [d]imidazole;
- (4(2-methylpyrrol-3-yl)-2-guanidisothiazole);
- 4-(4-(3-(imidazole)propoxy)phenyl)-2phenylthiazole;
- (E)-2-(2-(4-(3-(dipropylamino)butoxy)phenyl)-ethenyl) benzoxazole;
- (E)-2-(2-(4-(3-(dipropylamino)propoxy)phenyl)ethenyl)-benzothiazole;
- Benzeneamine, 2-[[(5-methoxy-1H-benzimidazol-2-yl) sulfinyl]methyl)-4-methyl-;
- Pumilacidin A;
- 2,3-dihydro-2-methoxycarbonylamino-1,2-benzisothiazol-3-one;
- 2-(2-ethylaminophenylmethylsulfinyl)-5,6-dimethoxybenzimidazole;
- 2-methyl-8-(phenylmethoxy)imidazo[1,2-a)pyridine-3-acetonitrile;
- 3-amino-2-methyl-8-phenylmethoxyimidazo[1,2-a)-pyrazine HC 1;
- 2-[[(3-chloro-4-morpholino-2-pyridyl)methyl]-sulfinyl)-5-methoxy-(1H)-benzinidazole;
- [3-butyryl-4-(2-methylphenylamino)-8-methoxy-quinoline);
- 2-indanyl 2-(2-pyridyl)-2-thiocarbamoylacetate HCl;
- 2,3-dihydro-2-(2-pyridinyl)-thiazolo (3,2-a)-benzimidazole;
- 3-cyanomethyl-2-methyl-8-(3-methyl-2-butenyloxy)-(1,2-a)imidazopyridine;
- zinc L-carnosine;
- or pharmaceutically acceptable salts thereof.

Rabeprazole is described in U.S. Pat. No. 5,045,552. Lansoprazole is described in U.S. Pat. No. 4,628,098. Pantoprazole is described in U.S. Pat. No. 4,758,579. These patents are incorporated herein by reference.

Preferably, the proton pump inhibitor is selected from (RS)-rabeprazole, (RS)-omeprazole, lansoprazole, pantoprazole, (R)-omeprazole, (S)-omeprazole, perprazole, (R)-rabeprazole, (S)-rabeprazole, or the alkaline salts thereof. The alkaline salts may be, for example, the lithium, sodium, potassium, calcium or magnesium salts.

Compositions of this invention comprising a pharmaceutically acceptable salt of a compound of formula (I) and a proton pump inhibitor may be administered as described above. Preferably the dose of each of the active ingredients in these compositions will be equal to or less than that which is approved or indicated in monotherapy with said active ingredient.

In another aspect of this invention, there is provided a kit comprising a pharmaceutically acceptable salt of a compound of formula (I) and a proton pump inhibitor. The kit is useful as a combined preparation for simultaneous, separate or sequential use in the treatment of patients suffering from gastrointestinal disorders.

In yet a further aspect of the present invention there is provided a method of making a pharmaceutical composition comprising a pharmaceutically acceptable salt of a compound of formula (I) substantially as described herein before and a proton pump inhibitor, comprising mixing said salt and said proton pump inhibitor with a pharmaceutically acceptable carrier or diluent.

The term "hydrocarbyl" is used herein to refer to monovalent groups consisting of carbon and hydrogen. Hydrocarbyl groups thus include alkyl, alkenyl and alkynyl groups (in both straight and branched chain forms), cycloalkyl (including polycycloalkyl groups such as bicyclooctyl and adamantyl), cycloalkenyl and aryl groups, and combinations of the foregoing, such as alkylcycloalkyl, alkylpolycycloalkyl, alkylaryl, alkenylaryl, alkynylaryl, cycloalkylaryl and cycloalkenylaryl groups.

Where reference is made to a carbon atom of a hydrocarbyl group being replaced by a N, O or S atom, what is intended is that

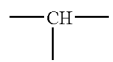

is replaced by

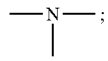

or that —CH$_2$— is replaced by —O— or —S—.

Where reference is made to an optionally substituted hydrocarbyl group, the hydrocarbyl group is substituted with 1, 2 or 3 groups independently selected from -L-Q wherein:

L is a bond, or a group of the formula —(CR$^{17}$R$^{18}$)$_v$—Y—(CR$^{17}$R$^{18}$)$_w$, wherein v and w are independently 0, 1, 2 or 3, and Y is a bond, —CR$^{15}$=CR$^{16}$—, phenyl, furanyl, thiophenyl, pyrrolyl, thiazolyl, imidazolyl, oxazolyl, isoxazolyl, pyrazolyl, isoxazolonyl, piperazinyl, piperidinyl, morpholinyl, pyrrolidinyl, isothiazolyl, triazolyl, oxadiazolyl, thiadiazolyl, pyridyl or pyridazyl;

Q is H, (C$_1$ to C$_6$ alkyl)oxy, [N-Z](C$_1$ to C$_6$ alkyl)oxy(C$_1$ to C$_6$ alkyl)amino, thio, (C$_1$ to C$_6$ alkyl)thio, carboxy(C$_1$ to C$_6$ alkyl)thio, carboxy, carboxy(C$_1$ to C$_6$ alkyl), carboxy (C$_1$ to C$_6$ alkenyl), [N-Z]carboxy(C$_1$ to C$_6$ alkyl)amino, carboxy(C$_1$ to C$_6$ alkyl)oxy, formyl, (C$_1$ to C$_6$ alkyl)carbonyl, (C$_1$ to C$_6$ alkyl)oxycarbonyl, (C$_1$ to C$_6$ alkyl)carbonyloxy, nitro, trihalomethyl, hydroxy, amino, [N-Z](C$_1$ to C$_6$ alkyl)amino, aminocarbonyl, (C$_1$ to C$_6$ alkyl)aminocarbonyl, di(C$_1$ to C$_6$ alkyl)aminocarbonyl, [N-Z](C$_1$ to C$_6$ alkyl)carbonylamino, C$_5$ to C$_8$ cycloalkyl, [N-Z](C$_1$ to C$_6$ alkyl)carbonyl(C$_1$ to C$_6$ alkyl)amino, halo, halo(C$_1$ to C$_6$ alkyl), sulfamoyl, [N-Z](C$_1$ to C$_6$ alkyl)sulfonylamino, (C$_1$ to C$_6$ alkyl)sulfonylaminocarbonyl, carboxy(C$_1$ to C$_6$ alkyl)sulfonyl, carboxy (C$_1$ to C$_6$ alkyl)sulfinyl, tetrazolyl, [N-Z]tetrazolylamino, cyano, amidino, amidinothio, SO$_3$H, formyloxy, formamido, C$_3$ to C$^8$ cycloalkyl, (C$_1$ to C$_6$ alkyl)sulphamoyl, di(C$_1$ to C$_6$ alkyl)sulphamoyl, (C$_1$ to C$_6$ alkyl)carbonylaminosulfonyl, 5-oxo-2,5-dihydro[1,2,4]oxadiazolyl, carboxy(C$_1$ to C$_6$ alkyl)carbonylamino, tetrazolyl(C$_1$ to C$_6$ alkyl)thio, [N-Z]tetrazolyl (C$_1$ to C$_6$ alkyl)amino, 5-oxo-2,5-dihydro[1,2,4] thiadiazolyl, 5-oxo-1,2-dihydro[1,2,4]triazolyl, [N-Z] (C$_1$ to C$_6$ alkyl)amino(C$_1$ to C$_6$ alkyl)amino, or a group of the formula

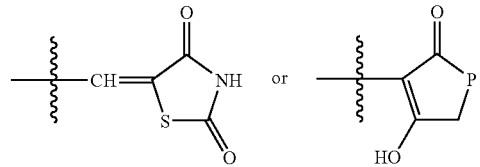

wherein P is O, S or NR$^{19}$;
and

Z is H, C$_1$ to C$_6$ alkyl, t-butoxycarbonyl, acetyl, benzoyl or benzyl.

The term "alkyl" is used herein to refer to both straight and branched chain forms. Further, the alkyl chain may include multiple bonds. Hence, the term "alkyl" also encompasses alkenyl and alkynyl groups. Likewise, the term "cycloalkyl" also encompasses cycloalkenyl groups. Preferably, alkyl and cycloalkyl groups as used in the present invention do not contain multiple bonds. Where there are preferred alkenyl groups, these are specified as alkenyl groups. However, specific reference to alkenyl groups is not to be construed as any limitation on the definition of alkyl groups as described above.

Where reference is made to dialkyl groups [e.g. di(C$_1$ to C$_6$ alkyl)amino groups], it is understood that the two alkyl groups may be the same or different.

In the interests of simplicity, terms which are normally used to refer to monovalent groups (such as "alkyl" or "phenyl") are also used herein to refer to divalent bridging groups which are formed from the corresponding monovalent group by the loss of one hydrogen atom. Whether such a term refers to a monovalent group or to a divalent group will be clear from the context. For example, when L is —(CR$^{17}$R$^{18}$)$_v$—Y—(CR$^{17}$R$^{18}$)$_w$—, it is clear that Y must be a divalent group. Thus, when Y is defined as thiazolyl, for example, this refers to a divalent group having the structure

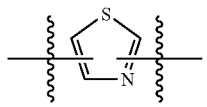

Where, as in this example, a divalent bridging group is formed from a cyclic moiety, the linking bonds may be on any suitable ring atom, subject to the normal rules of valency. Accordingly, by way of further example, the term pyrrolyl in the definition of Y includes all of the following groups:

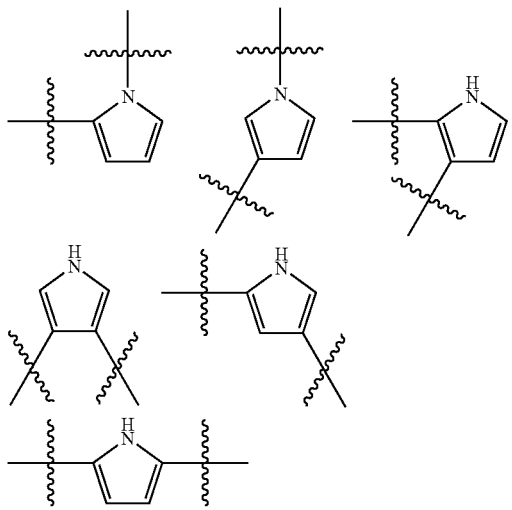

The term "halogen" or "halo" is used herein to refer to any of fluorine, chlorine, bromine and iodine. Most usually, however, halogen substituents in the compounds of the invention are chlorine and fluorine substituents. Groups such as halo($C_1$ to $C_6$ alkyl) includes mono-, di- or tri-halo substituted $C_1$ to $C_6$ alkyl groups. Moreover, the halo substitution may be at any position in the alkyl chain.

The prefix [N-Z] refers to possible substitution of an amino group in the following compound or substituent name. For example, [N-Z]alkylamino refers to groups of the form

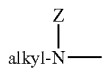

Similarly, [N-Z]tetrazolylamino, wherein Z is $C_1$ to $C_6$ alkyl, includes groups such as tetrazolyl[N-methyl]amino and tetrazolyl[N-ethyl]amino. Of course, when Z is H, no substitution is present.

In case there is any doubt, the group named as 5-oxo-2,5-dihydro[1,2,4]oxadiazolyl has the following formula

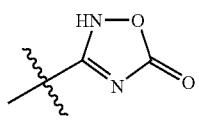

and comprehends tautomeric forms.

The invention is now further illustrated by means of the following Examples.

Experimental

All reactions were performed under an atmosphere of dry argon unless otherwise stated. Commercially available dichloromethane (DCM), tetrahydrofuran (THF) and N,N-dimethylformamide (DMF) were used. In reactions in which anilines were used, where necessary un-reacted aniline was removed either by chromatography or by stirring with excess methylisocyanate polystyrene HL resin (200-400 mesh, 2 mmol/g) in DCM (R. J. Booth, et. al., *J. Am. Chem. Soc.*, (1997), 119, 4882). Flash column chromatography was performed on Merck silica gel 60 (40-63 μm) using the reported solvent systems. $^1$H NMR spectra were recorded on a Bruker DRX-300 instrument at 300 MHz and the chemical shifts ($\delta_H$) were recorded relative to an internal standard. (2-Amino-phenyl)-cyclohexyl-methanone was prepared by a published method (M. S. Chambers, et. al., *Bioorg. Med. Chem. Lett.* (1993), 3, 1919), and (2-amino-phenyl)-cyclopentyl-methanone and 1-(2-amino-phenyl)-3-methyl-butan-1-one were prepared by a modification of this method. 2-Bromo-1-cyclopentyl-ethanone and 2-bromo-1-cyclohexyl-ethanone were prepared by a published method (M. Gaudry, A. Marquet, *Org. Synth.*, (1976), 55, 24), and 2-bromo-1-cyclopropyl-ethanone was prepared by a modification of this method. 2-Bromo-1-(1-methyl-cyclopentyl)-ethanone was prepared by a published method (T. S. Sorensen, *J. Am. Chem. Soc.*, (1969), 91, 6398). Substituted anilines were either obtained commercially, synthesized by the literature method indicated where first mentioned or prepared in a number of steps and from the starting material as indicated, using standard chemical transformations.

EXAMPLE 1

3-{2-[5-Cyclohexyl-1-(3,3-dimethyl-2-oxo-butyl)-2-oxo-1,2-dihydro-3H-1,3,4-benzotriazepin-3-yl]-acetylamino}-benzoic acid methyl ester Step a. {N'-[(2-Amino-phenyl)-cyclohexyl-methylene]-hydrazino}-acetic acid ethyl ester. A mixture of (2-amino-phenyl)-cyclohexyl-methanone (20.3 g, 0.1 mol), ethyl hydrazinoacetate hydrochloride (23.25 g, 0.15 mol) and pyridine (12.1 ml, 0.15 mol) was heated at reflux in EtOH (400 ml) for 72 h. On cooling, un-reacted ethyl hydrazinoacetate hydrochloride crystallised from the solution and was removed by filtration. The filtrate was evaporated and the residue was partitioned between saturated NaHCO$_3$ (250 ml) and EtOAc (250 ml). The organic phase was washed with brine (250 ml), dried over MgSO$_4$ then the solvent was evaporated under reduced pressure. The residue was purified by flash column chromatography (EtOAc-hexane (1:4)) to afford {NA-[(2-amino-phenyl)-cyclohexyl-methylene]-hydrazino}-acetic acid ethyl ester as a pale yellow foam (21.2 g, 71%) and un-reacted (2-amino-phenyl)-cyclohexyl-methanone (2.40 g). $^1$H NMR (CDCl$_3$) 7.17 (1H, dt), 6.98 (1H, dd), 6.80 (1H, dt), 6.73 (1H, dd), 5.32 (1H, t), 4.16 (2H, m), 3.95 (2H, br s), 3.89 (2H, m), 2.37 (1H, m), 1.80 (1H, m), 1.75-1.61 (4H, m), 1.33-1.19 (8H, m).

Step b. (5-Cyclohexyl-2-oxo-1,2-dihydro-3H-1,3,4-benzotriazepin-3-yl)-acetic acid ethyl ester. To a solution of the product of step a (23.39 g, 77.0 mmol) and triethylamine (26.8 ml, 0.19 mol) in DCM (300 ml) at 0° C., a solution of triphosgene (11.4 g, 39 mmol) in DCM (100 ml) was added drop-wise over 1 h. The reaction mixture was stirred at this temperature for 1 h, washed with H$_2$O (300 ml), saturated NaHCO$_3$ (300 ml) and brine (300 ml). The organic phase was dried over MgSO$_4$, filtered and the solvent was evaporated under reduced pressure. The crude product was re-crystallised from Et$_2$O-hexane (1:3) to afford the main product, (5-cyclohexyl-2-oxo-1,2-dihydro-3H-1,3,4-benzotriazepin-3-yl)-acetic acid ethyl ester (15.8 g, 62%), as a yellow solid. Concentration of the mother liquors and re-crystallisation of the residue from EtOAc-hexane (1:9) yielded the minor product, (1-chlorocarbonyl-5-cyclohexyl-2-oxo-1,2-dihydro-3H-1,3,4-benzotriazepin-3-yl)-acetic acid ethyl ester (2.1 g, 7.0%), as a pale yellow solid.

Major product: (5-Cyclohexyl-2-oxo-1,2-dihydro-3H-1,3,4-benzotriazepin-3-yl)-acetic acid ethyl ester. $^1$H NMR (CDCl$_3$) 7.35 (2H, m), 7.12 (1H, t), 6.85 (2H, m), 4.32 (2H, s), 4.18 (2H, m), 2.68 (1H, m), 1.81-1.68 (5H, m), 1.49-1.22 (8H, m).

Minor product: (1-Chlorocarbonyl-5-cyclohexyl-2-oxo-1,2-dihydro-3H-1,3,4-benzotriazepin-3-yl)-acetic acid ethyl ester. $^1$H NMR (CDCl$_3$) 7.65-7.49 (4H, m), 4.61-4.35 (2H, m), 4.15 (2H, m), 2.86 (1H, m), 2.00-1.22 (10H, m), 1.18 (3H, t).

Step c. [5-Cyclohexyl-1-(3,3-dimethyl-2-oxo-butyl)-2-oxo-1,2-dihydro-3H-1,3,4-benzotriazepin-3-yl]-acetic acid ethyl ester. To an ice cooled solution of the major product of step b (3.29 g, 10.0 mml) in DMF (30 ml) was added sodium hydride (60% dispersion in mineral oil, 480 mg, 12.0 mmol) in small portions. The mixture was stirred at room temperature for 30 min then 1-bromo-3,3-dimethyl-butan-2-one (1.60 ml, 12.0 mmol) was added. The reaction mixture was stirred at room temperature for 2 h, diluted with H$_2$O (200 ml) and extracted with EtOAc (30 ml×3). The combined organic extracts were washed with brine (50 ml), dried over MgSO$_4$, filtered and the solvent was evaporated under reduced pressure. The residue was purified by flash column chromatography (EtOAc-DCM (1:9)) to afford the product as a yellow foam (3.59 g, 84%). $^1$H NMR (CDCl$_3$) 7.37 (2H, m), 7.17 (1H, dt), 6.93 (1H, d), 4.66 (2H, s), 4.35 (1H, m), 4.13 (3H, m), 2.74 (1H, m), 1.90-1.70 (6H, m), 1.31-1.16 (16H, m).

Step d. [5-Cyclohexyl-1-(3,3-dimethyl-2-oxo-butyl)-2-oxo-1,2-dihydro-3H-1,3,4-benzotriazepin-3-yl]-acetic acid. A solution of the product of step c (3.57 g, 8.20 mmol), and 1.0M NaOH (8.70 ml, 8.70 mmol) in EtOH (30 ml) was stirred at room temperature for 16 h. The EtOH was evaporated under reduced pressure, the residue was diluted with H$_2$O (30 ml) and acidified to pH 3 with 1N HCl. The mixture was extracted with DCM (30 ml×2), the combined extracts were dried over MgSO$_4$, filtered and the solvent was evaporated under reduced pressure to afford the product as a pale yellow foam (3.10 g, 95%). $^1$H NMR (CDCl$_3$) 11.00 (1H, br s), 7.45 (2H, m), 7.25 (1H, m), 6.97 (1H, dd), 4.68 (2H, m), 4.25 (1H, d), 3.90 (1H, d), 2.80 (1H, m), 2.08-1.61 (6H, m), 1.44-1.18 (13H, m).

Step e. To a solution of the product of step d (1.60 g, 4.00 mmol), and 3-amino-benzoic acid methyl ester (600 mg, 4.00 mmol) in DMF (20 ml) was added 1-hydroxybenzotriazole (HOBt)(810 mg, 6.00 mmol), 4-dimethylaminopyridine (DMAP)(50 mg, 0.40 mmol) and 1-(3-dimethylaminopropyl)-3-ethylcarbodiimide hydrochloride (EDC)(1.15 g, 6.00 mmol). The solution was maintained at room temperature for 16 h, diluted with H$_2$O (100 ml) and the reaction mixture was extracted with EtOAc (50 ml×2). The combined extracts were washed with 5% KHSO$_4$ (60 ml), saturated NaHCO$_3$ (60 ml) and brine (60 ml). The organic phase was dried over MgSO$_4$, filtered and the solvent was evaporated under reduced pressure. The residue was triturated with Et$_2$O to afford the title compound as an off-white solid (1.51 g, 71%). $^1$H NMR (CDCl$_3$) 8.49 (1H, s), 7.92 (1H, m), 7.84 (1H, t), 7.74 (1H, dt), 7.48 (2H, m), 7.39-7.27 (2H, m), 7.03 (1H, d), 4.77 (1H, d), 4.60 (1H, d), 4.25 (2H, s), 3.91 (3H, s), 2.80 (1H, m), 2.05-1.73 (6H, m), 1.34-1.17 (13H, m). Found: C, 67.56; H, 6.83; N, 10.36%; C$_{30}$H$_{36}$N$_4$O$_5$ requires: C, 67.56; H, 6.81; N, 10.52%.

EXAMPLE 2

3-{2-[5-Cyclohexyl-1-(3,3-dimethyl-2-oxo-butyl)-2-oxo-1,2-dihydro-3H-1,3,4-benzotriazepin-3-yl]-acetylamino}-benzoic acid To a solution of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) (1.33 g, 2.49 mmol) in THF-H$_2$O (2:1/45 ml) was added lithium hydroxide monohydrate (318 mg, 7.58 mmol) and the mixture was stirred at room temperature for 16 h. The THF was evaporated under reduced pressure, the aqueous solution was diluted with H$_2$O (50 ml) and acidified to pH 3 with 1N HCl. The reaction mixture was extracted with DCM (30 ml×2), the combined extracts were washed with brine (50 ml), dried over MgSO$_4$, filtered and the solvent was evaporated under reduced pressure to afford the product as an off-white solid (1.28 g, 99%). $^1$H NMR (DMSO-d$_6$) 12.89 (1H, br s), 9.99 (1H, s), 8.16 (1H, s), 7.70 (1H, dd), 7.60-7.36 (4H, m), 7.26-7.15 (2H, m), 4.78 (2H, d), 4.30 (1H, d), 3.98 (1H, d), 2.87 (1H, m), 1.80-1.50 (6H, m), 1.34-1.13 (13H, m). The compound was further characterised as the N-methyl-D-glucamine salt. Found: C, 60.39; H, 7.31; N, 9.78%; C$_{29}$H$_{34}$N$_4$O$_5$·C$_7$H$_{17}$NO$_5$ requires: C, 60.57; H, 7.20; N, 9.81%.

EXAMPLE 3

2-[5-Cyclohexyl-1-(3,3-dimethyl-2-oxo-butyl)-2-oxo-1,2-dihydro-3H-1,3,4-benzotriazepin-3-yl]-N-(3-methylamino-phenyl)-acetamide Step a. (3-Nitro-phenyl)-carbamic acid tert-butyl ester. A solution of 3-nitrophenyl isocyanate (14.44 g, 88.0 mmol) in tert-butanol (80 ml) was heated at reflux for 2 h. After cooling the solvent was evaporated and the residue was dried under high vacuum, washed thoroughly with Et$_2$O to afford the product as a yellow solid (19.96 g, 95%). $^1$H NMR (CDCl$_3$) 8.30 (1H, s), 7.88 (1H, d), 7.71 (1H, d), 7.45 (1H, t), 6.68 (1H, br s), 1.55 (9H, s).

Step b. Methyl-(3-nitro-phenyl)-carbamic acid tert-butyl ester. To an ice-cooled solution of the product of step a (3.57 g, 15.0 mmol), in DMF (30 ml) was added sodium hydride (60% dispersion in mineral oil, 720 mg, 18.0 mmol) in small portions. After stirring at room temperature for 1 h, the reaction mixture was cooled externally with ice and iodomethane (1.4 ml, 22.5 mmol) was added. The reaction mixture was stirred at room temperature for 2 h, H$_2$O (150 ml) was added and extracted with EtOAc (50 ml×2). The combined extracts were washed with brine, dried (MgSO$_4$), filtered and the solvent was evaporated. The residue was purified by flash column chromatography (EtOAc-DCM (1:9)) to afford the product as a yellow foam (3.34 g, 88%). $^1$H NMR (CDCl$_3$) 8.16 (1H, t), 8.00 (1H, m), 7.63 (1H, m), 7.48 (1H, t), 3.34 (3H, s), 1.49 (9H, s).

Step c. (3-Amino-phenyl)-methyl-carbamic acid tert-butyl ester. A round bottom flask containing the product of step b (3.30 g, 13.1 mmol), 10% palladium on charcoal (300 mg) and THF-MeOH (1:1/50 ml) was evacuated and flushed with hydrogen three times. The mixture was stirred vigorously overnight under an atmosphere of hydrogen. The catalyst was removed by filtration through a pad of celite and the filtrate evaporated to afford the product as a white solid (2.90 g, 99%). $^1$H NMR (CDCl$_3$) 7.10 (1H, t), 6.62 (2H, m), 6.50 (1H, m), 3.66 (2H, br s), 3.22 (3H, s), 1.46 (9H, s).

Step d. (3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-phenyl)-methyl-carbamic acid tert-butyl ester (Example 3, step c) was used in place of 3-amino-benzoic acid methyl ester in step e. $^1$H NMR (CDCl$_3$) 8.29 (1H, s), 7.44 (3H, m), 7.29-7.11 (4H, m), 7.03-6.94 (2H, m), 4.67 (2H, m), 4.23 (2H, m), 3.23 (3H, s), 2.79 (1H, m), 2.05-1.52 (6H, m), 1.45 (9H, s), 1.37-1.23 (13H, m).

Step e. A solution of the product of step d (270 mg, 0.45 mmol) in trifluoroacetic acid (3 ml) was stirred at room temperature for 1 h. The trifluoroacetic acid was evaporated under reduced pressure, the residue was partitioned between saturated NaHCO$_3$ (20 ml) and EtOAc (20 ml). The organic phase was separated and dried over MgSO$_4$. Filtration and evaporation of the solvent gave the crude product, which was purified by flash column chromatography (EtOAc-DCM (1:9)) to afford the title compound, as a colourless foam (154 mg, 68%). $^1$H NMR (CDCl$_3$) 8.07 (1H, s), 7.48 (2H, m), 7.27 (1H, dt), 7.04 (2H, m), 6.91 (1H, t), 6.46 (1H, dd), 6.31 (1H, dd), 4.68 (2H, m), 4.35 (1H, d), 4.13 (1H, d), 3.72 (1H, br s), 2.80 (4H, m), 2.05-1.72 (6H, m), 1.27 (13H, m). Found: C, 68.77; H, 7.64; N, 13.69%; C$_{29}$H$_{37}$N$_5$O$_3$ requires: C, 69.16; H, 7.40; N, 13.91%.

EXAMPLE 4

2-[1-(3,3-Dimethyl-2-oxo-butyl)-2-oxo-5-phenyl-1,2-dihydro-3H-1,3,4-benzotriazepin-3-yl]-N-(3-methylamino-phenyl)-acetamide Step a. [1-(3,3-Dimethyl-2-oxo-butyl)-2-oxo-5-phenyl-1,2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d), except that 2-amino-benzophenone was used in step a instead of (2-amino-phenyl)-cyclohexyl-methanone. $^1$H NMR (CDCl$_3$) 7.61 (2H, dd), 7.49-7.42 (4H, m), 7.17 (2H, m), 7.05 (1H, d), 4.76 (2H, br m), 4.28 (2H, br d), 1.25 (9H, s).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that [1-(3,3-dimethyl-2-oxo-butyl)-2-oxo-5-phenyl-1,2-dihydro-3H-1,3,4-benzotriazepin-3-yl]-acetic acid (Example 4, step a) and (3-amino-phenyl)-methyl-carbamic acid tert-butyl ester (Example 3, step c) were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.01 (1H, s), 7.63 (2H, m), 7.55 (1H, m), 7.42 (3H, m), 7.25 (2H, m), 7.14 (1H, d), 7.00 (1H, t), 6.90 (1H, t), 6.40 (1H, dd), 6.29 (1H, dd), 4.76 (2H, m), 4.52 (1H, d), 4.34 (1H, d), 3.25 (1H, br s), 2.77 (3H, s), 1.26 (9H, s). Found: C, 68.44; H, 6.46; N, 13.80%; C$_{29}$H$_{31}$N$_5$O$_3$.0.6H$_2$O requires: C, 68.41; H, 6.39; N, 13.76%.

EXAMPLE 5

2-[1-(3,3-Dimethyl-2-oxo-butyl)-2-oxo-5-pyridin-2-yl-1,2-dihydro-3H-1,3,4-benzotriazepin-3-yl]-N-(3-methylamino-phenyl)-acetamide Step a. [1-(3,3-Dimethyl-2-oxo-butyl)-2-oxo-5-pyridin-2-yl-1,2-dihydro-3H-1,3,4-benzotriazepin-3-yl]-acetic acid was prepared using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d), except that (2-amino-phenyl)-pyridin-2-yl-methanone (G. Semple, et. al. *Synth. Commun.*, (1996), 26, 721) was used in step a instead of (2-amino-phenyl)-cyclohexyl-methanone. $^1$H NMR (DMSO-d$_6$) 12.50 (1H, br s), 8.57 (1H, m), 7.94 (2H, m), 7.50 (2H, m), 7.16 (3H, m), 4.78 (2H, s), 4.25 (2H, br s), 1.15 (9H, s).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that [1-(3,3-dimethyl-2-oxo-butyl)-2-oxo-5-pyridin-2-yl-1,2-dihydro-3H-1,3,4-benzotriazepin-3-yl]-acetic acid (Example 5, step a) and (3-amino-phenyl)-methyl-carbamic acid tert-butyl ester (Example 3, step c) were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.62 (1H, d), 8.10 (1H, d), 8.00 (1H, br s), 7.79 (1H, dt), 7.55 (1H, m), 7.29 (3H, m), 7.13 (1H, d), 7.01 (1H, t), 6.92 (1H, t), 6.48 (1H, dd), 6.30 (1H, dd), 4.68 (2H, br d), 4.45 (2H, br d), 2.80 (1H, br s), 2.78 (3H, s), 1.27 (9H, s). Found: C, 67.18; H, 6.28; N, 16.63%; C$_{28}$H$_{30}$N$_6$O$_3$ requires: C, 67.45; H, 6.06; N, 16.86%.

EXAMPLE 6

N-(3-Methylamino-phenyl)-2-[2-oxo-1-(2-oxo-2-pyrrolidin-1-yl-ethyl)-5-pyridin-2-yl-1,2-dihydro-3H-1,3,4-benzotriazepin-3-yl]-acetamide Step a. [2-Oxo-1-(2-oxo-2-pyrrolidin-1-yl-ethyl)-5-pyridin-2-yl-, 2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d), except that (2-amino-phenyl)-pyridin-2-yl-methanone was used in step a instead of (2-amino-phenyl)-cyclohexyl-methanone and 2-bromo-1-pyrrolidin-1-yl-ethanone (prepared from pyrrolidine and bromoacetyl bromide) replaced 1-bromo-3,3-dimethyl-butan-2-one in step c.

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that [2-oxo-1-(2-oxo-2-pyrrolidin-1-yl-ethyl)-5-pyridin-2-yl-1,2-dihydro-3H-1,3,4-benzotriazepin-3-yl]-acetic acid (Example 6, step a) and (3-amino-phenyl)-methyl-carbamic acid tert-butyl ester (Example 3, step c) were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.61 (1H, d), 8.07 (2H, m), 7.77 (1H, dt), 7.54 (2H, m), 7.36-7.24 (3H, m), 6.98 (1H, t), 6.88 (1H, s), 6.48 (1H, d), 6.28 (1H, d), 4.53-4.34 (4H, br m), 3.52-3.20 (5H, br m), 2.75 (3H, s), 1.97 (2H, m), 1.87 (2H, m). Found: C, 65.44; H, 6.00; N, 18.79%; C$_{28}$H$_{29}$N$_7$O$_3$ requires: C, 65.74; H, 5.71; N, 19.17%.

EXAMPLE 7

N-(3-Methylamino-phenyl)-2-[2-oxo-1-(2-oxo-2-o-tolyl-ethyl)-5-pyridin-2-yl-1,2-dihydro-3H-1,3,4-benzotriazepin-3-yl]-acetamide Step a. [2-Oxo-1-(2-oxo-2-o-tolyl-ethyl)-5-pyridin-2-yl-1,2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d), except (2-amino-phenyl)-pyridin-2-yl-methanone was used in step a instead of (2-amino-phenyl)-cyclohexyl-methanone and 2-bromo-1-o-tolyl-ethanone (H. Shinagawa, et. al. *Bioorg. Med. Chem.*, (1997), 5, 601) replaced 1-bromo-3,3-dimethyl-butan-2-one in step c.

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that [2-oxo-1-(2-oxo-2-o-tolyl-ethyl)-5-pyridin-2-yl-1,2-dihydro-3H-1,3,4-benzotriazepin-3-yl]-acetic acid (Example 7, step a) and (3-amino-phenyl)-methyl-carbamic acid tert-butyl ester (Example 3, step c) were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.64 (1H, d), 8.08 (1H, d), 8.03 (1H, s), 7.79 (1H, dt), 7.59 (2H, m), 7.39-7.26 (5H, m), 7.19 (2H, m), 7.01 (1H, t), 6.90 (1H, s), 6.47 (1H, dd), 6.30 (1H, dd), 4.98 (2H, s), 4.45 (2H, br m), 3.30 (1H, br s), 2.76 (3H, s), 2.47 (3H, s). Found: C, 69.63; H, 5.45; N, 15.59%; C$_{31}$H$_{28}$N$_6$O$_3$ requires: C, 69.91; H, 5.30; N, 15.78%.

EXAMPLE 8

1-[1-(3,3-Dimethyl-2-oxo-butyl)-2-oxo-5-pyridin-2-yl-1,2-dihydro-3H-1,3,4-benzotriazepin-3-ylmethyl]-3-(3-methylamino-phenyl)-urea Step a. (3-{3-[1-(3,3-Dimethyl-2-oxo-butyl)-2-oxo-5-pyridin-2-yl-1,2-dihydro-3H-1,3,4-benzotriazepin-3-ylmethyl]-ureido}-phenyl)-methyl-carbamic acid tert-butyl ester. To an ice-cooled solution of [1-(3,3-dimethyl-2-oxo-butyl)-2-oxo-5-pyridin-2-yl-1,2-dihydro-3H-1,3,4-benzotriazepin-3-yl]-acetic acid (Example 5, step a)(390 mg, 1.00 mmol) and triethylamine (180 µl, 1.30 mmol) in acetone (3 ml) was added ethyl chloroformate (120 µl, 1.30 mmol). The mixture was stirred for 20 min, and a solution of sodium azide (100 mg, 1.50 mmol) in H$_2$O (3 ml) was added. The reaction mixture was stirred at 0° C. for 1 h then poured into PhCH$_3$—H$_2$O (1:1/20 ml). The organic phase was separated, dried over MgSO$_4$, filtered and the filtrate heated at reflux for 1 h. After cooling to room temperature the solvent was evaporated under reduced pressure. The residue was dissolved in DCM (5 ml) and (3-amino-phenyl)-methyl-carbamic acid tert-butyl ester (Example 3, step c)(220 mg, 1.00 mmol) was added. The solution was stirred at room temperature for 1 h, diluted with DCM (15 ml), washed with saturated NaHCO$_3$ (20 ml) and dried over MgSO$_4$. Filtration and evaporation of the solvent gave the crude product which was purified by flash column chromatography (EtOAc-DCM (1:1)) to afford the product as a colourless foam (166 mg, 27%). $^1$H NMR (CDCl$_3$) 8.51 (1H, d), 8.05 (1H, d), 7.85 (1H, d), 7.67 (1H, t), 7.39 (1H, m), 7.25 (2H, m), 7.13-7.05 (4H, m), 6.95 (1H, d), 6.84 (1H, d), 6.18 (1H, br t), 5.04 (1H, br s), 4.86 (1H, br s), 4.65 (1H, br s), 4.32 (1H, br s), 3.15 (3H, s), 1.49 (9H, s), 1.18 (9H, s).

Step b. The title compound was obtained by reaction of (3-{3-[1-(3,3-dimethyl-2-oxo-butyl)-2-oxo-5-pyridin-2-yl-1,2-dihydro-3H-1,3,4-benzotriazepin-3-ylmethyl]-ureido}-phenyl)-methyl-carbamic acid tert-butyl ester (Example 8, step a), in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.56 (1H, d), 8.00 (1H, d), 7.71 (1H, dt), 7.43 (1H, m), 7.30-7.15 (4H, m), 7.02 (2H, m), 6.72 (1H, t), 6.52 (1H, dd), 6.29 (1H, dd), 6.09 (1H, br t), 4.97 (2H, br d), 4.70 (1H, br s), 4.44 (1H, br s), 3.90 (1H, br s), 2.76 (3H, s), 1.23 (9H, s). Found: C, 65.55; H, 6.27; N, 19.00%; C$_{28}$H$_{31}$N$_7$O$_3$ requires: C, 65.48; H, 6.08; N, 19.09%.

EXAMPLE 9

3-{2-[5-Cyclopentyl-1-(3,3-dimethyl-2-oxo-butyl)-2-oxo-1,2-dihydro-3H-1,3,4-benzotriazepin-3-yl]-acetylamino}-benzoic acid Step a. [5-Cyclopentyl-1-(3,3-dimethyl-2-oxo-butyl)-2-oxo-1,2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d), except that (2-amino-phenyl)-cyclopentyl-methanone was used in step a instead of (2-amino-phenyl)-cyclohexyl-methanone. $^1$H NMR (DMSO-d$_6$) 12.30 (1H, br s), 7.51-7.10 (4H, m), 4.77 (2H, s), 4.05 (2H, m), 3.39 (1H, m), 1.74-1.56 (8H, m), 1.12 (9H, s).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that [5-cyclopentyl-1-(3,3-dimethyl-2-oxo-butyl)-2-oxo-1,2-dihydro-3H-1,3,4-benzotriazepin-3-yl]-acetic acid (Example 9, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}- benzoic acid methyl ester (Example 1), according to the method of Example 2. $^1$H NMR (DMSO-d$_6$) 12.89 (1H, br s), 9.98 (1H, s), 8.16 (1H, s), 7.71-7.14 (7H, m), 4.79 (2H, m), 4.22 (1H, m), 4.00 (1H, m), 3.42 (1H, m), 1.75-1.54 (8H, m), 1.32-1.19 (9H, s). The compound was further characterised as the N-methyl-D-glucamine salt. Found: C, 57.08; H, 7.45; N, 9.60%; $C_{28}H_{32}N_4O_5 \cdot C_7H_{17}NO_5 \cdot 2.0H_2O$ requires: C, 57.13; H, 7.26; N, 9.52%.

EXAMPLE 10

2-[5-Cyclopentyl-1-(3,3-dimethyl-2-oxo-butyl)-2-oxo-1,2-dihydro-3H-1,3,4-benzotriazepin-3-yl]-[3-(2H-tetrazol-5-yl)-phenyl]-acetamide Step a. 2,2-Dimethyl-propionic acid 5-(3-{2-[5-cyclopentyl-1-(3,3-dimethyl-2-oxo-butyl)-2-oxo-1,2-dihydro-3H-1,3,4-benzotriazepin-3-yl]-acetylamino}-phenyl)-tetrazol-2-ylmethyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclopentyl-1-(3,3-dimethyl-2-oxo-butyl)-2-oxo-1,2-dihydro-3H-1,3,4-benzotriazepin-3-yl]-acetic acid (Example 9, step a) and 5-(3-amino-phenyl)-tetrazol-2-ylmethyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e. $^1$H NMR (CDCl$_3$) 8.00 (1H, s), 7.55-7.44 (3H, m), 7.27-7.22 (3H, m), 7.00 (2H, m), 6.29 (2H, s), 4.75 (1H, d), 4.65 (1H, d), 4.25 (1H, m), 4.11 (1H, m), 3.29 (1H, m), 2.00-1.30 (8H, m), 1.26-1.19 (18H, m).

Step b. 2,2-Dimethyl-propionic acid 5-(3-{2-[5-cyclopentyl-1-(3,3-dimethyl-2-oxo-butyl)-2-oxo-1,2-dihydro-3H-1,3,4-benzotriazepin-3-yl]-acetylamino}-phenyl)-tetrazol-2-ylmethyl ester (Example 10, step a)(120 mg, 0.22 mmol) was stirred overnight in saturated methanolic ammonia solution (10 ml) at room temperature. After concentration in vacuo, the residue was dissolved in H$_2$O-MeOH (10:1/22 ml) and acidified to pH 3 by the addition of 5% KHSO$_4$ solution. The title compound was isolated as a light pink solid by filtration of the reaction mixture and dried in vacuo (81 mg, 68%). $^1$H NMR (CDCl$_3$) 8.61 (1H, s), 7.50-7.44 (3H, m), 7.31-7.24 (2H, m), 7.14 (1H, m), 6.97 (2H, m), 4.95 (1H, d), 4.65 (1H, d), 4.17 (2H, m), 3.30 (1H, m), 1.80-1.58 (8H, m), 1.15 (9H, m). The compound was further characterised as the N-methyl-D-glucamine salt. Found: C, 54.46; H, 7.13; N, 16.28%; $C_{28}H_{32}N_8O_3 \cdot C_7H_{17}NO_5 \cdot 2.5H_2O$ requires: C, 54.67; H, 7.07; N, 16.39%.

EXAMPLE 11

2-[5-Cyclopentyl-1-(3,3-dimethyl-2-oxo-butyl)-2-oxo-1,2-dihydro-3H-1,3,4-benzotriazepin-3-yl]-N-(3-methylaminophenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclopentyl-1-(3,3-dimethyl-2-oxo-butyl)-2-oxo-1,2-dihydro-3H-1,3,4-benzotriazepin-3-yl]-acetic acid (Example 9, step a) and (3-amino-phenyl)-methyl-carbamic acid tert-butyl ester (Example 3, step c) were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. The product was characterised as the hydrochloride salt. $^1$H NMR (DMSO-d$_6$) 9.89 (1H, br s), 7.84-7.40 (6H, m), 7.20 (1H, m), 6.66 (1H, m), 4.78 (2H, m), 3.98 (1H, m), 3.68 (1H, m), 3.35 (1H, m), 2.73 (3H, s), 1.85-1.33 (8H, m), 1.13 (9H, s).

EXAMPLE 12

3-{2-[1-(3,3-Dimethyl-2-oxo-butyl)-5-isobutyl-2-oxo-1,2-dihydro-3H-1,3,4-benzotriazepin-3-yl]-acetylamino}-benzoic acid Step a. [1-(3,3-Dimethyl-2-oxo-butyl)-5-isobutyl-2-oxo-1,2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d), except that 1-(2-amino-phenyl)-3-methyl-butan-1-one was used in step a instead of (2-amino-phenyl)-cyclohexyl-methanone. $^1$H NMR (CDCl$_3$) 7.47-7.39 (2H, m), 7.24 (1H, m), 6.98 (1H, d), 4.60 (2H, br m), 4.10 (2H, br m), 2.60 (2H, br m), 1.93 (1H, m), 1.25 (9H, s), 0.95 (6H, br m).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [1-(3,3-dimethyl-2-oxo-butyl)-5-isobutyl-2-oxo-1,2-dihydro-3H-1,3,4-benzotriazepin-3-yl]-acetic acid (Example 12, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 13.0 (1H, br), 10.01 (1H, s), 8.17 (1H, t), 7.70 (1H, d), 7.60-7.49 (3H, m), 7.38 (1H, t), 7.24 (1H, t), 7.13 (1H, d), 4.74 (2H, br m), 4.35 (1H, br m), 4.02 (1H, br m), 2.85 (1H, br m), 2.35 (1H, br m), 1.74 (1H, m), 1.15 (9H, s), 0.85 (6H, br m). The compound was further characterised as the N-methyl-D-glucamine salt. Found: C, 56.58; H, 7.55; N, 9.54%; $C_{27}H_{32}N_4O_5 \cdot C_7H_{17}NO_5 \cdot 2.0H_2O$ requires C, 56.42; H, 7.38; N, 9.68%.

EXAMPLE 13

2-[1-(3,3-Dimethyl-2-oxo-butyl)-5-isobutyl-2-oxo-1,2-dihydro-3H-1,3,4-benzotriazepin-3-yl]-N-(3-methylaminophenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [1-(3,3-dimethyl-2-oxo-butyl)-5-isobutyl-2-oxo-1,2-dihydro-3H-1,3,4-benzotriazepin-3-yl]-acetic acid (Example 11, step a) and (3-amino-phenyl)-methyl-carbamic acid tert-butyl ester (Example 3, step c) were used in place of [5-cyclohexyl-1-(3,3-dimethyl-2-oxo-butyl)-2-oxo-1,2-dihydro- 3H-1,3,4-benzotriazepin-3-yl]-acetic acid (Example 1, step d) and 3-amino-benzoic acid methyl ester respectively in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. The compound was further characterised as the hydrochloride salt. $^1$H NMR (DMSO-d$_6$) 10.03 (1H, br s), 7.56-7.46 (3H, m), 7.28-7.20 (3H, m), 7.13 (1H, d), 6.89 (1H, d), 4.73 (2H, br s), 4.10 (2H, br), 3.85 (1H, br m), 2.78 (3H, s), 2.30 (1H, br m), 1.74 (1H, m), 1.15 (9H, s), 0.86 (6H, br m). Found: C, 61.02; H, 7.35; N, 13.18%; $C_{27}H_{35}N_5O_3 \cdot H_2O \cdot HCl$ requires C, 60.95, H, 7.20, N, 13.16%.

EXAMPLE 14

3-{2-[5-Cyclohexyl-1-methyl-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that iodomethane was used in step c instead of 1-bromo-3,3-dimethyl-butan-2-one, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.90 (1H, br s), 10.03 (1H, s), 8.16 (1H, s), 7.69 (1H, d), 7.60-7.50 (3H, m), 7.38 (1H, t), 7.31-7.22 (2H, m), 4.20 (2H, br d), 3.14 (3H, s), 2.85 (1H, m), 1.64-1.04 (10H, m). The compound was further characterised as the N-methyl-D-glucamine salt. Found: C, 56.92; H, 7.12; N, 10.58%; $C_{24}H_{26}N_4O_4 \cdot C_7H_{17}NO_5 \cdot 1.4H_2O$ requires: C, 56.82; H, 7.05; N, 10.69%.

EXAMPLE 15

3-{2-[5-Cyclohexyl-2-oxo-1-(2-oxo-2-o-tolyl-ethyl)-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2-bromo-1-o-tolyl-ethanone was used in step c instead of 1-bromo-3,3-dimethyl-butan-2-one, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 13.00 (1H, br s), 9.98 (1H, s), 8.15 (1H, s), 7.77 (1H, d), 7.70 (1H, dd), 7.60-7.51 (3H, m), 7.39 (2H, m), 7.26 (4H, m), 5.06 (2H, d), 4.32 (1H, d), 3.98 (1H, d), 2.85 (1H, m), 2.29 (3H, s), 1.65-1.54 (6H, m), 1.36-1.14 (4H, m). The compound was further characterised as the N-methyl-D-glucamine salt. Found: C, 60.58; H, 6.86; N, 8.86%; $C_{32}H_{32}N_4O_5 \cdot C_7H_{17}NO_5 \cdot 1.4H_2O$ requires: C, 60.45; H, 6.76; N, 9.04%.

EXAMPLE 16

3-{2-[5-Cyclohexyl-1-(3-methyl-butyl)-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 1-bromo-3-methyl-butane was used in step c instead of 1-bromo-3,3-dimethyl-butan-2-one, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 13.00 (1H, br s), 9.99 (1H, s), 8.14 (1H, s), 7.68 (1H, dd), 7.56 (3H, m), 7.40 (2H, m), 7.27 (1H, d), 4.33 (1H, d), 3.98 (2H, m), 3.60 (1H, m), 2.85 (1H, m), 1.65-1.06 (13H, m), 0.77 (6H, m). The compound was further characterised as the N-methyl-D-glucamine salt. Found: C, 59.05; H, 7.81; N, 10.02%; $C_{28}H_{34}N_4O_4 \cdot C_7H_{17}NO_5 \cdot 1.3H_2O$ requires: C, 59.23; H, 7.62; N, 9.87%.

EXAMPLE 17

3-{2-[1-(2-Adamantan-1-yl-2-oxo-ethyl)-5-cyclohexyl-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 1-adamantan-1-yl-2-bromo-ethanone was used in step c instead of 1-bromo-3,3-dimethyl-butan-2-one, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.51 (1H, s), 8.04 (1H, d), 7.84 (1H, s), 7.80 (1H, d), 7.52-7.23 (4H, m), 7.03 (1H, d), 4.75 (1H, d), 4.59 (1H, d), 4.26 (2H, m), 2.80 (1H, m), 2.07-1.70 (21H, m), 1.27 (4H, m). The compound was further characterised as the N-methyl-D-glucamine salt. Found: C, 60.07; H, 7.58; N, 8.37%; $C_{35}H_{40}N_4O_5 \cdot C_7H_{17}NO_5 \cdot 2.7H_2O$ requires: C, 60.05; H, 7.48; N, 8.34%.

EXAMPLE 18

3-{2-[5-Cyclohexyl-1-(2-ethoxy-ethyl)-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that bromoethyl-ethyl ether was used in step c instead of 1-bromo-3,3-dimethyl-butan-2-one, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.45 (1H, s), 7.97 (1H, dd), 7.80 (1H, d), 7.63 (1H, t), 7.57 (1H, dt), 7.48 (1H, d), 7.37

(3H, m), 4.44 (1H, d), 4.34 (1H, m), 4.16 (1H, d), 3.75 (1H, m), 3.55 (2H, m), 3.38 (2H, m), 2.81 (1H, m), 2.02-1.67 (6H, m), 1.28 (4H, m), 1.08 (3H, t). The compound was further characterised as the N-methyl-D-glucamine salt. Found: C, 56.72; H, 7.46; N, 9.69%; $C_{27}H_{32}N_4O_5 \cdot C_7H_{17}NO_5 \cdot 1.8H_2O$ requires: C, 56.72; H, 7.36; N, 9.73%.

EXAMPLE 19

3-{2-[5-Cyclohexyl-2-oxo-1-(terahydro-pyran-2-ylmethyl)-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2-bromomethyl-tetrahydro-pyran was used in step c instead of 1-bromo-3,3-dimethyl-butan-2-one, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.45 (1H, d), 7.98 (1H, d), 7.79 (1H, d), 7.64-7.54 (2H, m), 7.49-7.33 (3H, m), 7.25 (1H, m), 4.47-4.12 (3H, m), 3.80 (1H, m), 3.55-3.30 (2H, m), 3.23 (1H, m), 2.82 (1H, m), 2.05-1.20 (16H, m). The compound was further characterised as the N-methyl-D-glucamine salt. Found: C, 57.71; H, 7.53; N, 9.14%; $C_{29}H_{34}N_4O_5 \cdot C_7H_{17}NO_5 \cdot 2.1H_2O$ requires: C, 57.54; H, 7.40; N, 9.32%.

EXAMPLE 20

3-{2-[5-Cyclohexyl-2-oxo-1-(2-oxo-2-pyrrolidin-1-yl-ethyl)-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2-bromo-1-pyrrolidin-1-yl-ethanone was used in step c instead of 1-bromo-3,3-dimethyl-butan-2-one, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.59 (1H, s), 8.02 (1H, d), 7.85 (1H, s), 7.75 (1H, d), 7.48 (2H, m), 7.33 (3H, m), 4.50 (1H, d), 4.35 (1H, d), 4.80 (2H, s), 3.53 (4H, m), 2.78 (1H, m), 2.05-1.70 (10H, m), 1.26 (4H, m). The compound was further characterised as the N-methyl-D-glucamine salt. Found: C, 56.43; H, 7.30; N, 10.86%; $C_{29}H_{33}N_5O_5 \cdot C_7H_{17}NO_5 \cdot 2.3H_2O$ requires: C, 56.34; H, 7.16; N, 10.95%.

EXAMPLE 21

3-{2-[5-Cyclohexyl-2-oxo-1-(2-oxo-propyl)-1,2-dihydro-3H-1,3,4-benzotriazepin-3-yl]-acetylamino}-benzoic acid Step a. [5-Cyclohexyl-2-oxo-1-(2-oxo-propyl)-1,2-dihydro-3H-1,3,4-benzotriazepin-3-yl]-acetic acid ethyl ester. To a solution of (5-cyclohexyl-2-oxo-1,2-dihydro-3H-1,3,4-benzotriazepin-3-yl)-acetic acid ethyl ester (Example 1, major product of step b) (300 mg, 1.00 mmol in MeCN (5 ml) were added K$_2$CO$_3$ (166 mg, 1.20 mmol), KI (20 mg) and 1-chloro-propan-2-one (90 μl, 1.10 mmol). The reaction mixture was heated at reflux for 48 h, then 1-chloro-propan-2-one (180 μl, 2.20 mmol) was added and heating continued for 16 h. The reaction mixture was filtered and the filtrate was evaporated. The residue was partitioned between saturated NaHCO$_3$ (30 ml) and EtOAc (30 ml). The organic phase was dried (MgSO$_4$), filtered and the solvent was evaporated. The crude product was purified by flash column chromatography (EtOAc-DCM (1:19)) to afford the product as a colourless foam (297 mg, 77%). $^1$H NMR (CDCl$_3$) 7.40 (2H, m), 7.19 (1H, t), 6.98 (1H, d), 4.50-4.11 (6H, m), 2.73 (1H, m), 2.19 (3H, s), 1.98-1.60 (6H, m), 1.26 (7H, m).

Step b. The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-2-oxo-1-(2-oxo-propyl)-1,2-dihydro-3H-1,3,4-benzotriazepin-3-yl]-acetic acid ethyl ester (Example 21, step a) was used in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c) in step d, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.55 (1H, s), 7.99 (1H, d), 7.81 (2H, m), 7.54-7.31 (4H, m), 7.09 (1H, d), 4.66 (1H, d), 4.43 (1H, d), 4.27 (2H, m), 2.82 (1H, m), 2.21 (3H, s), 2.07-1.73 (6H, m), 1.24 (4H, m). The compound was further characterised as the N-methyl-D-glucamine salt. Found: C, 54.51; H, 7.23; N, 9.88%; $C_{26}H_{28}N_4O_5 \cdot C_7H_{17}NO_5 \cdot 2.9H_2O$ requires: C, 54.72; H, 7.07; N, 9.67%.

EXAMPLE 22

3-{2-[5-Cyclohexyl-1-(2-cyclopentyl-2-oxo-ethyl)-2-oxo-1,2-dihydro-3H-1,3,4-benzotriazepin-3-yl]-acetylamino}-benzoic acid Step a. [5-Cyclohexyl-1-(2-cyclopentyl-2-oxo-ethyl)-2-oxo-1,2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that 2-bromo-cyclopentyl-ethanone was used in step c instead of 1-bromo-3,3-dimethyl-butan-2-one. $^1$H NMR (CDCl$_3$) 11.00 (1H, br s), 7.45 (2H, m), 7.25 (1H, m), 7.01 (1H, d), 4.56 (2H, d), 4.23 and 3.95 (2H, 2×d), 2.97 (1H, m), 2.81 (1H, m), 2.03-1.58 (13H, m), 1.30 (5H, m).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.52 (1H, s), 8.02

(1H, dd), 7.85 (1H, s), 7.81 (1H, d), 7.49 (2H, m), 7.41 (1H, t), 7.32 (1H, t), 7.08 (1H, d), 4.69 (1H, d), 4.46 (1H, d), 4.27 (2H, m), 2.96 (1H, m), 2.81 (1H, m), 2.05-1.61 (13H, m), 1.29 (5H, m). The compound was further characterised as the N-methyl-D-glucamine salt. Found: C, 58.44; H, 7.42; N, 9.18%; $C_{30}H_{34}N_4O_5 \cdot C_7H_{17}NO_5 01.9H_2O$ requires: C, 58.43; H, 7.27; N, 9.21%.

EXAMPLE 23

2-[5-Cyclohexyl-1-(3,3-dimethyl-2-oxo-butyl)-2-oxo-1,2-dihydro-3H-1,3,4-benzotriazepin-3-yl]-N-[3-(2H-tetrazol-5-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2,2-dimethyl-propionic acid 5-(3-amino-phenyl)-tetrazol-2-ylmethyl ester was used in place of 3-amino-benzoic acid methyl ester in step e, followed by reaction of the product obtained, in place of 2,2-dimethyl-propionic acid 5-(3-{2-[5-cyclopentyl-1-(3,3-dimethyl-2-oxo-butyl)-2-oxo-1,2-dihydro-3H-1,3,4-benzotriazepin-3-yl]-acetylamino}-phenyl)-tetrazol-2-ylmethyl ester (Example 10, step a), according to the method of Example 10, step b. $^1$H NMR (CDCl$_3$) 8.86 (1H, s), 8.18 (1H, m), 7.79 (1H, m), 7.46-7.24 (6H, m), 6.97 (1H, m), 4.73 (1H, d), 4.63 (1H, d), 4.27 (1H, d), 4.22 (1H, d), 2.77 (1H, m), 1.97-1.68 (6H, m), 1.24-1.11 (13H, m). The compound was further characterised as the N-methyl-D-glucamine salt. Found: C, 55.36; H, 7.36; N, 16.01%; $C_{29}H_{34}N_8O_3 \cdot C7H_{17}NO5.2.5H_2O$ requires: C, 55.23; H, 7.21; N, 16.10%.

EXAMPLE 24

2-[5-Cyclohexyl-1-(3,3-dimethyl-2-oxo-butyl)-2-oxo-1,2-dihydro-3H-1,3,4-benzotriazepin-3-yl]-N-m-tolyl-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that m-toluidine was used instead of 3-amino-benzoic acid methyl ester in step e. $^1$H NMR (CDCl$_3$) 8.19 (1H, s), 7.48 (2H, m), 7.46 (2H, m), 7.28 (2H, m), 7.15 (1H, d), 6.87 (1H, m), 4.72 (1H, d), 4.65 (1H, d), 4.28 (1H, d), 4.20 (1H, d), 2.80 (1H, m), 2.30 (3H, s), 1.76-1.70 (6H, m), 1.29-1.19 (13H, m). Found: C, 70.23; H, 7.63; N, 11.09%; $C_{29}H_{36}N_4O_{3}0.5H_2O$ requires: C, 69.99; H, 7.49; N, 11.26%.

EXAMPLE 25

2-[5-Cyclohexyl-1-(3,3-dimethyl-2-oxo-butyl)-2-oxo-1,2-dihydro-3H-1,3,4-benzotriazepin-3-yl]-N-phenyl-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that aniline was used instead of 3-amino-benzoic acid methyl ester in step e. $^1$H NMR (CDCl3) 8.20 (1H, s), 7.48-7.41 (5H, m), 7.38-7.27 (2H, m), 7.03 (2H, m), 4.70 (1H, d), 4.64 (1H, d), 4.32 (1H, d), 4.18 (1H, d), 2.78 (1H, m), 2.00-1.53 (6H, m), 1.32-1.23 (13H, m). Found: C, 69.45; H, 7.37; N, 11.39%; C28H34N4O3.0.5H2O requires: C, 69.54; H, 7.29; N, 11.58%.

EXAMPLE 26

2-[5-Cyclohexyl-1-(3,3-dimethyl-2-oxo-butyl)-2-oxo-1,2-dihydro-3H-1,3,4-benzotriazepin-3-yl]-N-(3-methanesulfonylamino-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that N-(3-amino-phenyl)-methanesulfonamide was used instead of 3-amino-benzoic acid methyl ester in step e. $^1$H NMR (CDCl$_3$) 8.51 (1H, s), 7.61 (1H, s), 7.45 (2H, m), 7.29 (2H, m), 7.06 (4H, m), 4.75 (1H, d), 4.62 (1H, d), 4.26 (2H, m), 2.98 (3H, s), 2.79 (1H, m), 2.00-1.50 (6H, m), 1.32-1.23 (13H, m). Found: C, 56.14; H, 6.86; N, 10.97%; $C_{29}H_{37}N_5O_5S.3.0H_2O$ requires: C, 56.02; H, 6.97; N, 11.26%.

EXAMPLE 27

2-[5-Cyclohexyl-1-(3,3-dimethyl-2-oxo-butyl)-2-oxo-1,2-dihydro-3H-1,3,4-benzotriazepin-3-yl]-N-(3-pyrrolidin-1-yl-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-pyrrolidin-1-yl-phenylamine (prepared in two steps from 3-nitro-aniline) was used instead of 3-amino-benzoic acid methyl ester in step e. $^1$H NMR (CDCl$_3$) 8.01 (1H, s), 7.49 (2H, m), 7.24 (1H, m), 7.04 (2H, m), 6.72 (1H, s), 6.51 (1H, d), 6.26 (1H, d), 4.69 (2H, m), 4.42 (1H, d), 4.12 (1H, d), 3.25 (4H, m), 2.77 (1H, m), 2.00-1.69 (10H, m), 1.28-1.21 (13H, m). The compound was further characterised as the hydrochloride salt. Found: C, 57.06; H, 6.38; N, 10.59%; $C_{32}H_{41}N_5O_9$HCl requires: C, 56.82; H, 6.26; N, 10.36%.

EXAMPLE 28

4-{2-[5-Cyclohexyl-J-(3,3-dimethyl-2-oxo-butyl)-2-oxo-1,2-dihydro-3H-1,3,4-benzotriazepin-3-yl]-acetylamino}-benzoic acid methyl ester The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 4-amino-benzoic acid methyl ester was used instead of 3-amino-benzoic acid methyl ester in step e. $^1$H NMR (CDCl$_3$) 8.57 (1H, s), 7.98 (2H, d), 7.50 (4H, m), 7.24 (1H, m), 7.03 (1H, d), 4.69 (1H, d), 4.59 (1H, d), 4.22 (2H, m), 3.89 (3H, s), 2.79 (1H, m), 2.00-1.69 (6H, m), 1.28-1.21 (13H, m). Found: C, 66.21; H, 6.98; N, 10.42%; $C_{30}H_{36}N_4O_5.5.0H_2O$ requires: C, 66.52; H, 6.88; N, 10.34%.

EXAMPLE 29

(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-phenyl)-acetic acid methyl ester was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.28 (1H, s), 7.48 (2H, m), 7.34-7.22 (4H, m), 7.00 (2H, m), 4.72 (1H, d), 4.64 (1H, d), 4.28 (1H, d), 4.15 (1H, d), 3.48 (2H, s), 2.70 (1H, m), 1.79-1.36 (6H, m), 1.22-1.05 (13H, m). The compound was further characterised as the N-methyl-D-glucamine salt. Found: C, 58.04; H, 7.73; N, 9.14%; C$_{30}$H$_{36}$N$_4$O$_5$.C$_7$H$_{17}$NO$_5$.2.0H$_2$O requires: C, 58.18; H, 7.52; N, 9.17%.

EXAMPLE 30

2-[5-Cyclohexyl-1-(3,3-dimethyl-2-oxo-butyl)-2-oxo-1,2-dihydro-3H-1,3,4-benzotriazepin-3-yl]-N-(3-methoxy-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that m-anisidine was used instead of 3-amino-benzoic acid methyl ester in step e. $^1$H NMR (CDCl$_3$) 8.22 (1H, m), 7.45-7.30 (2H, m), 7.27 (1H, m), 7.20-7.12 (2H, m), 7.03 (1H, d), 6.84 (1H, d), 6.63 (1H, d), 4.73 (1H, d), 4.64 (1H, d), 4.28 (1H, d). 4.19 (1H, d), 3.79 (3H, s), 2.80 (1H, m), 1.76-1.55 (6H, m), 1.36-1.24 (13H, m). Found C, 68.01; H, 7.48; N, 11.01; C$_{29}$H$_{36}$N$_4$O$_4$.0.5H$_2$O requires C, 67.81; H, 7.26; N, 10.91%.

EXAMPLE 31

2-[5-Cyclohexyl-1-(3,3-dimethyl-2-oxo-butyl)-2-oxo-1,2-dihydro-3H-1,3,4-benzotriazepin-3-yl]-N-p-tolyl-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that p-toluidine was used instead of 3-amino-benzoic acid methyl ester in step e. $^1$H NMR (CDCl$_3$) 8.11 (1H, s), 7.47 (2H, m), 7.29-7.25 (2H, m), 7.08-7.00 (4H, m), 4.71 (1H, d), 4.64 (1H, d), 4.32 (1H, d), 4.16 (1H, d), 2.77 (1H, m), 2.29 (3H, s), 1.86-1.53 (6H, m), 1.33-1.21 (13H, m). Found C, 71.49; H, 7.54; N, 11.25; C$_{29}$H$_{36}$N$_4$O$_3$ requires C, 71.28; H, 7.43; N, 11.47%.

EXAMPLE 32

2-[5-Cyclohexyl-1-(3,3-dimethyl-2-oxo-butyl)-2-oxo-1,2-dihydro-3H-1,3,4-benzotriazepin-3-yl]-N-(4-methoxy-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that p-anisidine was used instead of 3-amino-benzoic acid methyl ester in step e. $^1$H NMR (CDCl$_3$) 8.11 (1H, m), 7.47 (2H, m), 7.32-7.24 (3H, m), 7.01 (1H, d), 6.82 (2H, m), 4.74 (1H, d), 4.60 (1H, d), 4.31 (1H, d), 4.16 (1H, d), 3.77 (3H, s), 2.78 (1H, m), 2.03-1.71 (6H, m), 1.36-1.13 (13H, m). Found C, 67.74; H, 7.53; N, 10.67; C29H36N4O4.0.5H2O requires C, 67.81; H, 7.26; N, 10.91%.

EXAMPLE 33

2-[5-Cyclohexyl-J-(3,3-dimethyl-2-oxo-butyl)-2-oxo-1,2-dihydro-3H-1,3,4-benzotriazepin-3-yl]-N-(3-dimethylamino-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that m-N,N-dimethylaminoaniline was used instead of 3-amino-benzoic acid methyl ester in step e. $^1$H NMR (CDCl$_3$) 8.08 (1H, s), 7.50 (2H, m), 7.28 (1H, m), 7.10 (2H, m), 6.88 (1H, m), 6.64 (1H, m), 6.45 (1H, m), 4.69 (1H, d), 4.67 (1H, d), 4.36 (1H, d), 4.14 (1H, d), 2.95 (6H, m), 2.74 (1H, m), 2.00-1.71 (6H, m), 1.36-1.17 (13H, m). The compound was further characterised as the hydrochloride salt. Found C, 61.26; H, 7.58; N, 11.82; C$_{30}$H$_{39}$N$_5$O$_3$.HCl.2.0H$_2$O requires C, 61.05; H, 7.51; N, 11.86%.

EXAMPLE 34

(6-{2-[5-Cyclohexyl-1-(3,3-dimethyl-2-oxo-butyl)-2-oxo-1,2-dihydro-3H-1,3,4-benzotriazepin-3-yl]-acetylamino}-2,3-dihydro-indol-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (6-amino-2,3-dihydro-indol-1-yl)-acetic acid methyl ester (prepared in two steps from 6-nitro-2,3-dihydro-1H-indole), was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.40 (1H, br s), 9.38 (1H, s), 7.53 (2H, m), 7.18 (2H, m), 6.86 (1H, d), 6.65 (1H, d), 6.54 (1H, s), 4.78 (2H, m), 4.25 (1H, d), 3.90 (1H, d), 3.78 (2H, s), 3.46 (2H, m), 2.84 (3H, m), 1.86-1.55 (6H, m), 1.25-1.17 (13H, m). The compound was further characterised as the N-methyl-D-glucamine salt. Found C, 56.11; H, 7.64; N, 9.87; C$_{32}$H$_{39}$N$_5$.5C$_7$H$_{17}$NO$_5$.3.5H$_2$O requires C, 56.30; H, 7.63; N, 10.10%.

EXAMPLE 35

2-[5-Cyclohexyl-1-(3,3-dimethyl-2-oxo-butyl)-2-oxo-1,2-dihydro-3H-1,3,4-benzotriazepin-3-yl]-N-(4-fluoro-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 4-fluoroaniline was used instead of 3-amino-benzoic acid methyl ester in step e. $^1$H NMR (CDCl$_3$) 8.31 (1H, s), 7.48-7.28 (5H, m), 6.96 (3H, m), 4.75 (1H, d), 4.55 (1H, d), 4.21 (2H, m), 2.74 (1H, m), 1.90-1.65 (6H, m), 1.34-1.15 (13H, m). Found C, 66.98; H, 7.09; N, 10.88; C$_{28}$H$_{33}$FN$_4$O$_3$.0.5H$_2$O requires C, 67.04; H, 6.82; N, 11.16%.

EXAMPLE 36

2-[5-Cyclohexyl-1-(3,3-dimethyl-2-oxo-butyl)-2-oxo-1,2-dihydro-3H-1,3,4-benzotriazepin-3-yl]-N-{4-[methyl-(2H-tetrazol-5-yl)-amino]-phenyl}-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2,2-dimethyl-propionic acid 5-[(3-amino-phenyl)-methyl-amino]-tetrazol-2-ylmethyl ester (J. L. Castro et al. *J. Med. Chem.* (1996), 39, 842) was used in place of 3-amino-benzoic acid methyl ester in step e, followed by reaction of the product obtained, in place of 2,2-dimethyl-propionic acid 5-(3-{2-[5-cyclopentyl-1-(3,3-dimethyl-2-oko-butyl)-2-oxo-1,2-dihydro-3H-1,3,4-benzotriazepin-3-yl]-acetylamino}-phenyl)-tetrazol-2-ylmethyl ester (Example 10, step a), according to the method of Example 10, step b. $^1$H NMR (DMSO-d$_6$) 9.84 (1H, s), 7.55-7.05 (8H, m), 4.78 (2H, m), 3.96 (1H, m), 3.55 (1H, m), 3.39 (3H, s), 2.86 (1H, m), 1.85-1.65 (6H, m), 1.33-1.10 (13H, m). The compound was further characterised as the N-methyl-D-glucamine salt. Found C, 57.86; H, 7.31; N, 18.31; C$_{30}$H$_{37}$N$_9$O$_3$.C$_7$H$_{17}$NO$_5$ requires C, 57.94; H, 7.10; N, 18.26%.

EXAMPLE 37

N-(3-Cyano-phenyl)-2-[5-cyclohexyl-1-(3,3-dimethyl-2-oxo-butyl)-2-oxo-1,2-dihydro-3H-1,3,4-benzotriazepin-3-yl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-aminobenzonitrile was used instead of 3-amino-benzoic acid methyl ester in step e. $^1$H NMR (CDCl$_3$) 8.76 (1H, s), 7.83 (2H, m), 7.50-7.29 (5H, m), 7.02 (1H, m), 4.81 (1H, d), 4.48 (1H, d), 4.28 (1H, d), 4.14 (1H, d), 2.79 (1H, m), 1.91-1.65 (6H, m), 1.36-1.17 (13H, m). Found C, 66.32; H, 6.89; N, 13.39; C$_{29}$H$_{33}$N$_5$O$_3$.1.5H$_2$O requires C, 66.14; H, 6.89; N, 13.29%.

EXAMPLE 38

(3-{2-[5-Cyclohexyl-1-(3,3-dimethyl-2-oxo-butyl)-2-oxo-1,2-dihydro-3H-1,3,4-benzotriazepin-3-yl]-acetylamino}-phenylsulfanyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-phenylsulfanyl)-acetic acid ethyl ester (S. Hagishita et al. *Bioorg. Med. Chem.* (1997), 5, 1433) was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (DMSO-d$_6$) 12.60 (1H, br s), 9.81 (1H, s), 7.50 (3H, m), 7.27-7.21 (4H, m), 6.97 (1H, m), 4.78 (2H, m), 4.27 (1H, d), 3.96 (1H, d), 3.72 (2H, s), 2.86 (1H, m), 1.83-1.65 (6H, m), 1.29-1.17 (13H, m). The compound was further characterised as the N-methyl-D-glucamine salt. Found C, 54.50; H, 7.36; N, 8.44; C$_{30}$H$_{36}$N$_4$O$_5$S.C$_7$H$_{17}$NO$_5$.3.0H$_2$O requires C, 54.59; H, 7.30; N, 8.60%.

EXAMPLE 39

5-{2-[5-Cyclohexyl-1-(3,3-dimethyl-2-oxo-butyl)-2-oxo-1,2-dihydro-3H-1,3,4-benzotriazepin-3-yl]-acetylamino}-isophthalic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 5-amino-isophthalic acid dimethyl ester was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 10.19 (1H, s), 8.33 (2H, s), 8.13 (1H, s), 7.53 (1H, d), 7.48 (1H, t), 7.23 (1H, t), 7.16 (1H, d), 4.80 (2H, br), 4.30 (1H, br), 4.00 (1H, br), 2.85 (1H, m), 1.90-1.50 (6H, m), 1.45-1.13 (13H, m). The compound was further characterised as the N-methyl-D-glucamine salt. Found: C, 54.69; H, 7.11; N, 8.70%; C$_{30}$H$_{34}$N$_4$O$_7$.C$_7$H$_{17}$NO$_5$.3.0H$_2$O requires C, 54.74; H, 7.08; N, 8.63%.

EXAMPLE 40

2-[5-Cyclohexyl-1-(3,3-dimethyl-2-oxo-butyl)-2-oxo-1,2-dihydro-3H-1,3,4-benzotriazepin-3-yl]-N-(3-methanesulfonylaminocarbonyl-phenyl)-acetamide Methanesulfonamide (96 mg, 1.00 mmol) was added to a solution of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid (Example 2)(409 mg, 0.80 mmol), EDC (207 mg, 1.08 mmol) and DMAP (122 mg, 1.00 mmol) in DCM (20 ml) at room temperature. After stirring for 17 h, the mixture was washed with 5% KHSO$_4$ (50 ml), brine (50 ml) and dried (MgSO$_4$). Filtration and evaporation of the solvent gave the crude product which was purified by flash column chromatography (MeOH-DCM (1:10) to afford the title compound as a white crystalline solid (392 mg, 83%). $^1$H NMR (DMSO-d$_6$) 9.99 (1H, s), 8.02 (1H, s), 7.63-7.36 (5H, m), 7.23 (1H, t), 7.13 (1H, d), 4.73 (2H, dd), 4.29 and 4.25 (2H, d×2), 3.24 (3H, s), 2.87 (1H, m), 1.80-1.48 (6H, m), 1.30-1.09 (13H, m). The compound was further characterised as the N-methyl-D-glucamine salt. Found: C, 53.93; H, 7.07; N, 10.17%; $C_{30}H_{37}N_5O_6S.C_7H_{17}NO_5.2.0H_2O$ requires: C, 53.74; H, 7.07; N, 10.16%.

EXAMPLE 41

2-[5-Cyclohexyl-1-(3,3-dimethyl-2-oxo-butyl)-2-oxo-1,2-dihydro-3H-1,3,4-benzotriazepin-3-yl]-N-(3-propylamino-phenyl)-acetamide Step a. (3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-propyl-carbamic acid tert-butyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-phenyl)-propyl-carbamic acid tert-butyl ester (obtained using steps b and c of the method employed in the preparation of (3-amino-phenyl)-methyl-carbamic acid tert-butyl ester (Example 3, step c) except that 1-bromopropane was used in step b instead of iodomethane), was used instead of 3-amino-benzoic acid methyl ester in step e.

Step b. 4.0M HCl in dioxan (5 ml, 20.0 mmol) was added to a solution of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-propyl-carbamic acid tert-butyl ester (Example 41, step a) (524 mg, 0.83 mmol) in dioxan (15 ml) at room temperature. The mixture was stirred for 2 h during which time a white precipitate formed. The solvent was evaporated, and the solid obtained was washed with Et$_2$O, isolated by filtration and dried, to afford the hydrochloride salt of the title compound (430 mg, 91%). $^1$H NMR (CDCl$_3$) 8.39 (1H, s), 7.61-7.27 (7H, m), 7.01 (1H, d), 4.69 (2H, br s), 4.60 (1H, d), 4.29 (2H, dd), 3.21 (2H, br s), 2.80 (1H, br s), 2.01-1.45 (6H, m), 1.43-1.19 (15H, m), 0.95 (3H, t). Found: C, 63.68; H, 7.65; N, 11.98%; $C_{31}H_{41}N_5O_3.HCl.H_2O$ requires: C, 63.52; H, 7.57; N, 11.95%.

EXAMPLE 42

2-[5-Cyclohexyl-1-(3,3-dimethyl-2-oxo-butyl)-2-oxo-1,2-dihydro-3H-1,3,4-benzotriazepin-3-yl]-N-[3-(2-ethoxy-ethylamino)-phenyl]-acetamide The title compound was obtained as the hydrochloride salt by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that (3-amino-phenyl)-2-ethoxy-ethyl-carbamic acid tert-butyl ester (obtained using the method employed in the preparation of (3-amino-phenyl)-methyl-carbamic acid tert-butyl ester (Example 3, step c) except that 2-bromoethyl-ethyl ether was used in step b instead of iodomethane) was used instead of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-propyl-carbamic acid tert-butyl ester (Example 41, step a) according to the method of Example 41 step b. $^1$H NMR (CDCl$_3$) 8.45 (1H, s), 7.61 (1H, s), 7.56-7.47 (2H, m), 7.36 (4H, m), 7.03 (1H, d), 4.70 (2H, dd), 4.26 (2H, dd), 3.73 (2H, br s), 3.51 (4H, m), 2.82 (1H, br s), 2.05-1.65 (6H, m), 1.30-1.17 (16H, m). Found: C, 63.90; H, 7.66; N, 11.58%; $C_{32}H_{43}N_5O_4.HCl.0.25H_2O$ requires: C, 63.77; H, 7.44; N, 11.62%.

EXAMPLE 43

5-Cyclohexyl-1-(3,3-dimethyl-2-oxo-butyl)-3-(2-oxo-2-m-tolyl-ethyl)-1,3-dihydro-3H-1,3,4-benzotriazepin-2-one Step a. 2-[5-Cyclohexyl-1-(3,3-dimethyl-2-oxo-butyl)-2-oxo-1,2-dihydro-3H-1,3,4-benzotriazepin-3-yl]-N-methoxy-N-methyl-acetamide was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that N,O-dimethylhydroxylamine hydrochloride and triethylamine were used instead of 3-amino-benzoic acid methyl ester in step e. $^1$H NMR (CDCl$_3$) 7.86 (2H, m), 7.17 (1H, m), 6.94 (1H, d), 4.70-4.14 (3H, m), 4.09 (1H, m), 3.68 (3H, s), 3.17 (3H, s), 2.72 (1H, m), 1.93-1.55 (6H, m), 1.43-1.22 (13H, m).

Step b. A 1.0M solution of m-tolylmagnesium chloride in THF (0.6 ml, 0.6 mmol) was added drop-wise to a solution of 2-[5-cyclohexyl-1-(3,3-dimethyl-2-oxo-butyl)-2-oxo-1,2-dihydro-3H-1,3,4-benzotriazepin-3-yl]-N-methoxy-N-methyl-acetamide (Example 43, step a)(220 mg, 0.5 mmol) in Et$_2$O (10 ml) at −78° C. The reaction mixture was allowed to warm to room temperature and stirred overnight. After solvent concentration, the reaction mixture was extracted with Et$_2$O, washed with saturated NH$_4$Cl solution, brine and dried (MgSO$_4$). Flash column chromatography (EtOAc-hexane (1:4)) afforded the title compound as a white solid (36 mg, 15%). $^1$H NMR (CDCl$_3$) 7.69 (2H, m), 7.39-7.31 (4H, m), 7.26 (1H, m), 6.95 (1H, dd), 5.20 (1H, m), 4.68 (3H, m), 2.79 (1H, m), 2.30 (3H, s), 1.80-1.62 (6H, m), 1.31-1.24 (13H, m). Found C, 73.14; H, 7.82; N, 8.51; $C_{29}H_{35}N_3O_3$ requires C, 73.54; H, 7.45; N, 8.87%.

EXAMPLE 44

3-{5-[5-Cyclohexyl-1-(3,3-dimethyl-2-oxo-butyl)-2-oxo-1,2-dihydro-3H-1,3,4-benzotriazepin-3-ylmethyl]-[1,3,4]oxadiazol-2-yl}-benzoic acid Step a. 3-(N'-{2-[5-Cyclohexyl-1-(3,3-dimethyl-2-oxo-butyl)-2-oxo-1,2-dihydro-3H-1,3,4-benzotriazepin-3-yl]-acetyl}-hydrazinocarbonyl)-benzoic acid methyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-hydrazinocarbonyl-benzoic acid methyl ester (prepared in two steps from isophthalic acid dimethyl ester) was used instead of 3-amino-benzoic acid methyl ester in step e.

Step b. 3-{5-[5-Cyclohexyl-1-(3,3-dimethyl-2-oxo-butyl)-2-oxo-1,2-dihydro-3H-1,3,4-benzotriazepin-3-ylmethyl]-[1,3,4]oxadiazol-2-yl}-benzoic acid methyl ester. A solution of the 3-(N'-{2-[5-cyclohexyl-1-(3,3-dimethyl-2-oxo-butyl)-2-oxo-1,2-dihydro-3H-1,3,4-benzotriazepin-3-yl]-acetyl}-hydrazinocarbonyl)-benzoic acid methyl ester (Example 44, step a)(94 mg, 0.16 mmol), triphenylphosphine (64 mg, 0.24 mmol) and 1,8-diazabicyclo[5.4.0]undec-7-ene (75 mg, 0.49 mmol) in CCl$_4$-MeCN (1:1/2 ml) was stirred at room temperature for 5 h. A further quantity of triphenylphosphine (43 mg, 0.16 mmol) was added after 3 h. The solvent was evaporated under reduced pressure and the residue purified by flash column chromatography (EtOAc-hexane (1:1)) to afford the product as a off-white solid (52 mg, 57%). $^1$H NMR (CDCl$_3$) 8.62 (1H, s), 8.19 (2H, m), 7.56 (1H, t), 7.39-7.35 (2H, m), 7.19 (1H, t), 6.97 (1H, d), 5.05 (1H, br d), 4.85 (1H, br d), 4.68 (2H, s), 3.96 (3H, s), 2.70 (1H, m), 1.80-1.60 (6H, br), 1.25 (13H, m).

Step c. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid (Example 2) except that 3-{5-[5-cyclohexyl-1-(3,3-dimethyl-2-oxo-butyl)-2-oxo-1,2-dihydro-3H-1,3,4-benzotriazepin-3-ylmethyl]-[1,3,4]oxadiazol-2-yl}-benzoic acid methyl ester (Example 44, step b) was used in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1). $^1$H NMR (CDCl$_3$) 8.69 (1H, s), 8.27 (2H, m), 7.61 (1H, t), 7.42-7.38 (2H, m), 7.20 (1H, t), 6.98 (1H, d), 5.10 (1H, br d), 4.90 (1H, br d), 4.70 (2H, s), 2.73 (1H, m), 1.90-1.60 (6H, m), 1.30-1.25 (13H, m). The compound was further characterised as the N-methyl-D-glucamine salt. Found: C, 56.75; H, 7.08; N, 10.61%; C$_{30}$H$_{33}$N$_5$O$_5$.C$_7$H$_{17}$NO$_5$.2.5H$_2$O requires: C, 56.69; H, 7.07; N, 10.72%.

EXAMPLE 45

3-({2-[5-Cyclohexyl-1-(3,3-dimethyl-2-oxo-butyl)-2-oxo-1,2-dihydro-3H-1,3,4-benzotriazepin-3-yl]-acetylamino}-methyl)-benzoic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-aminomethyl-benzoic acid methyl ester was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.02 (1H, d), 7.94 (1H, s), 7.51 (1H, d), 7.45-7.35 (2H, m), 7.21 (1H, dd), 7.14 (1H, d), 6.93 (1H, d), 6.75 (1H, br t), 4.66-4.53 (3H, m), 4.38-4.19 (3H, m), 2.64 (1H, br m), 1.88-1.49 (6H, m), 1.31-1.20 (13H, m). The compound was further characterised as the N-methyl-D-glucamine salt. Found: C, 58.33; H, 7.64; N, 8.95%; C$_{30}$H$_{36}$N$_4$O$_5$.C$_7$H$_{17}$NO$_5$.2.0H$_2$O requires C, 58.18; H, 7.52; N, 9.17%.

EXAMPLE 46

[5-Cyclohexyl-1-(3,3-dimethyl-2-oxo-butyl)-2-oxo-1,2-dihydro-3H-1,3,4-benzotriazepin-3-yl]-acetic acid N'-m-tolyl-hydrazide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that meta-tolyl-hydrazine was used instead of 3-amino-benzoic acid methyl ester in step e. $^1$H NMR (CDCl$_3$) 8.12 (1H, d), 7.43-7.41 (2H, m), 7.25 (1H, t), 7.09 (1H, m), 6.99 (1H, d), 6.70 (1H, d), 6.65-6.31 (2H, m), 6.01 (1H, d), 4.71 (1H, d), 4.63 (1H, d), 4.24 (2H, s), 2.80 (1H, m), 2.29 (3H, s), 2.10-1.60 (6H, m), 1.35-1.24 (13H, m). Found: C, 68.00; H, 7.69; N, 13.66%; C$_{29}$H$_{37}$N$_5$O$_3$.0.5H$_2$O requires C, 67.94; H, 7.47; N, 13.66%.

EXAMPLE 47

5-Cyclohexyl-1-(3,3-dimethyl-2-oxo-butyl)-3-(5-oxo-4-m-tolyl-4,5-dihydro-[1,3,4]oxadiazol-2-ylmethyl)-1,3-dihydro-3H-1,3,4-benzotriazepin-2-one A solution of [5-cyclohexyl-1-(3,3-dimethyl-2-oxo-butyl)-2-oxo-1,2-dihydro-3H-1,3,4-benzotriazepin-3-yl]-acetic acid N'-m-tolyl-hydrazide (Example 46)(300 mg, 0.60 mmol), 1,1'-carbonyldiimidzole (483 mg, 2.98 mmol) and triethylamine (181 mg, 1.79 mmol) in THF (6 ml) was stirred at room temperature for 19 h, then heated at reflux for 6 h. The solvent was evaporated under reduced pressure and the residue was purified by flash column chromatography (EtOAc-hexane (2:3-7:3)) to afford the title compound as an off-white solid (83 mg, 26%). $^1$H NMR (CDCl$_3$) 7.63-7.60 (2H, m), 7.41-7.37 (2H, m), 7.32 (1H, m), 7.20 (1H, t), 7.05 (1H, d), 6.96 (1H, d), 4.75 (1H, br d), 4.68 (2H, d), 4.55 (1H, br d), 2.75 (1H, m), 2.38 (3H, s), 1.95-1.60 (6H, m), 1.35-1.20 (13H, m). Found: C, 67.93; H, 6.78; N, 13.23%; C$_{30}$H$_{35}$N$_5$O$_4$ requires C, 68.03; H, 6.66; N, 13.22%.

EXAMPLE 48

2-[5-Cyclohexyl-1-(3,3-dimethyl-2-oxo-butyl)-2-oxo-1,2-dihydro-3H-1,3,4-benzotriazepin-3-yl]-N-(3-hydroxymethyl-phenyl)-acetamide Step a. Carbonic acid 3-{2-[5-cyclohexyl-1-(3,3-dimethyl-2-oxo-butyl)-2-oxo-1,2-dihydro-3H-1,3,4-benzotriazepin-3-yl]-acetylamino}-benzyl ester methyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that carbonic acid 3-amino-benzyl ester methyl ester was used instead of 3-amino-benzoic acid methyl ester in step e. $^1$H NMR (CDCl$_3$) 8.30 (1H, s), 7.51-7.39 (4H, m), 7.31-7.24 (2H, m), 5.11 (2H, s), 4.72 (1H, d), 4.64 (1H, d), 4.23 (1H, d), 4.14 (1H, d), 3.80 (3H, s), 2.89 (1H, m), 1.76-1.67 (6H, m), 1.29-1.24 (13H, m).

Step b. Carbonic acid 3-{2-[5-cyclohexyl-1-(3,3-dimethyl-2-oxo-butyl)-2-oxo-1,2-dihydro-3H-1,3,4-benzotriazepin-3-yl]-acetylamino}-benzyl ester methyl ester (Example 48, step a) was dissolved in THF-MeOH (1:1/40 ml) and 1% K$_2$CO$_3$ solution (30 ml) was added. The mixture was stirred at room temperature for 2 h. After concentration of the organic solvents, a precipitate formed, which was collected by filtration and dried in vacuo to afford the title compound as a yellow solid (790 mg, 89%). $^1$H NMR (CDCl$_3$) 8.31 (1H, s), 7.51-7.45 (3H, m), 7.31-7.28 (3H, m), 7.26-7.10 (2H, m), 4.70 (1H, d), 4.67 (2H, s), 4.64 (1H, d), 4.26 (1H, d), 4.22 (1H, d), 2.89 (1H, m), 1.85-1.55 (6H, m), 1.30-1.24 (13H, m). Found: C, 67.70; H, 7.40; N, 10.79%; C$_{29}$H$_{36}$N$_4$O$_4$.0.5H$_2$O requires: C, 67.81; H, 7.26; N, 10.91%.

EXAMPLE 49

N-(3-Carbamimidoylsulfanylmethyl-phenyl)-2-[5-cyclohexyl-1-(3,3-dimethyl-2-oxo-butyl)-2-oxo-1,2-dihydro-3H-1,3,4-benzotriazepin-3-yl]-acetamide Step a. N-(3-Chloromethyl-phenyl)-2-[5-cyclohexyl-1-(3,3-dimethyl-2-oxo-butyl)-2-oxo-1,2-dihydro-3H-1,3,4-benzotriazepin-3-yl]-acetamide. 2-[5-Cyclohexyl-1-(3,3-dimethyl-2-oxo-butyl)-2-oxo-1,2-dihydro-3H-1,3,4-benzotriazepin-3-yl]-N-(3-hydroxymethyl-phenyl)- acetamide (Example 48)(750 mg, 1.49 mmol) and triphenylphosphine polystyrene resin (1.20 mmol/g; 2.50 g, 3.00 mmol)(P. Hodge, G. Richardson, J C. S. *Chem. Commun.*, (1983), 622) were heated at reflux in $CCl_4$ (30 ml) for 3 h. After filtration and evaporation of the solvent the product was obtained as a pale pink solid (220 mg, 29%). $^1$H NMR ($CDCl_3$) 8.36 (1H, s), 7.50-7.28 (4H, m), 7.10-7.01 (4H, m), 4.75 (1H, d), 4.60 (1H, d), 4.54 (2H, s), 4.25 (1H, d), 4.22 (1H, d), 2.79 (1H, m), 2.05-1.62 (6H, m), 1.30-1.22 (13H, m).

Step b. N-(3-Chloromethyl-phenyl)-2-[5-cyclohexyl-1-(3,3-dimethyl-2-oxo-butyl)-2-oxo-1,2-dihydro-3H-1,3,4-benzotriazepin-3-yl]-acetamide (Example 49, step a) (52 mg, 0.0 mmol) was reacted with thiourea (7.6 mg, 0.0 mmol) and NaI (2 mg) in refluxing acetone (10 ml) for 3 h. After cooling, the solvents were concentrated in vacuo, affording the title compound as a yellow solid after trituration with $Et_2O$ (18 mg, 30%). $^1$H NMR (DMSO-$d_6$) 9.89 (1H, br s), 8.99 (3H, br s), 7.75-7.46 (3H, m), 7.29-7.04 (5H, m), 4.77 (2H, m), 4.40 (2H, m), 4.38 (1H, m), 3.93 (1H, m), 2.86 (1H, m), 1.73-1.64 (6H, m), 1.21-1.08 (13H, m).

EXAMPLE 50

(3-{2-[5-Cyclohexyl-1-(3,3-dimethyl-2-oxo-butyl)-2-oxo-1,2-dihydro-3H-1,3,4-benzotriazepin-3-yl]-acetylamino}-benzenesulfonyl)-acetic acid ethyl ester The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-benzenesulfonyl)-acetic acid ethyl ester (prepared in one step from (3-amino-phenylsulfanyl)-acetic acid ethyl ester) was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (DMSO-$d_6$) 13.08 (1H, br s), 10.26 (1H, s), 8.16 (1H, s), 7.77-7.45 (5H, m), 7.26-7.15 (2H, m), 4.80 (2H, m), 4.39 (2H, s), 4.38 (1H, d), 3.98 (1H, d), 2.86 (1H, m), 1.65-1.34 (6H, m), 1.25-1.13 (13H, m). The compound was further characterised as the N-methyl-D-glucamine salt. Found: C, 53.55; H, 6.90; N, 8.48%; $C_{30}H_{36}N_4O_7S.C_7H_{17}NO_5$92.0$H_2O$ requires: C, 53.67; H, 6.94; N, 8.46%.

EXAMPLE 51

[tert-Butoxycarbonyl-(3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-amino]-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [(3-amino-phenyl)-tert-butoxycarbonyl-amino]-acetic acid methyl ester (prepared in three steps from 1-isocyanato-3-nitro-benzene) was used instead of 3-amino-benzoic acid methyl ester in step e, followed by reaction of the product obtained, in place of 3-{2-[5-cyclohexyl-1-(3,3-dimethyl-2-oxo butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-$d_6$) 12.60 (1H, br s), 9.81 (1H, s), 7.52-7.47 (3H, m), 7.23-7.17 (4H, m), 6.89 (1H, d), 4.78 (2H, m), 4.25 (1H, d), 4.14 (2H, s), 3.92 (1H, d), 2.86 (1H, m), 1.86-1.51 (6H, m), 1.36-1.13 (22H, m). The compound was further characterised as the N-methyl-D-glucamine salt. Found: C, 55.18; H, 7.90; N, 9.20%; $C_{35}H_{45}N_5O_7.C_7H_{17}NO_5.4.0H_2O$ requires: C, 55.12; H, 7.71; N, 9.18%.

EXAMPLE 52

(3-{2-[5-Cyclohexyl-1-(3,3-dimethyl-2-oxo-butyl)-2-oxo-1,2-dihydro-3H-1,3,4-benzotriazepin-3-yl]-acetylamino}-phenylamino)-acetic acid

[tert-Butoxycarbonyl-(3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-amino]-acetic acid (Example 51)(137 mg, 0.21 mmol) was stirred in trifluoroacetic acid for 2 h at room temperature. After concentration, the resulting gum was dissolved in DCM, washed with saturated $NaHCO_3$ and then with 1N HCl. The organic phase was dried over $MgSO_4$, filtered and the solvent was evaporated to afford the title compound as a yellow solid (85 mg, 73%). $^1$H NMR (DMSO-$d_6$) 9.47 (1H, s), 7.55-7.27 (2H, m), 7.23-7.15 (2H, m), 6.97 (1H, t), 6.92-6.68 (2H, m), 6.25 (1H, m), 5.80 (2H, br s), 4.78 (2H, m), 4.25 (1H, d), 3.95 (1H, d), 3.72 (2H, s), 2.80 (1H, m), 1.86-1.51 (6H, m), 1.26-1.09 (13H, m). The compound was further characterised as the N-methyl-D-glucamine salt. Found: C, 57.66; H, 7.45; N, 9.07%; $C_{30}H_{36}N_4O_6.C_7H_{17}NO_5.1.5H_2O$ requires: C, 57.65; H, 7.32; N, 9.09%.

EXAMPLE 53

(3-{2-[5-Cyclohexyl-1-(3,3-dimethyl-2-oxo-butyl)-2-oxo-1,2-dihydro-3H-1,3,4-benzotriazepin-3-yl]-acetylamino}-phenoxy)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-phenoxy)-acetic acid methyl ester was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-$d_6$) 13.00 (1H, br s), 9.75 (1H, s), 7.50 (2H, m), 7.26-7.13 (4H, m), 7.04 (1H, d), 6.55 (1H, d), 4.78 (2H, s), 4.58 (2H, s), 4.27 (1H, d), 3.97 (1H, d), 2.85 (1H, m), 1.90-1.20 (10H, m), 1.13 (9H, s). The compound was further characterised as the N-methyl-D-glucamine salt. Found: C, 57.66; H, 7.45; N, 9.07%; $C_{30}H_{36}N_4O_6.C_7H_{17}NO_5.1.5H_2O$ requires: C, 57.65; H, 7.32; N, 9.09%.

EXAMPLE 54

3-{2-[5-Adamantan-1-yl-1-(3,3-dimethyl-2-oxo-butyl)$_2$-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that adamantan-1-yl-(2-amino-phenyl)-methanone (A. Cappelli, et. al., *J. Med. Chem.*, (1999), 42, 1556) was used in step a instead of (2-amino-phenyl)-cyclohexyl-methanone, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 13.0 (1H, br s), 9.89 (1H, s), 8.14 (1H, s), 7.67 (1H, m), 7.59 (2H, d), 7.42 (2H, m), 7.21 (2H, m), 4.79 (2H, m), 4.29 (1H, d), 3.93 (1H, d), 2.04-1.66 (15H, m), 1.13 (9H, s). The compound was further characterised as the N-methyl-D-glucamine salt. Found: C, 59.82; H, 7.66; N, 8.67%; $C_{33}H_{38}N_4O_5 \cdot C_7H_{17}NO_5 \cdot 2.0H_2O$ requires C, 59.91; H, 7.41; N, 8.73%.

EXAMPLE 55

3-{2-[5-Cycloheptyl-1-(3,3-dimethyl-2-oxo-butyl)$_2$-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-phenyl)-cycloheptyl-methanone (prepared according to the method of A. Cappelli, et. al., *J. Med. Chem.*, (1999), 42, 1556) was used in step a instead of (2-amino-phenyl)-cyclohexyl-methanone, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.49 (1H, s), 8.04 (1H, m), 7.87 (1H, m), 7.81 (1H, m), 7.50-7.26 (4H, m), 7.04 (1H, d), 4.78 (1H, d), 4.60 (1H, d), 4.27 (2H, s), 3.00 (1H, m), 2.05-1.44 (12H, m), 1.25 (9H, s). The compound was further characterised as the N-methyl-D-glucamine salt. Found: C, 57.03; H, 7.58; N, 8.77%; $C_{30}H_{36}N_4O_5 \cdot C_7H_{17}NO_5 \cdot 3.5H_2O$ requires: C, 56.84; H, 7.61; N, 8.95%.

EXAMPLE 56

(3-{2-[5-Cyclohexy-1-(2-cyclopentyl-2-oxo-ethyl)-2-oxo-1,2-dihydro-3H-1,3,4-benzotriazepin-3-yl]-acetylamino}-phenyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and (3-amino-phenyl)-acetic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 9.20 (1H, br s), 8.29 (1H, s), 7.46 (2H, m), 7.36-7.19 (4H, m), 7.06 (1H, d), 6.99 (1H, d), 4.66 (1H, d), 4.46 (1H, d), 4.32 (1H, d), 4.17 (1H, d), 3.58 (2H, s), 2.93 (1H, m), 2.78 (1H, m), 1.99-1.51 (13H, m), 1.27 (5H, m). The compound was further characterised as the N-methyl-D-glucamine salt. Found: C, 58.65; H, 7.44, N, 9.06%; $C_{31}H_{36}N_4O_5 \cdot C_7H_{17}NO_5 92.1H_2O$ requires: C, 58.70; H, 7.41; N, 9.01%.

EXAMPLE 57

2-[5-Cyclohexyl-1-(2-cyclopentyl-2-oxo-ethyl)-2-oxo-1,2-dihydro-3H-1,3,4-benzotriazepin-3-yl]-N-(3-methylaminophenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and (3-amino-phenyl)-methyl-carbamic acid tert-butyl ester (Example 3, step c) were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.07 (1H, s), 7.47 (2H, m), 7.27 (1H, m), 7.04 (2H, m), 6.92 (1H, t), 6.44 (1H, dd), 6.31 (1H, dd), 4.64 (1H, d), 4.48 (1H, d), 4.36 (1H, d), 4.13 (1H, d), 3.71 (1H, br s), 2.95 (1H, m), 2.80 (4H, m), 2.05-1.56 (13H, m), 1.27 (5H, m). The compound was further characterised as the hydrochloride salt. Found: C, 64.90; H, 7.02; N, 12.57%; $C_{30}H_{37}N_4O_3 \cdot HCl$ requires: C, 65.26; H, 6.94; N, 12.68%.

EXAMPLE 58

(3-{2-[5-Cyclohexyl-1-(2-cyclopentyl-2-oxo-ethyl)-2-oxo-1,2-dihydro-3H-1,3,4-benzotriazepin-3-yl]-acetylamino}-phenylsulfanyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and (3-amino-phenylsulfanyl)-acetic acid ethyl ester were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.41 (1H, s), 7.45 (2H, m), 7.31-7.17 (4H, m), 7.08 (2H, m), 6.12 (1H, br s), 4.66 (1H, d), 4.21 (1H, d), 4.23 (1H, d), 4.19 (1H, d), 3.65 (2H, s), 2.96 (1H, m), 2.79 (1H, m), 1.82-1.62 (13H, m), 1.29 (5H, m). The compound was further characterised as the N-methyl-D-glucamine salt. Found: C, 52.82; H, 7.43; N, 8.12%; $C_{31}H_{36}N_4O_5S \cdot C_7H_{17}NO_5 \cdot 5.0H_2O$ requires: C, 52.95; H, 7.36; N, 8.04%.

EXAMPLE 59

2-[5-Cyclohexyl-1-(3,3-dimethyl-2-oxo-butyl)-2-oxo-1,2-dihydro-3H-1,3,4-benzotriazepin-3-yl]-N-[3-(5-oxo-Z5-dihydro-[1,2,4]oxadiazol-3-yl)-phenyl]-acetamide A solution of [5-cyclohexyl-1-(3,3-dimethyl-2-oxo-butyl)-2-oxo-1,2-dihydro-3H-1,3,4-benzotriazepin-3-yl]-acetic acid (Example 1, step d)(200 mg, 0.5 mmol), EDC (140 mg, 0.74 mmol), HOBT (100 mg, 0.74 mmol) and DMAP (20 mg) in DMF (10 ml) was stirred at room temperature for 2 h. Thereafter, a solution of 3-(3-amino-phenyl)-2H-[1,2,4]oxadiazol-5-one trifluoroacetic acid salt (WO 93/19063)(170 mg, 0.58 mmol) and triethylamine (120 µl, 1.00 mmol) in DMF (2 ml) was added and the reaction mixture was stirred for 16 h. The mixture was diluted with EtOAc (20 ml), and the organic layer washed with aqueous 5% $KHSO_4$, brine and dried over $MgSO_4$. Filtration and evaporation of the solvent afforded an oil which was purified by flash column chromatography (acetone-DCM (1:6)) to give the title compound as an orange foam (62 mg, 22%). $^1$H NMR ($CDCl_3$) 8.83 (1H, s), 7.90 (1H, m), 7.53-7.25 (7H, m), 7.02 (1H, d), 4.76 (1H, d), 4.57 (1H, d), 4.22 (1H, d), 4.20 (1H, d), 2.80 (1H, m), 1.95-1.55 (6H, m), 1.28-1.20 (13H, m). The compound was further characterised as the N-methyl-D-glucamine salt. Found: C, 55.99; H, 7.15; N, 12.14%; $C_{30}H_{34}N_6O_5.C_7H_{17}NO_5.2.0H_2O$ requires: C, 56.26; H, 7.01; N, 12.41%.

EXAMPLE 60

3-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-acrylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-(3-amino-phenyl)-acrylic acid methyl ester was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR ($CDCl_3$) 8.43 (1H, s), 7.75-7.45 (5H, m), 7.35-7.23 (3H, m), 7.04 (1H, d), 6.42 (1H, d), 4.76 (1H, d), 4.61 (1H, d), 4.27 (2H, m), 2.79 (1H, m), 2.01-1.65 (6H, m), 1.28-1.23 (13H, m). Found: C, 60.70; H, 7.50; N, 9.60%; $C_{31}H_{36}N_4O_5.C_7H_{17}NO_5.0.5H_2O$ requires: C, 60.49; H, 7.26; N, 9.35%.

EXAMPLE 61

3-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-propionic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-(3-amino-phenyl)-propionic acid methyl ester (D. F. Biggs, et. al., *J. Med. Chem.* (1976), 19, 472) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR ($CDCl_3$) 9.05 (1H, br s), 8.35 (1H, s), 7.45 (2H, m), 7.31-7.18 (4H, m), 7.03 (1H, d), 6.92 (1H, d), 4.73 (1H, d), 4.63 (1H, d), 4.27 (1H, d), 4.20 (1H, d), 2.91 (2H, m), 2.79 (1H, m), 2.63 (2H, m), 1.90-1.35 (6H, m), 1.29-1.21 (13H, m). The compound was further characterised as the N-methyl-D-glucamine salt. Found: C, 57.25; H, 7.81; N, 9.02%; $C_{31}H_{38}N_4O_5.C_7H_{17}NO_5.3.0H_2O$ requires: C, 57.34; H, 7.72; N, 8.80%.

EXAMPLE 62

N-(3,5-Bis-hydroxymethyl-phenyl)-2-[5-cyclohexyl-1-(3,3-dimethyl-2-oxo-butyl)-2-oxo-1,2-dihydro-3H-1,3,4-benzotriazepin-3-yl]-acetamide The title compound was prepared by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that carbonic acid 3-amino-5-methoxycarbonyloxymethyl-benzyl ester methyl ester was used instead of 3-amino-benzoic acid methyl ester in step e, followed by reaction of the product obtained, in place carbonic acid 3-{2-[5-cyclohexyl-1-(3,3-dimethyl-2-oxo-butyl)-2-oxo-1,2-dihydro-3H-1,3,4-benzotriazepin-3-yl]-acetylamino}-benzyl ester methyl ester (Example 48, step a), according to the method of Example 48, step b. $^1$H NMR ($CDCl_3$) 8.37 (1H, s), 7.47 (2H, m), 7.30 (3H, m), 7.09 (1H, s), 7.02 (1H, d), 4.78-4.58 (6H, m), 4.23 (2H, m), 2.79 (1H, m), 2.04-1.44 (8H, m), 1.26 (13H, m). Found: C, 64.88; H, 7.45; N, 10.15%; $C_{30}H_{38}N_4O_5.1.2H_2O$ requires: C, 64.75; H, 7.32; N, 10.07%.

EXAMPLE 63

2-[5-Cyclohexyl-1-(3,3-dimethyl-2-oxo-butyl)-2-oxo-1,2-dihydro-3H-1,3,4-benzotriazepin-3-yl]-N-pyridin-2-yl-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2-aminopyridine was used instead of 3-amino-benzoic acid methyl ester in step e. $^1$H NMR ($CDCl_3$) 8.83 (1H, s), 8.20-8.14 (2H, m), 7.62 (1H, t), 7.46-7.40 (2H, m), 7.25 (1H, m), 6.98-6.93 (2H, m), 4.70 (1H, d), 4.66 (1H, d), 4.30 (1H, d), 4.20 (1H, m), 2.78 (1H, m), 2.03-1.60 (6H, m), 1.38-1.22 (13H, m). The compound was further characterised as the hydrochloride salt. Found: C, 61.20; H, 6.90; N, 13.04%; $C_{27}H_{33}N_5O_3.HCl.H_2O$ requires: C, 61.18; H, 6.85; N, 13.21%.

EXAMPLE 64

2-[5-Cyclohexyl-1-(3,3-dimethyl-2-oxo-butyl)-2-oxo-1,2-dihydro-3H-1,3,4-benzotriazepin-3-yl]-N-pyridin-3-yl-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-aminopyridine was used instead of 3-amino-benzoic acid methyl ester in step e. $^1$H NMR ($CDCl_3$) 8.52 (1H, br s), 8.36 (1H, d), 8.31-8.24 (2H, m), 7.48-7.44 (2H, m), 7.31-7.22

(2H, m), 7.02 (1H, d), 4.79 (1H, d), 4.56 (1H, d), 4.23 (2H, s), 2.80 (1H, br m), 2.01 (1H, br m), 1.87-1.62 (5H, m), 1.33-1.23 (13H, m). The compound was further characterised as the hydrochloride salt. Found: C, 60.81; H, 7.01; N, 12.93%; $C_{27}H_{33}N_5O_3 \cdot HCl \cdot H_2O$ requires: C, 61.18; H, 6.85; N, 13.21%.

EXAMPLE 65

[Acetyl-(3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-amino]-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [acetyl-(3-amino-phenyl)-amino]-acetic acid methyl ester (prepared in three steps from 3-nitroaniline) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1H$ NMR (DMSO-$d_6$) 13.00 (1H, br s), 10.01 (1H, s), 7.50 (4H, m), 7.33 (1H, t), 7.23 (1H, m), 7.16 (1H, d), 7.03 (1H, d), 4.79 (2H, s), 4.28 (1H, d), 4.17 (2H, s), 3.96 (1H, d), 2.86 (1H, m), 2.01 (1H, br m), 1.90-1.10 (10H, m), 1.76 (3H, s), 1.16 (9H, s). The compound was further characterised as the N-methyl-D-glucamine salt. Found: C, 55.77; H, 7.44; N, 9.81%; $C_{32}H_{39}N_5O_6 \cdot C_7H_{17}NO_5 \cdot 3.0H_2O$ requires: C, 55.83; H, 7.49; N, 10.02%.

EXAMPLE 66

N-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-succinamic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that N-(3-amino-phenyl)-succinamic acid methyl ester (prepared in three steps from 3-nitroaniline) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1H$ NMR (DMSO-$d_6$) 12.00 (1H, br s), 9.91 (1H, s), 9.75 (1H, s), 7.88 (1H, s), 7.50 (2H, m), 7.25-7.13 (5H, m), 4.78 (2H, s), 4.25 (1H, d), 3.96 (1H, d), 2.86 (1H, m), 2.48 (4H, s), 1.98-1.17 (10H, m), 1.13 (9H, s). The compound was further characterised as the N-methyl-D-glucamine salt. Found: C, 55.74; H, 7.69; N, 9.91%; $C_{32}H_{39}N_5O_6 \cdot C_7H_{17}NO_5 \cdot 3.0H_2O$ requires: C, 55.84; H, 7.49; N, 10.02%.

EXAMPLE 67

2-[5-Cyclohexyl-1-(3,3-dimethyl-2-oxo-butyl)-2-oxo-1,2-dihydro-3H-1,3,4-benzotriazepin-3-yl]-N-[3-(1H-tetrazol-5-ylmethyl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-(1H-tetrazol-5-yl-methyl)-aniline was used instead of 3-amino-benzoic acid methyl ester in step e. $^1H$ NMR (CDCl$_3$) 8.61 (1H, s), 7.44 (4H, m), 7.27 (4H, m), 6.98 (2H, m), 4.70 (2H, q), 4.25 (2H, d), 2.80 (1H, m), 2.04 (1H, br m), 1.84 (1H, br d), 1.67 (6H, m), 1.28 (2H, m), 1.19 (9H, s). The compound was further characterised as the N-methyl-D-glucamine salt. Found C, 56.69; H, 7.43; N, 16.08, $C_{30}H_{36}N_8O_3 \cdot C_7H_{17}NO_5 \cdot 1.9H_2O$ requires C, 56.57; H, 7.43; N, 16.77%.

EXAMPLE 68

3-{2-[5-Cyclohexyl-1-(2-morpholin-4-yl-2-oxo-ethyl)-2-oxo-1,2-dihydro-3H-1,3,4-benzotriazepin-3-yl]-acetylamino}-benzoic acid Step a. (1-tert-Butoxycarbonylmethyl-5-cyclohexyl-2-oxo-1,2-dihydro-3H-1,3,4-benzotriazepin-3-yl)-acetic acid ethyl ester was obtained by the method used in the preparation of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c) except that tert-butyl-bromoacetate was used in place of 1-bromo-3,3-dimethyl-butan-2-one. $^1H$ NMR (CDCl$_3$) 7.40 (2H, m), 7.18 (1H, dt), 7.10 (1H, d), 4.51-4.10 (6H, m), 2.72 (1H, m), 1.66 (6H, m), 1.45 (9H, s), 1.23 (7H, m).

Step b. (5-Cyclohexyl-3-ethoxycarbonylmethyl-2-oxo-2,3-dihydro-3H-1,3,4-benzotriazepin-1-yl)-acetic acid. (1-tert-Butoxycarbonylmethyl-5-cyclohexyl-2-oxo-1,2-dihydro-3H-1,3,4-benzotriazepin-3-yl)-acetic acid ethyl ester (Example 68, step a)(860 mg, 1.94 mmol) was dissolved in trifluoroacetic acid (5 ml) and the solution was stirred at room temperature for 2 h. The trifluoroacetic acid was evaporated, the residue was dissolved in DCM (20 ml) and washed with H$_2$O (20 ml×2). The organic phase was separated and dried over MgSO$_4$. Filtration and evaporation of the solvent afford the product (630 mg, 84%). $^1H$ NMR (CDCl$_3$) 9.50 (1H, br s), 7.43 (2H, m), 7.25 (1H, m), 7.14 (1H, d), 4.40 (4H, m), 4.15 (2H, m), 2.73 (1H, m), 1.75 (6H, m), 1.24 (7H, m).

Step c. [5-Cyclohexyl-1-(2-morpholin-3-yl-2-oxo-ethyl)-2-oxo-1,2-dihydro-3H-1,3,4-benzotriazepin-3-yl]-acetic acid ethyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that (5-cyclohexyl-3-ethoxycarbonylmethyl-2-oxo-2,3-dihydro-3H-1,3,4-benzotriazepin-1-yl)-acetic acid (Example 68, step b) and morpholine were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively. $^1H$ NMR (CDCl$_3$) 7.40 (2H, m), 7.18 (2H, m), 4.51 (2H, br d), 4.26 (2H, br d), 4.14 (2H, m), 3.69-3.50 (8H, m), 2.74 (1H, m), 1.74 (6H, m), 1.24 (7H, m).

Step d. The title compound was obtained using steps d and e of the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [5-cyclohexyl-1-(2-morpholin-3-yl-2-oxo-ethyl)-2-oxo-1,2-dihydro-3H-1,3,4-benzotriazepin-3-yl]-acetic acid ethyl ester (Example 68, step c) was used in step d instead of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.60 (1H, s), 8.09 (1H, dd), 7.90 (1H, t), 7.78 (1H, d), 7.52 (2H, m), 7.42-7.29 (2H, m), 7.20 (1H, d), 4.64 (1H, d), 4.41 (1H, d), 4.26 (2H, m), 3.70 (6H, br s), 3.50 (2H, br s), 2.80 (1H, m), 2.05-1.71 (6H, m), 1.25 (4H, m). The compound was further characterised as the N-methyl-D-glucamine salt. Found: C, 55.33; H, 7.19; N, 10.70%; $C_{29}H_{33}N_5O_6 \cdot C_7H_{17}NO_5 \cdot 2.2H_2O$ requires: C, 55.22; H, 7.01; N, 10.73%.

EXAMPLE 69

(3-{2-[5-(4-tert-Butyl-cyclohexyl)-1-(3,3-dimethyl-2-oxo-butyl)-2-oxo-1,2-dihydro-3H-1,3,4-benzotriazepin-3-yl]-acetylamino}-phenyl)-acetic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-phenyl)-(4-tert-butyl-cyclohexyl)-methanone (prepared from 1-bromo-4-tert-butyl-cyclohexane (A. L. J. Beckwith, et. al., *J. Chem. Soc. Perkin Trans. II*, (1983), 661) and 2-aminobenzonitrile) was used in step a instead of (2-amino-phenyl)-cyclohexyl-methanone, and (3-amino-phenyl)-acetic acid methyl ester replaced 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.28 (1H, s), 7.50-7.44 (2H, m), 7.33-7.21 (4H, m), 7.03-6.98 (2H, m), 4.76 (1H, d), 4.60 (1H, d), 4.31 (1H, d), 4.17 (1H, d), 3.61 (2H, s), 2.71 (1H, m), 2.11-1.66 (5H, m), 1.34-1.24 (10H, m), 1.21-1.02 (3H, br m), 0.86 (9H, s). The compound was further characterised as the N-methyl-D-glucamine salt. Found: C, 58.81; H, 8.24; N, 8.49%; $C_{34}HN_{44}O_5 \cdot C_7H_{17}NO_5 \cdot 3.0H_2O$ requires C, 58.76; H, 8.06; N, 8.36%.

EXAMPLE 70

(6-{2-[5-Cyclohexyl-1-(3,3-dimethyl-2-oxo-butyl)-2-oxo-1,2-dihydro-3H-1,3,4-benzotriazepin-3-yl]-acetylamino}-indol-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (6-amino-indol-1-yl)-acetic acid ethyl ester (prepared in two steps from 6-nitroindole) was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.33 (1H, s), 7.92 (1H, s), 7.45 (3H, m), 7.28 (1H, m), 7.02 (2H, m), 6.58 (1H, dd), 6.47 (1H, t), 4.84 (2H, s), 4.68 (2H, m), 4.40 (1H, d), 4.18 (1H, d), 2.78 (1H, m), 2.02-1.15 (19H, m). The compound was further characterised as the N-methyl-D-glucamine salt. Found: C, 58.25; H, 7.41; N, 10.61%; $C_{32}H_{37}N_5O_5 \cdot C_7H_{17}NO_5 \cdot 2.0H_2O$ requires: C, 58.38; H, 7.28; N, 10.47%.

EXAMPLE 71

(3-{2-[5-Cyclohexyl-1-(3,3-dimethyl-2-oxo-butyl)-2-oxo-1,2-dihydro-3H-1,3,4-benzotriazepin-3-yl]-acetylamino}-benzylsulfanyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-benzyl-sulfanyl)-acetic acid methyl ester (prepared in two steps from 3-bromomethyl nitrobenzene) was used instead of 3-amino-benzoic acid methyl ester in step e, followed by reaction of the product-obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.37 (1H, s), 7.51-7.45 (2H, m), 7.31-7.20 (4H, m), 7.01 (1H, d), 6.80 (1H, br s), 4.79 (1H, d), 4.60 (1H, d), 4.31 (1H, d), 4.17 (1H, d), 3.78 (2H, s), 3.10 (2H, s), 2.79 (1H, m), 1.99-1.71 (6H, m), 1.29-1.19 (13H, m). The compound was further characterised as the N-methyl-D-glucamine salt. Found: C, 52.84; H, 7.53; N, 8.10%; $C_{31}H_{38}N_4O_5S \cdot C_7H_{17}NO_5 \cdot 5.0H_2O$ requires: C, 52.82; H, 7.58; N, 8.10%.

EXAMPLE 72

2-{5-Cyclohexyl-1-[2-(4-methyl-piperazin-1-yl)-2-oxo-ethyl]-2-oxo-1,2-dihydro-3H-1,3,4-benzotriazepin-3-yl}-N-(3-methylamino-phenyl)-acetamide Step a. {5-Cyclohexyl-1-[2-(4-methyl-piperazin-1-yl)-2-oxo-ethyl]-2-oxo-1,2-dihydro-3H-1,3,4-benzotriazepin-3-yl}-acetic acid ethyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that (5-cyclohexyl-3-ethoxycarbonylmethyl-2-oxo-2,3-dihydro-3H-1,3,4-benzotriazepin-1-yl)-acetic acid (Example 68, step b) and 1-methylpiperazine were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively. $^1$H NMR (CDCl$_3$) 7.40 (2H, m), 7.19 (2H, m), 4.48 (2H, br d), 4.25-4.10 (4H, m), 3.59 (4H, br m), 2.77 (1H, m), 2.60 (4H, m), 2.41 (3H, s), 1.72 (6H, m), 1.24 (7H, m).

Step b. {5-Cyclohexyl-1-[2-(4-methyl-piperazin-1-yl)-2-oxo-ethyl]-2-oxo-1,2-dihydro-3H-1,3,4-benzotriazepin-3-yl)-acetic acid was obtained by the method used in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that {5-cyclohexyl-1-[2-(4-methyl-piperazin-1-yl)-2-oxo-ethyl]-2-oxo-1,2-dihydro-3H-1,3,4-benzotriazepin-3-yl}-acetic acid ethyl ester (Example 72, step a) was used in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c). $^1$H NMR (CDCl$_3$) 9.30 (1H, br s), 7.42 (2H, m), 7.21 (2H, m), 4.45 (2H, br s), 4.08-3.78 (6H, br m), 2.92 (4H, m), 2.76 (1H, m), 2.62 (3H, s), 1.98-1.44 (6H, m), 1.23 (4H, m).

Step c. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that {5-cyclohexyl-1-[2-(4-methyl-piperazin-1-yl)-2-oxo-ethyl]-2-oxo-1,2-dihydro-3H-1,3,4-benzotriazepin-3-yl)-acetic acid (Example 72, step b) and (3-amino-phenyl)-methyl-carbamic acid tert-butyl ester (Example 3, step c) were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.12 (1H, s), 7.46 (2H, m), 7.27 (2H, m), 7.03 (1H, t), 6.91 (1H, t), 6.46 (1H, dd), 6.30 (1H, dd), 4.52 (2H, m), 4.37 (1H, d), 4.14 (1H, d), 3.62 (2H, m), 3.49 (2H, m), 2.79 (5H, m), 2.40 (4H, m), 2.30 (3H, s), 2.00-1.75 (6H, m), 1.26 (4H, m). The compound was further characterised as the di-hydrochloride salt. Found: C, 53.60; H, 7.08; N, 14.50%; C$_{30}$H$_{39}$N$_7$O$_3$.2.0HCl.3.0H$_2$O requires: C, 53.54; H, 7.05; N, 14.57%.

EXAMPLES 73/74

3-{2-[5-Cyclohexyl-1-(3,3-dimethyl-2-oxo-butyl)-2-oxo-1,2-dihydro-3H-1,3,4-benzotriazepin-3-yl]-acetylamino}-5-methylamino-benzoic acid methyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that with 3-amino-5-[methyl-(2,2,2-trifluoro-acetyl)-amino]-benzoic acid methyl ester (prepared in four steps from 3-amino-5-nitrobenzoic acid) was used in place of 3-amino-benzoic acid methyl ester in step e, and following reaction of the product according to the method of Example 2, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), two compounds were isolated by chromatography.

EXAMPLE 73

3-{2-[5-Cyclohexyl-1-(3,3-dimethyl-2-oxo-butyl)-2-oxo-1,2-dihydro-3H-1,3,4-benzotriazepin-3-yl]-acetylamino}-5-methylamino-benzoic acid $^1$H NMR (CDCl$_3$) 8.30 (1H, s), 7.52-7.46 (3H, m), 7.35-7.29 (1H, m), 7.05-6.92 (3H, m), 4.77 (1H, d, 17.7), 4.68 (1H, d, 17.7), 4.36-4.12 (2H, m), 2.88-2.76 (4H, m), 1.88-1.69 (5H, m), 1.31-1.23 (14H, m). The compound was further characterised as the N-methyl-D-glucamine salt. Found: C, 56.60; H, 7.65; N, 10.44%; C$_{30}$H$_{37}$N$_5$O$_5$.C$_7$H$_{17}$NO$_5$.3.5H$_2$O requires: C, 56.40; H, 7.55; N, 10.67%.

EXAMPLE 74

3-{2-[5-Cyclohexyl-1-(3,3-dimethyl-2-oxo-butyl)-2-oxo-1,2-dihydro-3H-1,3,4-benzotriazepin-3-yl]-acetylamino}-5-methylamino-benzoic acid methyl ester $^1$H NMR (CDCl$_3$) 8.31 (1H, s), 7.61-7.41 (3H, m), 7.33-7.27 (1H, m), 7.04-6.92 (3H, m), 4.77-4.61 (2H, m), 4.33 (1H, d, 13.2), 4.19 (1H, d, 13.2), 3.88 (4H, br s), 2.86-2.76 (4H, m), 2.05-1.73 (5H, m), 1.31-1.19 (14H, m). Found: C, 65.98; H, 7.25; N, 12.20%; C$_{31}$H$_{39}$N$_5$O$_5$ requires: C, 66.29; H, 7.00; N, 12.47%.

EXAMPLE 75

2-(3{2-[5-Cyclohexyl-1-(3,3-dimethyl-2-oxo-butyl)-2-oxo-1,2-dihydro-3H-1,3,4-benzotriazepin-3-yl]-acetylamino}-phenylamino)-propionic acid The title compound was obtained as the hydrochloride salt by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2-[(3-amino-phenyl)-tert-butoxycarbonyl-amino]-propionic acid methyl ester (prepared in two steps from 3-nitro-N-tert-butoxycarbonylaniline) was used instead of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-propyl-carbamic acid tert-butyl ester (Example 41, step a) according to the method of Example 41, step b. $^1$NMR (DMSO-d$_6$) 9.53 (1H, s), 7.50 (2H, m), 7.25 (2H, m), 6.98 (2H, m), 6.73 (1H, d), 6.30 (1H, d), 5.00 (3H, br s), 4.79 (2H, s), 4.25 (1H, m), 3.91 (2H, m), 2.86 (1H, m), 2.00-1.00 (10H, m), 1.33 (3H, d), 1.13 (9H, s). Found: C, 60.48; H, 6.77; N, 11.18%; C$_{31}$H$_{39}$N$_5$O$_5$.HCl.H$_2$O requires: C, 60.43; H, 6.87; N, 11.37%.

EXAMPLE 76

(R)-1-(3-{2-[5-Cyclohexyl-1-(3,3-dimethyl-2-oxobutyl)-2-oxo-1,2-dihydro-3H-1,3,4-benzotriazepin-3-yl]-acetylamino}-phenyl)-pyrrolidine-2-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (R)-1-(3-amino-phenyl)-pyrrolidine-2-carboxylic acid methyl ester (prepared in three steps from 3-nitro-iodobenzene and L-proline) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.40 (1H, br s), 9.48 (1H, s), 7.50 (2H, m), 7.24 (2H, m), 7.01 (1H, t), 6.78 (1H, d), 6.68 (1H, s), 6.13 (1H, d), 4.78 (2H, s), 4.20 (1H, d), 4.06 (1H, d), 3.90 (1H, d), 3.21 (2H, m), 2.90 (1H, m), 2.20-1.20 (14H, m), 1.13 (9H, s). The compound was further characterised as the N-methyl-D-glucamine salt. Found: C, 60.09; H, 7.50; N, 10.41%; C$_{33}$H$_{41}$N$_5$O$_5$.C$_7$H$_{17}$NO$_5$.H$_2$O requires: C, 59.98; H, 7.55; N, 10.49%.

EXAMPLE 77

2-[5-Cyclohexyl-J-(3,3-dimethyl-2-oxo-butyl)-2-oxo-1,2-dihydro-3H-1,3,4-benzotriazepin-3-yl]-N-[3-(1H-imidazol-4-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]- acetylamino}-benzoic acid methyl ester (Example 1) except that 4-(3-amino-phenyl)-imidazole-1-carboxylic acid tert-butyl ester (prepared in three steps from 2-bromo-3'-nitroacetophenone) was used in place of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.35 (1H, s), 7.82 (1H, s), 7.68 (1H, s), 7.51-7.46 (3H, m), 7.33-7.19 (5H, m), 7.04 (1H, d, 8.1), 4.78 (1H, d, 17.1), 4.66 (1H, d, 17.1), 4.35 (1H, d, 16.5), 4.22 (1H, d, 16.5), 2.80 (1H, m), 2.05-1.62 (5H, m), 1.31-1.18 (14H, m). Found C, 62.46; H, 7.01; N, 14.35%; C$_{31}$H$_{36}$N$_6$O$_3$.3.0H$_2$O requires C, 62.61; H, 7.12; N, 14.13%.

EXAMPLE 78

3-{2-[5-Cyclohexyl-1 (–2-hydroxy-3,3-dimethyl-butyl)-2-oxo-1,2-dihydro-3H-1,3,4-benzotriazepin-3-yl]-acetylamino}-5-methylamino-benzoic acid methyl ester Sodium borohydride (5 mg, 0.13 mmol) was added to an ice-cooled solution of 3-{2-[5-cyclohexyl-1-(3,3-dimethyl-2-oxo-butyl)-2-oxo-1,2-dihydro-3H-1,3,4-benzotriazepin-3-yl]-acetylamino}-5-methylamino-benzoic acid methyl ester (Example 74)(64 mg, 0.11 mmol) in MeOH (2 ml). The reaction mixture was stirred at 0-5° C. for 40 mins, then at room temperature for 2 h. Saturated NH$_4$Cl solution (10 ml) was added and the product was extracted with CHCl$_3$ (15 ml). The organic phase was dried (MgSO$_4$), filtered and the filtrate was evaporated to afford the title compound (60 mg, 97%). $^1$H NMR (CDCl$_3$) 8.10-8.79 (1H, m), 7.55 (2H, m), 7.36 (2H, m), 7.24 (1H, m), 6.95 (1H, s), 6.70 (1H, m), 4.46 (1H, m), 4.29-4.04 (2H, m), 3.89 (4H, m), 3.82-3.60 (1H, m), 3.43-3.23 (1H, m), 2.81 (4H, m), 2.15-1.66 (7H, m), 1.33-1.24 (3H, m), 0.97 and 0.93 (9H, s×2). Found C, 63.17; H, 7.59; N, 11.85%; C$_{31}$H$_{41}$N$_5$O$_5$.1.5H$_2$O requires C, 63.03, H, 7.51, N 11.86%.

II. EXAMPLE 79

3-{2-[5-Cyclohexyl-1-(2-cyclohexyl-2-oxo-ethyl)-2-oxo-1,2-dihydro-3H-1,3,4-benzotriazepin-3-yl]-acetylamino}-benzoic acid Step a. [5-Cyclohexyl-1-(2-cyclohexyl-2-oxo-ethyl)-2-oxo-1,2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that 2-bromo-cyclohexyl-ethanone was used in step c instead of 1-bromo-3,3-dimethyl-butan-2-one. $^1$H NMR (CDCl$_3$) 7.45 (2H, m), 7.23 (1H, m), 7.01 (1H, d), 4.56 (2H, d), 4.25 (1H, d), 3.89 (1H, d), 2.82 (1H, m), 2.47 (1H, m), 2.08-1.61 (1H, m), 1.46-1.19 (9H, m).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [5-cyclohexyl-1-(2-cyclohexyl-2-oxo-ethyl)-2-oxo-1,2-dihydro-3H-1,3,4-benzotriazepin-3-yl]-acetic acid (Example 79, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.52 (1H, s), 8.03 (1H, d), 7.82 (2H, m), 7.49 (2H, m), 7.41 (1H, t), 7.32 (1H, t), 7.06 (1H, d), 4.69 (1H, d), 4.47 (1H, d), 4.27 (2H, m), 2.81 (1H, m) 2.48 (1H, m), 2.05-1.69 (11H, m), 1.48-1.23 (9H, m). The compound was further characterised as the N-methyl-D-glucamine salt. Found: C, 57.41; H, 7.60; N, 9.02%; C$_{31}$H$_{36}$N$_4$O$_5$.C$_7$H$_{17}$NO$_5$.2.9H$_2$O requires: C, 57.59; H, 7.48; N, 8.84%.

EXAMPLE 80

(3-{2-[5-Cyclohexyl-1-(2-cyclohexyl-2-oxo-ethyl)-2-oxo-1,2-dihydro-3H-1,3,4-benzotriazepin-3-yl]-acetylamino}-phenyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclohexyl-2-oxo-ethyl)-2-oxo-1,2-dihydro-3H-1,3,4-benzotriazepin-3-yl]-acetic acid (Example 79, step a) and (3-amino-phenyl)-acetic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.27 (1H, s), 7.47 (2H, m), 7.27 (4H, m), 7.04 (1H, d), 6.99 (1H, d), 4.64 (1H, d), 4.46 (1H, d), 4.31 (1H, d), 4.17 (1H, d), 3.60 (2H, s), 2.78 (1H, m) 2.46 (1H, m), 2.04-1.66 (11H, m), 1.44-1.23 (9H, m). The compound was further characterised as the N-methyl-D-glucamine salt. Found: C, 56.73; H, 7.67; N, 8.65%; C$_{32}$H$_{38}$N$_4$O$_5$.C$_7$H$_{17}$NO$_5$.3.9H$_2$O requires: C, 56.87; H, 7.68; N, 8.50%.

EXAMPLE 81

(3-{2-[1-(2-Cyclopentyl-2-oxo-ethyl)-2-oxo-5-pyridin-2-yl-1,2-dihydro-3H-1,3,4-benzotriazepin-3-yl]-phenyl)-acetic acid Step a. [1-(2-Cyclopentyl-2-oxo-ethyl)-2-oxo-5-pyridin-2-yl-1,2-dihydro-3H-1,3,4-benzotriazapin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that (2-amino-phenyl)-pyridin-2-yl-methanone was used in step a instead of (2-amino-phenyl)-cyclohexyl-methanone and 2-bromo-1-cyclopentyl-ethanone replaced 1-bromo-3,3-dimethyl-butan-2-one in step c.

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [1-(2-cyclopentyl-2-oxo-ethyl)-2-oxo-5-pyridin-2-yl-1,2-dihydro-3H-1,3,4-benzotriazapin-3-yl]-acetic acid and (3-amino-phenyl)-acetic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-$d_6$) 12.20 (1H, br s), 9.99 (1H, s), 8.57 (1H, d), 7.91 (2H, m), 7.43 (4H, m), 7.20 (4H, m), 6.91 (1H, d), 4.66 (2H, br s), 4.40 (2H, br m), 3.50 (2H, s), 3.00 (1H, m), 1.75-1.47 (8H, m). The compound was further characterised as the N-methyl-D-glucamine salt. Found: C, 56.91; H, 6.61; N, 10.65%; $C_{30}H_{29}N_5O_5 \cdot C_7H_{17}NO_5 \cdot 2.5H_2O$ requires: C, 56.99; H, 6.59; N, 10.78%.

EXAMPLE 82

[3-(2-{5-Cyclohexyl-1-[2-(1-methyl-cyclopentyl)-2-oxo-ethyl]-2-oxo-1,2-dihydro-3H-1,3,4-benzotriazepin-3-yl}-acetylamino)-phenyl]-acetic acid Step a. {5-Cyclohexyl-1-[2-(1-methyl-cyclopentyl)-2-oxo-ethyl]-2-oxo-1,2-dihydro-3H-1,3,4-benzotriazepin-3-yl}-acetic acid was obtained using a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that 2-bromo-1-(1-methyl-cyclopentyl)-ethanone was used in step c instead of 1-bromo-3,3-dimethyl-butan-2-one. $^1$H NMR (CDCl$_3$) 11.00 91H, br s), 7.45 (2H, m), 7.25 (1H, m), 6.99 (1H, d), 4.67 (2H, m), 4.24 (1H, d), 3.86 (1H, d), 2.83 (1H, m), 2.17-1.22 (21H, m).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that {5-cyclohexyl-1-[2-(1-methyl-cyclopentyl)-2-oxo-ethyl]-2-oxo-1,2-dihydro-3H-1,3,4-benzotriazepin-3-yl}-acetic acid (Example 82, step a) and (3-amino-phenyl)-acetic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.27 (1H, s), 7.46 (2H, m), 7.35-7.20 (4H, m), 7.03 (1H, d), 6.99 (1H, d), 4.75 (1H, d), 4.58 (1H, d), 4.30 (1H, d), 4.18 (1H, d), 3.61 (2H, s), 2.78 (1H, m), 2.15-1.23 (21H, m). The compound was further characterised as the N-methyl-D-glucamine salt. Found: C, 56.76; H, 7.92; N, 8.59%; $C_{32}H_{38}N_4O_5 \cdot C_7H_{17}NO_5 \cdot 4.0H_2O$ requires: C, 56.69; H, 7.69; N, 8.48%.

EXAMPLE 83

3-({2-[5-Cyclohexyl-1-(3,3-dimethyl-2-oxo-butyl)-2-oxo-1,2-dihydro-3H-1,3,4-benzotriazepin-3-yl]-acetyl}-methyl-amino)-benzoic acid Step a. 3-({2-[5-Cyclohexyl-1-(3,3-dimethyl-2-oxo-butyl)-2-oxo-1,2-dihydro-3H-1,3,4-benzotriazepin-3-yl]-acetyl}-methyl-amino)-benzoic acid methyl ester. Methyl trifluoromethane sulfonate (329 mg, 2.0 mmol) was added drop-wise to an ice-cooled solution of 1,1'-carbonyldiimidazole (162 mg, 1.0 mml) in nitromethane (2 ml). The solution was stirred at this temperature for 5 min, then added to a suspension of [5-cyclohexyl-1-(3,3-dimethyl-2-oxo-butyl)-2-oxo-1,2-dihydro-3H-1,3,4-benzotriazepin-3-yl]-acetic acid (Example 1, step d)(400 mg, 1.0 mmol) in nitromethane (2 ml). The resulting mixture was stirred for 10 min at room temperature, then a solution of 3-methylamino-benzoic acid methyl ester (165 mg, 1.0 mmol) in nitromethane (2 ml) was added. The mixture was stirred at room temperature for 19 h, diluted with H$_2$O (30 ml) and extracted with EtOAc (15 ml×3). The combined extracts were washed with H$_2$O (15 ml×2), and dried (MgSO$_4$). Filtration and evaporation of the solvent gave the crude product which was purified by flash column chromatography (EtOAc-hexane (4:1)) to give the product as an off-white solid (330 mg, 60%). $^1$H NMR (CDCl$_3$) 7.95 (1H, d), 7.85 (1H, s), 7.40-7.34 (4H, m), 7.14 (1H, t), 6.88 (1H, d), 4.65 (2H, br d), 4.25 (1H, br), 3.98 (1H, br), 3.94 (3H, s), 3.25 (3H, s), 2.75 (1H, br m), 2.00-1.60 (5H, m), 1.35-1.20 (14H, m).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid (Example 2) except that 3-({2-[5-cyclohexyl-1-(3,3-dimethyl-2-oxo-butyl)-2-oxo-1,2-dihydro-3H-1,3,4-benzotriazepin-3-yl]-acetyl}-methyl-amino)-benzoic acid methyl ester (Example 83, step a) was used in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1). $^1$H NMR (DMSO-$d_6$) 13.10 (1H, br), 7.85 (1H, m), 7.79 (1H, s), 7.51-7.41 (4H, m), 7.21 (1H, t), 7.11 (1H, d), 4.71 (2H, d), 4.15 (1H, br), 3.70 (1H, br), 3.12 (3H, s), 2.83 (1H, m), 1.85-1.00 (19H, m). The compound was further characterised as the N-methyl-D-glucamine salt. Found: C, 57.48; H, 7.61; N, 9.25%; $C_{30}H_{36}N_4O_5 \cdot C_7H_{17}NO_5 \cdot 2.5H_2O$ requires C, 57.50; H, 7.56; N, 9.06%.

EXAMPLE 84

2-[5-Cyclohexyl-1-(3,3-dimethyl-2-oxo-butyl)-2-oxo-1,2-dihydro-3H-1,3,4-benzotriazepin-3-yl]-N-(3-hydroxy-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-aminophenol was used instead of 3-amino-benzoic acid methyl ester in step e. $^1$H NMR (CDCl$_3$) 8.31 (1H, s), 7.68 (1H, s), 7.30 (2H, m), 7.26 (1H, m), 7.08 (2H, m), 6.60 (1H, m), 6.57 (1H, m), 6.41 (1H, m), 4.72 (1H, d), 4.65 (1H, d), 4.32 (1H, d), 4.22 (1H, d), 2.77 (1H, m), 1.98-1.69 (6H, m), 1.27-1.24 (13H, m). Found: C, 67.78; H, 7.28; Ni 1.27%; $C_{28}H_{34}N_4O_4 \cdot 0.4H_2O$ requires: C, 67.56; H, 7.04; N, 11.25%.

EXAMPLE 85

N-(3-Amino-phenyl)-2-[5-cyclohexyl-1-(3,3-dimethyl-2-oxo-butyl)-2-oxo-1,2-dihydro-3H-1,3,4-benzotriazepin-3-yl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-phenyl)-carbamic acid tert-butyl ester was used in place of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}- phenyl)-methyl-carbamic acid tert-butyl ester (Example 3, step d), according to the method of Example 3, step e. $^1$H NMR (CDCl$_3$) 11.28 (1H, br s), 8.85 (1H, s), 7.69 (1H, s), 7.57-7.27 (6H, m), 7.04 (1H, m), 4.76 (1H, d), 4.63 (1H, d), 4.21 (2H, m), 2.80 (1H, m), 2.18-1.35 (6H, m), 1.32-1.22 (13H, m). The product was further characterised as the hydrochloride salt. Found: C, 59.71; H, 7.33; N, 12.48%; C$_{28}$H$_{35}$N$_5$O$_3$.HCl.2.0H$_2$O requires: C, 59.83; H, 7.17; N, 12.46%.

EXAMPLE 86

2-[5-Cyclohexyl-1-(3,3-dimethyl-2-oxo-butyl)-2-oxo-1,2-dihydro-3H-1,3,4-benzotriazepin-3-yl]-N-[3-(4H-tetrazol-5-ylmethylsutfanyl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-(1H-tetrazol-5-ylmethylsulfanyl)-aniline was used instead of 3-amino-benzoic acid methyl ester in step e. $^1$H NMR (CDCl$_3$) 8.82 (1H, s), 7.72 (1H, br s), 7.40 (3H, m), 7.27 (1H, m), 7.15 (1H, t), 6.96 (3H, m), 4.70 (2H, q), 4.41 (2H, s), 4.24 (2H, s), 2.82 (1H, m), 2.1-1.6 (6H, m), 1.28 (4H, m), 1.22 (9H, s).

EXAMPLE 87

2-{5-Cyclohexyl-1-[2-(1-methyl-cyclopentyl)-2-oxo-ethyl]-2-oxo-1,2-dihydro-3H-1,3,4-benzotriazepin-3-yl}-N-[3-(5-oxo-2,5-dihydro-[1,2,4]oxadiazol-3-yl)-phenyl]-acetamide The title compound was obtained by the method used in the preparation of 2-[5-cyclohexyl-1-(3,3-dimethyl-2-oxo-butyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide (Example 59) except that {5-cyclohexyl-1-[2-(1-methyl-cyclopentyl)-2-oxo-ethyl]-2-oxo-1,2-dihydro-3H-1,3,4-benzotriazepin-3-yl}-acetic acid (Example 82, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d). $^1$H NMR (CDCl$_3$) 11.00 (1H, br s), 8.84 (1H, s), 7.91 (1H, s), 7.58 (2H, m), 7.44 (3H, m), 7.28 (1H, t), 7.04 (1H, d), 4.81 (1H, d), 4.55 (1H, d), 4.21 (2H, s), 2.80 (1H, m), 2.09-1.24 (21H, m). The compound was further characterised as the N-methyl-D-glucamine salt. Found: C, 56.28; H, 6.94; N, 11.95%; C$_{32}$H$_{36}$N$_6$O$_5$.C$_7$H$_{17}$NO$_5$.2.8H$_2$O requires: C, 56.45; H, 7.11; N, 11.82%.

EXAMPLE 88

3-(2-{5-Cyclohexyl-1-[2-(1-methyl-cyclopentyl)-2-oxo-ethyl]-2-oxo-1,2-dihydro-3H-1,3,4-benzotriazepin-3-yl}-acetylamino)-benzoic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that {5-cyclohexyl-1-[2-(1-methyl-cyclopentyl)-2-oxo-ethyl]-2-oxo-1,2-dihydro-3H-1,3,4-benzotriazepin-3-yl}-acetic acid (Example 82, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.51 (1H, s), 8.03 (1H, d), 7.87 (1H, s), 7.81 (1H, d), 7.53-7.27 (4H, m), 7.05 (1H, d), 4.78 (1H, d), 4.57 (1H, d), 4.26 (2H, m), 2.81 (1H, m), 2.16-1.23 (21H, m). The compound was further characterised as the N-methyl-D-glucamine salt. Found: C, 57.94; H, 7.53; N, 8.71%; C$_{31}$H$_{36}$N$_4$O$_5$.C$_7$H$_{17}$NO$_5$.2.8H$_2$O requires: C, 57.80; H, 7.47; N, 8.87%.

EXAMPLE 89

2-[5-Cyclohexyl-1-(3,3-dimethyl-2-oxo-butyl)-2-oxo-1,2-dihydro-3H-1,3,4-benzotriazepin-3-yl]-N-[3-(1H-imidazol-1-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-imidazol-1-yl-phenylamine (prepared in two steps from 1-fluoro-nitrobenzene and imidazole) was used instead of 3-amino-benzoic acid methyl ester in step e. $^1$H NMR (CDCl$_3$) 8.57 (1H, s), 7.86 (1H, s), 7.71 (1H, t, 1.8), 7.52-7.28 (6H, m), 7.19 (1H, s), 7.11-7.08 (1H, m), 7.04-7.01 (1H, m), 4.84 (1H, d, 17.7), 4.58 (1H, d, 17.7), 4.24-4.23 (2H, m), 2.83-2.77 (1H, m), 2.05-1.67 (6H, m), 1.38-1.19 (13H, m). Found: C, 68.06; H, 6.75; N, 15.09%; C$_{31}$H$_{36}$N$_6$O$_3$.0.4H$_2$O requires: C, 67.87; H, 6.78; N, 15.32%.

EXAMPLE 90

N-(3H-Benzimidazol-5-yl)-2-[5-cyclohexyl-1-(3,3-dimethyl-2-oxo-butyl)-2-oxo-1,2-dihydro-3H-1,3,4-benzotriazepin-3-yl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 6-amino-benzimidazole-1-carboxylic acid tert-butyl ester (prepared in two steps from 5(6)-nitro-benzimidazole) was used in place of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.44. (1H, s), 8.24 (1H, br s), 7.98 (1H, s), 7.60-7.47 (3H, m), 7.32-7.27 (1H, m), 7.04 (1H, d, 8.1), 6.84 (1H, br s), 4.77 (1H, d, 18), 4.67 (1H, d, 18), 4.40 (1H, d, 16.5), 4.25 (1H, d, 16.5), 2.84-2.76 (1H, m), 2.05-1.65 (6H, m), 1.45-1.24 (13H, m). Found C, 65.40; H, 6.89; N, 15.79%; C$_{29}$H$_{34}$N$_6$O$_3$.H$_2$O requires C, 65.39; H, 6.81; N, 15.78%.

EXAMPLE 91

3-{2-[5-Cyclohexyl-1-(3,3-dimethyl-2-oxo-butyl)-2-oxo-1,2-dihydro-3H-1,3,4-benzotriazepin-3-yl]-acetylamino}-5-methyl-benzoic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]- acetylamino}-benzoic acid methyl ester (Example 1) except that 3-amino-5-methyl-benzoic acid methyl ester (prepared in three steps from 4-bromo-3-methylbenzoic acid) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.44 (1H, s), 7.87 (1H, s), 7.62 (2H, m), 7.53-7.47 (2H, m), 7.34-7.28 (1H, m), 7.05 (1H, d, 8.1), 4.81-4.58 (2H, m), 4.26-4.19 (2H, m), 2.84-2.80 (1H, m), 2.39 (3H, s), 2.05-173 (6H, m), 1.41-1.19 (13H, m). The compound was further characterised as the N-methyl-D-glucamine salt. Found C, 58.77; H, 7.70; N, 9.33%; C$_{30}$H$_{36}$N$_4$O$_5$.C$_7$H$_{17}$NO$_5$.1.5H$_2$O requires C, 58.87; H, 7.48; N, 9.28%.

EXAMPLE 92

N-[3-(Acetyl-methyl-amino)-5-methylamino-phenyl]-2-[5-cyclohexyl-1-(3,3-dimethyl-2-oxo-butyl)-2-oxo-1,2-dihydro-3H-1,3,4-benzotriazepin-3-yl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that N-(3-amino-5-methylamino-phenyl)-N-methyl-acetamide (prepared in four steps from 3,5-difluoronitrobenzene) was used instead of 3-amino-benzoic acid methyl ester in step e. $^1$H NMR (CDCl$_3$) 8.29 (1H, s), 7.51-7.43 (2H, m), 7.30-7.24 (1H, m), 7.03 (1H, d, 8.4), 6.92 (1H, s), 6.39 (1H, s), 6.10 (1H, s), 4.79 (1H, d, 18), 4.62 (1H, d, 18), 4.29 (1H, d, 16.5), 4.21 (1H, d, 16.5), 3.21 (3H, s), 2.83-2.75 (4H, m), 2.04-1.67 (9H, m), 1.33-1.17 (13H, m).

EXAMPLE 93

3-[2-(1-Carboxymethyl-5-cyclohexyl-2-oxo-1,2-dihydro-3H-1,3,4-benzotriazepin-3-yl)-acetylamino]-benzoic acid Step a. (1-tert-Butoxycarbonylmethyl-5-cyclohexyl-2-oxo-1,2-dihydro-3H-1,3,4-benzotriazepin-3-yl)-acetic acid was obtained by the method used in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that (1-tert-butoxycarbonylmethyl-5-cyclohexyl-2-oxo-1,2-dihydro-3H-1,3,4-benzotriazepin-3-yl)-acetic acid ethyl ester (Example 68, step a) was used in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c). $^1$H NMR (CDCl$_3$) 7.45 (2H, m), 7.27 (1H, m), 7.14 (1H, d), 4.41-3.93 (4H, br m), 2.80 (1H, m), 2.02-1.45 (6H, m), 1.46 (9H, m), 1.21 (4H, m).

Step b. 3-[2-(1-tert-Butoxycarbonylmethyl-5-cyclohexyl-2-oxo-1,2-dihydro-3H-1,3,4-benzotriazepin-3-yl)-acetylamino]-benzoic acid methyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that (1-tert-butoxycarbonylmethyl-5-cyclohexyl-2-oxo-1,2-dihydro-3H-1,3,4-benzotriazepin-3-yl)-acetic acid was used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d). $^1$H NMR (CDCl$_3$) 8.51 (1H, s), 7.89 (1H, d), 7.80 (1H, t), 7.74 (1H, d), 7.50 (2H, m), 7.35 (2H, m), 7.18 (1H, d), 4.43-4.09 (4H, m), 3.91 (3H, s), 2.80 (1H, m), 2.05-1.60 (6H, m), 1.43 (9H, s), 1.24 (4H, m).

Step c. The title compound was obtained by the method used in the preparation of (5-cyclohexyl-3-ethoxycarbonylmethyl-2-oxo-2,3-dihydro-3H-1,3,4-benzotriazepin-1-yl)-acetic acid (Example 68, step b) except that 3-[2-(1-tert-butoxycarbonylmethyl-5-cyclohexyl-2-oxo-1,2-dihydro-3H-1,3,4-benzotriazepin-3-yl)-acetylamino]-benzoic acid methyl ester (Example 93, step b) was used instead of (1-tert-butoxycarbonylmethyl-5-cyclohexyl-2-oxo-1,2-dihydro-3H-1,3,4-benzotriazepin-3-yl)-acetic acid ethyl ester (Example 68, step a), followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 9.15 (2H, br s), 8.84 (1H, s), 8.03 (1H, d), 7.73 (1H, s), 7.67 (1H, d), 7.48 (2H, m), 7.30 (2H, m), 7.14 (1H, d), 4.62 (1H, d), 4.29 (3H, m), 2.81 (1H, m), 2.07-1.74 (6H, m), 1.27 (4H, m). The compound was further characterised as the bis(N-methyl-D-glucamine) salt. Found: C, 50.94; H, 7.29; N, 8.05%; C$_{25}$H$_{26}$N$_4$O$_6$.C$_{14}$H$_{34}$N$_2$O$_{10}$.3.0H$_2$O.1.2C$_4$H$_8$O$_2$ requires: C, 51.05; H, 7.41; N, 8.16%.

EXAMPLE 94

(6-{2-[5-Cyclohexyl-1-(3,3-dimethyl-2-oxo-butyl)-2-oxo-1,2-dihydro-3H-1,3,4-benzotriazepin-3-yl]-acetylamino}-benzimidazol-1-yl)-acetic acid The of title compound was obtained as the hydrochloride salt by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (5-amino-benzimidazol-1-yl)-acetic acid tert-butyl ester (prepared in two steps from 5(6)-nitro-benzimidazole) was used instead of 3-amino-benzoic acid methyl ester in step e, followed by reaction of the product obtained, in place of (1-tert-butoxycarbonylmethyl-5-cyclohexyl-2-oxo-1,2-dihydro-3H-1,3,4-benzotriazepin-3-yl)-acetic acid ethyl ester (Example 68, step a) according to the method of Example 68, step b. $^1$H NMR (DMSO-d$_6$) 10.27-10.23 (1H, br s), 9.23 and 9.10 (1H, s), 8.19 (1H, s), 7.77-7.73 (1H, m), 7.55-7.40 (3H, m), 7.26-7.15 (2H, m), 5.40 and 5.32 (2H, m), 4.79 (2H, s), 4.41 (1H, br d, 15), 3.99 (1H, br d, 15), 2.87 (1H, m), 1.83-1.65 (6H, m), 1.30-1.06 (13H, m). Found: C, 61.13; H, 6.08; N, 13.77%; C$_{31}$H$_{36}$N$_6$O$_5$.HCl requires: C, 61.13; H, 6.12; N, 13.77%.

EXAMPLE 95

3-[2-(1-tert-Butoxycarbonylmethyl-5-cyclohexyl-2-oxo-1,2-dihydro-3H-1,3,4-benzotriazepin-3-yl)-acetylamino]-benzoic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid (Example 2) except that 3-[2-(1-tert-butoxycarbonylmethyl-5-cyclohexyl-2-oxo-1,2-dihydro-3H-1,3,4-benzotriazepin-3-yl)-acetylamino]-benzoic acid methyl ester (Example 93, step b) was used in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1). $^1$H NMR (CDCl$_3$) 8.53 (1H, s), 8.02 (1H, d), 7.81 (2H, m), 7.50 (2H, m), 7.37 (2H, m), 7.18 (1H, d), 4.45-4.12 (4H, m), 2.81 (1H, m), 2.05-1.65 (6H, m), 1.44 (9H, s), 1.27 (4H, m). The compound was further characterised as the N-methyl-D-glucamine salt. Found: C, 56.81; H, 7.01; N, 8.72%; C$_{29}$H$_{34}$N$_4$O$_6$.C$_7$H$_{17}$NO$_5$.1.5H$_2$O.0.3C$_4$H$_8$O$_2$ requires: C, 57.04; H, 7.26; N, 8.94%.

EXAMPLE 96

[(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-methyl-amino]-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [(3-amino-phenyl)-methyl-amino]-acetic acid methyl ester (prepared in three steps from sarcosine and 3-nitro-iodobenzene) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.40 (1H, br s), 9.47 (1H, s), 7.50 (2H, m), 7.20 (2H, m), 7.02 (1H, t), 6.80 (2H, m), 6.33 (1H, m), 4.78 (2H, s), 4.25-3.75 (2H, m), 4.00 (2H, s) 2.91 (3H, s), 2.90 (1H, m), 2.00-1.16 (10H, m), 1.13 (9H, s). The compound was further characterised as the N-methyl-D-glucamine salt. Found: C, 58.95; H, 7.81; N, 10.76%. C$_{31}$H$_{39}$N$_6$O$_5$.C$_7$H$_{17}$NO$_5$.H$_2$O requires: C, 58.90; H, 7.55; N, 10.85%.

EXAMPLE 97

[4-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-imidazol-1-yl]-acetic acid The of title compound was obtained as the hydrochloride salt by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [4-(3-amino-phenyl)-imidazol-1-yl]-acetic acid tert-butyl ester (prepared in three steps from 2-bromo-3'-nitro-acetophenone) was used instead of 3-amino-benzoic acid methyl ester in step e, followed by reaction of the product obtained, in place of (1-tert-butoxycarbonylmethyl-5-cyclohexyl-2-oxo-1,2-dihydro-3H-1,3,4-benzotriazepin-3-yl)-acetic acid ethyl ester (Example 68, step a) according to the method of Example 68, step b. $^1$H NMR (DMSO-d$_6$/D$_2$O) 10.02 (1H, s), 8.89 and 8.79 (1H, s), 8.04 (1H, s), 7.95 and 7.91 (1H, s), 7.53-7.34 (5H, m), 7.26-7.12 (2H, m), 5.14 and 5.08 (2H, s), 4.76-4.74 (2H, m), 4.31 (1H, m), 4.01-3.96 (1H, m), 2.87-2.84 (1H, m), 1.82-1.64 (6H, m), 1.32-1.04 (13H, m). Found: C, 59.97; H, 6.48; N, 12.22%; C$_{33}$H$_{38}$N$_6$O$_5$.1.6HCl.0.5C$_4$H$_8$O$_2$ requires: C, 59.96; H, 6.27; N, 11.99%.

EXAMPLE 98

3-[2-(Carbamoylmethyl-5-cyclohexyl-2-oxo-1,2-dihydro-3H-1,3,4-benzotriazepin-3-yl)-acetylamino]-benzoic acid Step a. (1-Carbamoylmethyl-5-cyclohexyl-2-oxo-1,2-dihydro-3H-1,3,4-benzotriazepin-3-yl)-acetic acid ethyl ester.

To a solution of (5-cyclohexyl-3-ethoxycarbonylmethyl-2-oxo-2,3-dihydro-3H-1,3,4-benzotriazepin-1-yl)-acetic acid (Example 68, step b)(200 mg, 0.52 mmol) in DMF-THF (1:1/10 ml) were added EDC (150 mg, 0.77 mmol), HOBt (100 mg, 0.77 mmol) and DMAP (20 mg). The solution was stirred at room temperature for 1 h, and then ammonia was bubbled into the reaction mixture for 5 min. The reaction mixture was stirred at room temperature for 16 h, H$_2$O (30 ml) was added and the mixture was extracted with EtOAc (20 ml×2). The extracts were washed with brine, dried (MgSO$_4$) and the solvent was evaporated. The residue was purified by flash column chromatography (DCM-EtOAc (1:1)) to afford the product (141 mg, 71%). $^1$H NMR (300 MHz, CDCl$_3$) 7.41 (2H, m), 7.22 (2H, m), 6.61 (1H, br s), 5.66 (1H, br s), 4.31-4.11 (6H, m), 2.75 (1H, m), 1.75 (6H, m), 1.23 (7H, m).

Step b. The title compound was obtained using steps d and e of the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that (1-carbamoylmethyl-5-cyclohexyl-2-oxo-1,2-dihydro-3H-1,3,4-benzotriazepin-3-yl)-acetic acid ethyl ester (Example 98, step a) was used in step d instead of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.88 (1H, br s), 11.12 (1H, s), 9.97 (1H, s), 8.19 (1H, s), 7.80 (1H, d), 7.61 (1H, d), 7.55 (1H, m), 7.45 (1H, m), 7.25 (1H, dd), 5.60 (1H, m), 4.27 (2H, m), 3.80 (2H, m), 2.15 (1H, m), 1.67-0.87 (9H, m). The compound was further characterised as the N-methyl-D-glucamine salt. Found: C, 55.13; H, 6.93; N, 11.11%; C$_{25}$H$_{27}$N$_5$O$_5$.C$_7$H$_{17}$NO$_5$.1.3H$_2$O.0.7C$_4$H$_8$O$_2$ requires: C, 55.16; H, 6.94; N, 11.09%.

EXAMPLE 99

(6-{2-[5-Cyclohexyl-1-(3,3-dimethyl-2-oxo-butyl)-2-oxo-1,2-dihydro-3H-1,3,4-benzotriazepin-3-yl]-acetylamino}-indazol-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (6-amino-indazol-1-yl)-acetic acid methyl ester (prepared in two steps from 6-nitro-indazole) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 13.0 (1H, br s), 9.97 (1H, s), 7.95-7.94 (2H, m), 7.66-7.46 (3H, m), 7.27-7.03 (3H, m), 5.11 (2H, s), 4.80-4.79 (2H, m), 4.34 (1H, m), 4.03 (1H, m), 2.88-2.84 (1H, m), 1.90-1.65 (6H, m), 1.34-1.08 (13H, m).

EXAMPLE 100

(3-{2-[5-Cyclohexyl-1-(2-cyclohexyl-2-oxo-ethyl)-2-oxo-1,2-dihydro-3H-1,3,4-benzotriazepin-3-yl]-acetylamino}-phenylsulfanyl)-acetic acid The title compound was obtained by the method used in the preparation of 3-{2-[5-cyclohexyl-1-(3,3-dimethyl-2-oxobutyl)-2-oxo-1,2-dihydro-3H-1,3,4-benzotriazepin-3-yl]-acetylamino}-benzoic acid methyl ester (Example 1) except that [5-cyclohexyl-1-(2-cyclohexyl-2-oxo-ethyl)-2-oxo-1,2-dihydro-3H-1,3,4-benzotriazepin-3-yl]-acetic acid (Example 79, step a) and (3-amino-phenylsulfanyl)-acetic acid ethyl ester were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.44 (1H, s), 7.45 (3H, m), 7.38 (1H, d), 7.24 (2H, m), 7.11 (1H, d), 7.05 (1H, d), 6.70 (1H, br s), 4.70 (1H, d), 4.44 (1H, d), 4.21 (2H, m), 3.66 (2H, s), 2.80 (1H, m), 2.47 (1H, m), 2.18-1.66 (11H, m), 1.44-1.22 (9H, m). The compound was further characterised as the N-methyl-D-glucamine salt. Found: C, 56.91; H, 6.96; N, 8.36%; $C_{32}H_{38}N_4O_5S.C_7H_{17}NO_5.2.0H_2O$ requires: C, 56.99; H, 7.24; N, 8.52%.

EXAMPLE 101

2-[5-Cyclohexyl-1-(3,3-dimethyl-2-oxo-butyl)-2-oxo-1,2-dihydro-3H-1,3,4-benzotriazepin-3-yl]-N-(2-methylamino-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that N-methyl-benzene-1,2-diamine (prepared in two steps from 2-fluoro-nitrobenzene) was used instead of 3-amino-benzoic acid methyl ester in step e. $^1$H NMR (CDCl$_3$) 8.26 (1H, s), 7.48-7.41 (2H, m), 7.35-7.32 (1H, m), 7.26-7.20 (1H, m), 7.17-7.11 (1H, m), 7.00 (1H, d,), 6.74-6.68 (2H, m), 4.78 (1H, d), 4.60 (1H, d), 4.20-4.19 (3H, m), 2.84-2.76 (4H, m), 2.07-1.71 (6H, m), 1.44-1.02 (13H, m). Found: C, 66.60; H, 7.02; N, 13.15%; $C_{29}H_{37}N_5O_3.0.3CH_2Cl_2$ requires: C, 66.51; H, 7.16; N, 13.24%.

EXAMPLE 102

3-{2-[1-(3,3-Dimethyl-2-oxo-butyl)-5-(4-methyl-cyclohexyl)-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-phenyl)-(4-methyl-cyclohexyl)-methanone (prepared from 4-methyl-cyclohexanol by bromination using phosphorus pentabromide (A. L. J. Beckwith et al.: *J. Chem. Soc. Perkin Trans. II,* 1983, 661) and reaction of the corresponding Grignard reagent with 2-aminobenzonitrile (J. A. Robl, *Synthesis,* 1991, 56-58)) was used in step a instead of (2-amino-phenyl)-cyclohexyl-methanone, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.51 (1H, br s), 8.02 (1H, d), 7.85-7.79 (2H, m), 7.53-7.29 (4H, m), 7.03 (1H, d), 4.78 (1H, d), 4.60 (1H, d), 4.30 (1H, d), 4.22 (1H, d), 2.75 (1H, m), 2.00 (1H, br m), 1.90-1.65 (4H, br m), 1.50-1.20 (11H, m), 1.10-0.85 (5H, m). The compound was further characterised as the N-methyl-D-glucamine salt. Found: C, 59.10; H, 7.20; N, 9.07%; $C_{30}H_{36}N_4O_5.C_7H_{17}NO_5.H_2O$ requires C, 59.58; H, 7.43; N, 9.39%.

EXAMPLE 103

(3-{2-[1-(3,3-Dimethyl-2-oxo-butyl)-5-(4-methyl-cyclohexyl)-2-oxo-1,2-dihydro-3H-1,3,4-benzotriazepin-3-yl]-acetylamino}-phenyl)-acetic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-phenyl)-(4-methyl-cyclohexyl)-methanone was used in step a instead of (2-amino-phenyl)-cyclohexyl-methanone, and (3-amino-phenyl)-acetic acid methyl ester replaced 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.27 (1H, br), 7.47-7.44 (2H, m), 7.33-7.23 (4H, m), 7.03-6.98 (2H, m), 4.75 (1H, d), 4.61 (1H, d), 4.31 (1H, d), 4.17 (1H, d), 3.60 (2H, s), 2.70 (1H, m), 2.00 (1H, br), 1.85-1.65 (4H, m), 1.45-1.25 (2H, m), 1.23 (9H, s), 1.05-0.80 (5H, m). The compound was further characterised as the N-methyl-D-glucamine salt. Found: C, 59.28; H, 7.36; N, 8.90%; $C_{31}H_{38}N_4O_5.C_7H_{17}NO_5.1.5H_2O$ requires C, 59.36; H, 7.60; N, 9.11%.

EXAMPLE 104

N-(3,5-Bis-methylamino-phenyl)-2-[5-cyclohexyl-1-(3,3-dimethyl-2-oxo-butyl)-2-oxo-1,2-dihydro-3H-1,3,4-benzotriazepin-3-yl]-acetamide The title compound was obtained as the tri-hydrochloride salt by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-5-methylamino-phenyl)-methyl-carbamic acid tert-butyl ester (prepared in four steps from 3,5-difluoro-nitrobenzene) was used instead of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-propyl-carbamic acid tert-butyl ester (Example 41, step a) according to the method of Example 41, step b. $^1$H NMR (DMSO-d$_6$) 9.83 (1H, br s), 7.55-7.45 (2H, m), 7.26-7.14 (2H, m), 6.79 (2H, br s), 6.26 (1H, s), 4.77 (2H, s), 4.31-4.26 (1H, m), 3.96-3.91 (1H, m), 3.65 (4H, br s), 2.86 (1H, m), 2.72 (6H, m), 1.84-1.64 (6H, m), 1.34-1.10 (13H, m). Found: C, 55.92; H, 6.79; N, 12.84%; $C_{30}H_{40}N_6O_3.3.0HCl$ requires: C, 56.11; H, 6.75; N, 13.09%.

EXAMPLE 105

2-[5-Cyclohexyl-1-(3,3-dimethyl-2-oxo-butyl)-2-oxo-1,2-dihydro-3H-1,3,4-benzotriazepin-3-yl]-N-(4-methoxy-3-methylamino-phenyl)-acetamide The title compound was obtained as the hydrochloride salt by the method used in the preparation of 3-{2-[5-cyclohexyl- 1-(3,3-dimethyl-2-oxo-butyl)-2-oxo-1,2-dihydro-3H-1,3,4-benzotriazepin-3-yl]-acetylamino}-benzoic acid methyl ester (Example 1) except that (5-amino-2-methoxy-phenyl)-methyl-carbamic acid tert-butyl ester (prepared in two steps from 2-methoxy-5-nitrophenylisocyanate) was used instead of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-propyl-carbamic acid tert-butyl ester (Example 41, step a) according to the method of Example 41, step b. $^1$H NMR (CDCl$_3$) 11.00-10.00 (1H, br s), 8.16-8.12 (1H, m), 7.61-7.27 (5H, m), 7.02-6.89 (2H, m), 4.74-4.68 (2H, m), 4.37 (1H, d, 16.8), 4.18 (1H, d), 3.90 (3H, s), 2.99 (3H, s), 2.84 (1H, m), 2.05-1.70 (6H, m), 1.36-1.12 (13H, m). Found: C, 61.98; H, 7.12; N, 11.65%; C$_{30}$H$_{39}$N$_5$O$_4$.1.4HCl requires: C, 61.66; H, 6.97; N, 11.99%.

EXAMPLE 106

2-[5-Cyclohexyl-1-(3,3-dimethyl-2-oxo-butyl)-2-oxo-1,2-dihydro-3H-1,3,4-benzotriazepin-3-yl]-N-(6-hydroxymethyl-pyridin-2-yl)-acetamide The title compound was obtained by the method used in the preparation 3-({2-[5-cyclohexyl-1-(3,3-dimethyl-2-oxo-butyl)-2-oxo-1,2-dihydro-3H-1,3,4-benzotriazepin-3-yl]-acetyl}-methyl-amino)-benzoic acid methyl ester (Example 83, step a), except that (6-amino-pyridin-2-yl)-methanol (prepared from 6-amino-pyridine-2-carboxylic acid methyl ester (T. R. Kelly et al.: *J. Org. Chem.*, (1996), 61, 4633) by reaction with lithium aluminium hydride) was used instead of 3-amino-benzoic acid methyl ester. $^1$H NMR (CDCl$_3$) 7.38-7.33 (3H, m), 7.16 (1H, t), 6.93 (1H, d), 6.59 (1H, d), 6.39 (1H, d), 5.04 (2H, s), 4.67 (2H, s), 4.45 (1H, br), 4.40 (2H, br), 4.30 (1H, br), 2.70 (1H, m), 1.90-1.55 (7H, m), 1.40-1.15 (12H, m). Found: C, 66.28; H, 7.03; N, 13.60%; C$_{28}$H$_{35}$N$_5$O$_4$ requires C, 66.51; H, 6.98; N, 13.85%.

EXAMPLE 107

2-[5-Cyclohexyl-1-(3,3-dimethyl-2-oxo-butyl)-2-oxo-1,2-dihydro-3H-1,3,4-benzotriazepin-3-yl]-N-[3-(2-methyl-thiazol-4-yl]-phenyl 4-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-(2-methyl-thiazol-4-yl)-phenylamine (prepared in two steps from 2-bromo-3'-nitroacetophenone) was used instead of 3-amino-benzoic acid methyl ester in step e. $^1$H NMR (CDCl$_3$) 8.38 (1H, br s), 7.85 (1H, d), 7.62-7.59 (1H, m), 7.50-7.46 (3H, m), 7.35-7.27 (3H, m), 7.04-7.01 (1H, m), 4.77 (1H, d), 4.67 (1H, d), 4.35 (1H, d), 4.22 (1H, d), 2.84-2.78 (4H, m), 2.05-1.71 (6H, m), 1.31-1.22 (13H, m). Found: C, 66.74; H, 6.49; N, 12.05%; C$_{32}$H$_{37}$N$_5$O$_3$S.0.3H$_2$O requires: C, 66.62; H, 6.57; N, 12.14%.

EXAMPLE 108

4-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-thiazole-2-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 4-(3-amino-phenyl)-thiazole-2-carboxylic acid ethyl ester (prepared in two steps from 2-bromo-3'-nitroacetophenone) was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.49 (1H, br s), 8.09-8.07 (1H, m), 7.89 (1H, s), 7.63-7.61 (1H, m), 7.56-7.46 (3H, m), 7.40-7.28 (2H, m), 7.05 (1H, d, 7.8), 4.82 (1H, d), 4.62 (1H, d), 4.33-4.20 (2H, m), 2.81-2.77 (1H, m), 2.05-1.69 (6H, m), 1.44-1.16 (13H, m). The compound was further characterised as the N-methyl-D-glucamine salt. Found: C, 56.05; H, 6.47; N, 9.82%; C$_{32}$H$_{35}$N$_5$O$_5$S.C$_7$H$_{17}$NO$_5$.2.0H$_2$O requires: C, 56.24; H, 6.78; N, 10.09%.

EXAMPLE 109

(3-{2-[5-Cyclohexyl-1-(3,3-dimethyl-2-oxo-butyl)-2-oxo-1,2-dihydro-3H-1,3,4-benzotriazepin-3-yl]-acetylamino}-2-oxo-2H-pyridin-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (3-amino-2-oxo-2H-pyridin-1-yl)-acetic acid ethyl ester (prepared in two steps from 3-nitro-1H-pyridin-2-one) was used in place of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 9.04 (1H, s), 8.50 (1H, dd), 7.48-7.41 (2H, m), 7.25 (1H, m), 6.99-6.96 (2H, m), 6.37 (1H, t), 4.70-4.60 (4H, m), 4.46 (1H, d), 4.15 (1H, d), 2.75 (1H, m), 2.00-1.65 (6H, m), 1.40-1.23 (14H, m). The compound was further characterised as the N-methyl-D-glucaminen salt. Found: C, 55.03; H, 6.91; N, 10.29%; C$_{29}$H$_{35}$N$_5$O$_6$.C$_7$H$_{17}$NO$_5$.2.5H$_2$O requires C, 54.74; H, 7.27; N, 10.64%.

EXAMPLE 110

(3-{2-[5-Cyclohexyl-1-(4-hydroxy-3,3-dimethyl-2-oxo-butyl)-2-oxo-1,2-dihydro-3H-1,3,4-benzotriazepin-3-yl]-acetylamino}-phenyl)-acetic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that benzoic acid 4-bromo-2,2-dimethyl-3-oxo-butyl ester (prepared in four steps from 2,2-dimethyl-3-oxo-butyric acid ethyl ester) was used in step c instead 1-bromo-3,3-dimethyl-butan-2-one, and (3-amino-phenyl)-acetic acid methyl ester replaced 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.20 (1H, br s), 9.75 (1H, s), 7.55-7.11 (7H, m), 6.90 (1H, d), 4.90 (1H, br s), 4.79 (2H, s), 4.30-3.90 (2H, m), 3.48 (4H, s), 2.82 (1H, m), 2.00-1.10 (10H, m) 1.05 (6H, s). The compound was further characterised as the N-methyl-D-glucamine salt. Found: C, 56.88; H, 7.22; N, 8.66%. $C_{30}H_{36}N_4O_6 \cdot C_7H_{17}NO_5 \cdot 2.0H_2O$ requires: C, 56.98; H, 7.36; N, 8.98%.

EXAMPLE 111

2-[5-Cyclohexyl-1-(2-cyclohexyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide The title compound was obtained by the method used in the preparation of 2-{5-cyclohexyl-1-(3,3-dimethyl-2-oxo-butyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide (Example 59) except that [5-cyclohexyl-1-(2-cyclohexyl-2-oxo-ethyl)-2-oxo-1,2-dihydro-3H-1,3,4-benzotriazepin-3-yl]-acetic acid (Example 79, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d). $^1$H NMR (CDCl$_3$) 10.9 (1H, br s), 8.82 (1H, s), 7.85 (1H, s), 7.60 (2H, m), 7.45 (3H, m), 7.28 (1H, t), 7.04 (1H, d),), 4.73 (1H, d), 4.45 (1H, d), 4.20 (2H, s), 2.80 (1H, m), 2.47 (1H, m), 2.01-1.64 (11H, m), 1.47-1.17 (9H, m). The compound was further characterised as the N-methyl-D-glucamine salt. Found: C, 56.12; H, 6.88; N, 11.10%; $C_{32}H_{36}N_6O_5 \cdot C_7H_{17}NO_5 \cdot 2.8H_2O \cdot 0.4C_4H_{8O2}$ requires: C, 56.34; H, 7.20; N, 11.33%.

EXAMPLE 112

3-{2-[5-Cyclohexyl-1-(3,3-dimethyl-2-oxo-butyl)-8-methyl-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-4-methyl-phenyl)-cyclohexyl-methanone was used in step a instead of (2-amino-phenyl)-cyclohexyl-methanone, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.54 (1H, s), 8.05 (1H, d), 7.82 (1H, s), 7.79 (1H, d), 7.40 (2H, m), 7.11 (1H, d), 6.82 (1H, s), 4.65 (2H, q), 4.25 (2H, q), 2.78 (1H, m), 2.41 (3H, s), 2.00 (1H, br m), 1.75 (4H, m), 1.31 (5H, m), 1.24 (9H, s). The compound was further characterised as the N-methyl-D-glucamine salt. Found C, 58.49; H, 7.20; N, 8.34; $C_{30}H_{36}N_4O_5 \cdot C_7H_{17}NO_5 \cdot 1.3H_2O \cdot 0.6C_4H_8O_2$ requires C, 58.85; H, 7.57; N, 8.71%.

EXAMPLE 113

3-{2-[5-Cyclohexyl-1-(3,3-dimethyl-2-oxo-butyl)-6-fluoro-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-6-fluoro-phenyl)-cyclohexyl-methanone was used in step a instead of (2-amino-phenyl)-cyclohexyl-methanone, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.60 (1H, s), 8.07 (1H, d), 7.98 (1H, s), 7.82 (1H, d), 7.42 (2H, m), 7.02 (1H, t), 6.81 (1H, d), 4.81 (1H, d), 4.56 (1H, d), 4.25 (2H, q), 2.91 (1H, m), 2.10 (1H, br m), 1.9-1.6 (4H, m), 1.28 (5H, m), 1.29 (9H, s). The compound was further characterised as the N-methyl-D-glucamine salt. Found C, 56.33; H, 7.07; N, 8.60; $C_{29}H_{33}FN_4O_5 \cdot C_7H_{17}NO_5 \cdot 1.9H_2O \cdot 0.5C_4H_8O_2$ requires C, 56.34; H, 7.19; N, 8.64%.

EXAMPLE 114

3-{2-[5-Cyclohexyl-1-(3,3-dimethyl-2-oxo-butyl)-6-methyl-2-oxo-1,2-dihydro-3H-1,3,4-benzotriazepin-3-yl]-acetylamino}-benzoic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-6-methyl-phenyl)-cyclohexyl-methanone was used in step a instead of (2-amino-phenyl)-cyclohexyl-methanone, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.41 (1H, s), 8.11 (1H, d), 7.82 (1H, d), 7.75 (1H, s), 7.39 (2H, m), 7.17 (1H, d), 6.86 (1H, d), 4.76 (1H, d), 4.57 (1H, d), 4.37 (1H, d), 4.21 (1H, d), 2.66 (1H, m), 2.40 (3H, s), 2.00 (1H, br m), 1.75 (5H, m), 1.27 (4H, m), 1.26 (9H, s). The compound was further characterised as the N-methyl-D-glucamine. Found C, 57.70; H, 7.27; N, 8.30; $C_{30}H_{36}N_4O_5 \cdot C_7H_{17}NO_5 \cdot 2.5H_2O \cdot 0.6C_4H_8O_2$ requires C, 57.85; H, 7.62; N, 8.65%.

EXAMPLE 115

2-[5-Cyclohexyl-2-oxo-1-(pyrrolidine-1-carbonyl) 1,2-dihyhdro-3H-1,3,4-benzotriazepin-3-yl]-N-m-tolyl-acetamide Step a. [5-Cyclohexyl-2-oxo-1-(pyrrolidine-1-carbonyl)-1,2-dihydro-3H-1,3,4-benzotriazepin-3-yl]-acetic acid ethyl ester. A mixture of (1-chlorocarbonyl-5-cyclohexyl-2-oxo-1,2-dihydro-3H-1,3,4-benzotriazepin-3-yl)-acetic acid ethyl ester (Example 1, minor product of step b)(391 mg, 1.0 mmol), and pyrrolidine (156 mg, 2.2 mmol) in DCM (5 ml) was stirred at room temperature for 30 min. The solution was washed with dilute HCl, dried (MgSO$_4$), and the solvent evaporated under reduced pressure to afford the product as a white solid (417 mg, 98%). $^1$H NMR (CDCl$_3$) 8.12 (1H, d), 7.50 (1H, t), 7.39-7.31 (2H, m), 4.31 (2H, s), 4.16 (2H, q), 3.45 (4H, m), 2.81 (1H, m), 1.92-1.27 (14H, m), 1.22 (3H, t).

Step b. [5-Cyclohexyl-2-oxo-1-(pyrrolidine-1-carbonyl)-1,2-dihydro-3H-1,3,4-benzotriazepin-3-yl]-acetic acid was obtained by the method used in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that [5-cyclohexyl-2-oxo-1-(pyrrolidine-1-carbonyl)-1,2-dihydro-3H-1,3,4-benzotriazepin-3-yl]-acetic acid ethyl ester (Example 115, step a) was used in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c). $^1$H NMR (CDCl$_3$) 8.11 (1H, d), 7.50 (1H, t), 7.42-7.33 (2H, m), 4.26 (2H, s), 3.42 (4H, m), 2.85 (1H, m), 1.91-1.19 (10H, m).

Step c. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that [5-cyclohexyl-2-oxo-1-(pyrrolidine-1-carbonyl)-1,2-dihydro-3H-1,3,4-benzotriazepin-3-yl]-acetic acid (Example 115, step b) and m-toluidine were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively. $^1$H NMR (CDCl$_3$) 8.12 (1H, d), 8.10 (1H, br s), 7.59 (1H, t), 7.43 (2H, m), 7.16 (2H, m), 7.07 (1H, d), 6.88 (1H, d), 4.34 (2H, s), 3.45-3.35 (4H, m), 2.88 (1H, m), 2.31 (3H, s), 2.00-1.31 (14H, m). Found: C, 68.00; H, 6.73; N, 14.07%; C$_{28}$H$_{33}$N$_5$O$_3$.0.5H$_2$O requires: C, 67.72; H, 6.90; N, 14.10%.

EXAMPLE 116

(7-{2-[5-Cyclohexyl-1-(3,3-dimethyl-2-oxo-butyl)-2-oxo-1,2-dihydro-3H-1,3,4-benzotriazepin-3-yl]-acetylamino}-3,4-dihydro-1H-isoquinolin-2-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (7-amino-3,4-dihydro-1H-isoquinolin-2-yl)-acetic acid ethyl ester was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (DMSO-d$_6$) 9.90 (1H, brs), 7.54-7.42 (3H, m), 7.28-7.11 (4H, m), 4.78 (2H, m), 4.33 (2H, m), 4.09 (2H, m), 3.39 (3H, m), 3.00 (3H, m), 1.65-1.21 (6H, m), 1.12-1.04 (13H, m). The product was further characterised as the hydrochloride salt. Found: C, 47.05; H, 5.34; N, 7.72%; C$_{33}$H$_{41}$N$_5$O$_5$.HCl.3.4CH$_2$Cl$_2$ requires: C, 47.14; H, 5.48; N, 7.55%.

EXAMPLE 117

(5-{2-[5-Cyclohexyl-1-(3,3-dimethyl-2-oxo-butyl)-2-oxo-1,2-dihydro-3H-1,3,4-benzotriazepin-3-yl]-acetylamino}-indol-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (5-amino-indol-1-yl)-acetic acid ethyl ester (prepared in two steps from 5-nitroindole) was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.21 (1H, s), 7.70 (1H, s), 7.47 (2H, m), 7.27 (1H, m), 7.05 (4H, m), 6.47 (1H, d), 4.79 (2H, s), 4.68 (2H, m), 4.39 (1H, d), 4.20 (1H, d), 2.78 (1H, m), 2.18-1.07 (19H, m). The compound was further characterised as the N-methyl-D-glucamine salt. Found: C, 58.02; H, 7.08; N, 9.62%; C$_{32}$H$_{37}$N$_5$O$_5$.C$_7$H$_{17}$NO$_5$.1.9H$_2$O.0.6C$_4$H$_8$O$_2$ requires: C, 58.23; H, 7.39; N, 9.84%.

EXAMPLE 118

(5-{2-[5-Cyclohexyl-1-(3,3-dimethyl-2-oxo-butyl)-2-oxo-1,2-dihydro-3H-1,3,4-benzotriazepin-3-yl]-acetylamino}-indazol-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (5-amino-indazol-1-yl)-acetic acid methyl ester (prepared in two steps from 5-nitro-indazole) was used in place of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.43 (1H, s), 8.05 (1H, s), 7.52-7.45 (2H, m), 7.32-7.23 (3H, m), 7.04 (1H, d, 8.1), 5.12 (2H, s), 4.82 (1H, d, 17.4), 4.61 (1H, d, 17.4), 4.27-4.26 (2H, m), 2.79 (1H, m), 2.05-1.72 (6H, m), 1.48-1.19 (13H, m). The compound was further characterised as the N-methyl-D-glucamine salt. Found: C, 56.75; H, 6.90; N, 11.81%; C$_{31}$H$_{36}$N$_6$O$_5$.C$_7$H$_{17}$NO$_5$.2.3H$_2$O requires: C, 56.46; H, 7.17; N, 12.13%.

EXAMPLE 119

(3-{2-[5-Cyclohexyl1-1-(2-cyclopropyl-2-oxo-ethyl)-2-oxo-1,2-dihydro-3H-1,3,4-benzotriazepin-3-yl]-acetylamino}-phenyl)-acetic acid Step a. [5-Cyclohexyl-1-(2-cyclopropyl-2-oxo-ethyl)-2-oxo-1,2-dihydro-3H-1,3,4-benzotriazepin-3-yl]-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that 2-bromo-1-cyclopropyl-ethanone was used in step c instead of 1-bromo-3,3-dimethyl-butan-2-one. $^1$H NMR (CDCl$_3$) 10.80 (1H, br s), 7.46 (2H, m), 7.27 (1H, m), 7.04 (1H, d), 4.66 (2H, m), 4.28 (1H, d), 3.93 (1H, d), 2.85 (1H, m), 1.99-0.92 (15H, m).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e) except that [5-cyclohexyl-1-(2-cyclopropyl-2-oxo-ethyl)-2-oxo-1,2-dihydro-3H-1,3,4-benzotriazepin-3-yl]-acetic acid (Example 119, step a) and (3-amino-phenyl)-acetic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 10.80 (1H, br s), 8.30 (1H, s), 7.46 (2H, m), 7.26 (4H, m), 7.08 (1H, d), 6.98 (1H, d), 4.78 (1H, d), 4.57 (1H, d), 4.32 (1H, d), 4.18 (1H, d), 3.59 (2H, s), 2.78 (1H, m), 2.17-1.68 (7H, m), 1.24 (4H, m), 1.08 (2H, m), 0.93 (2H, m). The compound was further characterised as the N-methyl-D-glucamine salt. Found: C, 58.57; H, 7.22; N, 8.57%; C$_{29}$H$_{32}$N$_4$O$_5$.C$_7$H$_{17}$NO$_5$.1.2H$_2$O.0.9C$_4$H$_8$O$_2$ requires: C, 58.52; H, 7.27; N, 8.62%.

EXAMPLE 120

[3-(2-{5-Cyclohexyl-1-(2-cyclopropyl-2-oxo-ethyl)-2-oxo-1,2-dihydro-3H-1,3,4-benzotriazepin-3-yl]-acetylamino}-phenylsulfanyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except [5-cyclohexyl-1-(2-cyclopropyl-2-oxo-ethyl)-2-oxo-1,2-dihydro-3H-1,3,4-benzotriazepin-3-yl]-acetic acid (Example 119, step a) and (3-amino-phenylsulfanyl)-acetic acid ethyl ester were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.90 (1H, br s), 8.44 (1H, s), 7.49 (3H, m), 7.29 (2H, m), 7.19 (1H, t), 7.08 (2H, t), 4.81 (1H, d), 4.56 (1H, d), 4.22 (2H, m), 3.65 (2H, s), 2.79 (1H, m), 2.01-1.68 (7H, m), 1.26 (4H, m), 1.09 (2H, m), 0.93 (2H, m). The compound was further characterised as the N-methyl-D-glucamine salt. Found: C, 55.42; H, 6.74; N, 8.42%; C$_{29}$H$_{32}$N$_4$O$_5$S.C$_7$H$_{17}$NO$_5$.1.8H$_2$O.0.4C$_4$H$_8$O$_2$ requires: C, 55.65; H, 6.93; N, 8.63%.

EXAMPLE 121

2-[5-Cyclohexyl-1-(2-cyclopentyl-2-oxo-ethyl)-2-oxo-1,2-dihydro-3H-1,3,4-benzotriazepin-3-yl]-N-[3-(5-oxo-Z 5-dihydro-[1,2,4]oxadiazol-3-yl)-phenyl]-acetamide and salts thereof A. The title compound was obtained by the method used in the preparation of 2-[5-cyclohexyl-1-(3,3-dimethyl-2-oxo-butyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide (Example 59) except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) was used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d). $^1$H NMR (CDCl$_3$) 10.80 (1H, br s), 8.85 (1H, s), 7.85 (1H, s), 7.59 (2H, m), 7.43 (3H, m), 7.28 (1H, t), 7.05 (1H, d),), 4.73 (1H, d), 4.45 (1H, d), 4.22 (2H, s), 2.93 (1H, m), 2.80 (1H, m), 2.18-1.59 (13H, m), 1.28 (5H, m). The compound was further characterised as the N-methyl-D-glucamine salt. Found: C, 57.52; H, 6.80; N, 12.01%; C$_{31}$H$_{34}$N$_6$O$_5$.C$_7$H$_{17}$NO$_5$.1.7H$_2$O requires: C, 57.25; H, 6.89; N, 12.30%.

B. Potassium Salt: 2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide (5.7 g, 10 mmol) was suspended in i-PrOH (200 mL) and treated with potassium hydroxide (0.64 g of 88% KOH, 10 mmol). The mixture was heated until a clear solution was obtained. Heating was continued to remove some of the i-PrOH then allowed to stand at rt overnight. The precipitated white solid was collected by filtration and washed with i-PrOH and air-dried; mp: >250° C.

X-ray diffraction data was obtained for the potassium salt, as indicated below.

2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide, potassium salt

| Position [°2θ] | d-spacing [Å] | Relative Intensity [%] |
| --- | --- | --- |
| 5.127 | 17.238 | 100.00 |
| 6.817 | 12.967 | 1.15 |
| 8.871 | 9.969 | 61.09 |
| 10.239 | 8.640 | 5.04 |
| 12.386 | 7.146 | 9.88 |
| 13.101 | 6.758 | 6.62 |
| 14.354 | 6.171 | 9.75 |
| 14.735 | 6.012 | 1.91 |
| 15.318 | 5.785 | 10.06 |
| 15.886 | 5.579 | 14.25 |
| 16.226 | 5.463 | 10.24 |
| 16.974 | 5.224 | 4.19 |
| 17.355 | 5.110 | 8.91 |
| 17.741 | 5.000 | 2.77 |
| 18.176 | 4.881 | 3.51 |
| 19.031 | 4.663 | 21.09 |
| 19.604 | 4.528 | 6.16 |
| 20.225 | 4.391 | 4.39 |
| 20.532 | 4.326 | 6.57 |
| 21.285 | 4.175 | 10.23 |
| 21.946 | 4.050 | 11.31 |
| 23.115 | 3.848 | 23.68 |
| 23.477 | 3.789 | 5.61 |
| 24.941 | 3.570 | 15.86 |
| 25.735 | 3.462 | 7.57 |
| 26.363 | 3.381 | 10.51 |
| 26.793 | 3.327 | 4.43 |
| 27.424 | 3.252 | 11.04 |
| 28.056 | 3.180 | 2.17 |
| 29.291 | 3.049 | 2.64 |
| 29.733 | 3.005 | 3.67 |
| 30.241 | 2.956 | 3.28 |
| 31.260 | 2.861 | 2.48 |
| 34.056 | 2.632 | 1.57 |

C. Sodium Salt: NaOH (0.4 g, 10 mmol) was dissolved in 1 mL of warm water and diluted with i-PrOH (80 mL). 2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide (5.7 g, 10 mmol) was added and the mixture was heated to boiling to form a yellow clear solution. The hot solution was filtered through a small plug of celite and allowed to stand at rt. After cooling, the solution was filtered again through celite to remove some yellow deposits. The solution was allowed to stand at rt overnight. The salt was precipitated; MeOH (5 mL) was added and the mixture stirred for 15 min. The solid was collected by filtration, rinsed with i-PrOH (10 mL) and air-dried.

X-ray diffraction data was obtained for the sodium salt, as indicated below.

2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide, sodium salt

| Position [°2θ] | d-spacing [Å] | Relative Intensity [%] |
| --- | --- | --- |
| 7.370 | 11.995 | 100.00 |
| 7.773 | 11.374 | 36.30 |
| 8.856 | 9.985 | 3.77 |

-continued

2-[5-Cyclohexyl-1-(2-cyclopentyl-2-oxo-ethyl)-2-oxo-1,2-dihydro-
3H-1,3,4-benzotriazepin-3-yl]-N-[3-(5-oxo-2,5-dihydro-
[1,2,4]oxadiazol-3-yl)-phenyl]-acetamide, sodium salt

| Position [°2θ] | d-spacing [Å] | Relative Intensity [%] |
|---|---|---|
| 10.650 | 8.307 | 10.30 |
| 11.242 | 7.871 | 2.98 |
| 12.391 | 7.143 | 4.68 |
| 12.880 | 6.873 | 12.73 |
| 13.304 | 6.656 | 2.73 |
| 13.584 | 6.519 | 2.22 |
| 14.946 | 5.928 | 5.23 |
| 15.179 | 5.837 | 9.47 |
| 15.995 | 5.541 | 6.90 |
| 16.423 | 5.398 | 5.37 |
| 16.781 | 5.283 | 12.51 |
| 16.955 | 5.229 | 13.70 |
| 17.048 | 5.201 | 10.60 |
| 17.697 | 5.012 | 2.88 |
| 18.382 | 4.827 | 7.03 |
| 18.763 | 4.729 | 3.48 |
| 19.285 | 4.603 | 4.65 |
| 20.037 | 4.431 | 1.80 |
| 20.978 | 4.235 | 5.86 |
| 21.964 | 4.047 | 23.38 |
| 22.613 | 3.932 | 7.19 |
| 23.564 | 3.776 | 10.06 |
| 24.255 | 3.670 | 2.93 |
| 24.806 | 3.589 | 1.88 |
| 25.596 | 3.480 | 3.08 |
| 25.983 | 3.429 | 4.45 |
| 26.479 | 3.366 | 3.81 |
| 26.914 | 3.313 | 3.35 |
| 27.735 | 3.217 | 3.00 |
| 28.808 | 3.099 | 1.42 |
| 29.303 | 3.048 | 2.43 |
| 29.718 | 3.006 | 2.50 |
| 30.273 | 2.952 | 2.62 |
| 31.039 | 2.881 | 2.47 |
| 31.584 | 2.833 | 1.61 |
| 32.520 | 2.753 | 1.40 |
| 33.258 | 2.694 | 1.17 |
| 33.728 | 2.657 | 1.46 |

D. Choline Salt: 2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide (57 g, 100.2 mmol) was suspended in EtOAc (500 mL) and MeOH (100 mL) and then treated with choline hydroxide (26.6 g of 45% solution in MeOH, 99.6 mmol) at rt. The mixture was heated to boiling until a clear solution was obtained. The solution was filtered through celite then heated to evaporate some of the MeOH until the boiling temperature reached 66° C. (the volume kept constant at about 600 mL by occasional addition of EtOAc while heating). The solution was stirred at 20° C. for 3 h.

The resulting solid was collected by filtration, washed with EtOAc and air-dried; mp: 157-160° C.

X-ray diffraction data was obtained for the choline salt, as indicated below.

2-[5-Cyclohexyl-1-(2-cyclopentyl-2-oxo-ethyl)-2-oxo-1,2-dihydro-
3H-1,3,4-benzotriazepin-3-yl]-N-[3-(5-oxo-2,5-dihydro-
[1,2,4]oxadiazol-3-yl)-phenyl]-acetamide, choline salt

| Position [°2θ] | d-spacing [Å] | Relative Intensity [%] |
|---|---|---|
| 4.477 | 19.738 | 99.32 |
| 8.048 | 10.987 | 24.76 |

-continued

2-[5-Cyclohexyl-1-(2-cyclopentyl-2-oxo-ethyl)-2-oxo-1,2-dihydro-
3H-1,3,4-benzotriazepin-3-yl]-N-[3-(5-oxo-2,5-dihydro-
[1,2,4]oxadiazol-3-yl)-phenyl]-acetamide, choline salt

| Position [°2θ] | d-spacing [Å] | Relative Intensity [%] |
|---|---|---|
| 8.991 | 9.836 | 100.00 |
| 9.767 | 9.056 | 6.54 |
| 10.286 | 8.600 | 23.07 |
| 10.615 | 8.334 | 36.36 |
| 11.054 | 8.005 | 19.20 |
| 11.792 | 7.505 | 19.86 |
| 12.786 | 6.924 | 46.42 |
| 13.678 | 6.474 | 26.11 |
| 15.204 | 5.828 | 8.89 |
| 15.792 | 5.612 | 16.97 |
| 16.206 | 5.469 | 8.84 |
| 16.777 | 5.285 | 24.34 |
| 16.849 | 5.262 | 17.67 |
| 17.193 | 5.158 | 15.16 |
| 17.749 | 4.997 | 74.49 |
| 18.142 | 4.890 | 71.61 |
| 18.947 | 4.684 | 23.15 |
| 19.560 | 4.539 | 30.94 |
| 20.668 | 4.30 | 29.44 |
| 21.812 | 4.075 | 43.07 |
| 22.644 | 3.927 | 23.10 |
| 23.793 | 3.74 | 13.13 |
| 24.971 | 3.56 | 16.13 |
| 26.157 | 3.410 | 6.16 |
| 27.336 | 3.263 | 20.59 |
| 28.349 | 3.148 | 2.67 |
| 30.696 | 2.913 | 14.97 |
| 31.954 | 2.801 | 3.53 |
| 33.648 | 2.664 | 1.87 |

E. t-Butylamine Salt: 2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide (2.85 g, 5 mmol) was suspended in i-PrOH (50 mL) and treated with tert-butylamine (0.37 g, 5 mmol). The mixture was heated until a clear solution was obtained. Heating was continued to remove some of the i-PrOH (to a volume of about 25 mL), diluted with heptane (10 mL) then allowed to stand at rt for several days. The precipitated white solid was collected by filtration, washed with i-PrOH/heptane and air-dried, mp 166-170° C.

X-ray diffraction data was obtained for the tert-butylamine salt, as indicated below.

2-[5-Cyclohexyl-1-(2-cyclopentyl-2-oxo-ethyl)-2-oxo-1,2-dihydro-
3H-1,3,4-benzotriazepin-3-yl]-N-[3-(5-oxo-2,5-dihydro-
[1,2,4]oxadiazol-3-yl)-phenyl]-acetamide, tert-butylamine salt

| Position [°2θ] | d-spacing [Å] | Relative Intensity [%] |
|---|---|---|
| 4.314 | 20.483 | 49.83 |
| 4.918 | 17.969 | 35.47 |
| 5.840 | 15.134 | 100.00 |
| 7.156 | 12.354 | 14.96 |
| 8.551 | 10.341 | 4.16 |
| 11.642 | 7.602 | 13.20 |
| 13.565 | 6.528 | 1.94 |
| 15.979 | 5.547 | 26.42 |
| 16.781 | 5.283 | 47.86 |
| 18.055 | 4.913 | 27.14 |
| 19.247 | 4.612 | 25.08 |
| 19.955 | 4.450 | 25.12 |
| 20.891 | 4.252 | 20.21 |
| 22.208 | 4.003 | 29.44 |

-continued

2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide, tert-butylamine salt

| Position [°2θ] | d-spacing [Å] | Relative Intensity [%] |
|---|---|---|
| 23.434 | 3.796 | 15.06 |
| 25.605 | 3.479 | 9.24 |
| 26.184 | 3.403 | 8.22 |
| 27.591 | 3.233 | 4.31 |
| 28.292 | 3.154 | 3.46 |
| 30.614 | 2.920 | 3.63 |
| 32.354 | 2.767 | 2.28 |
| 33.612 | 2.666 | 2.39 |

EXAMPLE 122

2-[5-Cyclohexyl-1-(3,3-dimethyl-2-oxo-butyl)-2-oxo-1,2-dihydro-3H-1,3,4-benzotriazepin-3-yl]-N-[3-(5-methyl-[1,3,4]oxadiazol-2-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-(5-methyl-[1,3,4]oxadiazol-2-yl)-phenylamine (prepared in three steps from 3-nitrobenzoic acid) was used instead of 3-amino-benzoic acid methyl ester in step e. $^1$H NMR (CDCl$_3$) 8.57 (1H, s), 8.04 (1H, s), 7.78-7.70 (2H, m), 7.50-7.30 (4H, m), 7.02 (1H, m), 4.80-4.56 (2H, m), 4.25 (2H, s), 2.81 (1H, m), 2.61 (3H, s), 2.00-1.27 (10H, m), 1.24 (9H, s). Found: C, 66.70; H, 6.71; N, 14.98%; $C_{31}H_{36}N_6O_4$ requires: C, 66.89; H, 6.52; N, 15.10%.

EXAMPLE 123

2-[5-Cyclohexyl-1-(3,3-dimethyl-2-oxo-butyl)-2-oxo-1,2-dihydro-3H-1,3,4-benzotriazepin-3-yl]-N-(3-morpholin-4-yl-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 3-morpholin-4-yl-phenylamine (prepared in two steps from 3-fluoro-1-nitrobenzene) was used instead of 3-amino-benzoic acid methyl ester in step e. $^1$H NMR (CDCl$_3$) 8.22 (1H, br s), 7.50-7.44 (2H, m), 7.29-7.12 (3H, m), 7.03 (1H, d, 8.1), 6.75 (1H, d, 8.1), 6.63-6.60 (1H, m), 4.77 (1H, d, 17.7), 4.65 (1H, d, 17.7), 4.34 (1H, d, 16.8), 4.19 (1H, d, 16.8), 3.84 (4H, t, 4.8), 3.15 (4H, t, 4.8), 2.82-2.75 (1H, m), 2.05-1.74 (6H, m), 1.36-1.24 (13H, m). Found: C, 68.18; H, 7.42; N, 12.29%; $C_{32}H_{41}N_5O_4$.0.3H$_2$O requires: C, 68.10; H, 7.42; N, 12.41%.

EXAMPLE 124

2-[5-Cyclohexyl-1-(2-cyclopentyl-2-oxo-ethyl)-2-oxo-1,2-dihydro-3H-1,3,4-benzotriazepin-3-yl]-N-(3-[methyl-(2H-tetrazol-5-yl)-amino]-phenyl)-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 2,2-dimethyl-propionic acid 5-[(3-amino-phenyl)-methyl-amino]-tetrazol-2-ylmethyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 2,2-dimethyl-propionic acid 5-(3-{2-[5-cyclopentyl-1-(3,3-dimethyl-2-oxo-butyl)-2-oxo-1,2-dihydro-3H-1,3,4-benzotriazepin-3-yl]-acetylamino}-phenyl)-tetrazol-2-ylmethyl ester (Example 10, step a), according to the method of Example 10, step b. $^1$H NMR (DMSO-d$_6$) 9.85 (1H, s), 7.56-7.48 (3H, m), 7.30-7.20 (3H, m), 7.15 (1H, d), 7.06 (1H, d), 7.00 (1H, br m), 6.65 (1H, br m), 4.65 (2H, br m), 4.25 (1H, br d), 3.95 (1H, br d), 3.40 (3H, s), 3.05-2.85 (2H, m), 1.90-1.40 (9H, m), 1.40-0.95 (9H, m). The compound was further characterised as the N-methyl-D-glucamine salt. Found: C, 56.42; H, 7.05; N, 16.27%; $C_{31}H_{37}N_9O_3.C_7H_{17}NO_5.1.5CH_3CO_2H$ requires C, 56.67; H, 6.96; N, 16.12%.

EXAMPLE 125

2-[5-Cyclohexyl-1-(2-cyclopentyl-2-oxo-ethyl)-2-oxo-1,2-dihydro-3H-1,3,4-benzotriazepin-3-yl]-N-[3-(2H-tetrazol-5-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 2,2-dimethyl-propionic acid 5-(3-amino-phenyl)-tetrazol-2-ylmethyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 2,2-dimethyl-propionic acid 5-(3-{2-[5-cyclopentyl-1-(3,3-dimethyl-2-oxo-butyl)-2-oxo-1,2-dihydro-3H-1,3,4-benzotriazepin-3-yl]-acetylamino}-phenyl)-tetrazol-2-ylmethyl ester (Example 10, step a), according to the method of Example 10, step b. $^1$H NMR (d$_6$-DMSO) 10.11 (1H, s), 8.36 (1H, s), 7.68-7.46 (5H, m), 7.22 (1H, m), 7.16 (1H, d), 6.95 (1H, br), 6.65 (1H, br), 4.64 (2H, m br), 4.35 (1H, m br), 4.00 (1H, m br), 3.00-2.80 (2H, m), 1.95-1.45 (9H, m), 1.40-1.00 (9H, m). The compound was further characterised as the N-methyl-D-glucamine salt. Found: C, 56.11; H, 7.00; N, 14.82%; $C_{30}H_{34}N_8O_3.C_7H_{17}NO_5.0.8CH_3CO_2H.2.2CH_3OH$ requires C, 56.43; H, 7.31; N, 14.52%.

EXAMPLE 126

(6-{2-[5-Cyclohexyl-1-(2-cyclopentyl-2-oxo-ethyl)-2-oxo-1,2-dihydro-3H-1,3,4-benzotriazepin-3-yl]-acetylamino}-indol-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1, 2-dihydro-3H-1,3,4-benzotriazepin-3-yl]-acetic acid (Example 22, step a) and (6-amino-indol-1-yl)-acetic acid ethyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (DMSO-d$_6$) 9.65 (1H, s), 7.67 (1H, s), 7.58-7.47 (2H, m), 7.39 (1H, d), 7.28-7.15 (3H, m), 6.97 (1H, d), 6.31 (1H, d), 4.75-4.55 (4H, m), 4.30 (1H, br d), 3.95 (1H, br d), 3.00-2.88 (2H, m), 1.98-1.40 (14H, m), 1.35-1.10 (4H, m). The compound was further characterised as the N-methyl-D-glucamine salt. Found: C, 58.53; H, 6.80; N, 10.01%; $C_{33}H_{37}N_5O_5.C_7H_{17}NO_5.2.0H_2O$ requires C, 58.95; H, 7.17; N, 10.31%.

EXAMPLE 127

(4-{2-[5-Cyclohexyl-1-(3,3-dimethyl-2-oxo-butyl)-2-oxo-1,2-dihydro-3H-1,3,4-benzotriazepin-3-yl]-acetylamino}-indol-1-yl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (4-amino-indol-1-yl)-acetic acid ethyl ester (prepared in two steps from 4-nitroindole) was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.47 (1H, s), 7.84 (1H, d), 7.47 (2H, m), 7.27 (1H, m), 7.15 (1H, t), 7.05 (1H, d), 6.96 (1H, d), 6.87 (1H, t), 5.69 (1H, d), 4.75 (4H, m), 4.57 (1H, d), 4.25 (1H, d), 2.79 (1H, m), 1.99-1.09 (19H, m). The compound was further characterised as the N-methyl-D-glucamine salt. Found: C, 58.46; H, 7.08; N, 9.78%; $C_{32}H_{37}N_5O_5.C_7H_{17}NO_5.1.6H_2O.0.5C_4H_8O_2$ requires: C, 58.64; H, 7.35; N, 10.01%.

EXAMPLE 128

3-(3-{2-[5-Cyclohexyl-1-(2-cyclopentyl-2-oxo-ethyl)-2-oxo-1,2-dihydro-3H-1,3,4-benzotriazepin-3-yl]-acetylamino}-phenyl)-propionic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 3-(3-amino-phenyl)-propionic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.28 (1H, s), 7.47 (2H, m), 7.32-7.16 (4H, m), 7.07 (1H, d), 6.92 (1H, d), 4.67 (1H, d), 4.45 (1H, d), 4.32 (1H, d), 4.18 (1H, d), 2.95 (3H, m), 2.80 (1H, m), 2.66 (2H, m), 1.84-1.57 (14H, m), 1.30 (4H, m). The compound was further characterised as the N-methyl-D-glucamine salt. Found: C, 59.30; H, 7.18; N, 8.70%; $C_{32}H_{38}N_4O_5.C_7H_{17}NO_5.1.8H_2O$ requires: C, 59.63; H, 7.51; N, 8.91%.

EXAMPLE 129

2-[5-Cyclohexyl-1-(3,3-dimethyl-2-oxo-butyl)-2-oxo-1,2-dihydro-3H-1,3,4-benzotriazepin-3-yl]-N-[3-(4-methyl-piperazin-1-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 3-(4-methyl-piperazin-1-yl)-phenylamine (prepared in two steps from 3-fluoro-1-nitrobenzene) was used instead of 3-amino-benzoic acid methyl ester in step e. $^1$H NMR (CDCl$_3$) 8.17 (1H, br s), 7.50-7.44 (2H, m), 7.29-7.27 (1H, m), 7.16-7.09 (2H, m), 7.04 (1H, d, 8.1), 6.78-6.75 (1H, m), 6.64-6.61 (1H, m), 4.76-4.60 (2H, m), 4.36-4.12 (2H, m), 3.21-3.18 (4H, m), 2.82-2.74 (1H, m), 2.57-2.54 (4H, m), 2.35 (3H, s), 2.04-1.60 (6H, m), 1.45-1.23 (13H, m). Found: C, 68.32; H, 7.55; N, 14.16%; $C_{33}H_{44}N_6O_3.0.5H_2O$ requires: C, 68.19; H, 7.79; N, 14.46%.

EXAMPLE 130

(4-{2-[5-Cyclohexyl-1-(3,3-dimethyl-2-oxo-butyl)-2-oxo-1,2-dihydro-3H-1,3,4-benzotriazepin-3-yl]-acetylamino}-indazol-1-yl)-acetic acid Step a. (4-{2-[5-Cyclohexyl-1-(3,3-dimethyl-2-oxo-butyl)-2-oxo-1,2-dihydro-3H-1,3,4-benzotriazepin-3-yl]-acetylamino}-indazol-1-yl)-acetic acid tert-butyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (4-amino-indazol-1-yl)-acetic acid tert-butyl ester (prepared in two steps from 4-nitro-indazole) was used in place of 3-amino-benzoic acid methyl ester in step e.

Step b. (4-{2-[5-Cyclohexyl-1-(3,3-dimethyl-2-oxo-butyl)-2-oxo-1,2-dihydro-3H-1,3,4-benzotriazepin-3-yl]-acetylamino}-indazol-1-yl)-acetic acid tert-butyl ester (Example 130, step a)(522 mg, 0.82 mmol) was dissolved in trifluoroacetic acid (5 ml) and the solution was stirred at room temperature for 2 h. The solvent was evaporated, and the solid obtained was washed with Et$_2$O, isolated by filtration and dried to afford the trifluoroacetate salt of the title compound (430 mg, 91%). $^1$H NMR (CDCl$_3$) 8.98 (1H, s), 8.00-7.86 (3H, br m), 7.57-7.29 (5H, m), 7.10-7.05 (2H, m), 5.21 (2H, s), 4.77-4.62 (2H, m), 4.47-4.30 (2H, m), 2.80-2.76 (1H, m), 2.02-1.61 (6H, m), 1.30-1.16 (13H, m). Found: C, 57.90; H, 5.54; N, 12.51%; $C_{31}H_{36}N_6O_5.CF_3CO_2H$ requires: C, 57.72; H, 5.43; N, 12.24%.

EXAMPLE 131

2-[5-Cyclohexyl-1-(3,3-dimethyl-2-oxo-butyl)-2-oxo-1,2-dihydro-3H-1,3,4-benzotriazepin-3-yl]-N-[1-(1H-tetrazol-5-ylmethyl)-1H-indol-6-yl]-acetamide The title compound was obtained by the method used in the preparation of 3-{2-[5-cyclohexyl-1-(3,3-dimethyl-2-oxobutyl)-2-oxo-1,2-dihydro-3H-1,3,4-benzotriazepin-3-yl]-acetylamino}-benzoic acid methyl ester (Example 1), except that 2,2-dimethyl-propionic acid 5-(6-amino-indol-1-ylmethyl)-tetrazol-1-ylmethyl ester (prepared in four steps from 6-nitro-indole) was used in place of 3-amino-benzoic acid methyl ester in step e, followed by reaction of the product obtained, in place of 2,2-dimethyl-propionic acid 5-(3-{2-[5-cyclopentyl-1-(3,3-dimethyl-2-oxo-butyl)-2-oxo-1,2-dihydro-3H-1,3,4-benzotriazepin-3-yl]-acetylamino}-phenyl)-tetrazol-2-ylmethyl ester (Example 10, step a), according to the method of Example 10, step b. $^1$H NMR (CDCl$_3$) 8.66 (1H, s), 7.87 (1H, s), 7.38 (3H, m), 7.24 (1H, m), 7.14 (1H, d), 6.93 (1H, d), 6.66 (1H, d), 6.45 (1H, d), 5.39 (2H, s), 4.60 (2H, q), 4.13 (2H, q), 2.78 (1H, m), 2.00 (1H, m), 1.70 (5H, m), 1.25 (4H, m), 1.15 (9H, s).

EXAMPLE 132

(3-{2-[5-Cyclohexyl-1-(3,3-dimethyl-2-oxo-butyl)-6-methyl-2-oxo-1,2-dihydro-3H-1,3,4-benzotriazepin-3-yl]-acetylamino}-phenyl)-acetic acid The title compound was obtained using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that (2-amino-6-methyl-phenyl)-cyclohexyl-methanone was used in step a instead of (2-amino-phenyl)-cyclohexyl-methanone, and (3-amino-phenyl)-acetic acid methyl ester replaced 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.22 (1H, s), 7.31 (4H, m), 7.10 (1H, d), 7.00 (1H, d), 6.84 (1H, d), 4.73 (1H, d), 4.56 (1H, d), 4.34 (1H, d), 4.16 (1H, d), 3.61 (2H, s), 2.63 (1H, m), 2.35 (3H, s), 2.00 (1H, br m), 1.75 (5H, m), 1.24 (13H, m).

EXAMPLE 133

[3-(2-{5-Cyclohexyl-1-[2-(1-methyl-cyclohexyl)-2-oxo-ethyl]-2-oxo-1,2-dihydro-3H-1,3,4-benzotriazepin-3-yl}-acetylamino)-phenyl]-acetic acid Step a. {5-Cyclohexyl-1-[2-(1-methyl-cyclohexyl)-2-oxo-ethyl]-2-oxo-1,2-dihydro-3H-1,3,4-benzotriazepin-3-yl}-acetic acid was obtained using steps a-d of the method employed in the preparation of [5-cyclohexyl-1-(3,3-dimethyl-2-oxo-butyl)-2-oxo-1,2-dihydro-3H-1,3,4-benzotriazepin-3-yl]-acetic acid (Example 1, step d) except that 2-bromo-1-(1-methyl-cyclohexyl)-ethanone (prepared from 1-methyl-cyclohexane-carboxylic acid in two steps) was used in step c instead of 1-bromo-3,3-dimethyl-butan-2-one. $^1$H NMR (CDCl$_3$) 10.80 (1H, br s), 7.45 (2H, m), 7.24 (1H, t), 6.96 (1H, d), 4.67 (2H, m), 4.22 (1H, d), 3.90 (1H, d), 2.82 (1H, m), 2.01-1.17 (23H, m).

Step b. The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that {5-cyclohexyl-1-[2-(1-methyl-cyclohexyl)-2-oxo-ethyl]-2-oxo-1,2-dihydro-3H-1,3,4-benzotriazepin-3-yl}-acetic acid (Example 133, step a) and (3-amino-phenyl)-acetic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.28 (1H, s), 7.47 (2H, m), 7.37-7.20 (4H, m), 7.00 (2H, t), 4.66 (2H, m), 4.25 (2H, m), 3.60 (2H, s), 2.78 (1H, m), 2.18-1.23 (20H, m), 1.19 (3H, s). The compound was further characterised as the N-methyl-D-glucamine salt. Found: C, 60.87; H, 7.66; N, 8.38%; $C_{33}H_{40}N_4O_5 \cdot C_7H_{17}NO_5 \cdot 0.9H_2O \cdot 0.6C_4H_8O_2$ requires: C, 60.84; H, 7.66; N, 8.37%.

EXAMPLE 134

[3-(2-{5-Cyclohexyl-1-[2-(1-methyl-cyclohexyl)-2-oxo-ethyl]-2-oxo-1,2-dihydro-3H-1,3,4-benzotriazepin-3-yl}-acetylamino)-phenylsulfanyl]-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that {5-cyclohexyl-1-[2-(1-methyl-cyclohexyl)-2-oxo-ethyl]-2-oxo-1,2-dihydro-3H-1,3,4-benzotriazepin-3-yl}-acetic acid (Example 133, step a) and (3-amino-phenylsulfanyl)-acetic acid ethyl ester were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.40 (1H, s), 7.48 (3H, m), 7.31 (2H, m), 7.20 (1H, t), 7.10 (1H, d), 7.02 (1H, d), 4.76 (1H, d), 4.58 (1H, d), 4.23 (2H, m), 3.67 (2H, s), 2.79 (1H, m), 1.99-1.25 (20H, m), 1.19 (3H, s). The compound was further characterised as the N-methyl-D-glucamine salt. Found: C, 58.41; H, 7.21; N, 8.18%; $C_{33}H_{40}N_4O_5S \cdot C_7H_{17}NO_5 \cdot 1.4H_2O$ requires: C, 58.17; H, 7.31; N, 8.48%.

EXAMPLE 135

5-{2-[5-Cyclohexyl-1-(3,3-dimethyl-2-oxo-butyl)-2-oxo-1,2-dihydro-3H-1,3,4-benzotriazepin-3-yl]-acetylamino}-1H-indole-2-carboxylic acid ethyl ester The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 5-amino-1H-indole-2-carboxylic acid ethyl ester was used instead of 3-amino-benzoic acid methyl ester in step e. $^1$H NMR (CDCl$_3$) 8.75 (1H, s), 8.24 (1H, s), 7.90 (1H, s), 7.48-7.19 (6H, m), 7.04 (1H, d), 4.68 (1H, d), 4.45 (1H, d), 4.41-4.25 (4H, m), 2.79 (1H, m), 2.05-1.39 (6H, m), 1.28-1.23 (16H, m). Found: C, 67.04; H, 6.98; N, 11.19%; $C_{33}H_{39}N_5O_5 \cdot 0.4CH_3CO_2C_2H_5$ requires: C, 66.93; H, 6.85; N, 11.28%.

EXAMPLE 136

2-[5-Cyclohexyl-1-(2-cyclopentyl-2-oxo-ethyl)-2-oxo-1,2-dihydro-3H-1,3,4-benzotriazepin-3-yl]-N-[3-(2-methyl-thiazol-4-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 3-(2-methyl-thiazol-4-yl)-phenylamine were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e. $^1$H NMR (CDCl$_3$) 8.39 (1H, s), 7.84 (1H, t), 7.61 (1H, d), 7.47 (3H, t), 7.30 (3H, m), 7.08 (1H, d), 4.57 (2H, m), 4.26 (2H, m), 2.95 (1H, m), 2.82 (1H, m), 2.77 (3H, s), 1.82-1.26 (18H, m). Found: C, 67.52; H, 6.42; N, 11.83%; $C_{33}H_{37}N_5O_3S.0.2H_2O$ requires: C, 67.44; H, 6.42; N, 11.92%.

EXAMPLE 137

4-(3-{2-[5-Cyclohexyl-1-(2-cyclopentyl-2-oxo-ethyl)-2-oxo-1,2-dihydro-3H-1,3,4-benzotriazepin-3-yl]-acetylamino}-phenyl)-thiazole-2-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 4-(3-amino-phenyl)-thiazole-2-carboxylic acid ethyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.51 (1H, s), 8.05 (1H, s), 7.88 (1H, s), 7.63 (1H, d), 7.49 (3H, m), 7.40-7.27 (2H, m), 7.07 (1H, d), 4.70 (1H, d), 4.45 (1H, d), 4.27 (2H, m), 2.95 (1H, m), 2.81 (1H, m), 2.06-1.56 (14H, m), 1.28 (4H, m). The compound was further characterised the N-methyl-D-glucamine salt. Found: C, 57.65; H, 6.41; N, 9.83%; $C_{33}H_{35}N_5O_5S.C_7H_{17}NO_5.1.5H_2O$ requires: C, 57.51; H, 6.63; N, 10.06%.

EXAMPLE 138

(3-{2-[1-(3,3-Dimethyl-2-oxo-butyl)-2-oxo-5-pyridin-2-yl-1,2-dihydro-3H-1,3,4-benzotriazepin-3-yl]-acetylamino}-phenylsulfanyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [1-(3,3-dimethyl-2-oxo-butyl)-2-oxo-5-pyridin-2-yl-1,2-dihydro-3H-1,3,4-benzotriazepin-3-yl]-acetic acid (Example 5, step a) and (3-amino-phenylsulfanyl)-acetic acid ethyl ester were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.63 (1H, m), 8.36 (1H, m), 8.02 (1H, m), 7.81 (1H, t), 7.36 (2H, m), 7.23 (3H, m), 7.11 (4H, m), 5.05 (1H, br s), 4.72 (2H, m), 4.36 (2H, m), 3.61 (2H, s), 1.27 (9H, s).

EXAMPLE 139

(3-{2-[1-(3,3-Dimethyl-2-oxo-butyl)-2-oxo-5-phenyl-1,2-dihydro-3H-1,3,4-benzotriazepin-3-yl]-acetylamino}-phenylsulfanyl)-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that [1-(3,3-dimethyl-2-oxo-butyl)-2-oxo-5-phenyl-1,2-dihydro-3H-1,3,4-benzotriazepin-3-yl]-acetic acid (Example 4, step a) and (3-amino-phenylsulfanyl)-acetic acid ethyl ester were used instead of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1, step d. $^1$H NMR (CDCl$_3$) 8.60 (1H, br s), 8.40 (1H, s), 7.63-7.40 (7H, m), 7.25-7.14 (6H, m), 4.76 (2H, m), 4.43 (2H, s), 3.58 (2H, s), 1.25 (9H, s). The compound was further characterised as the N-methyl-D-glucamine salt. Found: C, 50.02; H, 6.04; N, 7.59%; $C_{30}H_{30}N_5O_5S.C_7H_{17}NO_5.1.8C_4H_8O_2.2.2CH_2Cl_2$ requires: C, 50.06; H, 5.96; N, 7.55%.

EXAMPLE 140

2-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-oxazole-4-carboxylic acid methyl ester The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 2-(3-amino-phenyl)-oxazole-4-carboxylic acid methyl ester (prepared in three steps from serine methyl ester and 3-nitrobenzoic acid) was used instead of 3-amino-benzoic acid methyl ester in step e. $^1$H NMR (CDCl$_3$) 8.51 (1H, br s), 8.28 (1H, s), 8.00 (1H, t, 1.8), 7.86-7.83 (1H, m), 7.76-7.73 (1H, m), 7.54-7.34 (4H, m), 7.05 (1H, d, 1.8), 4.81 (1H, d, 17.7), 4.64 (1H, d, 17.7), 4.26-4.25 (2H, m), 3.96 (3H, s), 2.83-2.77 (1H, m), 2.05-1.70 (6H, m), 1.38-1.18 (13H, m). Found: C, 64.43; H, 6.10; N, 11.25%; $C_{33}H_{37}N_6O_5.0.8H_2O$ requires: C, 64.56; H, 6.33; N, 11.41%.

EXAMPLE 141

2-[5-Cyclohexyl-1-(3,3-dimethyl-2-oxo-butyl)-2-oxo-1,2-dihydro-3H-1,3,4-benzotriazepin-3-yl]-N-[3-(1-methyl-1H-imidazol-4-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 3-(1-methyl-1H-imidazol-4-yl)-phenylamine (prepared in three steps from 2-bromo-3'-nitroacetophenone) was used instead of 3-amino-benzoic acid methyl ester in step e. $^1$H NMR (CDCl$_3$) 8.25 (1H, br s), 7.85 (1H, t, 1.8), 7.54-7.44 (4H, m), 7.30-7.24 (2H, m), 7.19 (2H, m), 7.04 (1H, d, 7.8), 4.71-4.68 (2H, m), 4.37 (1H, d, 16.2), 4.21 (1H, d, 16.2), 3.72 (3H, s), 2.79 (1H, m), 2.05-1.72 (6H, m), 1.32-1.24 (13H, m). Found: C, 68.00; H, 6.90; N, 14.55%; C$_{32}$H$_{38}$N$_6$O$_3$.0.7H$_2$O requires: C, 67.77; H, 7.00; N, 14.82%.

EXAMPLE 142

(4-{2-[5-Cyclohexyl-1-(3,3-dimethyl-2-oxo-butyl)-2-oxo-1,2-dihydro-3H-1,3,4-benzotriazepin-3-yl]-acetylamino}-indazol-2-yl)-acetic acid The title compound was obtained as the trifluoroacetate salt by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that (4-amino-indazol-2-yl)-acetic acid tert-butyl ester (prepared in two steps from 4-nitro-indazole) was used instead of 3-amino-benzoic acid methyl ester in step e, followed by reaction of the product obtained, in place of (4-{2-[5-cyclohexyl-1-(3,3-dimethyl-2-oxo-butyl)-2-oxo-1,2-dihydro-3H-1,3,4-benzotriazepin-3-yl]-acetylamino}-indazol-1-yl)-acetic acid tert-butyl ester (Example 130, step a), according to the method of Example 130, step b. $^1$H NMR (CDCl$_3$) 10.04-9.95 (2H, br s), 9.06 (1H, s), 8.13 (1H, s), 7.53-7.20 (6H, m), 7.06 (1H, d, 6), 5.26 (2H, s), 4.80 (1H, d, 18), 4.63 (1H, d, 18), 4.29 (2H, s), 2.81-2.78 (1H, m), 2.07-1.67 (6H, m), 1.37-1.19 (13H, m). Found: C, 56.82; H, 5.42; N, 11.88%; C$_{31}$H$_{36}$N$_6$O$_5$.CF$_3$CO$_2$H.0.7H$_2$O requires: C, 56.72; H, 5.53; N, 12.03%.

EXAMPLE 143

2-[5-Cyclohexyl-1-(3,3-dimethyl-2-oxo-butyl)-2-oxo-1,2-dihydro-3H-1,3,4-benzotriazepin-3-yl]-N-{3-[methyl-(2-methylamino-ethyl)-amino]-phenyl}-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that {2-[(3-amino-phenyl)-methyl-amino]-ethyl}-methyl-carbamic acid tert-butyl ester (prepared in three steps from 3-fluoro-1-nitrobenzene and N,N'-dimethylethylenediamine) was used instead of 3-amino-benzoic acid methyl ester in step e, followed by reaction of the product obtained, in place of (3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-methyl-carbamic acid tert-butyl ester (Example 3, step d), according to the method of Example 3, step e. $^1$H NMR (CDCl$_3$) 8.09 (1H, s), 7.50-7.45 (2H, m), 7.29-7.24 (1H, m), 7.12-7.01 (3H, m), 6.53-6.46 (2H, m), 4.69-4.67 (2H, m), 4.38 (1H, d, 13.8), 4.17 (1H, d, 13.8), 3.50-3.44 (2H, m), 2.93 (3H, s), 2.86-2.74 (3H, m), 2.49 (3H, s), 2.04-1.58 (7H, m), 1.31-1.19 (13H, m). Found: C, 65.52; H, 7.53; N, 14.12%; C$_{32}$H$_{44}$N$_6$O$_5$.0.4CH$_2$Cl$_2$ requires: C, 65.58; H, 7.61; N, 14.17%.

EXAMPLE 144

2-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-oxazole-4-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid (Example 2) except that 2-(3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-oxazole-4-carboxylic acid methyl ester (Example 140) was used instead of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1). $^1$H NMR (CDCl$_3$) 8.58 (1H, m), 8.36 (1H, s), 8.08 (1H, t, 1.2), 7.83-7.81 (1H, m), 7.76-7.73 (1H, m), 7.54-7.32 (4H, m), 7.05 (1H, d, 8.1), 4.83 (1H, d, 17.4), 4.63 (1H, d, 17.4), 4.26 (2H, s), 2.84-2.78 (1H, m), 2.06-1.73 (6H, m), 1.36-1.18 (13H, m). The compound was further characterised as the N-methyl-D-glucamine salt. Found: C, 57.95; H, 6.68; N, 10.18%; C$_{32}$H$_{35}$N$_6$O$_5$.C$_7$H$_{17}$NO$_5$.1.6H$_2$O requires: C, 57.85; H, 6.87; N, 10.38%.

EXAMPLE 145

5-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-furan-2-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 5-(3-amino-phenyl)-furan-2-carboxylic acid methyl ester (prepared in two steps from 5-(3-nitrophenyl)-2-furoic acid) was used in place of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.34 (1H, br s), 7.63-7.50 (5H, m), 7.40-7.27 (3H, m), 7.05 (1H, d), 6.77 (1H, m), 4.79 (1H, d), 4.65 (1H, d), 4.39 (1H, d), 2.81 (1H, m), 2.05-1.72 (6H, m), 1.36-1.23 (13H, m). The compound was further characterised as the N-methyl-D-glucamine salt. Found: C, 59.03; H, 6.69; N, 8.48%; C$_{33}$H$_{36}$N$_4$O$_6$.C$_7$H$_{17}$NO$_5$.1.7H$_2$O requires: C, 59.34; H, 7.01; N, 8.65%.

EXAMPLE 146

3'-{2-[5-Cyclohexyl-1-(3,3-dimethyl-2-oxo-butyl)-2-oxo-1,2-dihydro-3H-1,3,4-benzotriazepin-3-yl]-acetylamino}-biphenyl-4-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 3'-amino-biphenyl-4-carboxylic acid methyl ester (prepared by catalytic hydrogenation of 3'-nitro-biphenyl-4-carboxylic acid methyl ester (Y. Matsushita, et. al., *Syn. Comm.*, (1994), 24, 3307)) was used in place of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.9 (1H, br s), 9.90 (1H, s), 8.02 (2H, d), 7.88 (1H, s), 7.71 (2H, d), 7.57-7.38 (5H, m), 7.26-7.16 (2H, m), 4.80-4.79 (2H, m), 4.37-4.31 (1H, m), 4.01 (1H, m), 2.87 (1H, m), 1.75-1.65 (6H, m), 1.34-1.13 (13H, m). The compound was further characterised as the N-methyl-D-glucamine salt. Found: C, 61.82; H, 7.05; N, 8.19%; $C_{35}H_{38}N_4O_5 \cdot C_7H_{17}NO_5 \cdot 1.7H_2O$ requires: C, 61.51; H, 7.17; N, 8.54%.

EXAMPLE 147

2-[5-Cyclohexyl-1-(3,3-dimethyl-2-oxo-butyl)-2-oxo-1,2-dihydro-3H-1,3,4-benzotriazepin-3-yl]-N-[3-(2,4-dioxo-thiazolidin-5-ylidenemethyl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 5-(3-amino-benzylidene)-thiazolidine-2,4-dione (prepared in two steps from 3-nitro-benzaldehyde) was used in place of 3-amino-benzoic acid methyl ester in step e. $^1$H NMR (DMSO-d$_6$) 9.84 (1H, br s), 7.62-7.45 (4H, m), 7.33-7.15 (4H, m), 4.80-4.76 (2H, m), 4.32-4.30 (1H, br m), 4.03-3.94 (1H, br m), 2.87 (1H, m), 1.86-1.53 (6H, m), 1.34-1.10 (13H, m). Found: C, 61.16; H, 5.89; N, 11.08%; $C_{32}H_{44}N_6O_5S \cdot 1.4H_2O$ requires: C, 61.34; H, 6.07; N, 11.18%.

EXAMPLE 148

2-(3-{2-[5-Cyclohexyl-1-(2-cyclopentyl-2-oxo-ethyl)-2-oxo-1,2-dihydro-3H-1,3,4-benzotriazepin-3-yl]-acetylamino}-phenyl)-oxazole-4-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 2-(3-amino-phenyl)-oxazole-4-carboxylic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.60 (1H, s), 8.35 (1H, s), 8.08 (1H, s), 7.83-7.81 (1H, m), 7.74-7.72 (1H, m), 7.61-7.32 (4H, m), 7.09 (1H, d), 4.73 (1H, d), 4.49 (1H, d), 4.26 (2H, s), 3.01-2.91 (1H, m), 2.81 (1H, m), 2.13-1.58 (14H, m), 1.31-1.25 (4H, m). The compound was further characterised as the N-methyl-D-glucamine salt. Found: C, 57.97; H, 6.50; N, 9.95%; $C_{33}H_{35}N_5O_6 \cdot C_7H_{17}NO_5 \cdot 1.8H_2O$ requires: C, 58.20; H, 6.79; N, 10.18%.

EXAMPLE 149

5-(3-{2-[5-Cyclohexyl-1-(2-cyclopentyl-2-oxo-ethyl)-2-oxo-1,2-dihydro-3H-1,3,4-benzotriazepin-3-yl]-acetylamino}-phenyl)-furan-2-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 5-(3-amino-phenyl)-furan-2-carboxylic acid methyl ester were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.35 (1H, s), 7.63-7.50 (5H, m), 7.41-7.32 (3H, m), 7.11 (1H, d), 6.80 (1H, d), 4.71 (1H, d), 4.51 (1H, d), 4.45 (1H, d), 4.24 (1H, d), 3.01-2.91 (1H, m), 2.85-2.79 (1H, m), 2.06-1.60 (14H, m), 1.31-1.30 (4H, m). The compound was further characterised as the N-methyl-D-glucamine salt. Found: C, 60.14; H, 6.70; N, 8.49%; $C_{34}H_{36}N_4O_6 \cdot C_7H_{17}NO_5 \cdot 1.5H_2O$ requires: C, 60.16; H, 6.89; N, 8.56%.

EXAMPLE 150

2-[5-Cyclohexyl-1-(3,3-dimethyl-2-oxo-butyl)-2-oxo-1,2-dihydro-3H-1,3,4-benzotriazepin-3-yl]-N-[3-(2-methylamino-thiazol-4-yl)-phenyl]-acetamide The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [4-(3-amino-phenyl)-thiazol-2-yl]-methyl-amine (prepared in two steps from 2-bromo-3'-nitroacetophenone) was used in place of 3-amino-benzoic acid methyl ester in step e. $^1$H NMR (CDCl$_3$) 8.28 (1H, s), 7.77 (1H, s), 7.55-7.25 (7H, m), 7.04 (1H, d), 6.71 (1H, s), 5.12 (1H, d), 4.77 (1H, d), 4.67 (1H, d), 4.36 (1H, d), 4.22 (1H, d), 3.04 (3H, d), 2.79 (1H, m), 2.05-1.73 (6H, m), 1.45-1.19 (13H, m). Found: C, 64.64; H, 6.57; N, 14.05%; $C_{32}H_{38}N_6O_3S \cdot 0.5H_2O$ requires: C, 64.57; H, 6.59; N, 14.12%.

EXAMPLE 151

3'-{2-[5-Cyclohexyl-1-(3,3-dimethyl-2-oxo-butyl)-2-oxo-1,2-dihydro-3H-1,3,4-benzotriazepin-3-yl]-acetylamino}-biphenyl-3-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 3'-amino-biphenyl-3-carboxylic acid ethyl ester (prepared in two steps from 3-nitrophenylboronic acid) was used instead of 3-amino-benzoic acid methyl ester in step e, followed by reaction of the product obtained, in place of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), according to the method of Example 1,

87 step d. ¹H NMR (CDCl₃) 8.40 (1H, s), 8.29 (1H, t), 8.12-8.08 (1H, m), 7.85-7.81 (1H, m), 7.64-7.61 (1H, m), 7.57-7.47 (4H, m), 7.41-7.27 (3H, m), 7.06 (1H, d), 4.80 (1H, d), 4.65 (1H, d), 4.39 (1H, d), 4.25 (1H, d), 2.84-2.77 (1H, m), 2.02-1.70 (6H, m), 1.44-1.16 (13H, m). The compound was further characterised as the N-methyl-D-glucamine salt. Found: C, 61.19; H, 7.07; N, 8.48%; $C_{35}H_{38}N_4O_5 \cdot C_7H_{17}NO_5 \cdot 1.9H_2O$ requires: C, 61.21; H, 7.19; N, 8.50%.

EXAMPLE 152

(3-{2-[1-(2-tert-Butyl-allyl)-5-cyclohexyl-2-oxo-1,2-dihydro-3H-1,3,4-benzotriazepin-3-yl]-acetylamino}-phenyl)-acetic acid The title compound was obtained by using the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2-bromomethyl-3,3-dimethyl-but-1-ene (E. Lee, et al., *J. Org. Chem.* (1994), 59, 1444) was used instead of 1-bromo-3,3-dimethyl-butan-2-one in step c, and (3-amino-phenyl)-acetic acid methyl ester replaced 3-aminobenzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. ¹H NMR (DMSO-d₆) 12.10 (1H, br s), 9.79 (1H, s), 7.58-7.34 (5H, m), 7 21 (2H, m), 6.90 (1H, d), 4.79 (1H, s), 4.68 (2H, m), 4.32 (2H, br t), 3.95 (1H, d), 3.48 (2H, s), 2.80 (1H, m), 2.00-1.10 (10H, m), 1.04 (9H, s). The compound was further characterised as the N-methyl-D-glucamine salt. Found: C, 58.80; H, 7.60; N, 8.73%; $C_{31}H_{38}N_4O_4 \cdot C_7H_{17}NO_5 \cdot 3.0H_2O$ requires: 58.52; H, 7.88; N, 8.97%.

EXAMPLE 153

5-(3-{2-[1-(2-tert-Butyl-allyl)-5-cyclohexyl-2-oxo-1,2-dihydro-3H-1,3,4-benzotriazepin-3-yl]-acetylamino]-phenyl)-furan-2-carboxylic acid The title compound was obtained by the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that 2-bromomethyl-3,3-dimethyl-but-1-ene was used instead of 1-bromo-3,3-dimethyl-butan-2-one in step c, and 5-(3-amino-phenyl)-furan-2-carboxylic acid methyl ester replaced 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. ¹H NMR (DMSO-d₆) 13.00 (1H, br s), 10.01 (1H, s), 7.59-7.34 (7H, m), 7.25 (2H, m), 7.03 (1H, d), 4.80 (1H, s), 4.68 (1H, s), 4.60-4.04 (2H, br m), 4.30 (2H, br m), 2.90 (1H, m), 2.00-1.20 (10H, m), 1.04 (9H, s). The compound was further characterised as the N-Methyl-D-glucamine salt. Found: C, 58.88; H, 7.03; N, 8.13%; $C_{34}H_{38}N_4O_6 \cdot C_7H_{17}NO_5 \cdot 3.0H_2O$ requires: C, 59.19; H, 7.39; N, 8.41%.

88

EXAMPLE 154

3'-{2-[5-Cyclohexyl-1-(3,3-dimethyl-2-oxo-butyl)-2-oxo-1,2-dihydro-3H-1,3,4-benzotriazepin-3-yl]-acetylamino}-biphenyl-2-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 3'-amino-biphenyl-2-carboxylic acid methyl ester (prepared in two steps from 3-nitrophenylboronic acid) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. ¹H NMR (CDCl₃) 8.52 (1H, s), 7.91 (1H, d), 7.63-7.20 (9H, m), 7.11 (1H, d), 7.03 (1H, d), 4.82 (1H, d), 4.61 (1H, d), 4.30 (1H, d), 4.16 (1H, d), 2.82-2.75 (1H, m), 2.05-1.57 (6H, m), 1.44-1.00 (13H, m). The compound was further characterised as the N-methyl-D-glucamine salt. Found: C, 61.11; H, 6.88; N, 8.29%; $C_{35}H_{38}N_4O_5 \cdot C_7H_{17}NO_5 \cdot 1.8H_2O$ requires: C, 61.40; H, 7.18; N, 8.53%.

EXAMPLE 155

2-Acetylamino-3-(3-{2-[5-cyclohexyl-1-(3,3-dimethyl-2-oxo-butyl)-2-oxo-1,2-dihydro-3H-1,3,4-benzotriazepin-3-yl]-acetylamino}-phenyl)-acrylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 2-acetylamino-3-(3-amino-phenyl)-acrylic acid methyl ester (prepared in three steps from 3-nitro-benzaldehyde and N-acetyl-glycine) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. ¹H NMR (CDCl₃) 8.43 (1H, s), 7.99 (1H, s), 7.61-7.00 (9H, m), 4.80 (1H, d), 4.61 (1H, d), 4.22-4.16 (2H, m), 2.79 (1H, m), 2.19-1.65 (9H, m), 1.44-1.19 (13H, m). The compound was further characterised as the N-methyl-D-glucamine salt. Found: C, 56.61; H, 6.99; N, 9.44%; $C_{33}H_{39}N_5O_6 \cdot C_7H_{17}NO_5 \cdot 3.2H_2O$ requires: C, 56.22; H, 7.36; N, 9.83%.

EXAMPLE 156

3-{2-[1-(tert-Butylcarbamoyl-methyl)-5-cyclohexyl-2-oxo-1,2-dihydro-3H-1,3,4-benzotriazepin-3-yl]-acetylamino}-benzoic acid Step a. [1-(tert-Butylcarbamoyl-methyl)-5-cyclohexyl-2-oxo-1,2-dihydro-3H-1,3,4-benzotriazepin-3-yl]-acetic acid ethyl ester was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1, step e), except that (5-cyclohexyl-3-ethoxycarbonylmethyl-2-oxo-2,3-dihydro-3H-1,3,4-benzotriazepin-1-yl)-acetic acid (Example 68, step b) and tert-butylamine were used instead of [5-cyclohexyl-1-(3,3-dimethyl-2-oxo-butyl)-2-oxo-1,2-dihydro-3H-1,3,4- benzotriazepin-3-yl]-acetic acid (Example 1, step d) and 3-amino-benzoic acid methyl ester respectively. $^1$H NMR (CDCl$_3$) 7.40 (2H, m), 7.22 (2H, m), 6.63 (1H, s), 4.27-4.09 (6H, m), 2.75 (1H, m), 2.00-1.55 (6H, m), 1.30-1.20 (16H, m).

Step b. The title compound was obtained using steps d and e of the method employed in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [1-(tert-butylcarbamoyl-methyl)-5-cyclohexyl-2-oxo-1,2-dihydro-3H-1,3,4-benzotriazepin-3-yl]-acetic acid ethyl ester (Example 156, step a) was used in step d instead of [5-cyclohexyl-1-(3,3-dimethyl-2-oxo-butyl)-2-oxo-1,2-dihydro-3H-1,3,4-benzotriazepin-3-yl]-acetic acid ethyl ester (Example 1, step c), followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.59 (1H, s), 7.95 (1H, d), 7.78-7.75 (2H, m), 7.54-7.45 (2H, m), 7.40-7.28 (3H, m), 6.49 (1H, s), 4.35-4.09 (4H, m), 2.81 (1H, m br), 2.05 (1H, br), 1.88 (1H, br), 1.80-1.60 (4H, m), 1.35-1.20 (13H, m). The compound was further characterised as the N-methyl-D-glucamine salt. Found: C, 55.95; H, 7.01; N, 10.29%; C$_{29}$H$_{35}$N$_5$O$_5$.C$_7$H$_{17}$NO$_5$.0.7CH$_2$Cl$_2$ requires C, 55.92; H, 6.83; N, 10.66%.

EXAMPLE 157

5-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-thiophene-2-carboxylic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that 5-(3-amino-phenyl)-thiophene-2-carboxylic acid methyl ester (prepared in three steps from 5-bromo-2-thiophenecarboxylic acid) was used instead of 3-amino-benzoic acid methyl ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.47 (1H, s), 7.85 (1H, d), 7.62-7.47 (4H, m), 7.37-7.27 (4H, m), 7.06 (1H, d), 4.81 (1H, d), 4.64 (1H, d), 4.36 (1H, d), 4.25 (1H, d), 2.84-2.78 (1H, m), 2.07-1.70 (6H, m), 1.30-1.19 (13H, m). The compound was further characterised as the N-methyl-D-glucamine salt. Found: C, 58.29; H, 6.63; N, 8.22%; C$_{33}$H$_{36}$N$_4$O$_5$S.C$_7$H$_{17}$NO$_5$.1.7H$_2$O requires: C, 58.10; H, 6.88; N, 8.46%.

EXAMPLE 158

[2-(3-{2-[5-Cyclohexyl-1-(3,3-dimethyl-2-oxo-butyl)-2-oxo-1,2-dihydro-3H-1,3,4-benzotriazepin-3-yl]-acetylamino}-phenyl)-pyrrol-1-yl]-acetic acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [2-(3-amino-phenyl)-pyrrol-1-yl]-acetic acid methyl ester (prepared in four steps from 1-(tert-butoxycarbonyl)-pyrrole-2-boronic acid and 1-bromo-3-nitrobenzene) was used instead of 3-amino-benzoic acid methyl, ester in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (CDCl$_3$) 8.46 (1H, s), 7.47-7.43 (3H, m), 7.32-7.23 (3 h, m), 7.09-7.00 (2H, m), 6.77-6.75 (1H, m), 6.27-6.21 (2H, m), 4.79-4.56 (4H, m), 4.31 (1H, d), 4.21 (1H, d), 2.81-2.75 (1H, m), 2.05-1.71 (6H, m), 1.36-1.19 (13H, m). The compound was further characterised as the N-methyl-D-glucamine salt. Found: C, 59.36; H, 7.02; N, 9.65%; C$_{34}$H$_{39}$N$_5$O$_5$.C$_7$H$_{17}$NO$_5$.2.2H$_2$O requires: C, 59.12; H, 7.31; N, 10.09%.

EXAMPLE 159

4-(3-{2-[5-Cyclohexyl-1-(2-cyclopentyl-2-oxo-ethyl)-2-oxo-1,2-dihydro-3H-1,3,4-benzotriazepin-3-yl]-acetylamino}-phenyl-butyric acid The title compound was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), except that [5-cyclohexyl-1-(2-cyclopentyl-2-oxo-ethyl)-2-oxo-1,2-dihydro-3H-1,3,4-benzotriazepin-3-yl]-acetic acid (Example 22, step a) and 4-(3-amino-phenyl)-butyric acid methyl ester (J. P. Weichert, et. al., *J. Med. Chem.* (1995), 38, 636) were used in place of [5-cyclohexyl-1-(3,3-dimethyl-2-oxo-butyl)-2-oxo-1,2-dihydro-3H-1,3,4-benzotriazepin-3-yl]-acetic acid (Example 1, step d) and 3-amino-benzoic acid methyl ester respectively in step e, followed by reaction of the product obtained, in place of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1), according to the method of Example 2. $^1$H NMR (DMSO-d$_6$) 12.00 (1H, br s), 9.67 (1H, s), 7.50 (2H, m), 7.32-7.15 (5H, m), 6.84 (1H, d), 4.63 (2H, m), 4.25 (1H, br d), 3.99 (1H, br d), 3.00 (1H, m), 2.88 (1H, m), 2.52 (2H, t), 2.19 (2H, t), 2.00-1.00 (20H, m). The compound was further characterised as the N-methyl-D-glucamine salt. Found: C, 59.52; H, 7.41; N, 8.62%; C$_{33}$H$_{40}$N$_4$O$_5$.C$_7$H$_{17}$NO$_5$.2.0H$_2$O requires: C, 59.76; H, 7.65; N, 8.71%.

EXAMPLE 160

2-(5-Cyclohexyl-1-methyl-2-oxo-4-oxy-1,2-dihydro-3H-1,3,4-benzotriazepin-3-yl)-N-phenyl-acetamide Step a. 2-(5-Cyclohexyl-1-methyl-2-oxo-1,2-dihydro-3H-1,3,4-benzotriazepin-3-yl)-N-phenyl-acetamide was obtained by the method used in the preparation of 3-{2-[5-cyclohexyl-1-(3,3-dimethyl-2-oxo-butyl)-2-oxo-1,2-dihydro-3H-1,3,4-benzotriazepin-3-yl]-acetylamino}-benzoic acid methyl ester (Example 1) except that iodomethane was used in step c instead of 1-bromo-3,3-dimethyl-butane-2-one, and aniline was used in step e instead of 3-amino-benzoic acid methyl ester. $^1$H NMR (CDCl$_3$) 8.25 (1H, s), 7.55 (1H, t), 7.44 (1H, d), 7.32-7.21 (6H, m), 7.06 (1H, t), 4.47 (1H, d), 4.14 (1H, d), 3.29 (3H, s), 2.76 (1H, m), 2.00-1.00 (10H, m).

Step b. To a solution of the product of step a (390 mg, 1.00 mmol) in DCM (10 ml) was added 3-chloroperoxybenzoic acid (1.23 g of 70%, 5.00 mmol) and the solution stirred at room temperature for 16 hr. After dilution with DCM (50 ml) the solution was washed with 5% Na$_2$CO$_3$ (2×50 ml), then brine (50 ml). The organic phase was dried over MgSO$_4$, and the solvent evaporated under reduced pressure. The residue was purified by flash column chromatography (EtOAc-DCM (1:9) to afford the product as a white solid (94 mg, 23%) $^1$H NMR (CDCl$_3$) 8.17 (1H br.s), 7.51 (2H, d), 7.39-7.22 (6H, m), 7.06 (1H, m), 4.60 (1H, d), 4.23 (1H, d), 3.39 (3H, s), 3.15 (1H, m), 2.00-1.00 (10H, m). Found: C, 67.73; H, 6.46; N, 13.71%; C$_{23}$H$_{26}$N$_4$O$_3$ requires: C, 67.96; H, 6.45; N, 13.78%.

Gastrin (CCK$_2$) Antagonist Activity

The compounds of the examples were tested for gastrin (CCK$_2$) antagonist activity in an immature rat stomach assay. The procedure was as follows:

The oesophagus of immature rats (33-50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4-5 ml of unbuffered solution was flushed through the stomach to ensure the preparation was not leaking. The stomach was lowered into a jacketed organ bath containing 40 ml of buffered solution containing 3×10$^{-8}$ M 5-methylfurmethide, maintained at 37° and gassed vigorously with 95% O$_2$/5% CO$_2$. The stomach was continuously perfused at a rate of 1 ml min$^{-1}$ with unbuffered solution gassed with 100% O$_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et al., *Br. J. Pharmacol.*, 1985, 86, 581.

The results obtained at gastrin (CCK$_2$) receptors are set out in the following Table.

| Example No | Structure | pKB rat stomach |
|---|---|---|
| 1 | | 8.55 ± 0.32 |
| 2 | | 9.18 ± 0.31 |
| 3 | | 8.1 ± 0.13 |

-continued
| Example No | | pKB rat stomach |
|---|---|---|
| 4 | 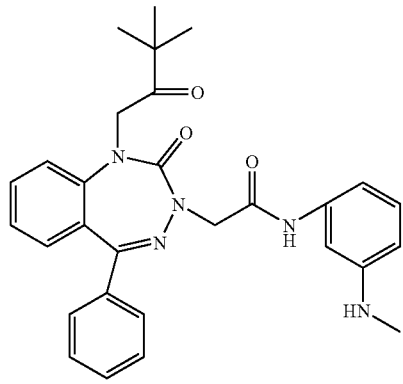 | 6.88 ± 0.29 |
| 5 | 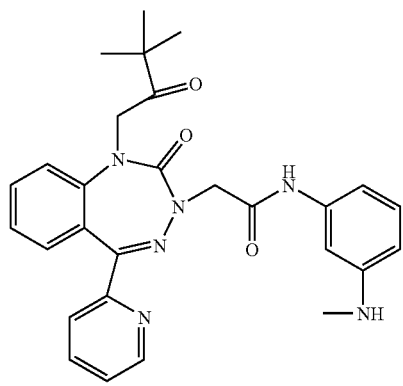 | 6.62 ± 0.27 |
| 6 | 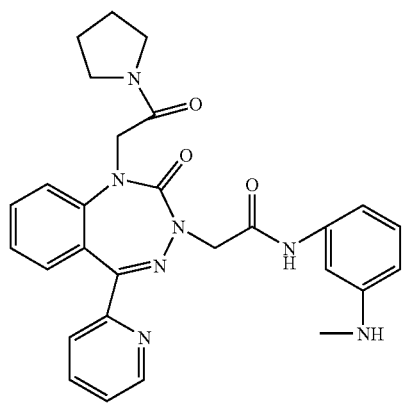 | 5.98 ± 0.27 |
| 7 | 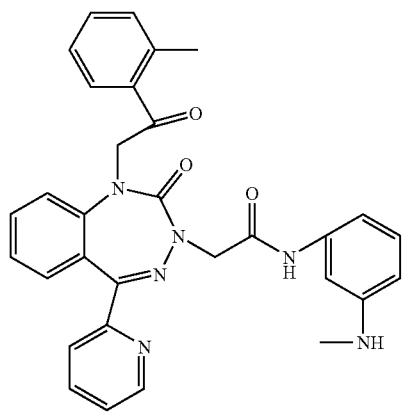 | 7.30 ± 0.26 |

-continued
| Example No | pKB rat stomach |
|---|---|
| 8 | 6.58 ± 0.24 |
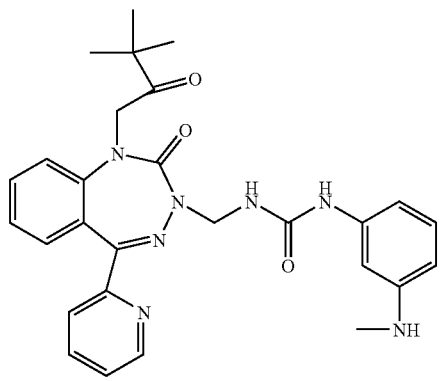
| | |
|---|---|
| 9 | 7.12 ± 0.26 |
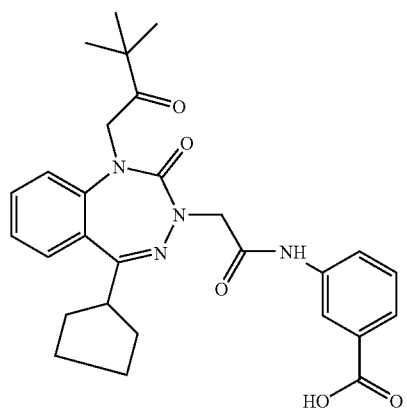
| | |
|---|---|
| 10 | 7.05 ± 0.18 |
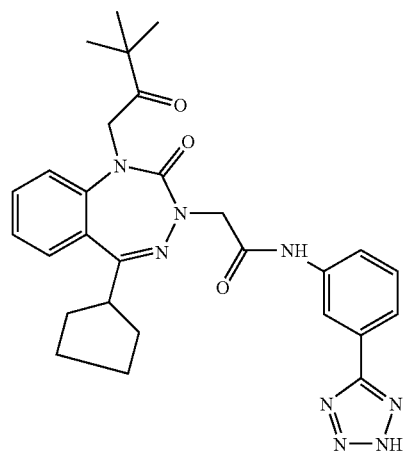

-continued
| Example No | | pKB rat stomach |
|---|---|---|
| 11 | 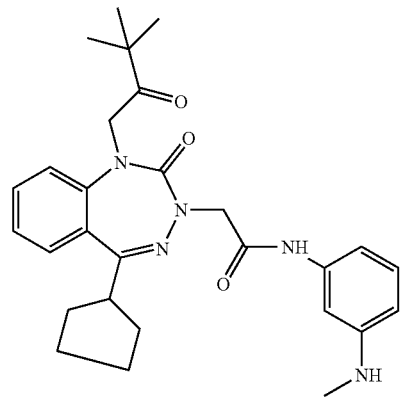 | 7.35 ± 0.17 |
| 12 | 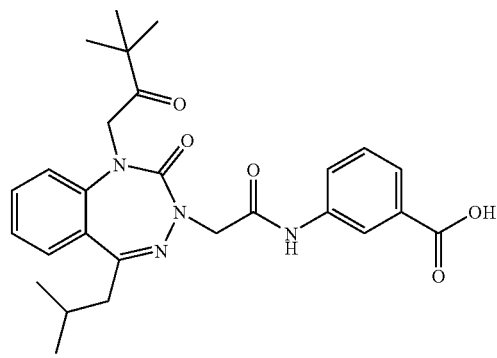 | |
| 13 | 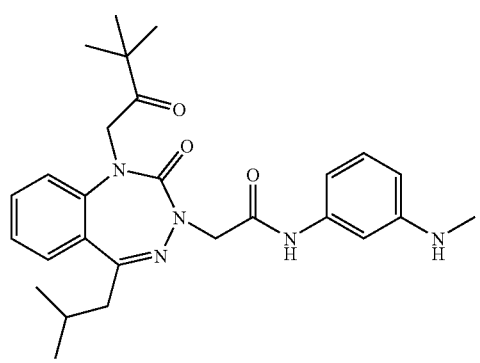 | 7.29 ± 0.28 |
| 14 | 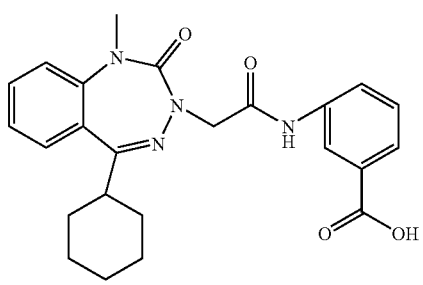 | |

-continued
| Example No | | pKB rat stomach |
|---|---|---|
| 15 | 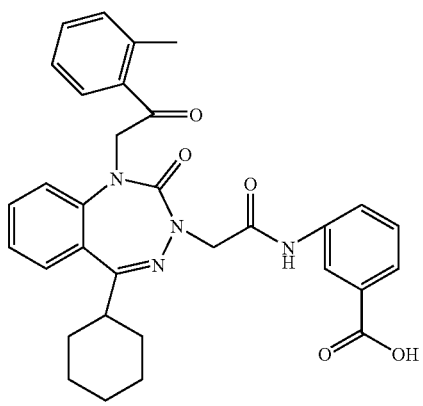 | 8.02 ± 0.27 |
| 16 | 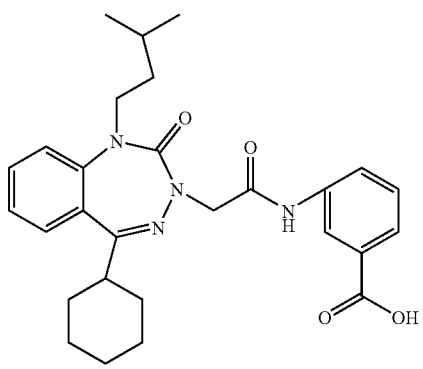 | 7.37 ± 0.38 |
| 17 | 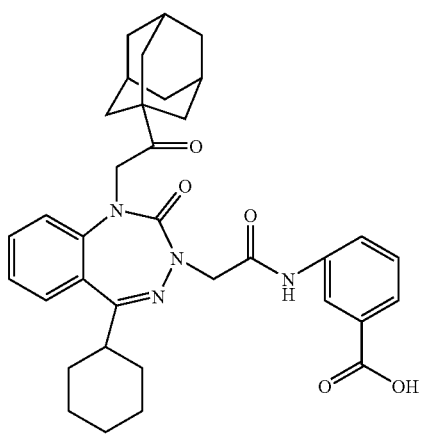 | 6.94 ± 0.18 |
| 18 | 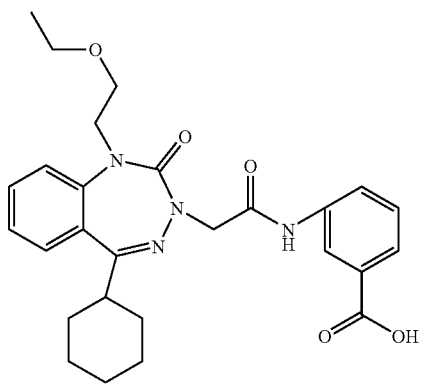 | |

-continued
| Example No | | pKB rat stomach |
|---|---|---|
| 19 | 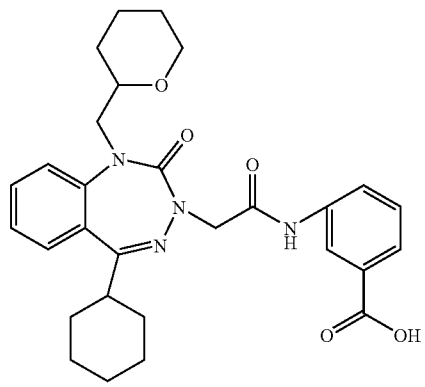 | |
| 20 | 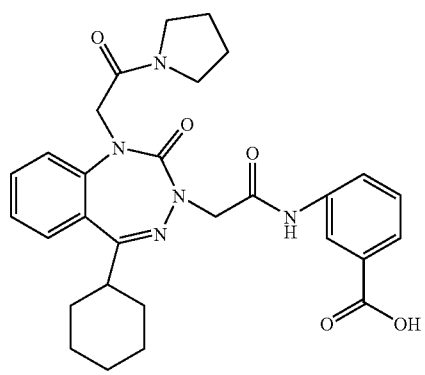 | 7.23 ± 0.41 |
| 21 | 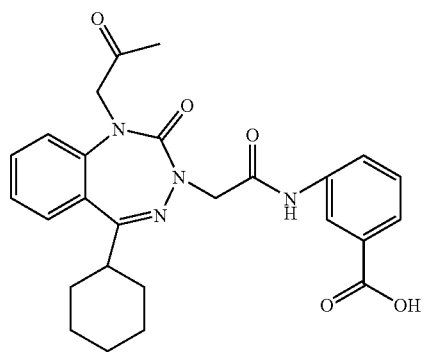 | |
| 22 | 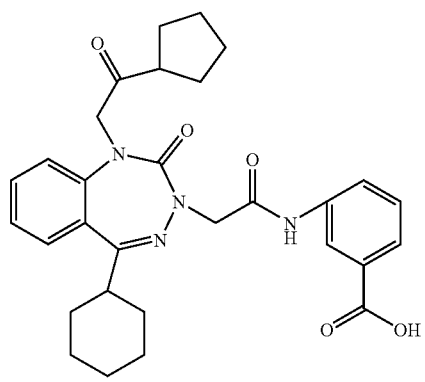 | 8.73 ± 0.44 |

-continued
| Example No | pKB rat stomach |
|---|---|
| 23 | 7.95 ± 0.26 |
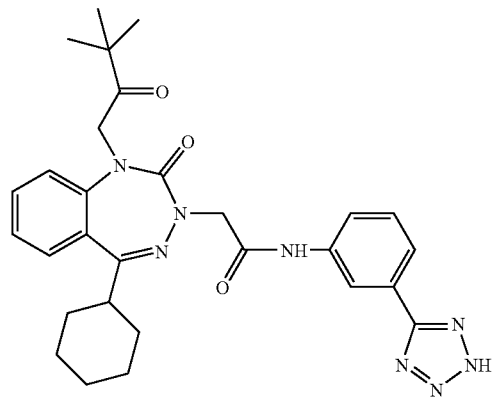
24
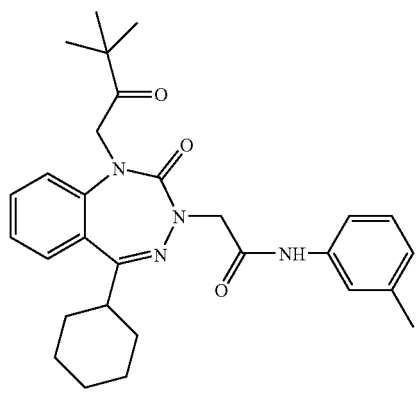
25
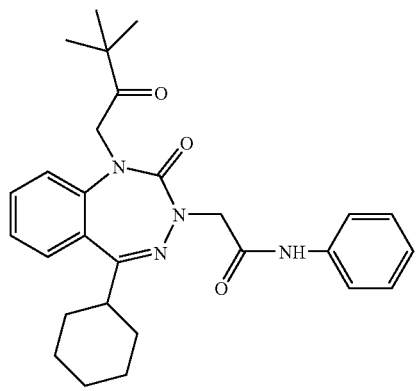

-continued
| Example No | pKB rat stomach |
|---|---|
| 26 | 6.34 ± 0.31 |
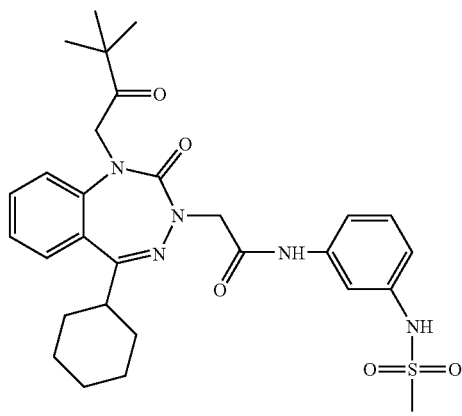
| | |
|---|---|
| 27 | 6.84 ± 0.26 |
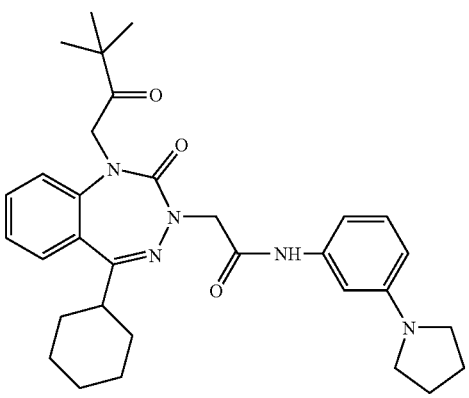
28
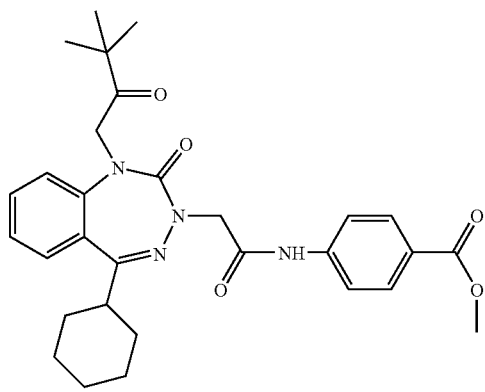

| Example No | | pKB rat stomach |
|---|---|---|
| 29 | 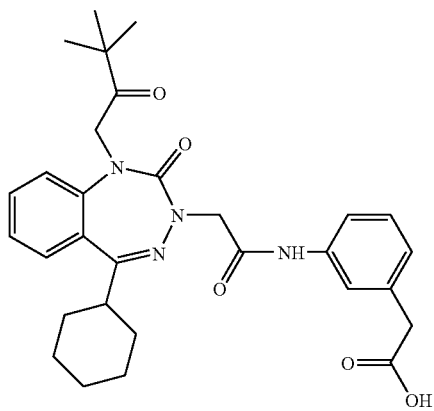 | 7.21 ± 0.25 |
| 30 | 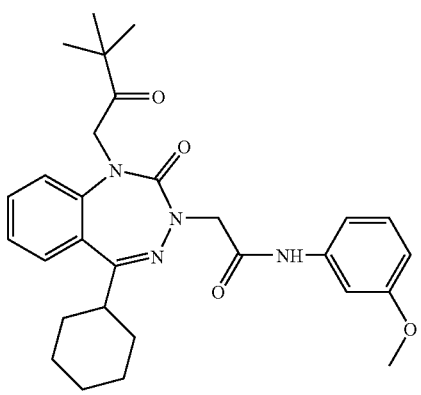 | |
| 31 | 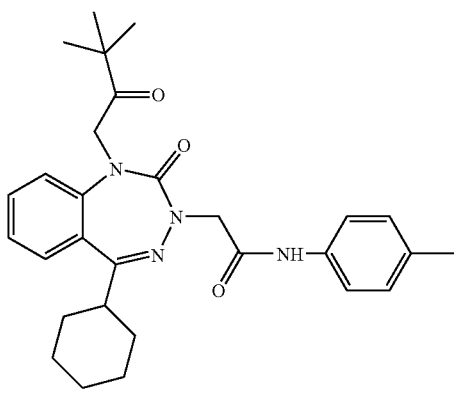 | |
| 32 | 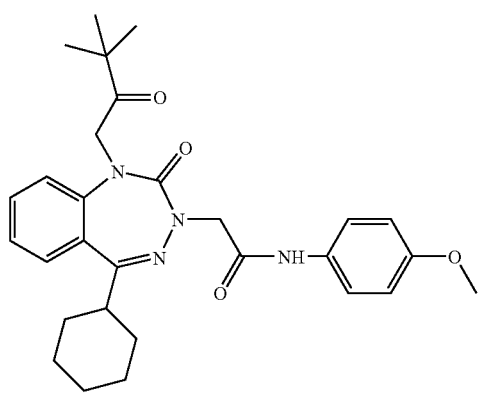 | 7.11 ± 0.29 |

-continued
| Example No | | pKB rat stomach |
|---|---|---|
| 33 | 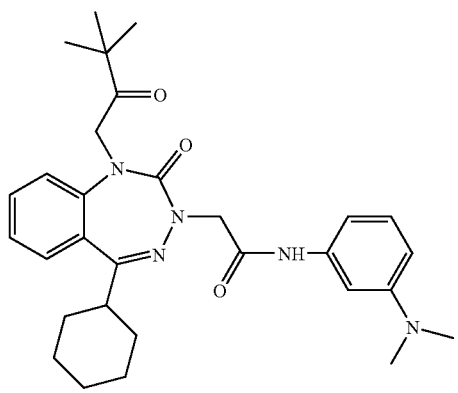 | 7.04 ± 0.28 |
| 34 | 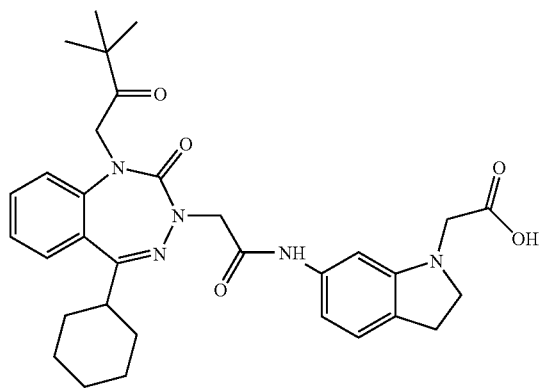 | 7.80 ± 0.30 |
| 35 | 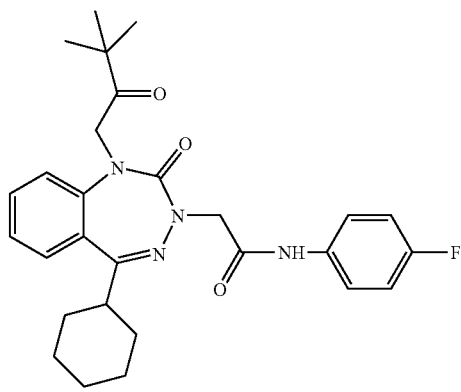 | 7.64 ± 0.45 |
| 36 | 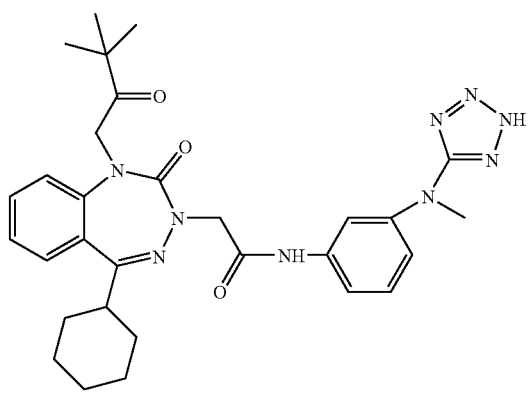 | |

-continued
| Example No | pKB rat stomach |
|---|---|
| 37 | |
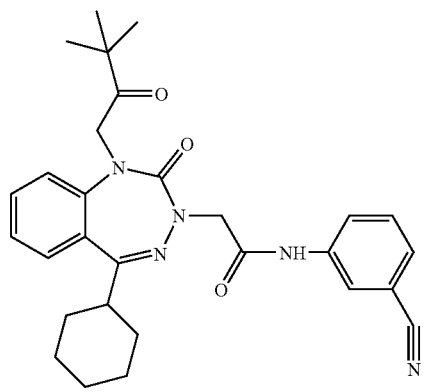
| 38 | 8.18 ± 0.36 |
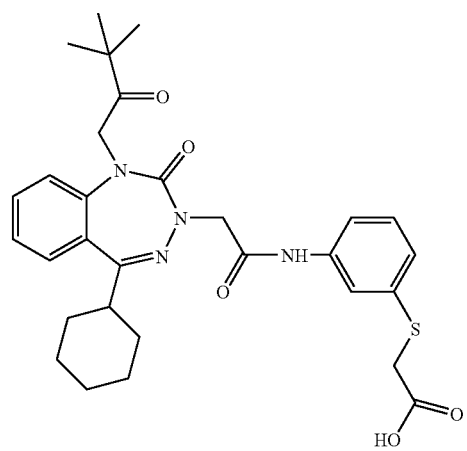
| 39 | 8.12 ± 0.18 |
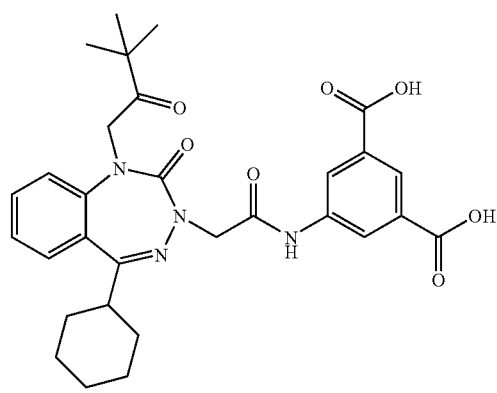

-continued
| Example No | pKB rat stomach |
|---|---|
| 40 | 7.64 ± 0.40 |
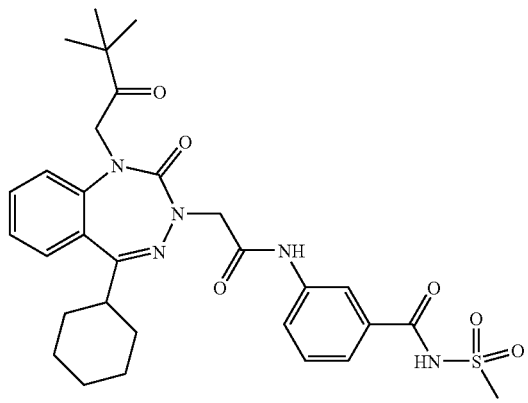
41
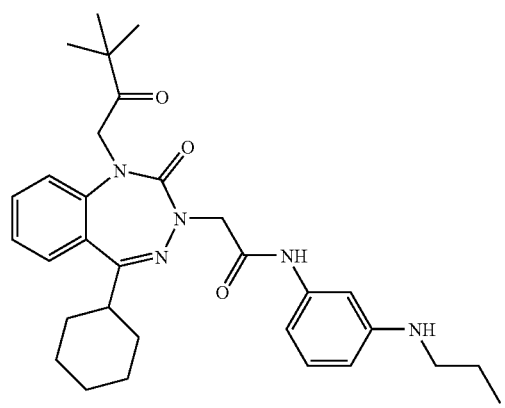
42 | 6.98 ± 0.40
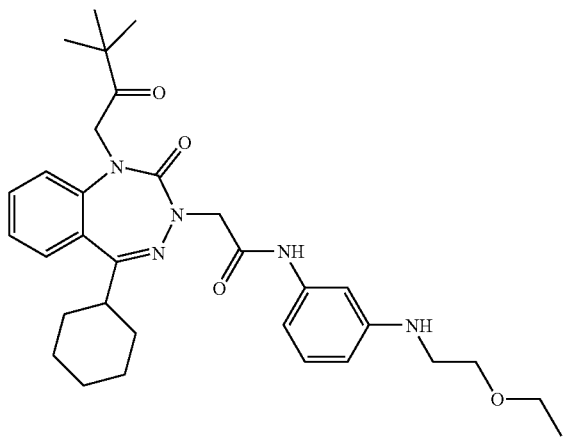

-continued
| Example No | | pKB rat stomach |
|---|---|---|
| 43 | 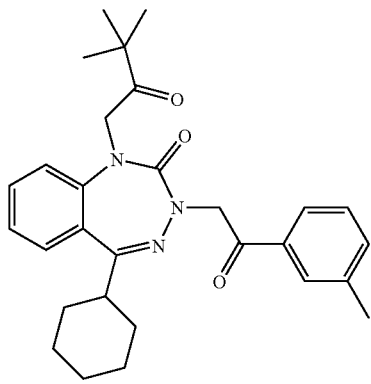 | |
| 44 | 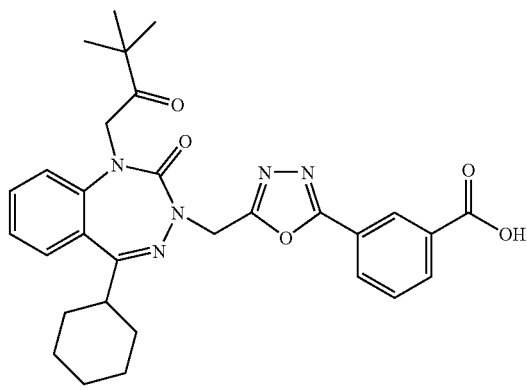 | |
| 45 | 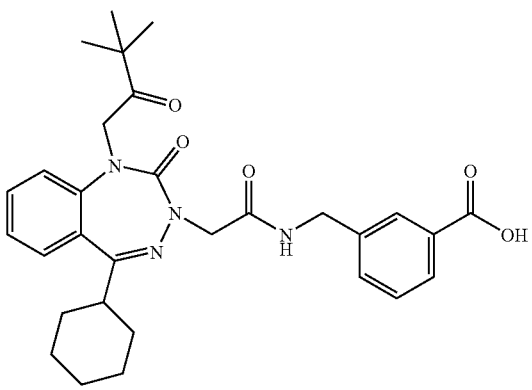 | 7.03 ± 0.30 |
| 46 | 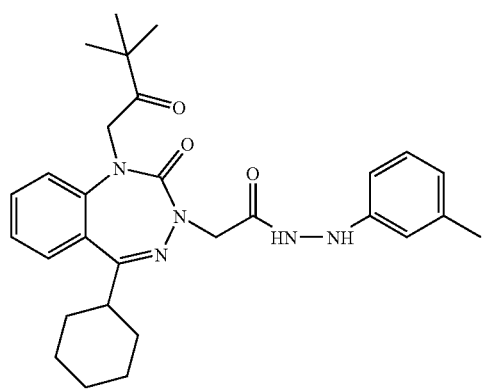 | 6.76 ± 0.36 |

-continued
| Example No | pKB rat stomach |
|---|---|
| 47 | |
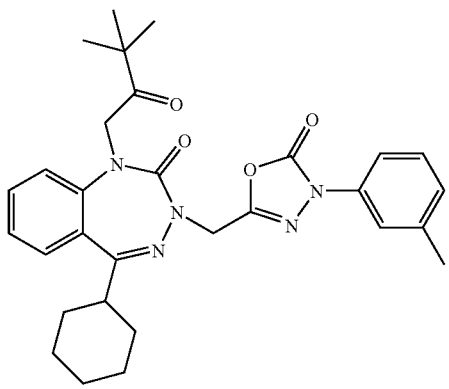
| 48 | 7.77 ± 0.28 |
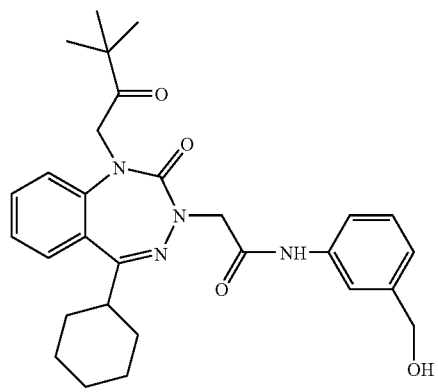
| 49 | 7.00 ± 0.27 |
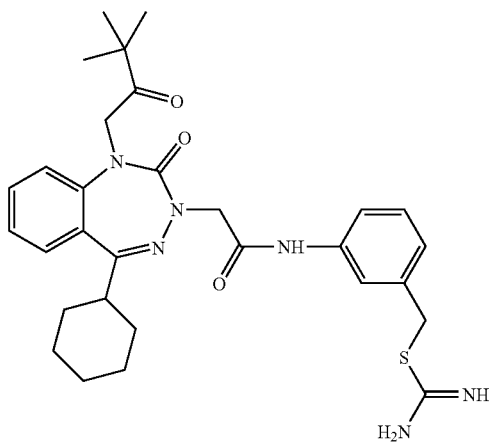

-continued
| Example No | | pKB rat stomach |
|---|---|---|
| 50 | 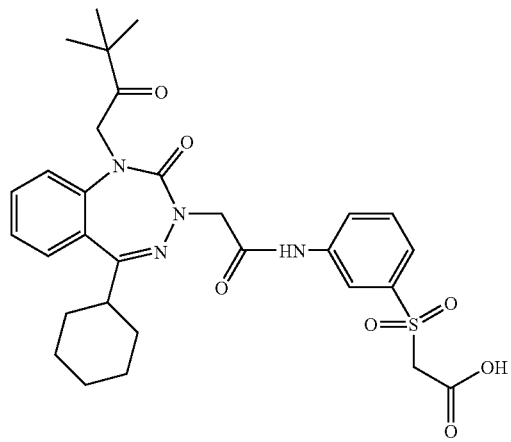 | 7.96 ± 0.34 |
| 51 | 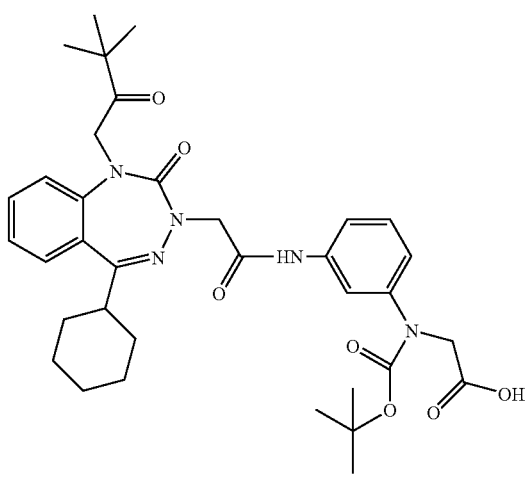 | |
| 52 | 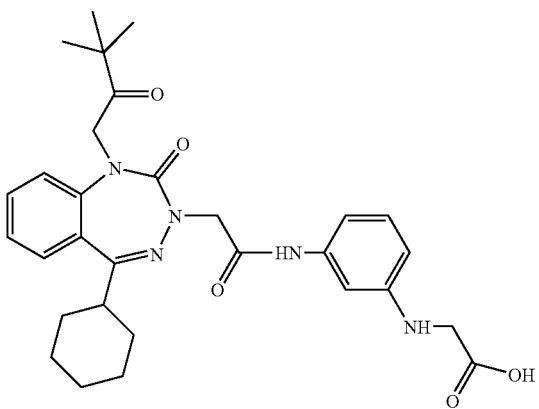 | 7.49 ± 0.24 |

-continued
| Example No | | pKB rat stomach |
|---|---|---|
| 53 | 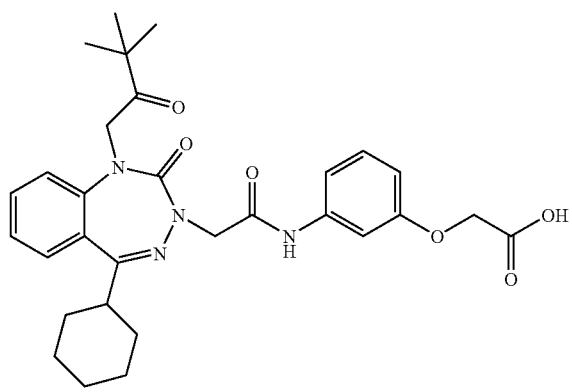 | 7.68 ± 0.34 |
| 54 | 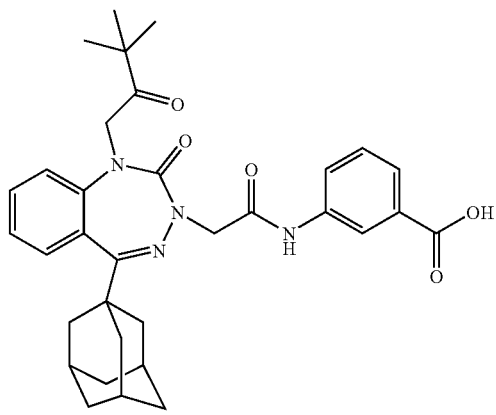 | 7.77 ± 0.43 |
| 55 | 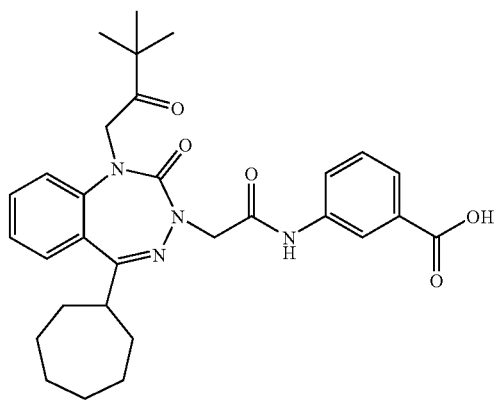 | 9.16 ± 0.28 |
| 56 | 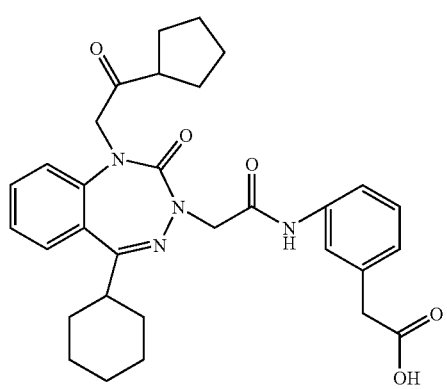 | 9.13 ± 0.22 |

-continued
| Example No | pKB rat stomach |
|---|---|
| 57 | 8.93 ± 0.47 |
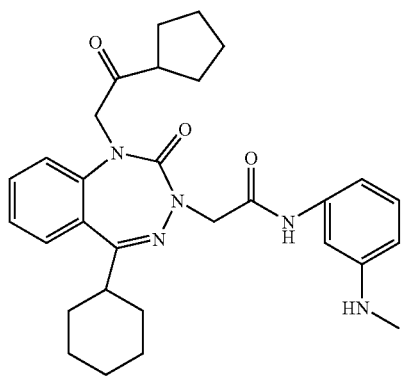
| 58 | 8.83 ± 0.18 |
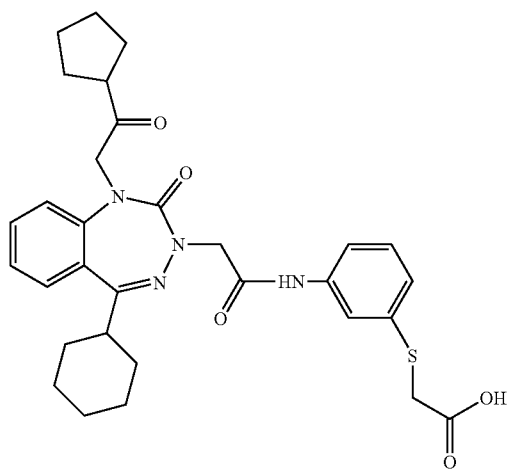
| 59 | 8.02 ± 0.37 |
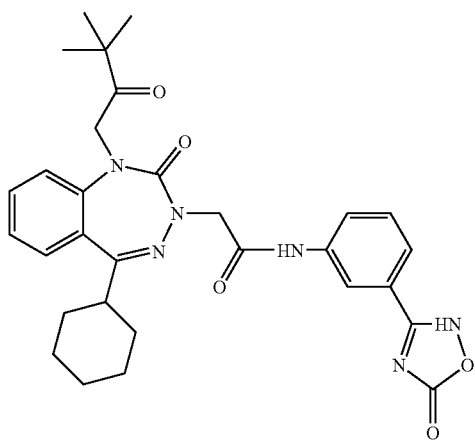

-continued
| Example No | | pKB rat stomach |
|---|---|---|
| 60 | 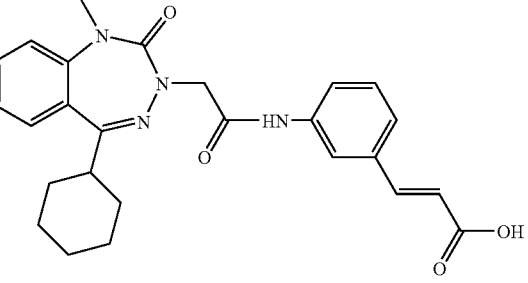 | 8.46 ± 0.28 |
| 61 | 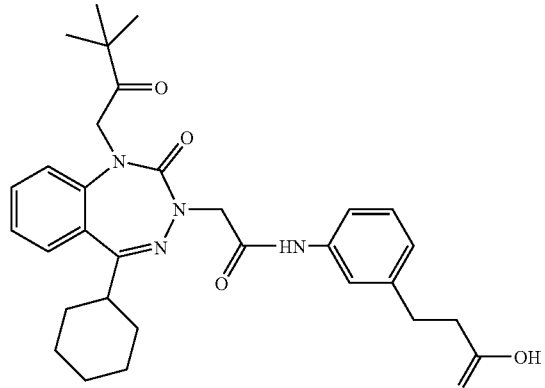 | 8.35 ± 0.22 |
| 62 | 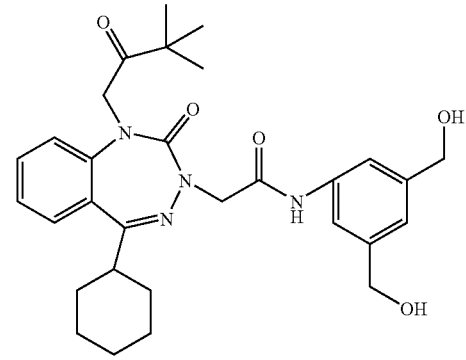 | |
| 63 | 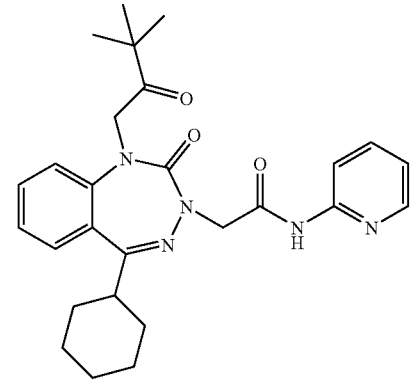 | 6.18 ± 0.29 |

-continued
| Example No | | pKB rat stomach |
|---|---|---|
| 64 | 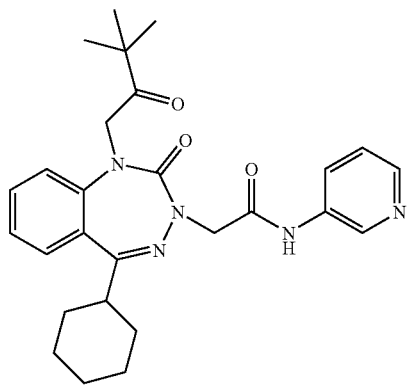 | |
| 65 | 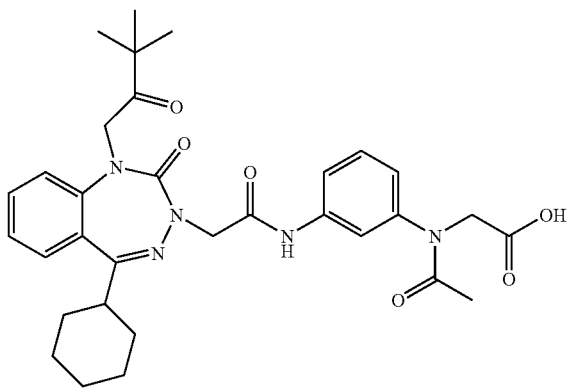 | 7.28 ± 0.25 |
| 66 | 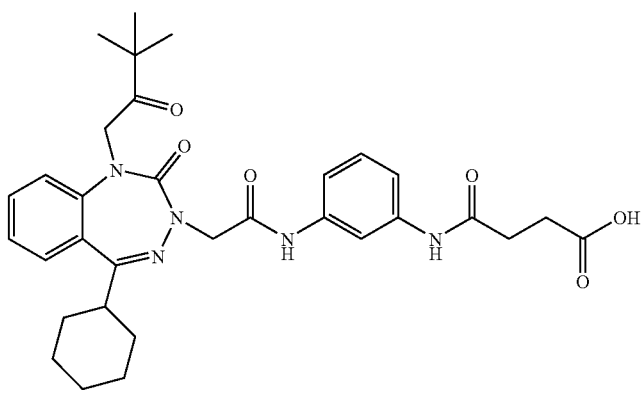 | 7.13 ± 0.26 |
| 67 | 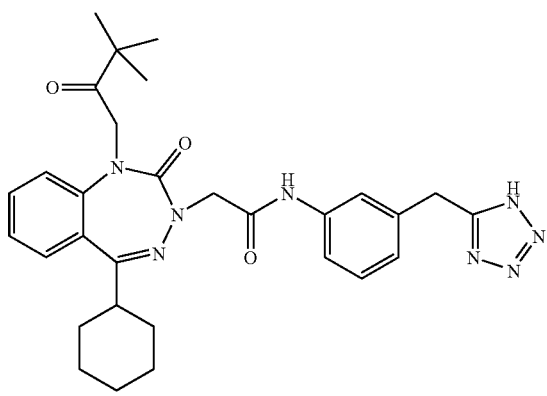 | 7.11 ± 0.21 |

-continued
| Example No | pKB rat stomach |
|---|---|
| 68 | 7.09 ± 0.28 |
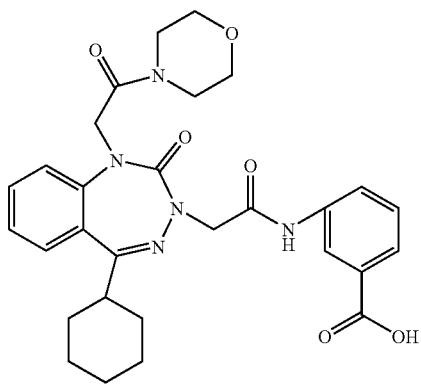
69
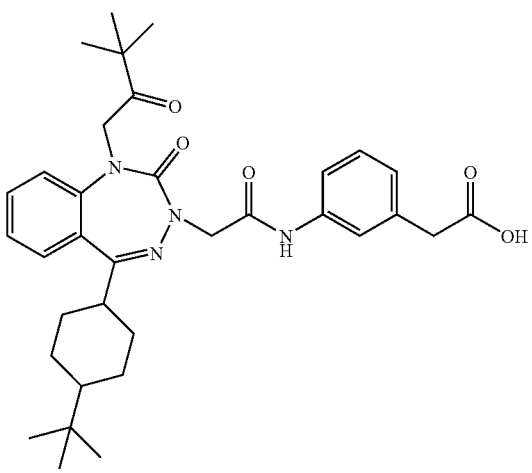
70  9.07 ± 0.23
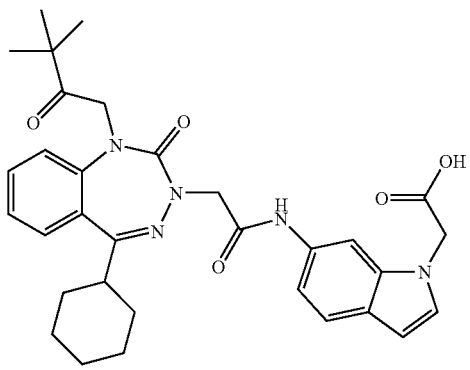

-continued
| Example No | | pKB rat stomach |
|---|---|---|
| 71 | 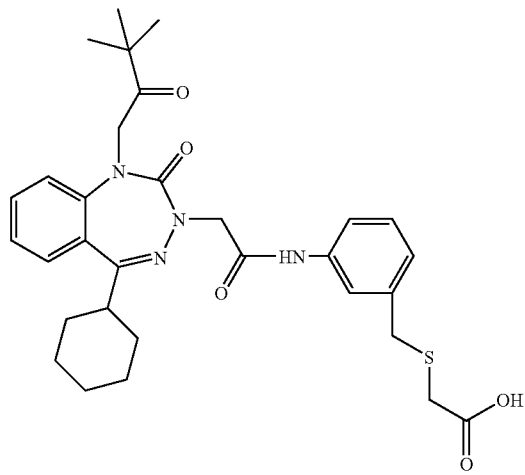 | 8.42 ± 0.24 |
| 72 | 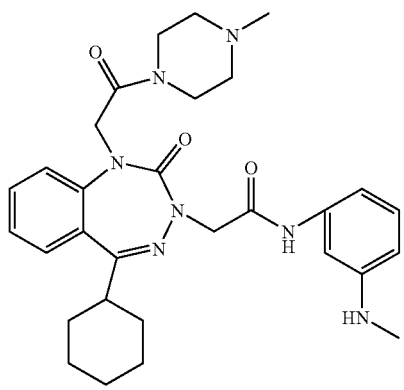 | 6.58 ± 0.16 |
| 73 | 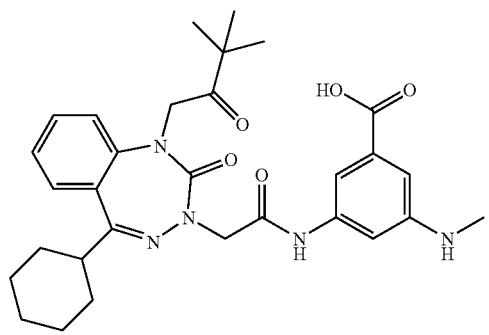 | 7.17 ± 0.27 |
| 74 | 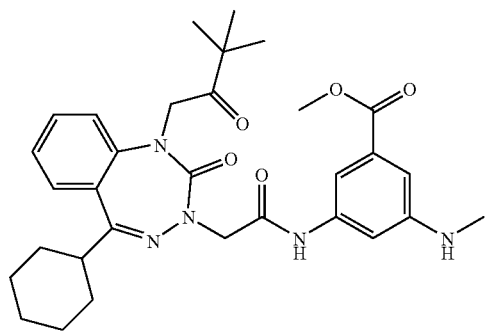 | 6.43 ± 0.17 |

-continued
| Example No | | pKB rat stomach |
|---|---|---|
| 75 | 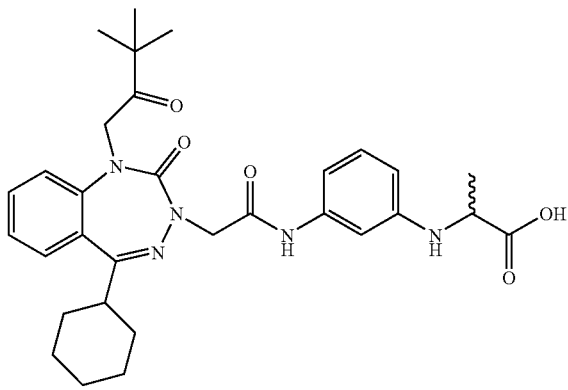 | 6.68 ± 0.30 |
| 76 | 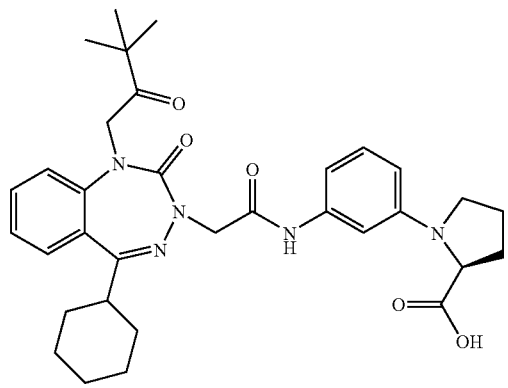 | 6.96 ± 0.16 |
| 77 | 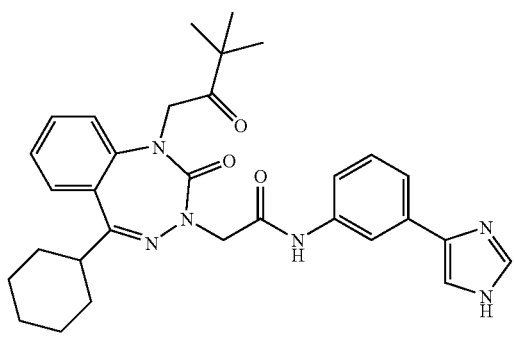 | |
| 78 | 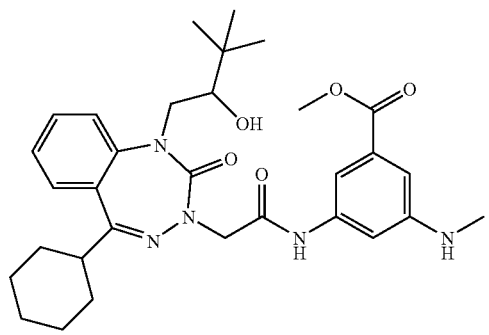 | 6.49 ± 0.33 |

-continued
| Example No | | pKB rat stomach |
|---|---|---|
| 79 | 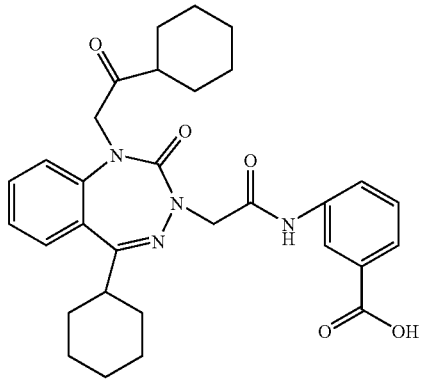 | 8.60 ± 0.40 |
| 80 | 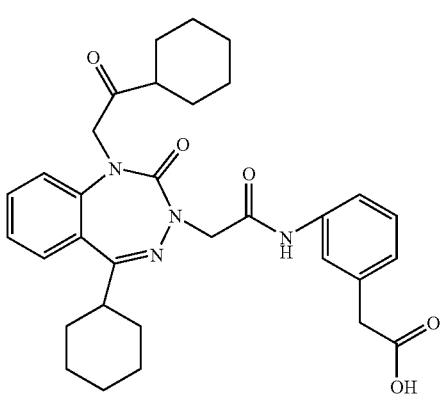 | 8.47 ± 0.36 |
| 81 | 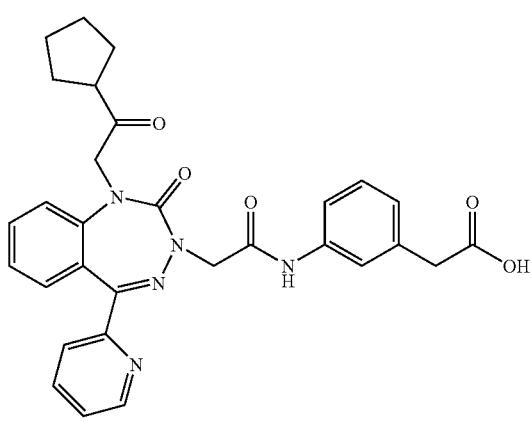 | 7.14 ± 0.35 |
| 82 | 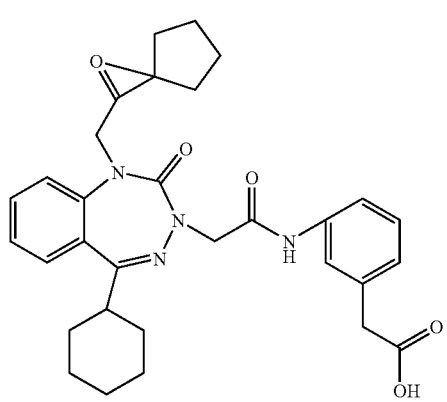 | 8.02 ± 0.27 |

-continued
| Example No | pKB rat stomach |
|---|---|
| 83 | |
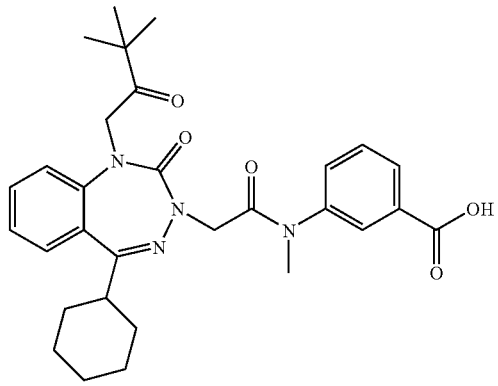
| 84 | 7.56 ± 0.32 |
|---|---|
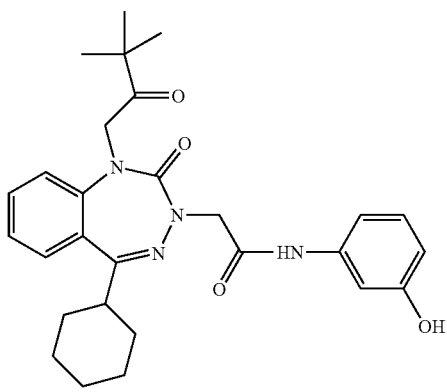
| 85 | 7.44 ± 0.30 |
|---|---|
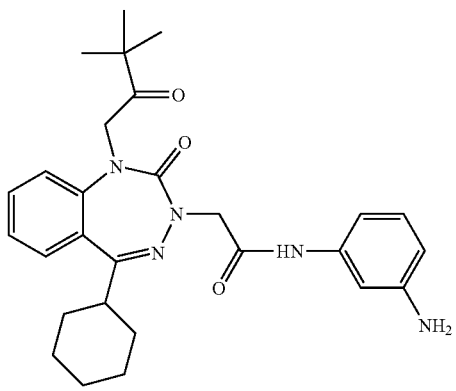
| 86 | 8.47 ± 0.31 |
|---|---|
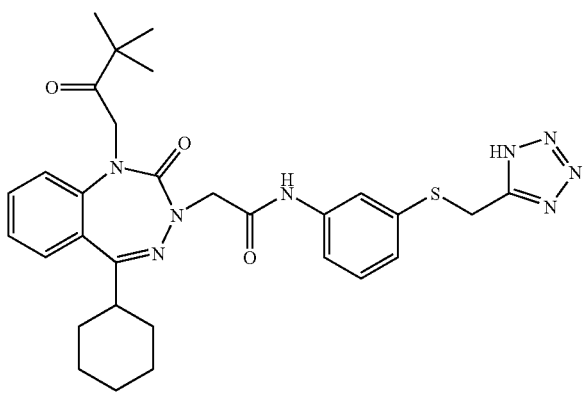

-continued
| Example No | | pKB rat stomach |
|---|---|---|
| 87 | 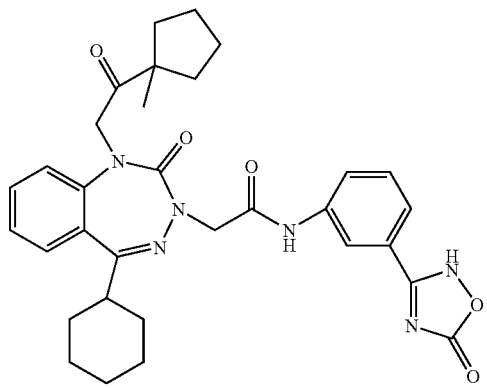 | 8.50 ± 0.28 |
| 88 | 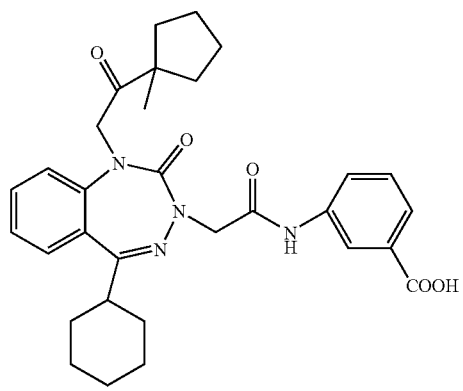 | 7.93 ± 0.30 |
| 89 | 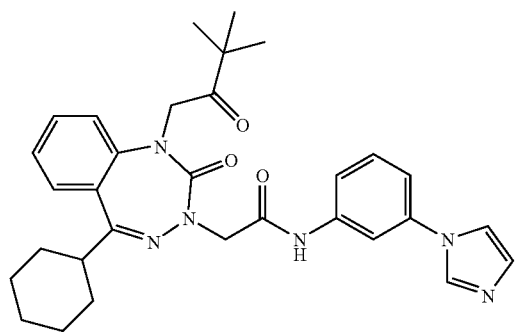 | 6.06 ± 0.19 |
| 90 | 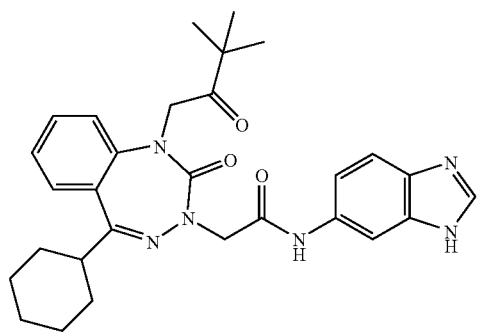 | |

-continued
| Example No | | pKB rat stomach |
|---|---|---|
| 91 | 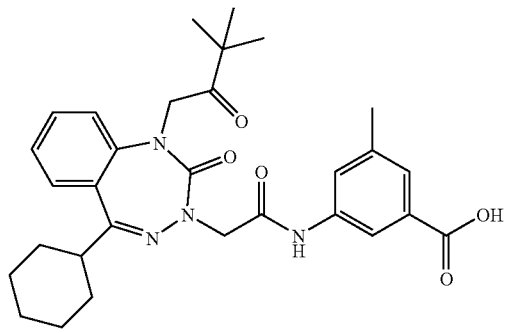 | 7.39 ± 0.34 |
| 92 | 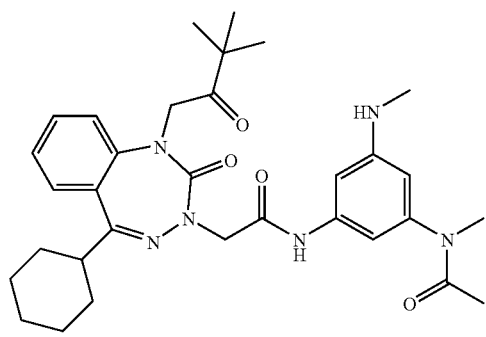 | |
| 93 | 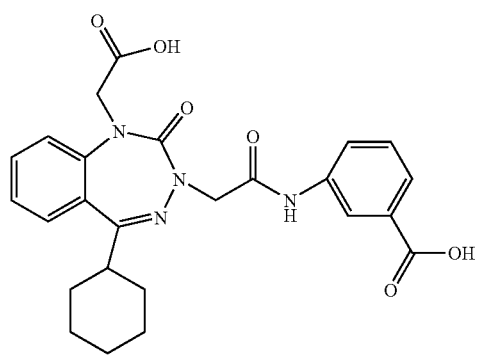 | |
| 94 | 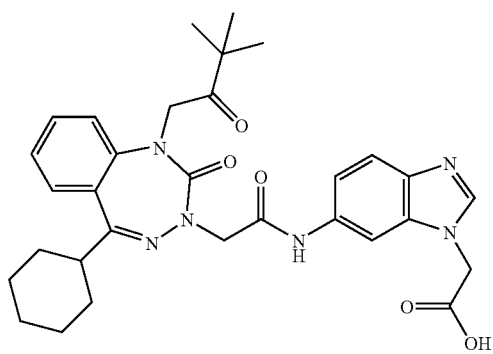 | 6.81 ± 0.41 |

-continued
| Example No | | pKB rat stomach |
|---|---|---|
| 95 | 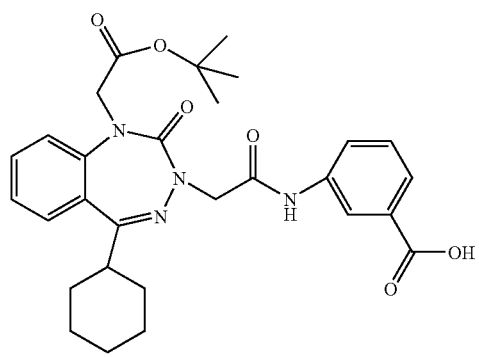 | 8.40 ± 0.25 |
| 96 | 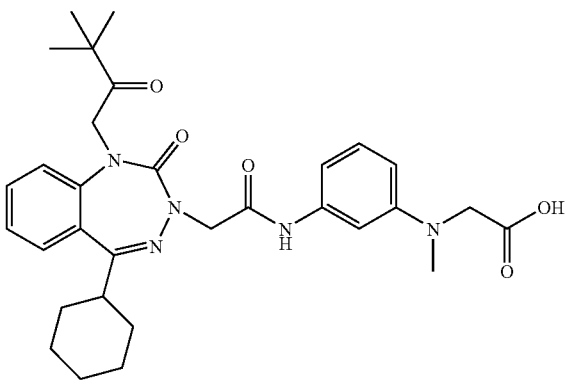 | 8.14 ± 0.31 |
| 97 | 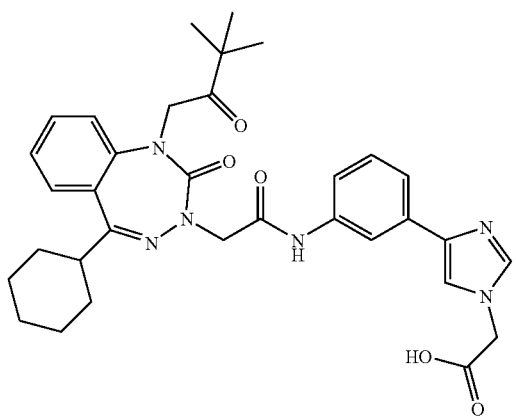 | 7.59 ± 0.30 |
| 98 | 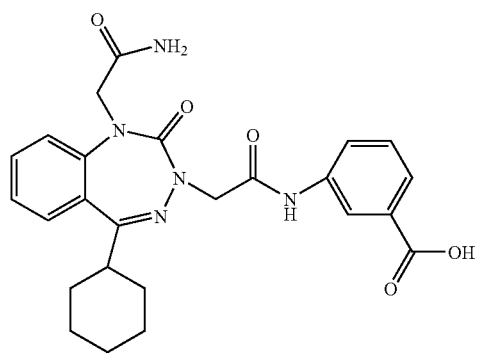 | |

-continued
| Example No | | pKB rat stomach |
|---|---|---|
| 99 | 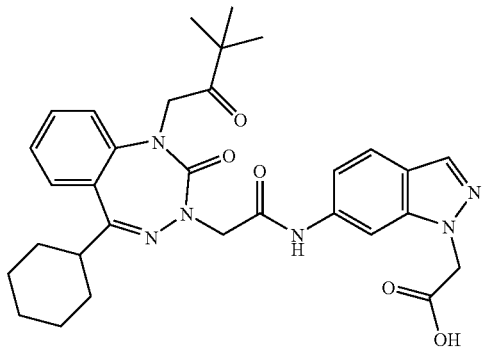 | 7.85 ± 0.20 |
| 100 | 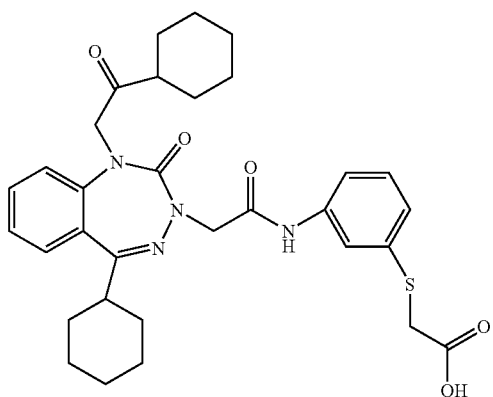 | 9.24 ± 0.34 |
| 101 | 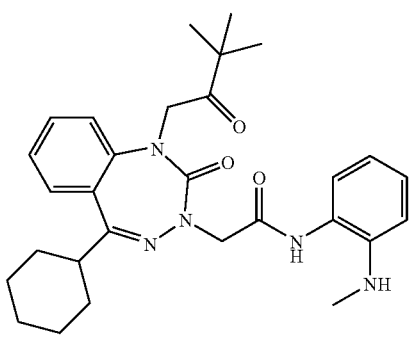 | 6.89 ± 0.21 |
| 102 | 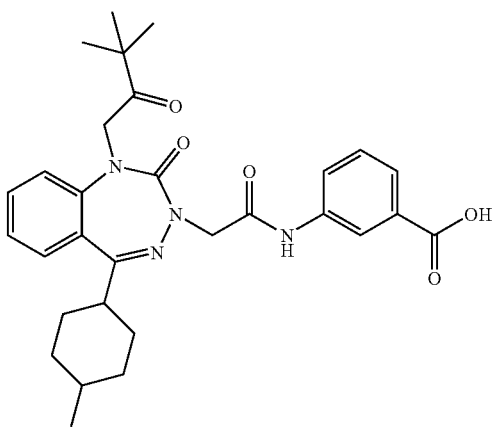 | 9.11 ± 0.36 |

-continued
| Example No | pKB rat stomach |
|---|---|
| 103 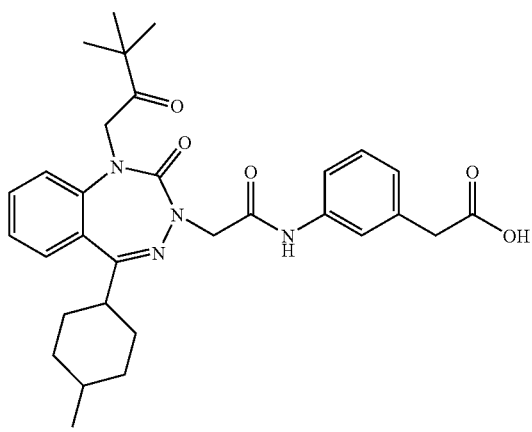 | 8.40 ± 0.28 |
| 104 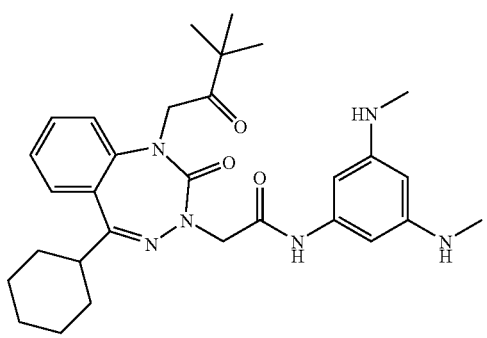 | 7.35 ± 0.18 |
| 105 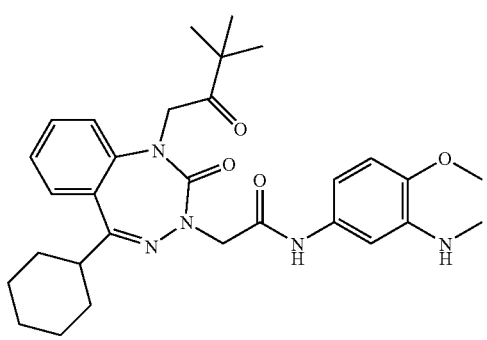 | 7.56 ± 0.26 |
| 106 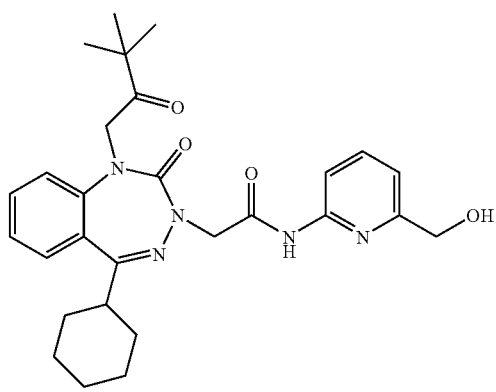 | 6.89 ± 0.26 |

-continued
| Example No | | pKB rat stomach |
|---|---|---|
| 107 | 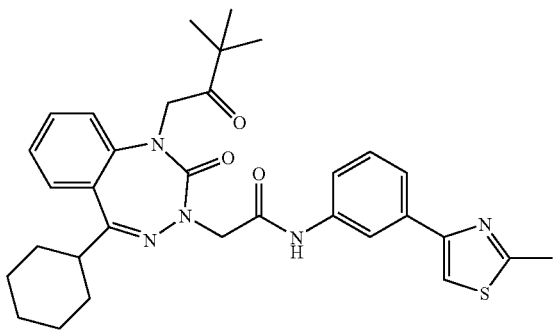 | 8.48 ± 0.32 |
| 108 | 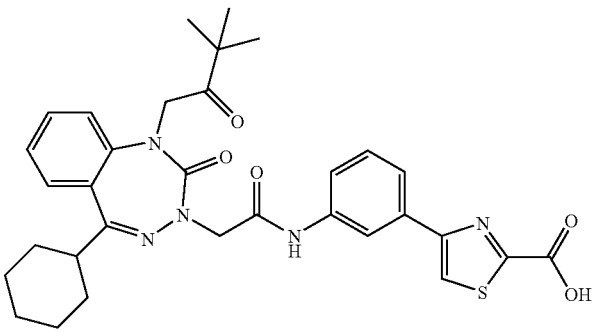 | 7.43 ± 0.11 |
| 109 | 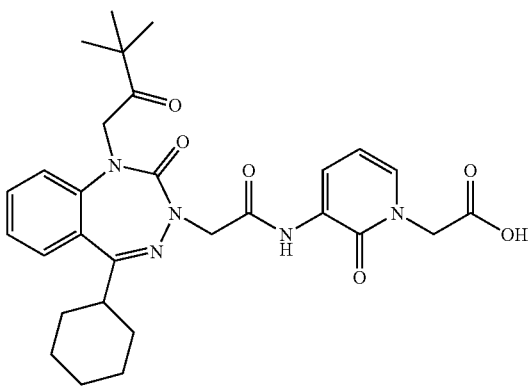 | |
| 110 | 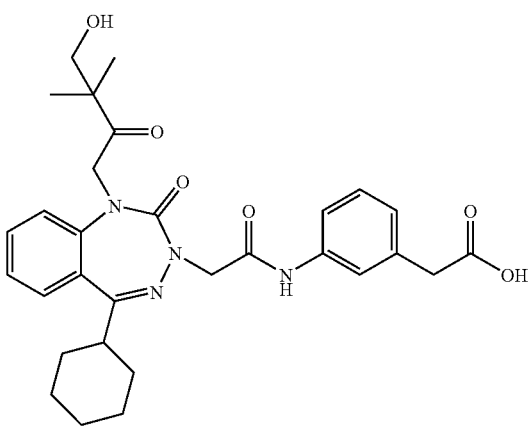 | 7.03 ± 0.24 |

-continued
| Example No | | pKB rat stomach |
|---|---|---|
| 111 | 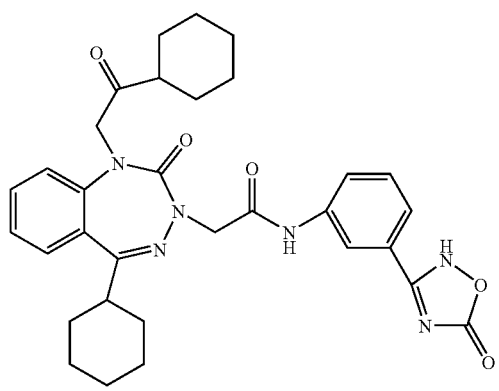 | 8.66 ± 0.33 |
| 112 | 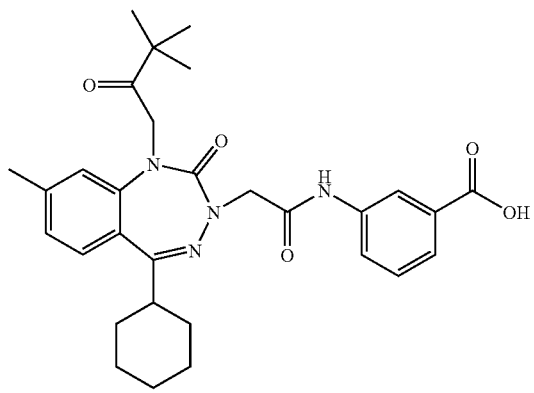 | 7.39 ± 0.48 |
| 113 | 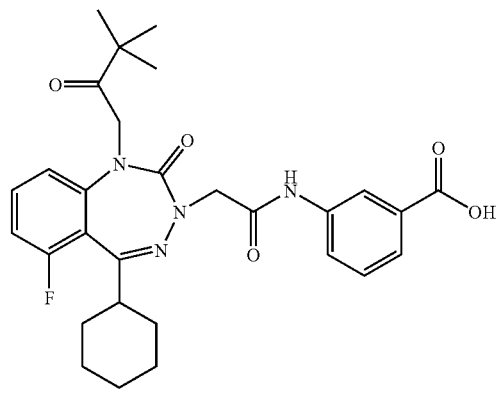 | 8.22 ± 0.29 |
| 114 | 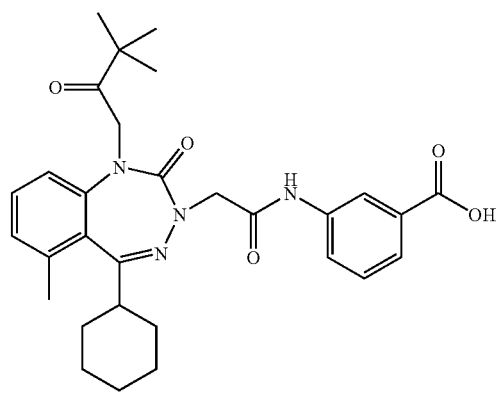 | 7.45 ± 0.43 |

| Example No | pKB rat stomach |
|---|---|
| 115 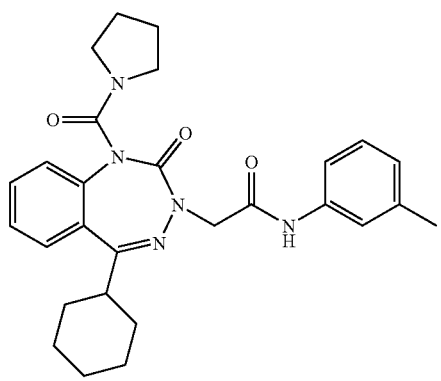 | |
| 116 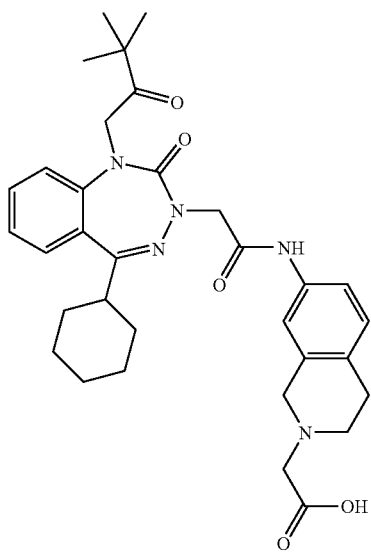 | |
| 117 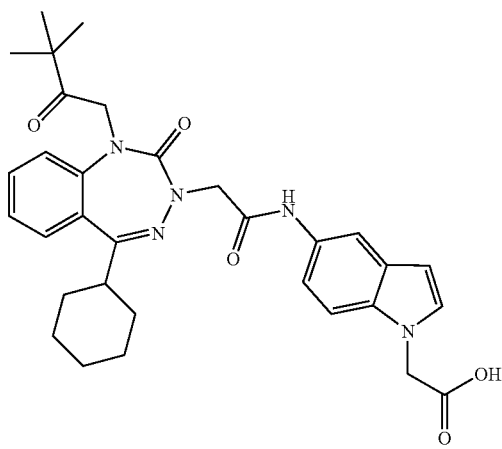 | 7.56 ± 0.17 |

-continued
| Example No | | pKB rat stomach |
|---|---|---|
| 118 | 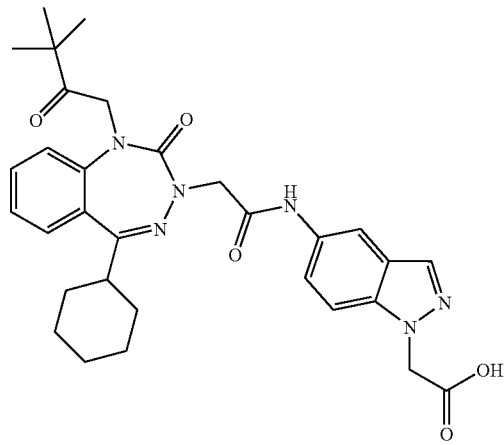 | |
| 119 | 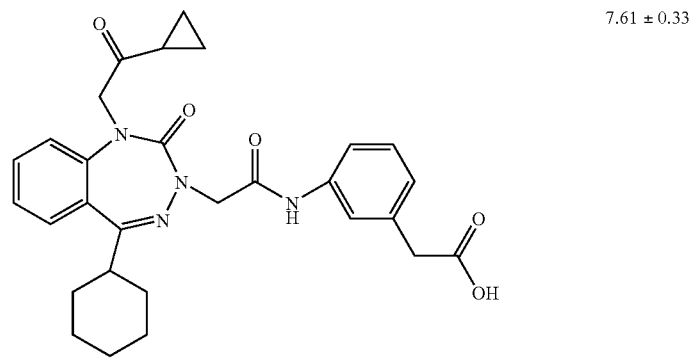 | 7.61 ± 0.33 |
| 120 | 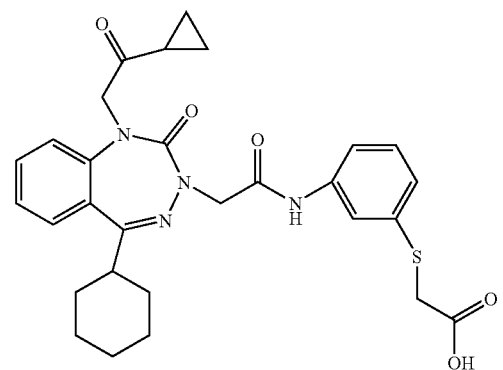 | 7.43 ± 0.44 |
| 121 | 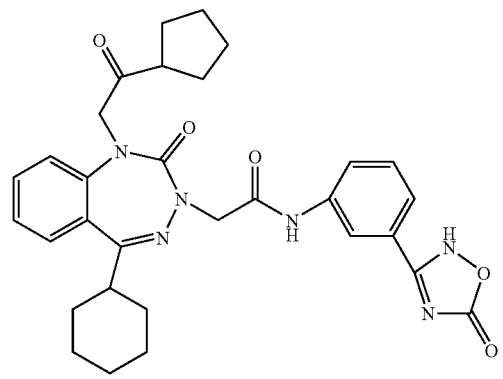 | 9.53 ± 0.22 |

-continued
| Example No | | pKB rat stomach |
|---|---|---|
| 122 | 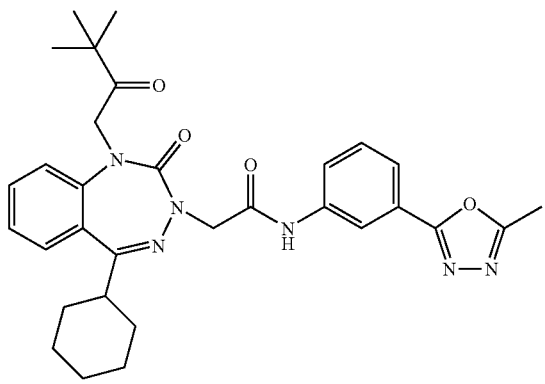 | |
| 123 | 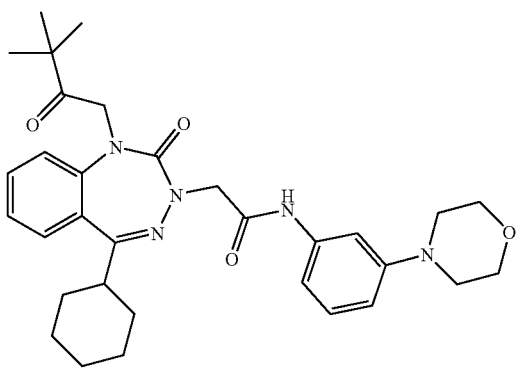 | 7.74 ± 0.36 |
| 124 | 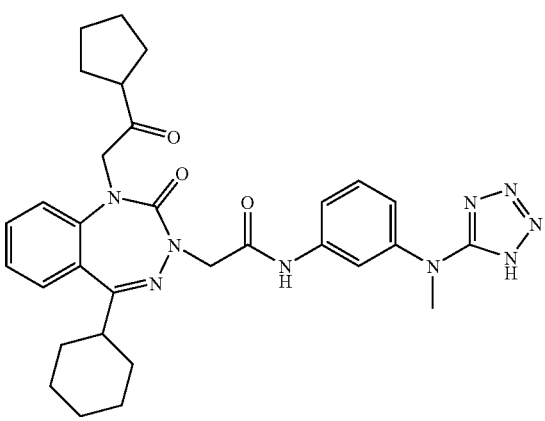 | 8.67 ± 0.39 |
| 125 | 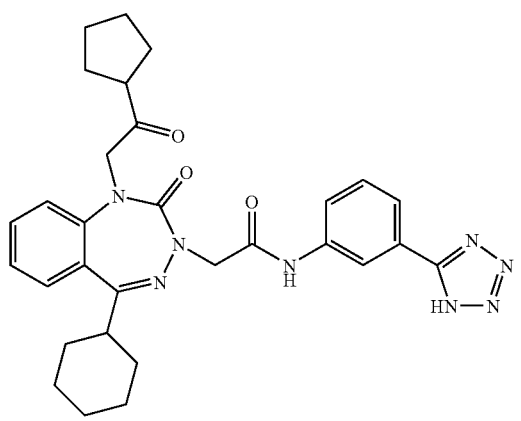 | 8.36 ± 0.34 |

-continued
| Example No | pKB rat stomach |
|---|---|
| 126 | 10.24 ± 0.39 |
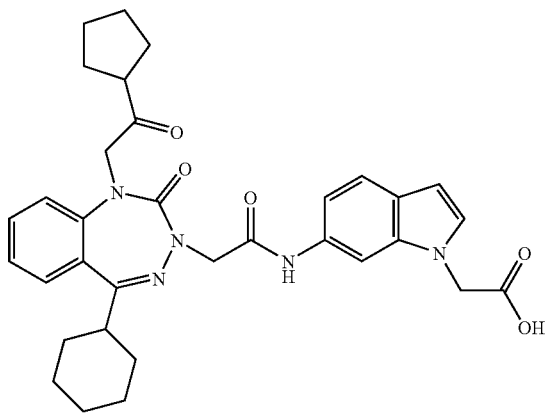
| 127 | 8.68 ± 0.19 |
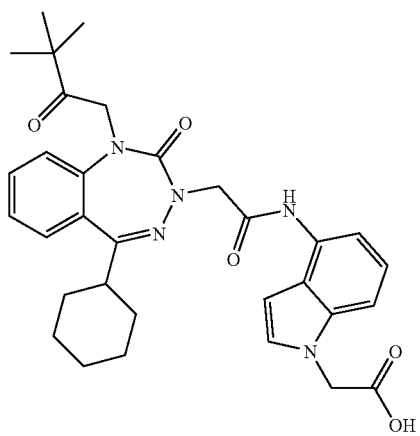
| 128 | 8.91 ± 0.20 |
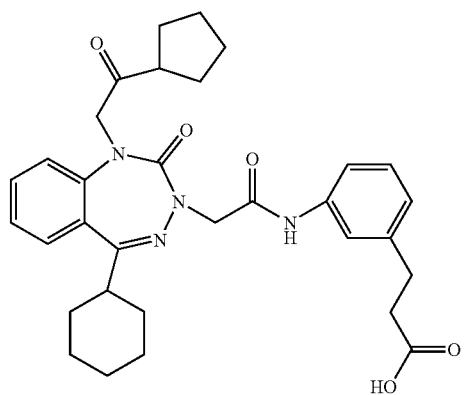

-continued
| Example No | | pKB rat stomach |
|---|---|---|
| 129 | 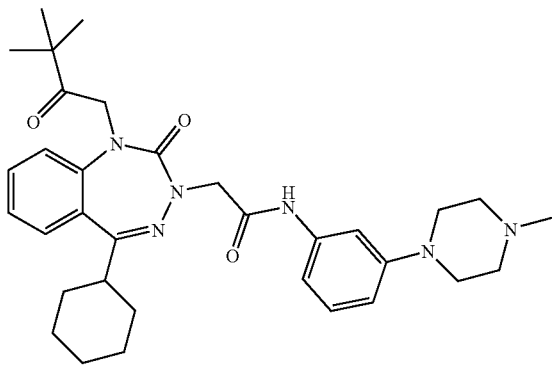 | |
| 130 | 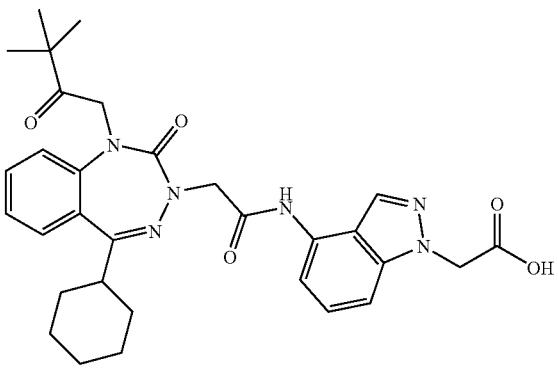 | 7.35 ± 0.27 |
| 131 | 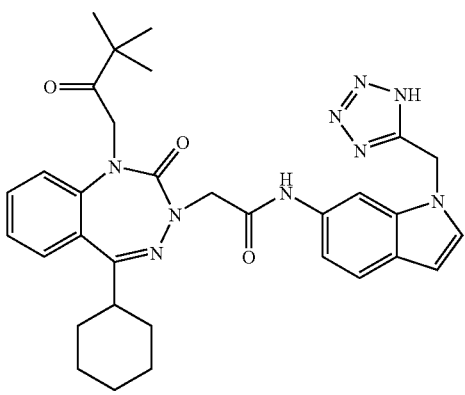 | 8.79 ± 0.23 |
| 132 | 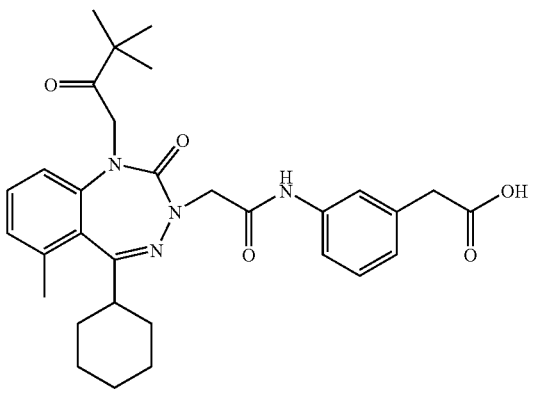 | 7.18 ± 0.36 |

-continued
| Example No | | pKB rat stomach |
|---|---|---|
| 133 | 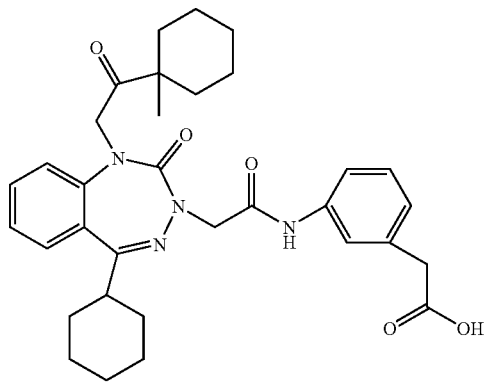 | 7.85 ± 0.22 |
| 134 | 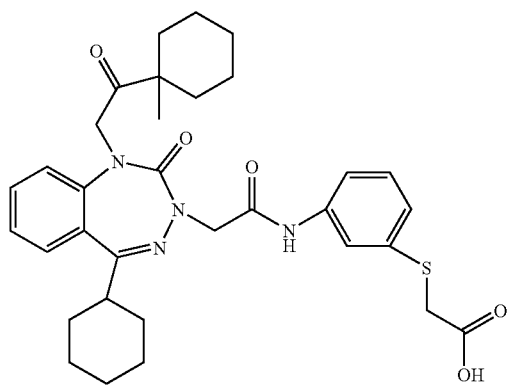 | 7.76 ± 0.28 |
| 135 | 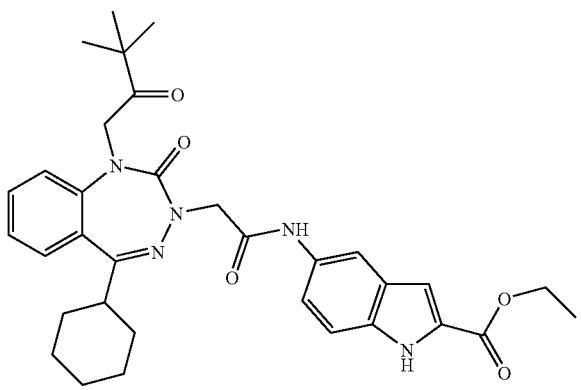 | |
| 136 | 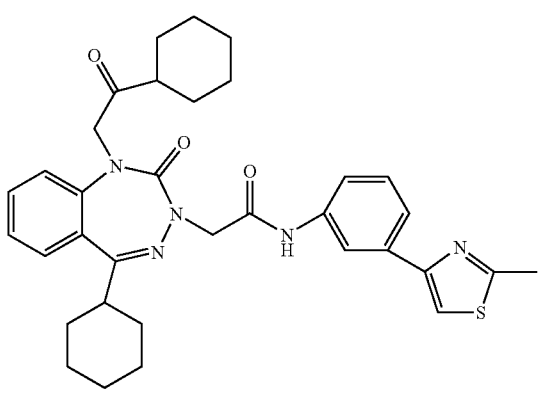 | 8.22 ± 0.47 |

| Example No | pKB rat stomach |
|---|---|
| 137 | 8.54 ± 0.42 |
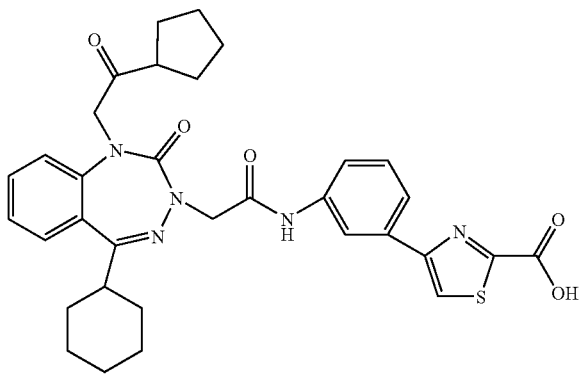
138
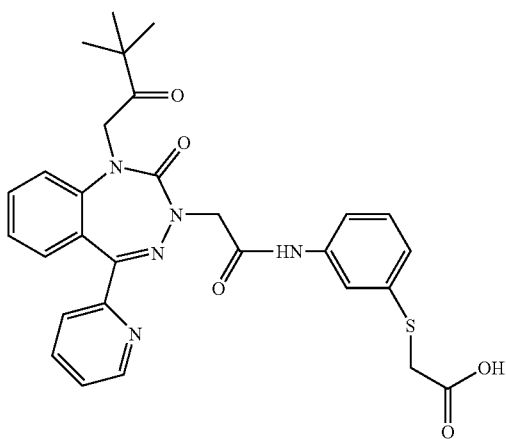
139
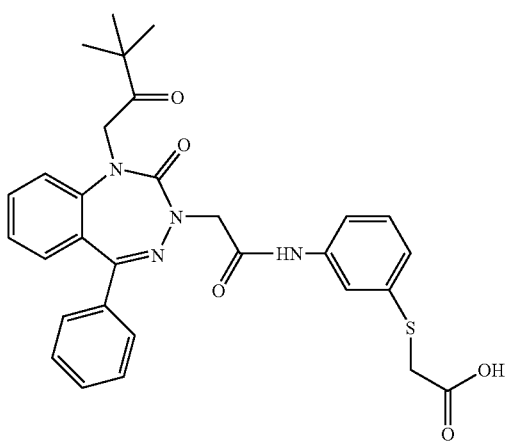

-continued
| Example No | | pKB rat stomach |
|---|---|---|
| 140 | 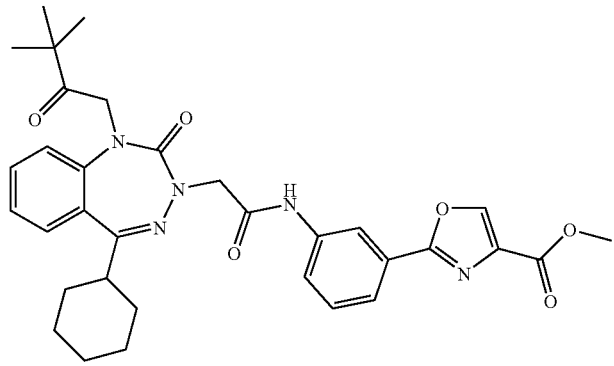 | 8.95 ± 0.41 |
| 141 | 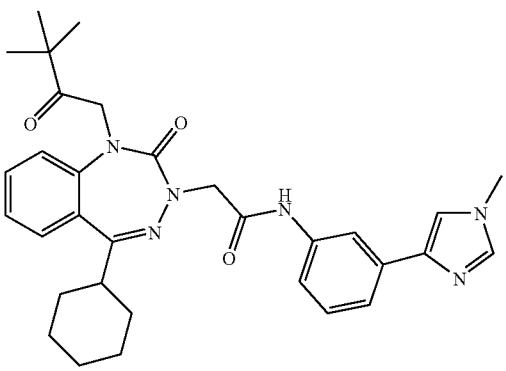 | |
| 142 | 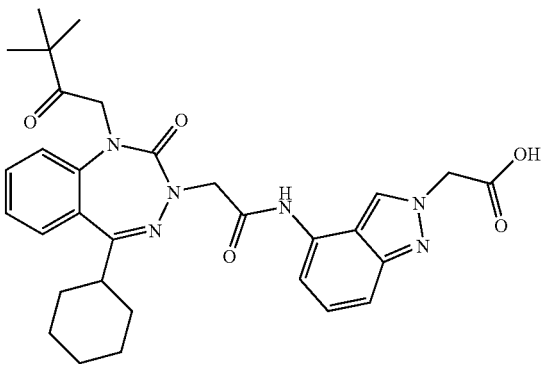 | 7.81 ± 0.29 |
| 143 | 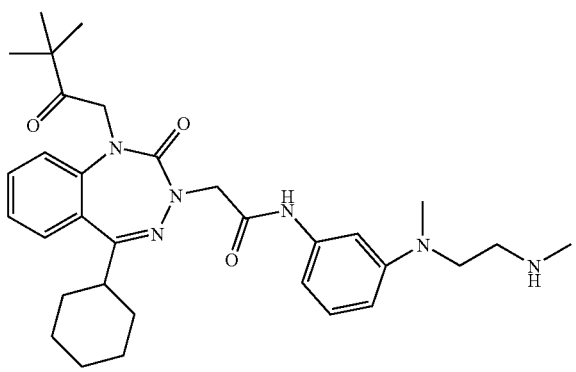 | 6.93 ± 0.40 |

-continued
| Example No | | pKB rat stomach |
|---|---|---|
| 144 | 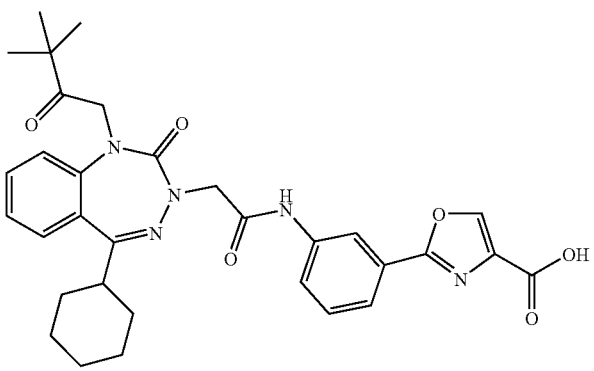 | 8.38 ± 0.44 |
| 145 | 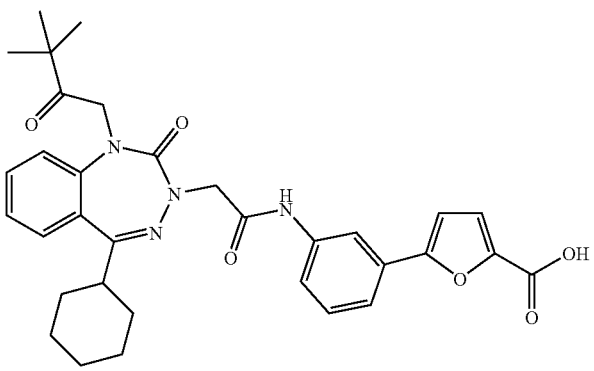 | 8.47 ± 0.26 |
| 146 | 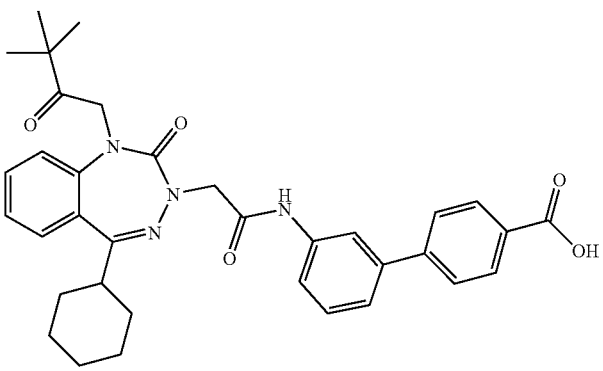 | 8.15 ± 0.30 |
| 147 | 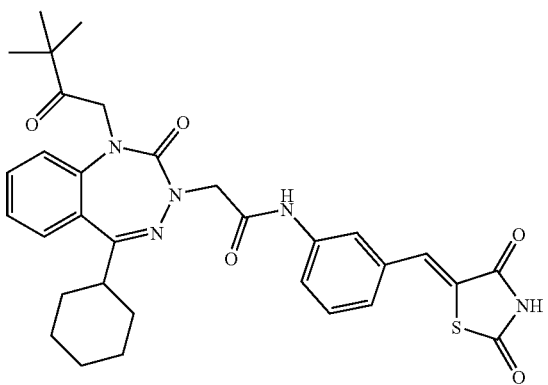 | 8.08 ± 0.35 |

-continued
| Example No | | pKB rat stomach |
|---|---|---|
| 148 | 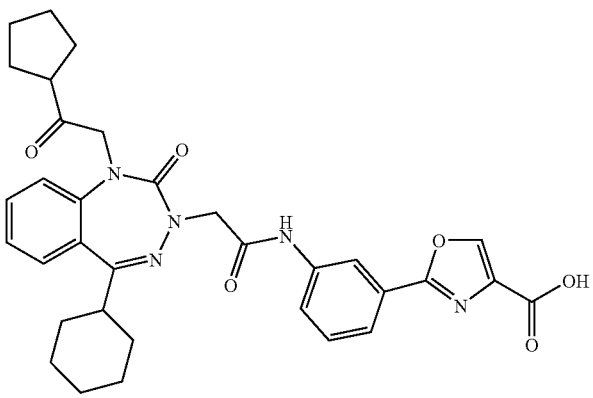 | 8.41 ± 0.47 |
| 149 | 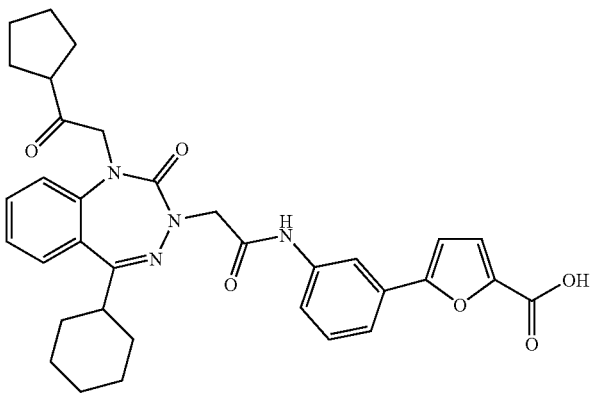 | 8.96 ± 0.48 |
| 150 | 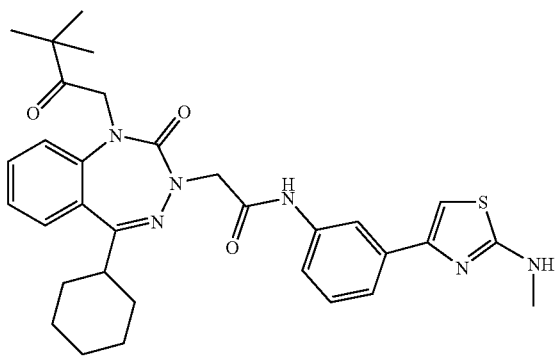 | 8.89 ± 0.42 |
| 151 | 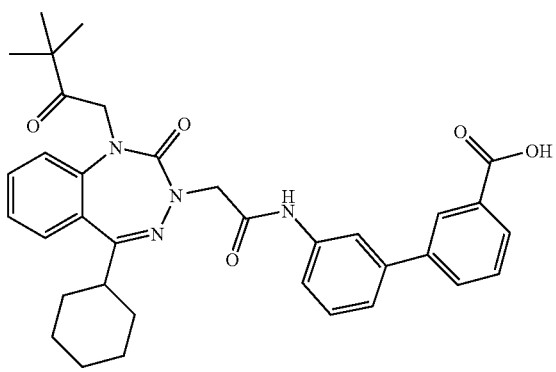 | 7.94 ± 0.33 |

-continued
| Example No | | pKB rat stomach |
|---|---|---|
| 152 | 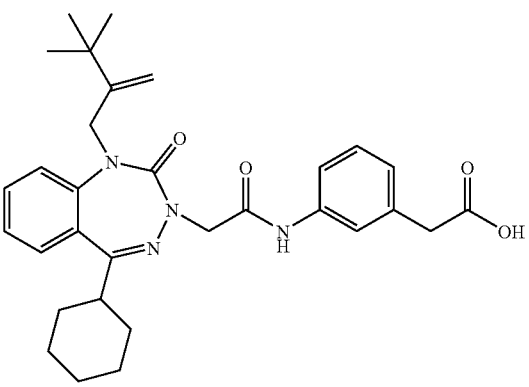 | 7.30 ± 0.50 |
| 153 | 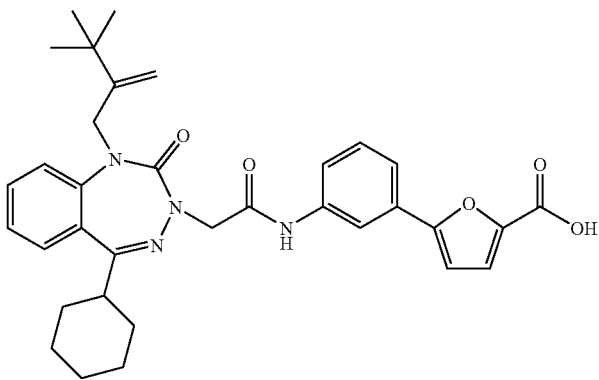 | |
| 154 | 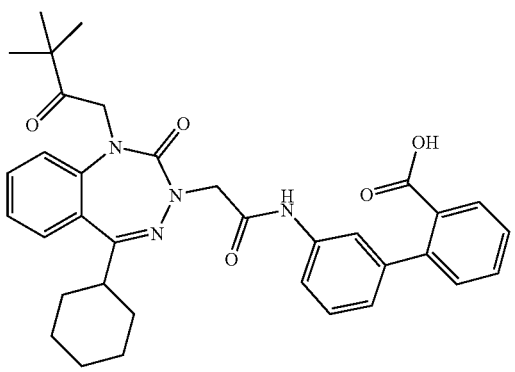 | 8.49 ± 0.2 |
| 155 | 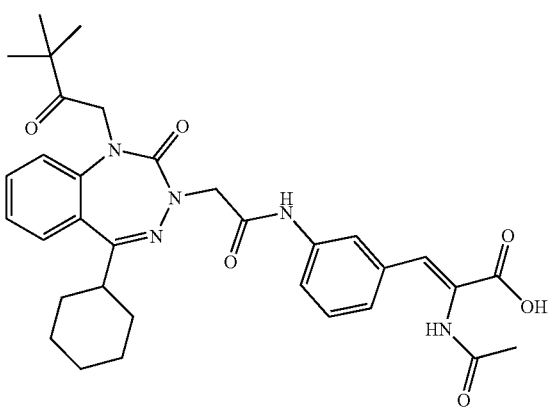 | 7.15 ± 0.2 |

-continued
| Example No | | pKB rat stomach |
|---|---|---|
| 156 | 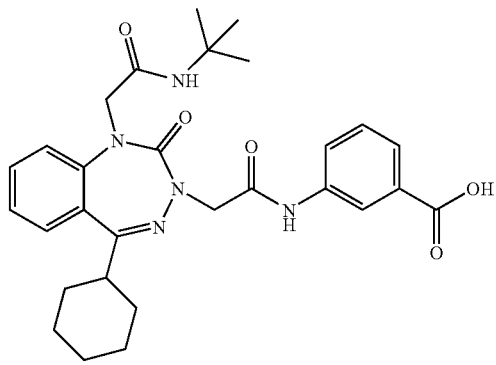 | |
| 157 | 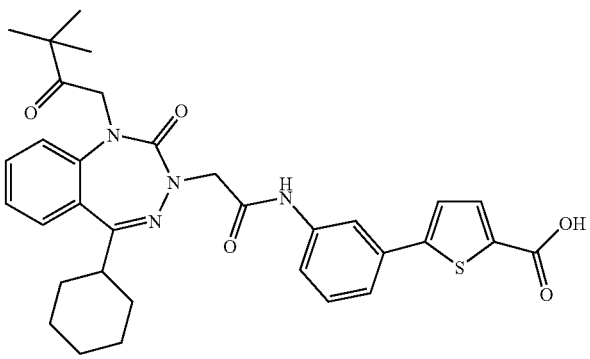 | 8.11 ± 0.2 |
| 158 | 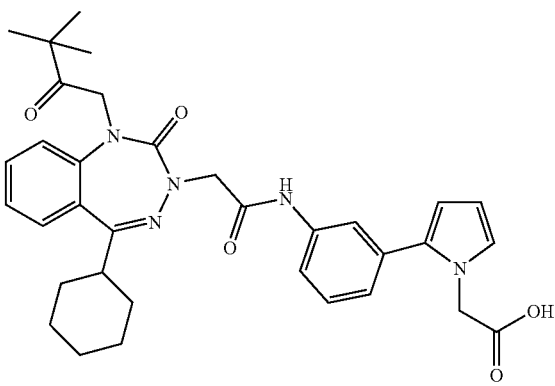 | 8.37 ± 0.3 |
| 159 | 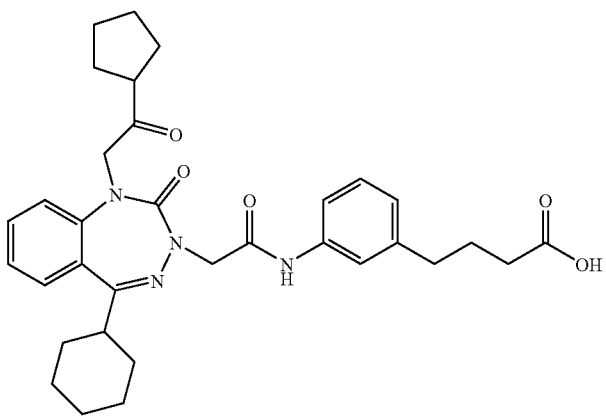 | 8.90 ± 0.3 |

| Example No | pKB rat stomach |
|---|---|
| 160 | 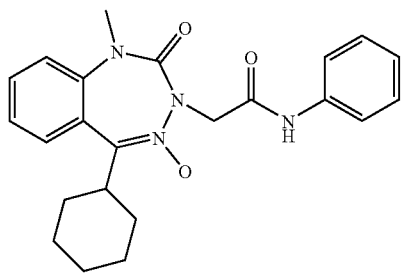 |

A number of compounds were tested at human gastrin (CCK$_2$) receptors which have been cloned into an NIH3T3 cell line as follows:

Step a: Subcloning of IMAGE Clone Encoding the Human CCK$_2$R into a Mammalian Expression Vector I.M.A.G.E. (Integrated Molecular Analysis of Genomes and their Expression) clone number 3504160 (Lennon et al. Genomics 33, 151-152 (1996)) was purchased from the HGMP (Human Genome Mapping Project, Cambridge). The cDNA encoding the mRNA for the human CCK$_2$R, corresponding to accession number BC000740, was present in vector pOTB7 in host cell DH10B. The cells, initially streaked on to LB-Agar plates containing 20 µg/ml chloramphenicol, were then grown in LB containing 20 µg/ml chloramphenicol with shaking at 37° C. according to standard techniques (Current Protocols in Molecular Biology, Wiley). DNA was prepared using the QIAGEN® EndoFree™ plasmid Maxi kit (Qiagen Ltd.) according to the manufacturer's protocol. The DNA was then amplified by PCR (polymerase chain reaction) from the start codon to the stop codon using primers containing restriction sites, Eco R1 and Xba I respectively, to facilitate uni-directional cloning. The start codon primer also contained a Kozak consensus site (Kozak M, *Nucleic Acids Res.* 1984 Jan. 25; 12(2):857-72) for optimal initiation of translation. Primers 1 and 2 (see Table 1) were synthesised to HPLC grade by Invitrogen. The PCR was performed in 20 mM Tris-HCl (pH 8.4), 50 mM KCl containing 2 mM MgCl$_2$, 0.2 mM dNTP (Invitrogen) and 0.1 µM of each primer. A hot start PCR was used: the samples were denatured for 2 min at 95° C., cooled to 75° C., then 1U Taq Polymerase (Invitrogen) was added and the reactions were cycled 30 times at 95° C. for 1 min, 60° C. for 30 sec and 72° C. for 3 min. The samples were cooled to 4° C., after a final extension at 72° C. for 5 min.

The PCR product was purified using the QIAGEN® MinElute™ PCR purification kit, according to the manufacturer's instructions. The PCR product and a mammalian expression vector were digested using both Eco RI (Promega Corp.) and Xba I (Promega Corp.) in 1× Buffer H (90 mM Tris-HCl, 10 mM MgCl$_2$, 50 mM NaCl, pH 7.5) (Promega Corp.) and 0.1 µg/ml BSA. The digested DNA bands of the correct size, analysed by ethidium bromide stained agarose/TBE gels, were excised and purified using QIAGEN® MinElute™ gel extraction kit, according to the manufacturer's instructions. The PCR product was then ligated into the vector using the Lightning™ DNA Ligation kit (Bioline) and transformed into *Escherichia coli*, strain XL1-Blue cells (Stratagene) according to the manufacturer's instructions.

Colonies were selected and screened using restriction digestion of DNA prepared from small-scale cultures (5 ml) using QIAGEN® plasmid Mini-prep columns. One positive clone was cultured on a larger scale (100 ml) using standard techniques (Current Protocols in Molecular Biology, Wiley) and DNA was prepared using QIAGEN® plasmid Maxi-prep columns. The DNA was then custom sequenced by MWG Biotech AG using primers 3, 4 and 5 (Table A). The sequence contained the correct sequence of primers 1 and 2 and the sequence of the coding region exactly matched that of accession number BC000740.

Step b: Generation of Stable Cell Line

NIH3T3 cells from (ECACC) were cultured in Dulbecco's modified Eagle's medium (DMEM)(Invitrogen), containing 2 mM Glutamax I (Invitrogen), 10% heat inactivated newborn calf serum (Invitrogen). Cells (4×10$^5$) were seeded into 35 mm×10 mm dishes (Corning) and transfected using the Transfast™ reagent (Promega Corp.) according to the manufacturers instructions using 10 µg of the hCCK$_2$R plasmid DNA at a ratio of 1:1 (DNA:Transfast™ reagent). Untransfected cells and cells transfected with vector only were also prepared as controls. After 48 h the cells were trypsinised using standard techniques (Culture of Animal Cells, A Manual of Basic Techniques 4$^{th}$ Ed, R. Ian Freshney) and dilutions were plated on 35 mm×10 mm dishes in media containing 800 µg/ml G-418 (Invitrogen). Cells were selected for 2 weeks until individual, separate colonies appeared. In the untransfected cells all cells had died after this time, confirming adequate selection. Using cloning rings and trypsinisation, according to standard techniques (Culture of Animal Cells, A Manual of Basic Techniques 4$^{th}$ Ed, R. Ian Freshney), individual colonies were picked from plates containing cells transfected with the vector only and cells transfected with the hCCK$_2$R plasmid construct. The cells were expanded and analysed by radioligand binding analysis (see below).

TABLE A

Primers used in the cloning and sequence analysis of human CCK$_{2S}$R

| Primer Name | Primer Orientation | Sequence (5'-3') | Gene specific or vector | Restriction Site |
|---|---|---|---|---|
| 1 | Forward | TCTGAATTCGCCGCC<u>ATG</u>GAGCTGCTA (SEQ ID NO:1) | GENE | Eco RI |
| 2 | Reverse | GTATCTAGAC<u>TCA</u>GCCAGGGCCCAGTG (SEQ ID NO:2) | GENE | Xba I |
| 3 (T7) | Forward | TAATACGACTCACTATAGG (SEQ ID NO:3) | VECTOR | — |
| 4 (T3) | Reverse | ATTAACCCTCACTAAAGGG (SEQ ID NO:4) | VECTOR | — |
| 5 | Forward | TGTCCGGACTACTCATGGTG (SEQ ID NO:5) | GENE | — |

Restrictions site in bold. Start codon underlined. Stop codon italic and underlined.

Step c: Clonal Selection

Stable clones expressing hCCK$_2$R were screened for their ability to specifically bind [$^{125}$I]-BH-CCK-8S in tissue concentration curve studies (0.3×10$^4$-1×10$^6$ cells per tube) using the assay conditions described below. Of those tested, clone 7 gave the highest amount of specifically bound and % specific bound label whilst also meeting the criteria that the amount of total bound label did not exceed 10% of the total added radio label (e.g. 4.2%). In addition there was a direct linear correlation between the amount of specific bound label and the cell concentration up to and including 2.5×10$^5$ cells per ml. Based on the above, this clone was chosen for expansion and full binding characterisation.

Step d: Membrane Preparation

Cultured clone 7 cells were stored as frozen pellets at −70° C. until required. Cell pellets were thawed in CCK$_2$ assay buffer ((mM): 10 Hepes; 130 NaCl; 5 MgCl$_2$; 4.7 KCl; 1 EGTA (pH7.2 at 21° C.) with 0.125 g Bacitracin added to each liter), and homogenised using a Polytron (4×1 s). The resulting membrane preparation was centrifuged at 39,800 g for 15 min at 4° C. Each cell pellet was re-suspended in fresh buffer and re-centrifuged as above. The final pellet was resuspended by homogenisation (Teflon-in-glass), to the appropriate membrane concentration.

Step e: Incubation Conditions

For saturation and competition studies, the cell membranes prepared as in step d (3×10$^4$ cells per 400 µl) were incubated for 150 min at 21° C. in a final volume of 0.5 ml with CCK$_2$ assay buffer containing [$^{125}$I]-BH-CCK-8S (50 µl; 200 pM). Total and non-specific binding of [$^{125}$I]-BH-CCK-8S were defined, respectively using 50 µl of buffer and 50 µl of 10 µYM022. The assays were terminated by rapid filtration through pre-soaked Whatman GF/B filters which were washed (3×3 ml) with ice-cold 50 mM Tris HCl (Ph 7.4 @ 4° C.). Filters were transferred to plastic gamma counter vials and bound radioactivity determined by counting (1 min) in a Clini-gamma counter.

Step f: Saturation Analysis

The binding of [$^{125}$I]-BH-CCK-8S to the hCCK$_2$ receptor isoform was saturable. Scatchard plots appeared linear and the mean slope of the corresponding Hill plots was not significantly different from unity (0.97±0.08; n=4). The equilibrium dissociation constant (pK$_D$) and Bmax values were 10.75±0.08 and 1.1±0.3 fmol per 1×10$^5$ cells, respectively (n=4±s.e. mean). Saturation data were analysed using the curve-fitting programmes, Radlig and Ligand.

Step g: Competition Studies

A number of compounds of the invention as well as reference compounds were tested for their ability to displace [$^{125}$I]-BH-CCK-8S from the receptors prepared as above. Briefly, dilution and addition of test compounds, radioligand and cell membranes were performed using a Beckman Biomek 2000. The ability of compounds to inhibit the specific binding of to hCCK$_2$ receptors was determined in triplicate over a range of concentrations at half-log intervals. Total and non-specific binding was determined for each compound. Each compound was tested in a minimum of three experiments. Competition data were fitted to the Hill equation using Graph-pad Prism software to obtain estimates of the IC$_{50}$ (mid-point location parameter) and n$_H$ (mid-point slope parameter). Dissociation constants (K$_I$) were determined using the Cheng & Prusoff equation (1973) to correct for the receptor occupancy by the radioligand. All compounds were dissolved in DMF to give a stock concentration of either 1 or 10 mM and subsequent dilutions were made in assay buffer. The pK$_I$ for representative examples together with a number of reference compounds are shown in the table below. All Hill slopes were not significantly different from unity.

| Example no or reference | pKi ± s.e.mean |
|---|---|
| Ex 22 | 9.45 ± 0.04 |
| Ex 56 | 9.79 ± 0.03 |
| Ex 58 | 9.48 ± 0.08 |
| Ex 59 | 9.66 ± 0.05 |
| Ex 121 | 9.96 ± 0.01 |
| Ex 128 | 9.69 ± 0.03 |
| Ex 160 | 5.49 ± 0.05 |
| L-365, 260 | 8.45 ± 0.09 |
| YM022 | 10.19 ± 0.03 |

Compounds of certain examples were also tested in a CCK$_1$ binding assay. All the examples tested were found to have a CCK$_1$ pK$_i$ not exceeding 6.5.

It is found that the compositions and products of the present invention comprising a compound of formula (I) and a proton pump inhibitor reduce hyperplasia, associated with administration of proton pump inhibitors. This was measured according to the following experimental protocol.

Animals and Treatment:

40 male SPF Wistar rats (200 g) were divided into 4 treatment groups and 2 strata. The treatment of the 20 rats in the second stratum started 2 weeks after the treatment of the first stratum. The design of the study was completely randomised double blind with individual blinding; all rats were placed in a separate cage. Animals had continuous access to water and food.

Animals were treated once daily during 14 days:
Control group: 1 ml gastrin test drug vehicle+1 ml p.o. (gavage) 0,25% Methocel (Dow Corning)
PPI group: 1 ml gastrin test drug vehicle+1 ml p.o. (gavage) 25 mg/kg Rabeprazole in 0.25% Methocel.
GRA group: 1 ml gastrin test drug+1 ml p.o. (gavage) 0,25% Methocel
GRA-PPI group: 1 ml gastrin test drug+1 ml p.o. (gavage) 25 mg/kg Rabeprazole in 0.25% Methocel.
Gastrin test drug made up to an appropriate dose in physiologically compatible solvent.

Preparation of Tissue:

After removal of the fundus, the stomach were rinsed with phosphate buffered saline prior to fixation with 4% formalin in Millonig buffer. After 4 hours immersion in fixative solutions at room temperature, tissue was rinsed in phosphate buffered saline (PBS), dehydrated and embedded in paraffin using the Leitz paraffin embedding station (Leitz TP 1050; Germany) dehydration module and paraffin embedding module (Leitz EG 1160; Germany).

Cross sections (3 μm thick) of the oxyntic part of the stomach were made at 3 levels, each separated by a distance of 400 μm.

Immunostaining

The following indirect immunofluorescence labeling method was used:
removal of paraffin and rehydratation of the sections followed by a blocking step
primary antibodies: polyclonal guinea pig anti-histidine decarboxylase, 1/2000 (from Euro-Diagnostica) and monoclonal mouse anti PCNA 1/2500 (Clone PC10 from Sigma). All antibodies were diluted in a 0.2% BSA solution. Sections were incubated overnight at 4° C. and then washed with a BSA solution.
secondary antibodies: goat anti guinea pig coupled to CY5, 1/500 (from Jackson Laboratories) and goat anti-mouse coupled to Cy3, 1/250 (from Jackson Laboratories); incubation for 4 hours at 37° C. After rinsing with BSA and PBS solutions, sections were mounted with slow-fade (Molecular Probes Europe BV), and stored at 4° C.

Imaging

Fluorescence labelling was observed with an epifluorescence microscope or a Zeiss LSM510 (Carl Zeiss Jena GmbH) confocal microscope.

By using CY5- and CY3-coupled antibodies, the high autofluorescence properties of the oxyntic mucosa were circumvented when sections are illuminated by a 488 nm (FITC channel) light source. Negative controls, by omitting the primary antibodies, and an isotype control staining for PCNA showed complete absence of staining. The specific labelling of PCNA was checked using double staining with TOPRO-3® (Molecular Probes Europe BV), a nuclear stain. Only in the most luminal located epithelial cells, non-specific cytoplasmic labelling was present. In the glandular part of the mucosa, non-specific PCNA-staining was absent.

For determination of the labelling index of ECL cells, at least 80 confocal images per rat were taken from the 3 slides at the 3 different levels. The ratio of double labelled cells (HDC+PCNA) and all HDC labelled cells yielded the labelling index of ECL cells.

Proliferation activity of ECL cells in the PPI group is expected to be increased compared with sham, GRA and GRA-PPI groups (Eissele, R., Patberg, H., Koop, H., Krack, W., Lorenz, W., McKnight, A. T., and Arnold, R. Effect of gastrin receptor blockade on endrocine cells in rats during achlorhydria. *Gastroenterology,* 103, 1596-1601, 1992). Increased proliferation by PPI will be completely blocked by GRA.

The invention claimed is:

1. A pharmaceutically acceptable choline salt of a compound of formula (I)

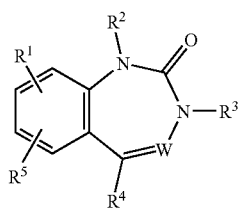

(I)

wherein:

W is N or $N^+$—$O^-$;

$R^1$ and $R^5$ are independently H, $C_1$ to $C_6$ alkyl, ($C_1$ to $C_6$ alkyl)oxy, mercapto, ($C_1$ to $C_6$ alkyl)mercapto, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino, ($C_1$ to $C_6$ alkyl)aminocarbonyl, di($C_1$ to $C_6$ alkyl)aminocarbonyl, [N-Z]($C_1$ to $C_6$ alkyl)carbonylamino, formyloxy, formamido, ($C_1$ to $C_6$ alkyl)aminosulfonyl, di($C_1$ to $C_6$ alkyl)aminosulfonyl, [N-Z]($C_1$ to $C_6$ alkyl)sulfonylamino or cyano; or $R^1$ and $R^5$ together form a methylenedioxy group;

$R^2$ is H or a $C_1$ to $C_{18}$ alkyl, alkenyl, alkynyl, cycloalkyl, polycycloalkyl, cycloalkenyl, or aryl group, or a combination thereof, optionally substituted with 1, 2, or 3 -L-$Q^2$ groups up to three C atoms of each alkyl, alkenyl, alkynyl, cycloalkyl, polycycloalkyl, cycloalkenyl, or aryl group may optionally be replaced by N, O and/or S atoms;

$R^3$ is —$(CR^{11}R^{12})_m$—X—$(CR^{13}R^{14})_p$—$R^9$;

m is 0, 1, 2, 3 or 4;

p is 0, 1 or 2;

X is a bond, —$CR^{15}$=$CR^{16}$—, —C≡C—, C(O)NH, NHC(O), C(O)NMe, NMeC(O), C(O)O, NHC(O)NH, NHC(O)O, OC(O)NH, NH, O, CO, $SO_2$, $SO_2$NH, C(O)NHNH,

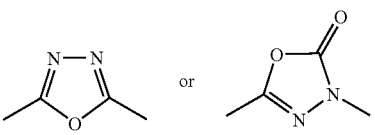

$R^9$ is H; $C_1$ to $C_6$ alkyl; or phenyl, naphthyl, pyridyl, benzimidazolyl, indazolyl, quinolinyl, isoquinolinyl, tetrahydroisoquinolinyl, indolinyl, isoindolinyl, indolyl, isoindolyl or 2-pyridonyl substituted with

-L-Q wherein:

L is a bond, or a group of the formula —$(CR^{17}R^{18})_v$—Y—$(CR^{17}R^{18})_w$, wherein v and w are independently 0, 1, 2 or 3, and Y is a bond, —$CR^{15}$=$CR^{16}$—, phenyl, furanyl, thiophenyl, pyrrolyl, thiazolyl, imidazolyl, oxazolyl, isoxazolyl, pyrazolyl, isoxazolonyl, piperazinyl, piperidinyl, morpholinyl, pyrrolidinyl, isothiazolyl, triazolyl, oxadiazolyl, thiadiazolyl, pyridyl or pyridazyl; and Q is 5-oxo-2,5-dihydro[1,2,4]oxadiazolyl;

$Q^2$ is H, ($C_1$ to $C_6$ alkyl)oxy, [N-Z]($C_1$ to $C_6$ alkyl)oxy($C_1$ to $C_6$ alkyl)amino, mercapto, ($C_1$ to $C_6$ alkyl)mercapto, carboxy($C_1$ to $C_6$ alkyl)thiol, carboxy, carboxy($C_1$ to $C_6$ alkyl), carboxy($C_1$ to $C_6$ alkenyl), [N-Z]carboxy($C_1$ to $C_6$ alkyl)amino, carboxy($C_1$ to $C_6$ alkyl)oxy, formyl, ($C_1$ to $C_6$ alkyl)carbonyl, ($C_1$ to $C_6$ cycloalkyl)carbonyl, ($C_1$ to $C_6$ alkyl)oxycarbonyl, ($C_1$ to $C_6$ alkyl)carbonyloxy, nitro, trihalomethyl, hydroxy, amino, [N-Z]($C_1$ to $C_6$ alkyl)amino, aminocarbonyl, ($C_1$ to $C_6$ alkyl)aminocarbonyl, di($C_1$ to $C_6$ alkyl)aminocarbonyl, [N-Z]($C_1$ to $C_6$ alkyl)carbonylamino, $C_5$ to $C_8$ cycloalkyl, [N-Z]($C_1$ to $C_6$ alkyl)carbonyl($C_1$ to $C_6$ alkyl)amino, halo, halo($C_1$ to $C_6$ alkyl), sulfamoyl, [N-Z]($C_1$ to $C_6$ alkyl)sulfonylamino, ($C_1$ to $C_6$ alkyl)sulfonylaminocarbonyl, carboxy ($C_1$ to $C_6$ alkyl)sulfonyl, carboxy($C_1$ to $C_6$ alkyl)sulfinyl, tetrazolyl, [N-Z]tetrazolylamino, cyano, amidino, amidinothio, $SO_3H$, formyloxy, formamido, $C_3$ to $C_8$ cycloalkyl, ($C_1$ to $C_6$ alkyl)sulphamoyl, di($C_1$ to $C_6$ alkyl)sulphamoyl, ($C_1$ to $C_6$ alkyl)carbonylaminosulfonyl, 5-oxo-2,5-dihydro[1,2,4]oxadiazolyl, carboxy($C_1$ to $C_6$ alkyl)carbonylamino, tetrazolyl($C_1$ to $C_6$ alkyl)thio, [N-Z]tetrazolyl($C_1$ to $C_6$ alkyl)amino, 5-oxo-2,5-dihydro[1,2,4]thiadiazolyl, 5-oxo-1,2-dihydro[1,2,4]triazolyl, [N-Z]($C_1$ to $C_6$ alkyl)amino($C_1$ to $C_6$ alkyl)amino, or a group of the formula

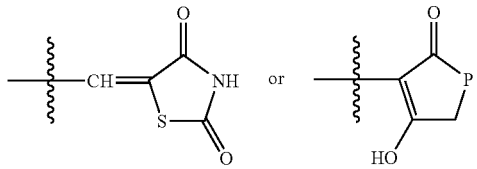

P is O, S or $NR^{19}$;

Z is H, $C_1$ to $C_6$ alkyl, t-butoxycarbonyl, acetyl, benzoyl or benzyl;

$R^4$ is H or a $C_1$ to $C_{18}$ alkyl, alkenyl, alkynyl, cycloalkyl, polycycloalkyl, cycloalkenyl, or aryl group, or a combination thereof, optionally substituted with 1, 2, or 3 -L-$Q^2$ groups wherein up to three C atoms of each alkyl, alkenyl, alkynyl, cycloalkyl, polycycloalkyl, cycloalkenyl, or aryl group may optionally be replaced by N, O and/or S atoms;

$R^{11}$, $R^{12}$, $R^{13}$, $R^{14}$, $R^{15}$, $R^{17}$, $R^{18}$ and $R^{19}$ are independently H or $C_1$ to $C_3$ alkyl; and $R^{16}$ is H, $C_1$ to $C_3$ alkyl, or acetylamino.

2. The salt of claim 1 wherein W is N.
3. The salt of claim 1 wherein $R^1$ and $R^5$ are both H.
4. The salt of claim 1 wherein $R^2$ is:

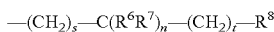

wherein:
$R^6$ and $R^7$ are independently selected from H, $C_1$ to $C_6$ alkyl or OH; or $R^6$ and $R^7$ together represent an =O group;
n is 0 or 1;
s is 0, 1, 2 or 3;
t is 0, 1, 2 or 3; and
$R^8$ is selected from H, $C_1$ to $C_{12}$ alkyl, ($C_1$ to $C_{12}$ alkyl)oxy, $C_3$ to $C_{12}$ cycloalkyl, phenyl, naphthyl, pyridyl, pyrrolyl, imidazolyl, pyrazolyl, pyridazinyl, pyrimidinyl, triazolyl, furanyl, thienyl, furazanyl, oxazolyl, isoxazolyl, thiazolyl, thiazinyl, indolyl, indolinyl, isoindolyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxanyl (all optionally substituted with 1, 2 or 3 groups independently selected from $C_1$ to $C_6$ alkyl, ($C_1$ to $C_6$ alkyl)oxy, mercapto, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino or cyano).

5. The salt of claim 4 wherein s is 1, n is 1, and $R^6$ and $R^7$ together represent an =O group.
6. The salt of claim 4 wherein t is 0 and $R^8$ is a $C_3$ to $C_{12}$ cycloalkyl group optionally substituted with a methyl group or a branched $C_3$ to $C_{12}$ alkyl group.
7. The salt of claim 4 wherein $R^8$ is a t-butyl, cyclohexyl, 1-methylcyclohexyl, 1-methylcyclopentyl or cyclopentyl group.
8. The salt of claim 1 wherein m is 1, $R^{11}$ is H and $R^{12}$ is H.
9. The salt of claim 1 wherein p is 0.
10. The salt of claim 1 wherein X is C(O)NH.
11. The salt of claim 1 wherein $R^4$ is

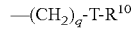

wherein:
q is 0, 1, 2 or 3;
T is a bond, O, S, NH or N($C_1$ to $C_6$ alkyl); and
$R^{10}$ is $C_1$ to $C_{12}$ alkyl, $C_3$ to $C_{12}$ cycloalkyl, phenyl, naphthyl, pyridyl, pyrrolyl, imidazolyl, pyrazolyl, pyridazinyl, pyrimidinyl, triazolyl, furanyl, thienyl, furazanyl, oxazolyl, isoxazolyl, thiazolyl, thiazinyl, indolyl, indolinyl, isoindolyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxanyl (all optionally substituted with 1, 2 or 3 groups independently selected from $C_1$ to $C_6$ alkyl, ($C_1$ to $C_6$ alkyl)oxy, $C_3$ to $C_8$ cycloalkyl, ($C_3$ to $C_8$ cycloalkyl)oxy, mercapto, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino or cyano).

12. The salt of claim 11 wherein q is 0, T is a bond and $R^{10}$ is $C_1$ to $C_{12}$ alkyl, $C_3$ to $C_{12}$ cycloalkyl, pyridyl or phenyl, wherein the $C_1$ to $C_{12}$ alkyl, $C_3$ to $C_{12}$ cycloalkyl, pyridyl and phenyl groups are optionally substituted with OMe, $NMe_2$, $CF_3$, Me, F, Cl, Br or I.
13. The salt of claim 1 wherein $R^4$ is cyclohexyl.
14. The salt of claim 1 wherein $R^3$ is —$CH_2$—X—$R^9$, X is C(O)NH, $R^9$ is phenyl-L-Q, L is a bond and Q is 5-oxo-2,5-dihydro[1,2,4]oxadiazolyl.
15. The salt of claim 1 that is
2-[5-Cyclohexyl-1-(2-cyclopentyl-2-oxo-ethyl)-2-oxo-1,2-dihydro-3H-1,3,4-benzotriazepin-3-yl]-N-[3-(5-oxo-2,5-dihydro-[1,2,4]oxadiazol-3-yl)-phenyl]-acetamide, choline salt.

* * * * *